United States Patent
Aspnes et al.

(10) Patent No.: US 11,858,916 B2
(45) Date of Patent: Jan. 2, 2024

(54) GLP-1 RECEPTOR AGONISTS AND USES THEREOF

(71) Applicant: Pfizer Inc., New York, NY (US)

(72) Inventors: Gary Erik Aspnes, Biberach an der Riss (DE); Scott W. Bagley, Mystic, CT (US); Edward L. Conn, Griswold, CT (US); John M. Curto, Mystic, CT (US); David J. Edmonds, Basel (CH); Mark E. Flanagan, Gales Ferry, CT (US); Kentaro Futatsugi, Sharon, MA (US); David A. Griffith, Sudbury, MA (US); Kim Huard, Berkeley, CA (US); Chris Limberakis, Pawcatuck, CT (US); Alan M. Mathiowetz, Waltham, MA (US); David W. Piotrowski, Waterford, CT (US); Roger B. Ruggeri, Waterford, CT (US)

(73) Assignee: Pfizer Inc., New York, NY (US)

( * ) Notice: Subject to any disclaimer, the term of this patent is extended or adjusted under 35 U.S.C. 154(b) by 559 days.

(21) Appl. No.: 17/251,929

(22) PCT Filed: Jun. 13, 2019

(86) PCT No.: PCT/IB2019/054961
§ 371 (c)(1),
(2) Date: Dec. 14, 2020

(87) PCT Pub. No.: WO2019/239371
PCT Pub. Date: Dec. 19, 2019

(65) Prior Publication Data
US 2021/0332034 A1    Oct. 28, 2021

Related U.S. Application Data

(60) Provisional application No. 62/685,656, filed on Jun. 15, 2018.

(51) Int. Cl.
*C07D 405/14* (2006.01)
*C07D 401/14* (2006.01)
*C07D 403/14* (2006.01)
*C07D 413/14* (2006.01)
*C07D 471/04* (2006.01)

(52) U.S. Cl.
CPC ......... *C07D 405/14* (2013.01); *C07D 401/14* (2013.01); *C07D 403/14* (2013.01); *C07D 413/14* (2013.01); *C07D 471/04* (2013.01)

(58) Field of Classification Search
CPC .. C07D 405/14; C07D 401/14; C07D 403/14; C07D 413/14; C07D 471/04
See application file for complete search history.

(56) References Cited

U.S. PATENT DOCUMENTS

| | | | |
|---|---|---|---|
| 10,208,019 B2 | 2/2019 | Aspnes et al. | |
| 10,669,259 B2 | 6/2020 | Aspnes et al. | |
| 10,676,465 B2 | 6/2020 | Aspnes et al. | |
| 10,683,281 B2 | 6/2020 | Aspnes et al. | |
| 10,851,081 B2 | 12/2020 | Aspnes et al. | |
| 10,934,279 B2 | 3/2021 | Aspnes et al. | |
| 2004/0127504 A1 | 7/2004 | Cowart et al. | |
| 2005/0143381 A1 | 6/2005 | Yu et al. | |

FOREIGN PATENT DOCUMENTS

| | | | |
|---|---|---|---|
| WO | 2007/115077 | 10/2007 | |
| WO | 2011/143365 | 11/2011 | |
| WO | 2018/109607 | 6/2018 | |
| WO | WO-2020103815 A1 * | 5/2020 | ......... A61K 31/4427 |

OTHER PUBLICATIONS

PCT/IB2019/054961 International Search Report dated Nov. 12, 2019.
PCT/IB2019/054961 Written Opinion of the International Searching Authority dated Nov. 12, 2019.

* cited by examiner

*Primary Examiner* — Matthew P Coughlin
(74) *Attorney, Agent, or Firm* — Feng Shao

(57) ABSTRACT

Provided herein are 6-carboxylic acids of benzimidazoles and 4-aza-, 5-aza-, and 7-aza-benzimidazoles as GLP-1R agonists, processes to make said compounds, and methods comprising administering said compounds to a mammal in need thereof.

20 Claims, No Drawings

GLP-1 RECEPTOR AGONISTS AND USES THEREOF

This application is a national phase filing under 35 U.S.C. § 371 of international patent application number PCT/IB2019/054961 filed Jun. 13, 2019, which in turn claims the benefit of priority to U.S. Provisional Patent Application Ser. No. 62/685,656 filed Jun. 15, 2018, the disclosure of each of these applications is hereby incorporated by reference in its entirety.

FIELD OF INVENTION

Provided herein are 6-carboxylic acids of benzimidazoles and 4-aza-, 5-aza-, and 7-aza-benzimidazoles as GLP-1R agonists, processes to make said compounds, and methods comprising administering said compounds to a mammal in need thereof.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. *Use of Antidiabetic Drugs in the U.S., 2003-2012, Diabetes Care* 2014, 37, 1367-1374). These may be grouped into six major classes, each acting through a different primary mechanism: (A) Insulin secretogogues, including sulphonyl-ureas (e.g., glipizide, glimepiride, glyburide), meglitinides (e.g., nateglidine, repaglinide), dipeptidyl peptidase IV (DPP-IV) inhibitors (e.g., sitagliptin, vildagliptin, alogliptin, dutogliptin, linagliptin, saxogliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP-IV inhibitors have limited efficacy. Marketed GLP-1R agonists are peptides administered by subcutaneous injection. Liraglutide is additionally approved for the treatment of obesity. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents, and frequent use may also lead to weight gain and carries a risk of hypoglycemia. (F) sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs have limited efficacy and do not address the most important problems, the declining β-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier, et al. *Biodrugs.* 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. *Diabetes.* 2001. 50; 609-613).

Holst (*Physiol. Rev.* 2007, 87, 1409) and Meier (*Nat. Rev. Endocrinol.* 2012, 8, 728) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need for an easily-administered prevention and/or treatment for cardiometabolic and associated diseases.

DETAILED DESCRIPTION OF THE INVENTION

The present invention concerns compounds of Formula I:

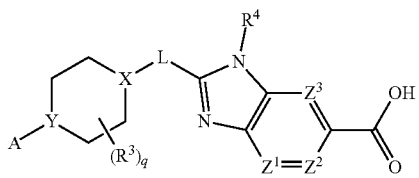

I or a pharmaceutically acceptable salt thereof, wherein A is A1 or A2,

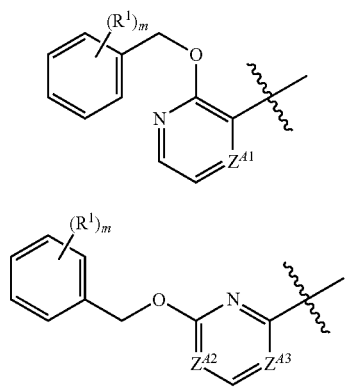

A1

A2 and wherein
  each $R^1$ is independently halogen, —CN, —$C_{1-3}$alkyl, or —$OC_{1-3}$alkyl, wherein the alkyl of $C_{1-3}$alkyl and $OC_{1-3}$alkyl is substituted with 0 to 3 F atoms;
  m is 0, 1, 2, or 3;
  X-L is N—$CH_2$, $CHCH_2$, or cyclopropyl;
  Y is CH or N;
  $Z^{A1}$ is CH, $CR^2$, or N;
  $Z^{A2}$ is CH, $CR^2$, or N;
  $Z^{A3}$ is CH, $CR^2$, or N, provided that $Z^{A2}$ and $Z^{A3}$ are not simultaneously N; and further provided that one of $Z^{A2}$ and $Z^{A3}$ is N when X-L is N—$CH_2$;
  each $R^2$ is independently F, Cl, or —CN;
  each $R^3$ is independently F, —OH, —CN, —$C_{1-3}$alkyl, —$OC_{1-3}$alkyl, or —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;
q is 0, 1, or 2;
$R^4$ is —$C_{1-3}$alkyl, —$C_{0-3}$alkylene-$C_{3-6}$cycloalkyl, —$C_{0-3}$alkylene-$R^5$, or —$C_{1-3}$alkylene-$R^6$, wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, and —$N(R^N)_2$, and
wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —$N(R^N)_2$;
$R^5$ is a 4- to 6-membered heterocycloalkyl, wherein said heterocycloalkyl may be substituted with 0 to 2 substituents as valency allows independently selected from:
  0 to 1 oxo (=O),
  0 to 1 —CN,
  0 2 F atoms, and
  0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
  0 to 3 F atoms,
  0 to 1 —CN, and
  0 to 1 —$OR^O$;
$R^6$ is a 5- to 6-membered heteroaryl, wherein said heteroaryl may be substituted with 0 to 2 substituents as valency allows independently selected from:
  0 to 2 halogens,
  0 to 1 substituent selected from —$OR^O$ and —$N(R^N)_2$, and
  0 to 2 —$C_{1-3}$alkyl, wherein the alkyl may be substituted with 0 to 3 substituents as valency allows independently selected from:
    0 to 3 F atoms, and
    0 to 1 —$OR^O$;
each $R^O$ is independently H, or —$C_{1-3}$alkyl, wherein $C_{1-3}$alkyl may be substituted with 0 to 3 F atoms;
each $R^N$ is independently H, or —$C_{1-3}$alkyl;
$Z^1$, $Z^2$, and $Z^3$ are each —$CR^Z$, or
one of $Z^1$, $Z^2$, and $Z^3$ is N and the other two are —$CR^Z$; and
each $R^Z$ is independently H, F, Cl, or —$CH_3$.

Another embodiment concerns a compound of Formula II

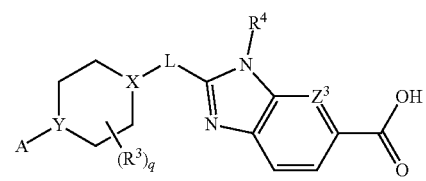

II or a pharmaceutically acceptable salt thereof, wherein A is A1 or A2,

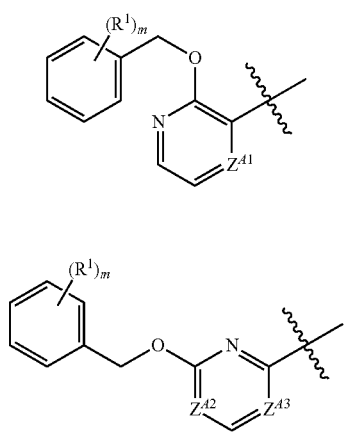

and wherein
each $R^1$ is independently F, Cl, or —CN; and
m is 0, 1, or 2.

Another embodiment concerns a compound of Formula III

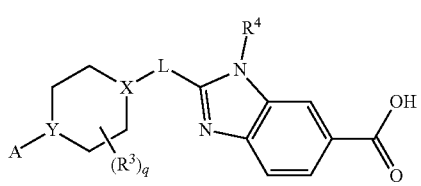

or a pharmaceutically acceptable salt thereof, wherein A is A1 or A2,

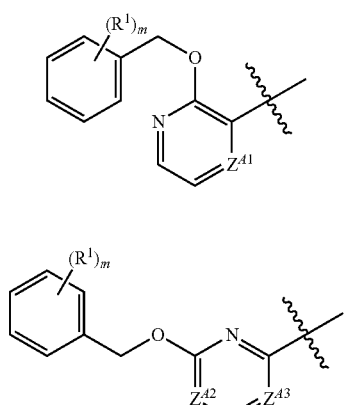

and wherein
each $R^1$ is independently F, Cl, or —CN; and
m is 0, 1, or 2.

Another embodiment concerns a compound of Formulas I, II, or III, wherein A is A1, or a pharmaceutically acceptable salt thereof.

Another embodiment concerns a compound of Formula IV

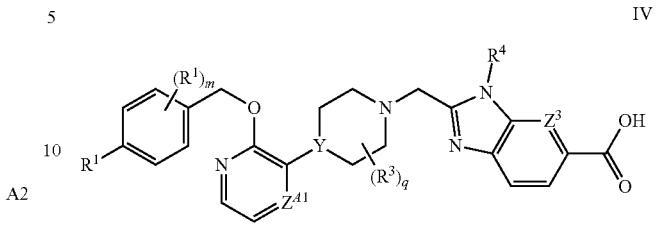

or a pharmaceutically acceptable salt thereof, wherein
each $R^1$ is independently F, Cl, or —CN;
m is 0, or 1;
q is 0 or 1; and
$R^3$ is —CH$_3$.

Another embodiment concerns a compound of Formulas I, II, III, or IV, wherein $Z^{A1}$ is CH, or CR$^2$; and $R^2$ is F; or a pharmaceutically acceptable salt thereof.

Another embodiment concerns a compound of Formulas I, II, III, or IV, wherein $Z^{A1}$ is N, or a pharmaceutically acceptable salt thereof.

Another embodiment concerns a compound of Formulas I, II, or OII, wherein A is A2,
q is 0 or 1; and
$R^3$ is —CH$_3$;
or a pharmaceutically acceptable salt thereof.

Another embodiment concerns a compound of Formulas I, II, or III, wherein $Z^{A2}$ is CH, or CR$^2$; and $Z^{A3}$ is N, or a pharmaceutically acceptable salt thereof.

Another embodiment concerns a compound of Formulas I, II, or III, wherein $Z^{A2}$ is N and $Z^{A3}$ is CH, or CR$^2$, or a pharmaceutically acceptable salt thereof.

Another embodiment concerns a compound of Formula I,

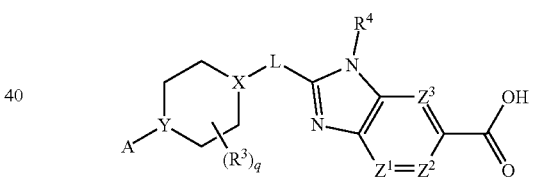

or a pharmaceutically acceptable salt thereof, wherein A is A1 or A2,

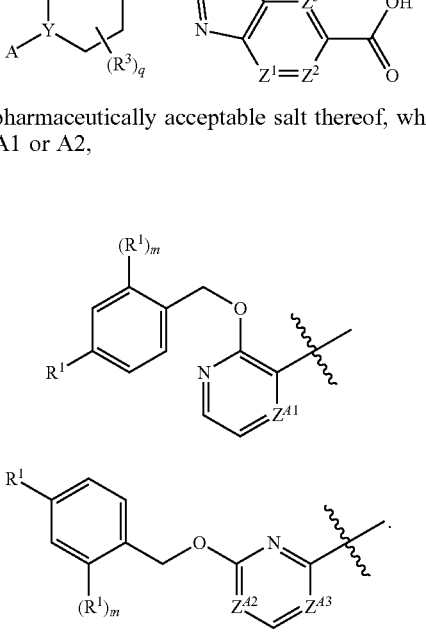

and wherein
each $R^1$ is independently F, Cl, or —CN; and
m is 0, or 1.

Another embodiment concerns compounds of other embodiments herein, e.g., compounds of Formulas I, II, or III, or a pharmaceutically acceptable salt thereof, wherein X-L is N—CH$_2$; and Y is CH or N. From the embodiments described herein, in such a case, X is N and L is CH$_2$.

Another embodiment concerns compounds of other embodiments herein, e.g., compounds of Formulas I, II, or III, or a pharmaceutically acceptable salt thereof, wherein X-L is CHCH$_2$; and Y is N. From the embodiments described herein, in such a case, X is CH and L is CH$_2$.

Another embodiment concerns compounds of other embodiments herein, e.g., compounds of Formulas I, II, or III, or a pharmaceutically acceptable salt thereof, wherein X-L is CHCH$_2$; and Y is CH. From the embodiments described herein, in such a case, X is CH and L is CH$_2$.

Another embodiment concerns compounds of other embodiments herein, e.g., compounds of Formulas I, or II, or a pharmaceutically acceptable salt thereof, wherein X-L is cyclopropyl; and Y is N.

In the embodiments where X-L is cyclopropyl, X-L being cyclopropyl would provide:

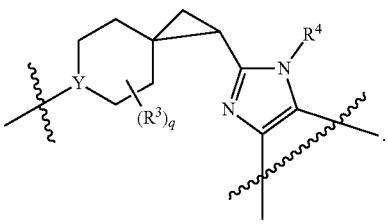

Another embodiment concerns a compound of Formula V

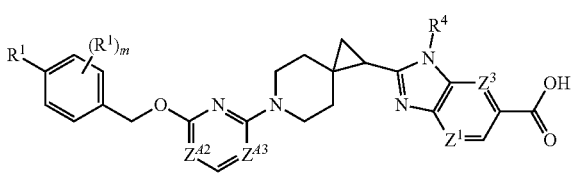

V or a pharmaceutically acceptable salt thereof, wherein
each R$^1$ is independently F, Cl, or —CN;
m is 0, or 1;
Z$^{A2}$ is CH, CR$^2$, or N;
Z$^{A3}$ is CH, CR$^2$, or N, provided that Z$^{A2}$ and Z$^{A3}$ are not simultaneously N; and
each R$^2$ is F.

Another embodiment concerns compounds a compound of Formula VI

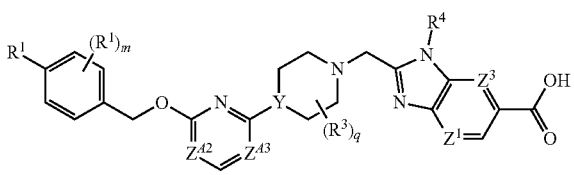

VI or a pharmaceutically acceptable salt thereof, wherein
each R$^1$ is independently F, Cl, or —CN;
m is 0, or 1;
R$^3$ is —CH$_3$;
q is 0, 1, or 2;
Z$^{A2}$ is CH, CR$^2$, or N;
Z$^{A3}$ is CH, CR$^2$, or N, Z$^{A2}$ and Z$^{A3}$ are not simultaneously N;
R$^2$ is F; and
Y is CH or N.

Another embodiment concerns compounds of any of Formulas I, II, III, IV, V, or IV and any embodiments thereof, wherein R$^4$ is —CH$_2$—R$^5$, wherein R$^5$ is the 4- to 5-membered heterocycloalkyl, wherein said heterocycloalkyl may be substituted with 0 to 2 substituents as valency allows independently selected from:
0 to 2 F atoms, and
0 to 1 substituent selected from oxo (═O), —OCH$_3$ and —CH$_2$OCH$_3$;
or a pharmaceutically acceptable salt thereof.

In the embodiments concerning a compound of Formulas II, III, IV, V, or VI, where a variable is not defined, it takes on the definition provided in Formula I.

Another embodiment concerns compounds of Formulas I, II, III, IV, V, or VI, wherein R$^4$ is —CH$_2$CH$_2$OCH$_3$, C$_{1-3}$alkylene-R$^5$, or C$_{1-3}$alkylene-R$^6$, or a pharmaceutically acceptable salt thereof.

Another embodiment concerns compounds of Formulas I, II, III, IV, V, or VI, wherein R$^4$ is —C$_{1-3}$alkyl, wherein said alkyl may be substituted as valency allows with 0 to 1 substituent selected from —C$_{0-1}$alkylene-OR$^O$, and —N(R$^N$)$_2$, or a pharmaceutically acceptable salt thereof.

Another embodiment concerns compounds of Formulas I, II, III, IV, V, or VI, wherein R$^4$ is —(CH$_2$)$_2$OCH$_3$, or —(CH$_2$)$_2$N(CH$_3$)$_2$, or a pharmaceutically acceptable salt thereof.

Another embodiment concerns compounds of Formulas I, II, III, IV, V, or VI, wherein R$^4$ is —CH$_2$—R$^5$, wherein R$^5$ is the 4- to 5-membered heterocycloalkyl, wherein said heterocycloalkyl may be substituted with 0 to 1 substituent that is oxo (═O), or a pharmaceutically acceptable salt thereof.

Another embodiment concerns compounds of Formulas I, II, III, IV, V, or VI, wherein R$_4$ is —CH$_2$—R$^5$, wherein R$^5$ is the 4- to 5-membered heterocycloalkyl, wherein said heterocycloalkyl may be substituted with 0 to 2 substituents as valency allows independently selected from:
0 to 2 F atoms, and
0 to 1 substituent selected from —OCH$_3$ and —CH$_2$OCH$_3$;
or a pharmaceutically acceptable salt thereof.

Another embodiment concerns compounds of any of Formulas I, II, III, IV, V, or IV and any embodiments thereof, wherein R$_4$ is —CH$_2$—R$^6$, wherein R$^6$ is the 5-membered heteroaryl, wherein said heteroaryl may be substituted with 0 to 2 substitutents as valency allows independently selected from:
0 to 2 halogens, wherein the halogen is independently selected from F and Cl,
0 to 1 —OCH$_3$, and
0 to 1 —CH$_3$, —CH$_2$CH$_3$, —CF$_3$, or —CH$_2$CH$_2$OCH$_3$;
or a pharmaceutically acceptable salt thereof.

Another embodiment concerns compounds of any of Formulas I, II, III, IV, V, or IV and any embodiments thereof, wherein R$_4$ is —C$_{1-3}$alkyl, wherein said alkyl may be substituted as valency allows with 0 to 3 substituents independently selected from 0 to 3 F atoms and 0 to 1 substituent that is —C$_{0-1}$alkylene-OR$^O$.

Another embodiment concerns compounds of Formulas I, II, III, IV, V, or VI, wherein the heterocycloalkyl is

[chemical structures: oxetane, tetrahydropyran, azetidine, pyrrolidine, piperidine, oxazolidine, imidazolidine, morpholine, dioxane, oxazinane (NH), and hexahydropyrimidine (NH)]

wherein the heterocycloalkyl may be substituted with 0 to 2 substituents as valency allows, e.g., replacing hydrogen, independently selected from:
  0 to 1 oxo (O═),
  0 to 1 —CN,
  0 to 2 F atoms, and
  0 to 2 substituents independently selected from —C$_{1-3}$ alkyl and —OC$_{1-3}$alkyl, wherein the alkyl of C$_{1-3}$alkyl and OC$_{1-3}$alkyl may be independently substituted with 0 to 3 substituents as valency allows independently selected from:
    0 to 3 F atoms,
    0 to 1 —CN, and
    0 to 1 —OR$^O$,
or a pharmaceutically acceptable salt thereof.

Another embodiment concerns compounds of Formulas I, II, III, IV, V, or VI, wherein the heterocycloalkyl is

[chemical structures: oxetane, tetrahydrofuran, tetrahydropyran, azetidine, pyrrolidine, piperidine, morpholine, and dioxane]

wherein the heterocycloalkyl may be substituted with 0 to 2 substituents as valency allows, e.g., replacing hydrogen, independently selected from:
  0 to 1 —CN,
  0 2 F atoms, and
  0 to 2 substituents independently selected from —C$_{1-3}$alkyl and —OC$_{1-3}$alkyl, wherein the alkyl of C$_{1-3}$alkyl and OC$_{1-3}$alkyl may be independently substituted with 0 to 3 substituents as valency allows independently selected from:
    0 to 3 F atoms,
    0 to 1 —CN, and
    0 to 1 —OR$^O$, or a pharmaceutically acceptable salt thereof.

Another embodiment concerns compounds of Formulas I, II, III, IV, V, or VI, wherein the heterocycloalkyl is

[chemical structures: pyrrolidinone, piperidinone, morpholinone, oxazolidinone, imidazolidinone, 1,3-dioxan-2-one, and tetrahydropyrimidinone]

wherein the heterocycloalkyl may be substituted with 0 to 1 substituent as valency allows, e.g., replacing hydrogen, selected from:
  —CN,
  F atom, and
  0 to 1 substituent independently selected from —C$_{1-3}$ alkyl and —OC$_{1-3}$alkyl, wherein the alkyl of C$_{1-3}$alkyl and OC$_{1-3}$alkyl may be substituted with 0 to 3 substituents as valency allows independently selected from:
    0 to 3 F atoms,
    0 to 1 —CN, and
    0 to 1 —OR$^O$,
or a pharmaceutically acceptable salt thereof.

Another embodiment concerns compounds of Formulas I, II, III, IV, V, or VI, wherein the heterocycloalkyl is

[chemical structures: oxetanyl, tetrahydrofuranyl, oxazolidinonyl, and tetrahydrofuranyl]

or a pharmaceutically acceptable salt thereof.

Another embodiment concerns compounds of Formulas I, II, III, IV, V, or VI, wherein the heterocycloalkyl is

[chemical structures: oxetanyl, tetrahydrofuranyl, or tetrahydrofuranyl]

wherein the heterocycloalkyl may be substituted as valency allows with 0 to 1 methyl, wherein said methyl may be substituted with 0 to 3 F atoms, or a pharmaceutically acceptable salt thereof.

Another embodiment concerns compounds of Formulas I, II, III, IV, V, or VI, wherein the heterocycloalkyl is

[chemical structure: oxetanyl]

wherein the heterocycloalkyl is unsubstituted, or a pharmaceutically acceptable salt thereof.

Another embodiment concerns compounds of Formulas I, II, III, IV, V, or VI, wherein —CH$_2$—R$^5$ and the nitrogen to which R$^4$ is attached provides:

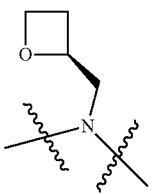 [SMILES: *N(*)C[C@@H]1CCO1]

or a pharmaceutically acceptable salt thereof.

Another embodiment concerns compounds of Formulas I, II, III, IV, V, or VI, wherein the heteroaryl is

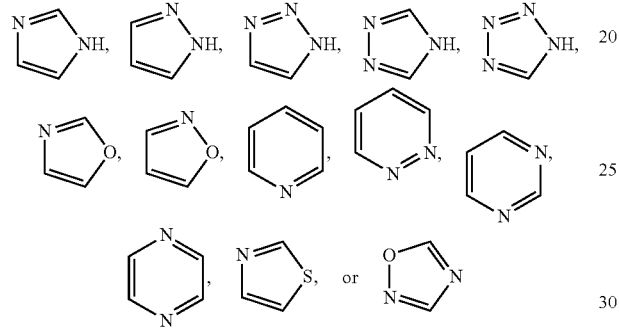

wherein said heteroaryl may be substituted with 0 to 2 substituents as valency allows, e.g., replacing hydrogen, independently selected from:
  0 to 2 halogens, wherein the halogen is independently selected from F and Cl,
  0 to 1 substituent selected from —OR$^O$ and —N(R$^N$)$_2$, or
  0 to 2 —C$_{1-3}$alkyl, wherein the alkyl may be substituted with 0 to 3 substituents as valency allows independently from:
    0 to 3 F atoms, and
    0 to 1 —OR$^O$;
or a pharmaceutically acceptable salt thereof.

Another embodiment concerns compounds of Formulas I, II, III, IV, V, or VI, wherein the heteroaryl is

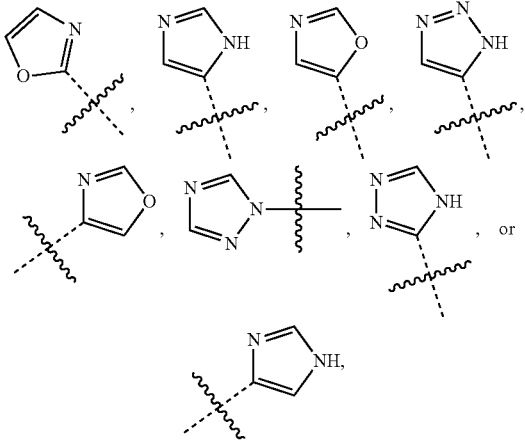

wherein said heteroaryl may be substituted with 0 to 1 substituent as valency allows with —C$_{1-2}$alkyl, wherein the alkyl may be substituted with 0 to 3 substituents as valency allows independently selected from:
  0 to 3 F atoms, and
  0 to 1 —OR$^O$; and
  each R$^O$ is independently H, or —C$_{1-3}$alkyl;
or a pharmaceutically acceptable salt thereof. One will recognize that any substituent would replace H on the carbon or nitrogen being substituted. A non-limiting example of substituted heteroaryls are:

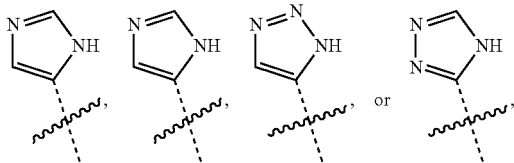

One will recognize that H is replaced with a substituent, e.g., R$^{6s}$ (substituent allowed on any heteroaryl of R$^6$), to provide:

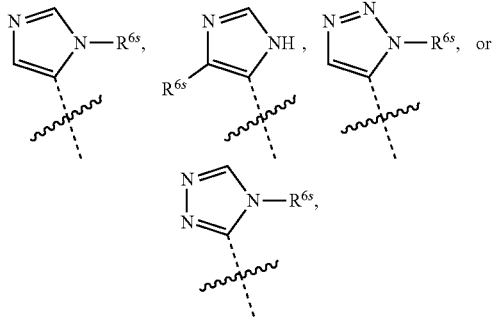

wherein R$^{6s}$ is —C$_{1-2}$alkyl, wherein the alkyl may be substituted with 0 to 3 substituents as valency allows independently selected from:
  0 to 3 F atoms, and
  0 to 1 —OR$^O$; and
  each R$^O$ is independently H, or —C$_{1-3}$alkyl;
or a pharmaceutically acceptable salt thereof.

Another embodiment concerns compounds of Formulas I, II, III, IV, V, or VI, wherein the heteroaryl is

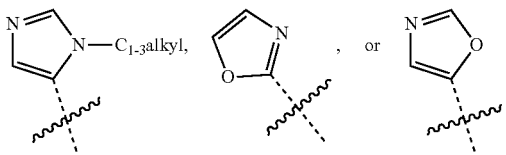

or a pharmaceutically acceptable salt thereof.

Another embodiment concerns any one or more compound that is
2-[(4-{2-[(4-chloro-2-fluorobenzyl)oxy]pyridin-3-yl} piperidin-1-yl)methyl]-1-[(2S)-oxetan-2-ylmethyl]-1H-benzimidazole-6-carboxylic acid;
2-[(4-{2-[(4-chloro-2-fluorobenzyl)oxy]pyridin-3-yl}piperidin-1-yl)methyl]-1-(1,3-oxazol-2-ylmethyl)-1H-benzimidazole-6-carboxylic acid;

2-[(4-{2-[(4-cyano-2-fluorobenzyl)oxy]pyridin-3-yl}piperidin-1-yl)methyl]-1-(1,3-oxazol-2-ylmethyl)-1H-benzimidazole-6-carboxylic acid;

2-[(4-{2-[(4-cyano-2-fluorobenzyl)oxy]pyridin-3-yl}piperidin-1-yl)methyl]-1-[(2S)-oxetan-2-ylmethyl]-1H-benzimidazole-6-carboxylic acid; or 2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylic acid;

or a pharmaceutically acceptable salt thereof.

Another embodiment concerns any one or more compound that is 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylic acid;

2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylic acid;

2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid;

2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylic acid; or 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylic acid;

or a pharmaceutically acceptable salt thereof.

Another embodiment concerns any one or more compound that is

2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylic acid;

2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylic acid; or 2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic acid;

or a pharmaceutically acceptable salt thereof.

Another embodiment concerns compounds, wherein the compound is 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylic acid, wherein chirality comes from C79;

2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylic acid, wherein chirality comes from P7;

2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid, wherein chirality comes from P7;

2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylic acid; or 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylic acid, wherein chirality comes from C93;

or a pharmaceutically acceptable salt thereof.

Another embodiment concerns compounds, wherein the compound is 2-[(4-{2-[(4-chloro-2-fluorobenzyl)oxy]pyridin-3-yl}piperidin-1-yl)methyl]-1-[(2S)-oxetan-2-ylmethyl]-1H-benzimidazole-6-carboxylic acid, or a pharmaceutically acceptable salt thereof.

Another embodiment concerns compounds, wherein the compound is 2-[(4-{2-[(4-chloro-2-fluorobenzyl)oxy]pyridin-3-yl}piperidin-1-yl)methyl]-1-(1,3-oxazol-2-ylmethyl)-1H-benzimidazole-6-carboxylic acid, or a pharmaceutically acceptable salt thereof.

Another embodiment concerns compounds, wherein the compound is 2-[(4-{2-[(4-cyano-2-fluorobenzyl)oxy]pyridin-3-yl}piperidin-1-yl)methyl]-1-(1,3-oxazol-2-ylmethyl)-1H-benzimidazole-6-carboxylic acid, or a pharmaceutically acceptable salt thereof.

Another embodiment concerns compounds, wherein the compound is 2-[(4-{2-[(4-cyano-2-fluorobenzyl)oxy]pyridin-3-yl}piperidin-1-yl)methyl]-1-[(2S)-oxetan-2-ylmethyl]-1H-benzimidazole-6-carboxylic acid, or a pharmaceutically acceptable salt thereof.

Another embodiment concerns compounds, wherein the compound is 2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylic acid, or a pharmaceutically acceptable salt thereof.

Another embodiment concerns compounds, wherein the compound is 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylic acid, or a pharmaceutically acceptable salt thereof.

Another embodiment concerns compounds, wherein the compound is 2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylic acid, or a pharmaceutically acceptable salt thereof.

Another embodiment concerns compounds, wherein the compound is 2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid;

2-[(1S)-6-{2-[(4-chloro-2-fluorobenzyl)oxy]-5-fluoropyrimidin-4-yl}-6-azaspiro[2.5]oct-1-yl]-1-(1,3-oxazol-2-ylmethyl)-1H-benzimidazole-6-carboxylic acid; or 2-[(1R)-6-{2-[(4-chloro-2-fluorobenzyl)oxy]-5-fluoropyrimidin-4-yl}-6-azaspiro[2.5]oct-1-yl]-1-(1,3-oxazol-2-ylmethyl)-1H-benzimidazole-6-carboxylic acid; or a pharmaceutically acceptable salt thereof.

Another embodiment concerns compounds, wherein the compound is 2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylic acid;

2-[(1S)6-{6-[(4-cyano-2-fluorobenzyl)oxy]-5-fluoropyridin-2-yl}-6-azaspiro[2.5]oct-1-yl]-1-[(2S)-oxetan-2-ylmethyl]-1H-benzimidazole-6-carboxylic acid; or 2-[(1R)6-{6-[(4-cyano-2-fluorobenzyl)oxy]-5-fluoropyridin-2-yl}-6-azaspiro[2.5]oct-1-yl]-1-[(2S)-oxetan-2-ylmethyl]-1H-benzimidazole-6-carboxylic acid;

or a pharmaceutically acceptable salt thereof.

Another embodiment concerns compounds, wherein the compound is 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylic acid;

2-[(1S)6-{6-[(4-cyano-2-fluorobenzyl)oxy]-3-fluoropyridin-2-yl}-6-azaspiro[2.5]oct-1-yl]-1-[(2S)-oxetan-2-ylmethyl]-1H-benzimidazole-6-carboxylic acid; or 2-[(1R)6-{6-[(4-cyano-2-fluorobenzyl)oxy]-3-fluoropyridin-2-yl}-6-azaspiro[2.5]oct-1-yl]-1-[(2S)-oxetan-2-ylmethyl]-1H-benzimidazole-6-carboxylic acid;

or a pharmaceutically acceptable salt thereof.

Another embodiment concerns compounds, wherein the compound is 2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylic acid, or a pharmaceutically acceptable salt thereof.

Another embodiment concerns compounds, wherein the compound is 2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylic acid, or a pharmaceutically acceptable salt thereof.

Another embodiment concerns compounds, wherein the compound is 2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic acid, or a pharmaceutically acceptable salt thereof.

Another embodiment concerns compounds of other embodiments herein, e.g., compounds of Formulas I, II, III, IV, V, or VI, wherein $Z^1$, $Z^2$, and $Z^3$ are each $CR^Z$, or a pharmaceutically acceptable salt thereof.

Another embodiment concerns compounds of other embodiments herein, e.g., compounds of Formulas I, II, III, IV, V, or VI, wherein $R^Z$ is H, or a pharmaceutically acceptable salt thereof.

Another embodiment concerns compounds of other embodiments herein, e.g., compounds of Formulas I, II, III, IV, V, or VI, wherein $Z^1$, $Z^2$, and $Z^3$ are each CH, or a pharmaceutically acceptable salt thereof.

Another embodiment concerns compounds of other embodiments herein, e.g., compounds of Formulas I, II, III, IV, V, or VI, wherein each $R^2$ is F, or a pharmaceutically acceptable salt thereof.

Another embodiment concerns compounds of other embodiments herein, e.g., compounds of Formulas I, II, III, IV, V, or VI, wherein q is 0, or a pharmaceutically acceptable salt thereof. One will recognize that when q is 0, $R^3$ is absent.

Another embodiment concerns compounds of other embodiments herein, e.g., compounds of Formulas I, II, III, IV, V, or VI, wherein $R^3$ is —CH$_3$, or —CF$_3$; and q is 1, or a pharmaceutically acceptable salt thereof.

Another embodiment concerns compounds of other embodiments herein, e.g., compounds of Formulas I, II, III, IV, V, or VI, wherein $R^3$ is —CH$_3$; and q is 1, or a pharmaceutically acceptable salt thereof.

Another embodiment concerns compounds of other embodiments herein, e.g., compounds of Formulas I, II, III, IV, V, or VI, wherein each $R^1$ is independently F, Cl, or —CN, or a pharmaceutically acceptable salt thereof.

Another embodiment concerns compounds of other embodiments herein, e.g., compounds of Formulas I, II, III, IV, V, or VI, wherein $R_4$ is —CH$_2$—R$^5$, or a pharmaceutically acceptable salt thereof.

Another embodiment concerns compounds of other embodiments herein, e.g., compounds of Formulas I, II, III, IV, V, or VI, wherein $R_4$ is —CH$_2$—R$^6$, or a pharmaceutically acceptable salt thereof.

Another embodiment concerns compounds of other embodiments herein, e.g., compounds of Formulas I, II, III, IV, V, or VI, wherein the compound is the free acid.

In another embodiment, the invention provides a pharmaceutical composition comprising a compound of Formulas I, II, III, IV, V, or VI, or a pharmaceutically acceptable salt thereof, as defined in any of the embodiments described herein, in admixture with at least one pharmaceutically acceptable excipient. This would include a pharmaceutical composition comprising a compound of Formulas I, II, III, IV, V, or VI or a pharmaceutically acceptable salt thereof, as defined in any of the embodiments described herein, in admixture with at least one pharmaceutically acceptable excipient and one or more other therapeutic agent discussed herein.

The invention also includes the following embodiments:
- a compound of Formulas I, II, III, IV, V, or VI, or a pharmaceutically acceptable salt thereof, as defined in any of the embodiments described herein, for use as a medicament;
- a compound of Formulas I, II, III, IV, V, or VI, or a pharmaceutically acceptable salt thereof, as defined in any of the embodiments described herein, for use in the prevention and/or treatment of cardiometabolic and associated diseases discussed herein, including T2DM, pre-diabetes, NASH, and cardiovascular disease;
- a method of treating a disease for which an agonist of GLP-1R is indicated, in a subject in need of such prevention and/or treatment, comprising administering to the subject a therapeutically effective amount of a compound of Formulas I, II, III, IV, V, or VI, or a pharmaceutically acceptable salt thereof, as defined in any of the embodiments described herein;
- the use of a compound of Formulas I, II, III, IV, V, or VI, or a pharmaceutically acceptable salt thereof, as defined in any of the embodiments described herein, for the manufacture of a medicament for treating a disease or condition for which an agonist of the GLP-1R is indicated;
- a compound of Formulas I, II, III, IV, V, or VI, or a pharmaceutically acceptable salt thereof, as defined in any of the embodiments described herein, for use in the treatment of a disease or condition for which an agonist of GLP-1R is indicated; or
- a pharmaceutical composition for the treatment of a disease or condition for which an agonist of the GLP-1R is indicated, comprising a compound of Formulas I, II, III, IV, V, or VI, or a pharmaceutically acceptable salt thereof, as defined in any of the embodiments described herein.

Every Example or pharmaceutically acceptable salt thereof may be claimed individually or grouped together in any combination.

The invention also relates to a pharmaceutical composition comprising a compound of Formulas I, II, III, IV, V, or VI, or a pharmaceutically acceptable salt thereof, as defined in any of the embodiments described herein, for use in the treatment and/or prevention of cardiometabolic and associated diseases discussed herein, including T2DM, pre-diabetes, NASH, and cardiovascular disease.

Another embodiment of the invention concerns a compound of Formulas I, II, III, IV, V, or VI, or a pharmaceutically acceptable salt thereof, as defined in any of the embodiments described herein, for use in the treatment and/or prevention of cardiometabolic and associated diseases including diabetes (T1D and/or T2DM, including pre-diabetes), idiopathic T1D (Type 1b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, prevention or treatment of Polycystic Ovary Syndrome and treatment of addiction (e.g., alcohol and/or drug abuse).

Abbreviations used herein are as follows:

The term "alkyl", as used herein, means a straight or branched chain monovalent hydrocarbon group of formula —$C_nH_{(2n+1)}$. Non-limiting examples include methyl, ethyl, propyl, butyl, 2-methyl-propyl, 1,1-dimethylethyl, pentyl and hexyl.

The term "alkylene", as used herein, means a straight or branched chain divalent hydrocarbon group of formula —$C_nH_{2n}$—. Non-limiting examples include ethylene, and propylene.

The term "cycloalkyl", as used herein, means a cyclic, monovalent hydrocarbon group of formula —$C_nH_{(2n-1)}$ containing at least three carbon atoms. Non-limiting examples include cyclopropyl, cyclobutyl, cyclopentyl and cyclohexyl.

The term "halogen", as used herein, refers to fluoride, chloride, bromide, or iodide.

The term "heterocycloalkyl", as used herein, refers to a cycloalkyl group in which one or more of the ring methylene groups (—CH$_2$—) has been replaced with a group selected from —O—, —S— or nitrogen, wherein the nitrogen may provide a point of attachment or may be substituted as provided within each embodiment. Where nitrogen provides a point of attachment, a structural drawing of a heterocycloalkyl would have an hydrogen on said nitrogen. Generally, the heterocycloalkyl may be substituted with 0 to 2 substituents as valency allows independently selected from oxo, —CN, halogen, alkyl and —Oalkyl and the alkyl may be further substituted. One will note that when there is 0 substitution, the heterocycloalkyl is unsubstituted.

The term "heteroaryl", as used herein, refers to a monocyclic aromatic hydrocarbon containing from 5 to 6 carbon atoms in which at least one of the ring carbon atoms has been replaced with a heteroatom selected from oxygen, nitrogen and sulfur. Such a heteroaryl group may be attached through a ring carbon atom or, where valency permits, through a ring nitrogen atom. Generally, the heteroaryl may be substituted with 0 to 2 substituents as valency allows independently selected from halogen, OH, alkyl, O-alkyl, and amino (e.g., NH$_2$, NHalkyl, N(alkyl)$_2$), and the alkyl may be further substituted. One will note that when there is 0 substitution, the heteroaryl is unsubstituted.

Room temperature: RT.
Methanol: MeOH.
Ethanol: EtOH.
Isopropanol: iPrOH.
Ethyl acetate: EtOAc.
Tetrahydrofuran: THF.
Toluene: PhCH$_3$.
Cesium carbonate: Cs$_2$CO$_3$.
Lithium bis(trimethylsilyl)amide: LiHMDS.
Sodium t-butoxide: NaOtBu.
Potassium t-butoxide: KOtBu.
Lithium diisopropylamide: LDA.
Triethylamine: Et$_3$N.
N,N-diisopropylethyl amine: DIPEA.
Potassium carbonate: K$_2$CO$_3$.
Dimethyl formamide: DMF.
Dimethyl acetamide: DMAc.
Dimethyl sulfoxide: DMSO.
N-Methyl-2-pyrrolidinone: NMP.
Sodium hydride: NaH.
Trifluoroacetic acid: TFA.
Trifluoroacetic anhydride: TFAA.
Acetic anhydride: Ac$_2$O.
Dichloromethane: DCM.
1,2-Dichloroethane: DCE.
Hydrochloric acid: HCl.
1,8-Diazabicyclo[5.4.0]undec-7-ene: DBU.
Borane-dimethylsulfide complex: BH$_3$-DMS.
Borane-tetrahydrofuran complex: BH$_3$-THF.
Lithium aluminum hydride: LAH.
Acetic acid: AcOH.
Acetonitrile: MeCN.
p-Toluenesulfonic acid: pTSA.
Dibenzylidine acetone: DBA.
2,2'-Bis(diphenylphosphino)-1,1'-binaphthalene: BINAP.
1,1'-Ferrocenediyl-bis(diphenylphosphine): dppf.
1,3-Bis(diphenylphosphino)propane: DPPP.
3-Chloroperbenzoic acid: m-CPBA.
Tert-Butyl methyl ether: MTBE.
Methanesulfonyl: Ms.
N-Methylpyrrolidinone: NMP.
Thin layer chromatography: TLC.
Supercritical fluid chromatography: SFC.
4-(Dimethylamino)pyridine: DMAP.
Tert-Butyloxycarbonyl: Boc.
1-[Bis(dimethylamino)methylene]-1H-1,2,3-triazolo[4,5-b]pyridinium 3-oxid hexafluorophosphate: HATU.
Petroleum ether: PE.
2-(1H-Benzotriazole-1-yl)-1,1,3,3-tetramethyluronium hexafluorophosphate: HBTU.
2-Amino-2-(hydroxymethyl)propane-1,3-diol: tris.
tris(dibenzylideneacetone)dipalladium: Pd$_2$(dba)$_3$ $^1$H Nuclear magnetic resonance (NMR) spectra were in all cases consistent with the proposed structures. Characteristic chemical shifts (δ) are given in parts-per-million relative to the residual proton signal in the deuterated solvent (CHCl$_3$ at 7.27 ppm; CD$_2$HOD at 3.31 ppm; MeCN at 1.94 ppm; DMSO at 2.50 ppm) and are reported using conventional abbreviations for designation of major peaks: e.g. s, singlet; d, doublet; t, triplet; q, quartet; m, multiplet; br, broad.

As used herein, a wavy line, "⁓" denotes a point of attachment of a substituent to another group.

The compounds and intermediates described below were named using the naming convention provided with ACD/ChemSketch 2012, File Version C10H41, Build 69045 (Advanced Chemistry Development, Inc., Toronto, Ontario, Canada). The naming convention provided with ACD/ChemSketch 2012 is well-known by those skilled in the art and it is believed that the naming convention provided with ACD/ChemSketch 2012 generally comports with the IUPAC (International Union for Pure and Applied Chemistry) recommendations on Nomenclature of Organic Chemistry and the CAS Index rules. One will note that the chemical names may have only parentheses or may have parentheses and brackets. The stereochemical descriptors may also be placed different locations within the name itself, depending on the naming convention. One of ordinary skill in the art will recognize these formatting variations and understand they provide the same chemical structure.

Pharmaceutically acceptable salts of the compounds of Formula I include acid addition and base salts.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinafoate salts.

Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-Amino-2-(hydroxymethyl)propane-1,3-diol (tris or tromethamine) and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:
(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'.

Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The compounds of Formula I may exhibit polymorphism and/or one or more kinds of isomerism (e.g. optical, geometric or tautomeric isomerism). The compounds of Formula I may also be isotopically labelled. Such variation is implicit to the compounds of Formula I defined as they are by reference to their structural features and therefore within the scope of the invention.

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

The pharmaceutically acceptable salts of compounds of Formula I may also contain a counterion which is optically active (e.g. d-lactate or l-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, a racemic precursor containing a chiral ester may be separated by enzymatic resolution (see, for example, Int J Mol Sci 29682-29716 by A. C. L. M. Carvaho et. al. (2015)). In the case where the compound of Formula I contains an acidic or basic moiety, a salt may be formed with an optically pure base or acid such as 1-phenylethylamine or tartaric acid. The resulting diastereomeric mixture may be separated by fractional crystallization and one or both of the diastereomeric salts converted to the corresponding pure enantiomer(s) by means well known to a skilled person. Alternatively, the racemate (or a racemic precursor) may be covalently reacted with a suitable optically active compound, for example, an alcohol, amine or benzylic chloride. The resulting diastereomeric mixture may be separated by chromatography and/or fractional crystallization by means well known to a skilled person to give the separated diastereomers as single enantiomers with 2 or more chiral centers. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (SFC with Packed Columns), pp. 223-249 and references cited therein). In some relevant examples herein, columns were obtained from Chiral Technologies, Inc, West Chester, Pennsylvania, USA, a subsidiary of Daicel® Chemical Industries, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

It must be emphasised that the compounds of Formula I have been drawn herein in a single tautomeric form, all possible tautomeric forms are included within the scope of the invention.

The present invention includes all pharmaceutically acceptable isotopically-labeled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

One way of carrying out the invention is to administer a compound of Formula I in the form of a prodrug. Thus, certain derivatives of a compound of Formula I which may have little or no pharmacological activity themselves can, when administered into or onto the body, be converted into a compound of Formula I having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Prodrugs as Novel Delivery Systems', Vol. 14, *ACS Symposium Series* (T. Higuchi and W. Stella) and 'Bioreversible Carriers in Drug Design', Pergamon Press, 1987 (Ed. E. B. Roche, American Pharmaceutical Association). Reference can also be made to *Nature Reviews/Drug Discovery*, 2008, 7, 355 and *Current Opinion in Drug Discovery and Development*, 2007, 10, 550.

Prodrugs in accordance with the invention can, for example, be produced by replacing appropriate functionalities present in the compounds of Formula I with certain moieties known to those skilled in the art as 'pro-moieties' as described, for example, in 'Design of Prodrugs' by H. Bundgaard (Elsevier, 1985) and Y. M. Choi-Sledeski and C. G. Wermuth, 'Designing Prodrugs and Bioprecursors' in Practice of Medicinal Chemistry, (Fourth Edition), Chapter 28, 657-696 (Elsevier, 2015).

Thus, a prodrug in accordance with the invention is (a) an ester or amide derivative of a carboxylic acid in a compound of Formula I; (b) an ester, carbonate, carbamate, phosphate or ether derivative of a hydroxyl group in a compound of Formula I; (c) an amide, imine, carbamate or amine derivative of an amino group in a compound form Formula I; (d) an oxime or imine derivative of a carbonyl group in a compound of Formula I; or (e) a methyl, primary alcohol or aldehyde group that can be metabolically oxidized to a carboxylic acid in a compound of Formula I.

Some specific examples of prodrugs in accordance with the invention include:

(i) where the compound of Formula I contains a carboxylic acid functionality (—COOH), an ester thereof, such as a compound wherein the hydrogen of the carboxylic acid functionality of the compound of Formula I is replaced by $C_1$-$C_8$ alkyl (e.g. ethyl) or ($C_1$-$C_8$ alkyl)C(=O)OCH$_2$— (e.g. $^t$BuC(=O)OCH$_2$—);

(ii) where the compound of Formula I contains an alcohol functionality (—OH), an ester thereof, such as a compound wherein the hydrogen of the alcohol functionality of the compound of Formula I is replaced by —CO($C_1$-$C_8$ alkyl) (e.g. methylcarbonyl) or the alcohol is esterified with an amino acid;

(iii) where the compound of Formula I contains an alcohol functionality (—OH), an ether thereof, such as a compound wherein the hydrogen of the alcohol functionality of the compound of Formula I is replaced by ($C_1$-$C_8$ alkyl)C(=O)OCH$_2$— or —CH$_2$OP(=O)(OH)$_2$;

(iv) where the compound of Formula I contains an alcohol functionality (—OH), a phosphate thereof, such as a compound wherein the hydrogen of the alcohol functionality of the compound of Formula I is replaced by —P(=O)(OH)$_2$ or —P(=O)(ONa)$_2$ or —P(=O)(O$^-$)$_2$Ca$^{2+}$;

(v) where the compound of Formula I contains a primary or secondary amino functionality (—NH$_2$ or —NHR where R≠H), an amide thereof, for example, a compound wherein, as the case may be, one or both hydrogens of the amino functionality of the compound of Formula I is/are replaced by ($C_1$-$C_{10}$)alkanoyl, —COCH$_2$NH$_2$ or the amino group is derivatised with an amino acid;

(vi) where the compound of Formula I contains a primary or secondary amino functionality (—NH$_2$ or —NHR where R≠H), an amine thereof, for example, a compound wherein, as the case may be, one or both hydrogens of the amino functionality of the compound of Formula I is/are replaced by —CH$_2$OP(=O)(OH)$_2$;

(vii) where the carboxylic acid group within compound of Formula I is replaced by a methyl group, a —CH$_2$OH group or an aldehyde group.

Certain compounds of Formula I may themselves act as prodrugs of other compounds of Formula I. It is also possible for two compounds of Formula I to be joined together in the form of a prodrug. In certain circumstances, a prodrug of a compound of Formula I may be created by internally linking two functional groups in a compound of Formula I, for instance by forming a lactone.

References to compounds of Formula I are taken to include the compounds themselves and prodrugs thereof. The invention includes such compounds of Formula I as well as pharmaceutically acceptable salts of such compounds and pharmaceutically acceptable solvates of said compounds and salts.

Administration and Dosing

Typically, a compound of the invention is administered in an amount effective to treat a condition as described herein. The compounds of the invention can be administered as compound per se, or alternatively, as a pharmaceutically acceptable salt. For administration and dosing purposes, the compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, or topically.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the invention is typically from about 0.001 to about 100 mg/kg (i.e., mg compound of the invention per kg body weight) for the treatment of the indicated conditions discussed herein. In another embodiment, total daily dose of the compound of the invention is from about 0.01 to about 30 mg/kg, and in another embodiment, from about 0.03 to about 10 mg/kg, and in yet another embodiment, from about 0.1 to about 3. It is not uncommon that the administration of the compounds of the invention will be repeated a plurality of times in a day (typically no greater than 4 times). Multiple doses per day typically may be used to increase the total daily dose, if desired.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the invention include mammalian subjects. In one embodiment, humans are suitable subjects. Human subjects may be of either gender and at any stage of development.

Pharmaceutical Compositions

In another embodiment, the invention comprises pharmaceutical compositions. Such pharmaceutical compositions comprise a compound of the invention presented with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Co-Administration

The compounds of the invention can be used alone, or in combination with other therapeutic agents. The invention provides any of the uses, methods or compositions as defined herein wherein the compound of any embodiment of Formula I herein, or pharmaceutically acceptable salt thereof, or pharmaceutically acceptable solvate of said compound or salt, is used in combination with one or more other therapeutic agent discussed herein. This would include a pharmaceutical composition comprising a compound of Formulas I, II, III, IV, V, or VI or a pharmaceutically acceptable salt thereof, as defined in any of the embodiments described herein, in admixture with at least one pharmaceutically acceptable excipient and one or more other therapeutic agent discussed herein.

The administration of two or more compounds "in combination" means that all of the compounds are administered closely enough in time that each may generate a biological effect in the same time frame. The presence of one agent may alter the biological effects of the other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the invention provides methods of treatment that include administering compounds of the present invention in combination with one or more other pharmaceutical agents, wherein the one or more other pharmaceutical agents may be selected from the agents discussed herein.

In one embodiment, the compounds of this invention are administered with an anti-diabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of this invention are administered with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buprorion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of this invention are administered with an agent to treat NASH including but not limited to PF-05221304, an FXR agonist (e.g., obeticholic acid), a PPAR α/δ agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the compound of Formulas I, II, III, IV, V, or VI, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

Another aspect of the invention provides kits comprising the compound of Formulas I, II, or III or pharmaceutical compositions comprising the compound of Formulas I, II, or III of the invention. A kit may include, in addition to the compound of Formulas I, II, or III, of the invention or pharmaceutical composition thereof, diagnostic or therapeutic agents. A kit may also include instructions for use in a diagnostic or therapeutic method. In some embodiments, the kit includes the compound of Formulas I, II, III, IV, V, or VI, or a pharmaceutical composition thereof and a diagnostic agent. In other embodiments, the kit includes the compound of Formulas I, II, III, IV, V, or VI, or a pharmaceutical composition thereof.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

Preparation

The compounds of Formulas I, II, III, IV, V, or VI, may be prepared by the general and specific methods described below, using the common general knowledge of one skilled in the art of synthetic organic chemistry. Such common general knowledge can be found in standard reference books such as Comprehensive Organic Chemistry, Ed. Barton and Ollis, Elsevier; Comprehensive Organic Transformations: A Guide to Functional Group Preparations, Larock, John Wiley and Sons; and Compendium of Organic Synthetic Methods, Vol. I-XII (published by Wiley-Interscience). The starting materials used herein are commercially available or may be prepared by routine methods known in the art.

In the preparation of the compounds of Formulas I, II, III, IV, V, or VI, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I compounds.

The Schemes described below are intended to provide a general description of the methodology employed in the preparation of the compounds of the present invention. Some of the compounds of the present invention may contain single or multiple chiral centers with the stereochemical designation (R) or (S). It will be apparent to one skilled in the art that all of the synthetic transformations can be conducted in a similar manner whether the materials are enantioenriched or racemic. Moreover the resolution to the desired optically active material may take place at any desired point in the sequence using well known methods such as described herein and in the chemistry literature. For example, intermediates (e.g., S29, S32, S37 and S48) and finals (e.g., S49) may be separated using chiral chromatographic methods. Alternatively, chiral salts may be utilized to isolate enantiomerically enriched intermediates and final compounds.

In the Schemes that follow, the variables A, A1, A2, X, Y, L, $Z^1$, $Z^2$, $Z^3$, $Z^{A1}$, $Z^{A2}$, $Z^{A3}$, $R^1$, $R^2$, $R^3$, $R^4$, $R^5$, $R^6$, m, and q are as described herein for compounds of Formulas I, II, III, IV, V, or VI unless otherwise noted. For the Schemes provided below, each p is independently 0 or 1. For the Schemes provided below, each $X^1$, $X^2$, $X^3$, and $X^4$ can independently be a leaving group such as any alkyl or aryl sulfonate (e.g., mesylate, tosylate, or triflate), or a halogen or any other group that can be displaced by an amine or utilized in a metal mediated coupling reaction. $X^4$ may also be a protected carboxylic acid (i.e., ester). When the protecting group is identified as $Pg^1$, it can be an alkyl amine protecting group such as benzyl, benzhydryl, or the like; a carbamate protecting group such as Boc, Cbz, or the like; or an amide protecting group such trifluoroacetamide. When the protecting group is identified as $Pg^2$, it can be acid protecting group such as methyl, ethyl, benzyl, t-butyl or the like. $R^{4a}$ is $C_{1-2}$alkyl, $C_{0-2}$alkylene-$C_{3-6}$cycloalkyl, $C_{0-2}$alkylene-$R^5$, or $C_{1-2}$alkylene-$R^6$, wherein said alkyl, alkylene, or cycloalkyl may be independently substituted as valency allows with 0 to 3 F atoms and 0 to 1 substituent independently selected from $C_{0-1}$alkylene-$OR^O$ and —$N(R^N)_2$.

The substituted piperidine of general structure S6 where Y=CH may be prepared as discussed in Scheme 1. The heterocycle of general structure S1 may be reacted with a substituted boronic acid or boronate ester (S2) in the presence of a palladium catalyst and ligand complex in the manner of a Suzuki reaction (Maluenda and Navarro, Molecules, 2015, 20, 7528-7557) to provide compounds of the general formula S3. When $Z^{A1}$ is CH or $CR_2$, a preferred $X_1$ leaving group is F or $SO_2Me$ (from oxidation of SMe, as described in Scheme 3) and preferred $X_2$ substituents include Br and I. When $Z^{A1}$ is N, Cl is preferred for both $X_1$ and $X_2$. Reduction of the olefin to provide compounds of general structure S4 could be performed under an atmosphere of hydrogen (15-100 psi $H_2$) in an alcoholic solvent such as MeOH or EtOH or alternatively an aprotic organic solvent such as EtOAc or THF in the presence of an appropriate catalyst such as palladium on carbon, $Pd(OH)_2$ on carbon (Pearlman's catalyst), $PtO_2$ (Adams catalyst), or tris(triphenylphosphine)rhodium(I) chloride (Wilkinson's catalyst). Transfer hydrogenation reagents, for example ammonium formate or dihydrobenzene, or similar, may be employed using suitable catalyst. Alternatively, the reduction may be accomplished by alternative methods know to those skilled in the art using reagents such as triethyl silane or other silanes, under acid or metallic catalysis, or metallic reductants, such as magnesium or similar. Alternatively, the olefin can be functionalized by methods known to one skilled in the art to introduce $R^3$ groups. For example, the olefin could be hydroborated to produce an alcohol that could be alkylated or further converted to a nitrile, F or alkyl group. Conversion to compounds of general structure S6 can be accomplished by such manner as a Buchwald-Hartwig C—O coupling (Lundgren and Stradiotto, Aldrich Chimica Acta, 2012, 45, 59-65) between compounds of the general structure S4 and an appropriately substituted benzyl alcohol S5 in the presence of a palladium or copper catalyst and ligand complex. A preferred $X_1$ halogen is Cl. These reactions are generally performed between 0 and 110° C. in aprotic organic solvents such as but not limited to 1,4-dioxane and $PhCH_3$ with added base such as $Cs_2CO_3$, LiHMDS or NaOtBu. Alternatively, reaction of S4 with an appropriately substituted benzyl alcohol S5 in an aprotic solvent such as DMF or THF in the presence of a strong base such as NaH, KOtBu or LiHMDS can deliver compounds of the general structure S6. Preferred $X_1$ substituents for this reaction include F and Cl or sulfones (e.g. $SO_2Me$).

The substituted piperazine of general structure S6 where Y=N may be prepared as discussed in Scheme 2. Conversion of S1 to compounds of general structure S7 can be accomplished by reaction of S1 with an appropriately substituted benzyl alcohol S5 in an aprotic solvent such as DMF or THF in the presence of a strong base such as NaH, KOtBu or LiHMDS, to deliver compounds of the general structure S7. When $Z^{A1}$ is CH or $CR_2$, a preferred $X_1$ leaving group is F, and preferred $X_2$ substituents include Br and I. When $Z^{A1}$ is N, Cl is preferred for both $X_1$ and $X_2$. Conversion of S7 to compounds of general structure S6 where Y=N may be accomplished by such manner as a Buchwald-Hartwig C—N coupling between compounds of the general structure S7 and an appropriately substituted and protected piperazine S8 in the presence of a palladium or copper catalyst and ligand complex. These reactions are generally performed between 0 and 110° C. in aprotic organic solvents such as but not limited to 1,4-dioxane and $PhCH_3$ with added base such as $Cs_2CO_3$, LiHMDS or NaOtBu.

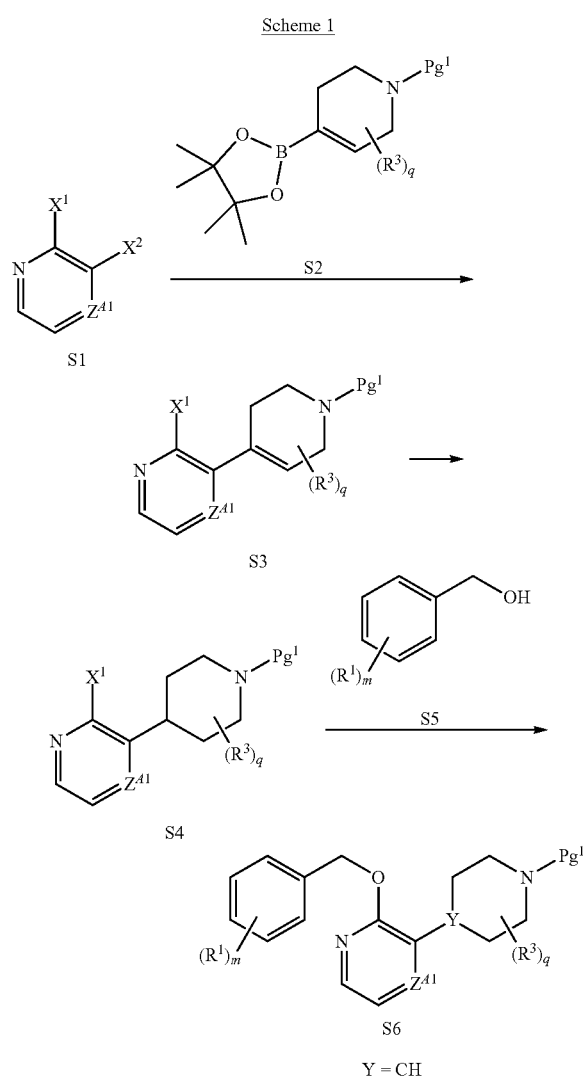

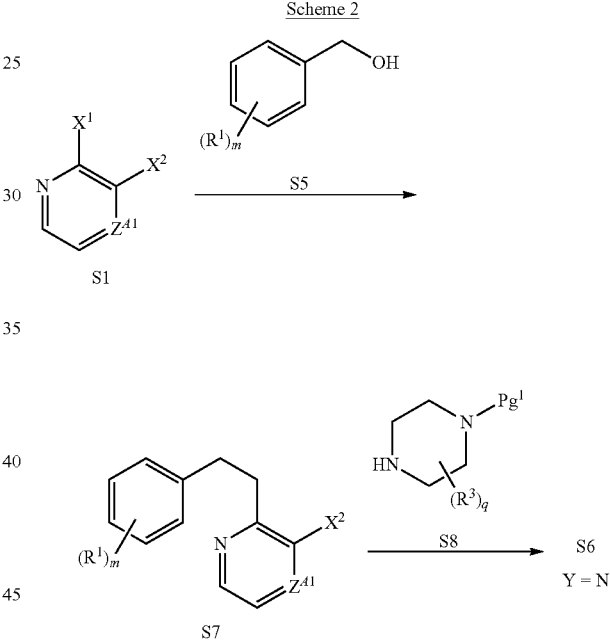

As shown in Scheme 3, appropriately substituted piperidine esters of general structure S9 can be reacted with pyrimidines S11 in the presence of strong base such as LiHMDS or LDA or other suitable base in an aprotic organic solvent such as THF to deliver compounds of the general structure S12. In reactions of S9 with S11, $X^1$ is preferably Cl or more preferably SMe, $X^2$ is preferably Cl. Removal of $Pg^2$ through ester hydrolysis and decarboxylation of the resulting carboxylic acids may deliver piperidines S13 ($X^1$=SMe) or S14 ($X^1$=Cl). When $X^1$ is SMe, oxidation of the thioether with a peroxide such as meta-chloroperbenzoic acid may provide sulfoxides or sulfones S14 ($X^1$=S(O)Me, $SO_2Me$). Reaction of pyrimidine S14 ($X^1$=Cl, S(O)Me, $SO_2Me$) with an appropriately substituted benzyl alcohol S5 in an aprotic solvent such as DMF or THF in the presence of a strong base such as NaH, KOtBu, LiHMDS, or NaHMDS may deliver compounds of the general structure S15.

Scheme 3

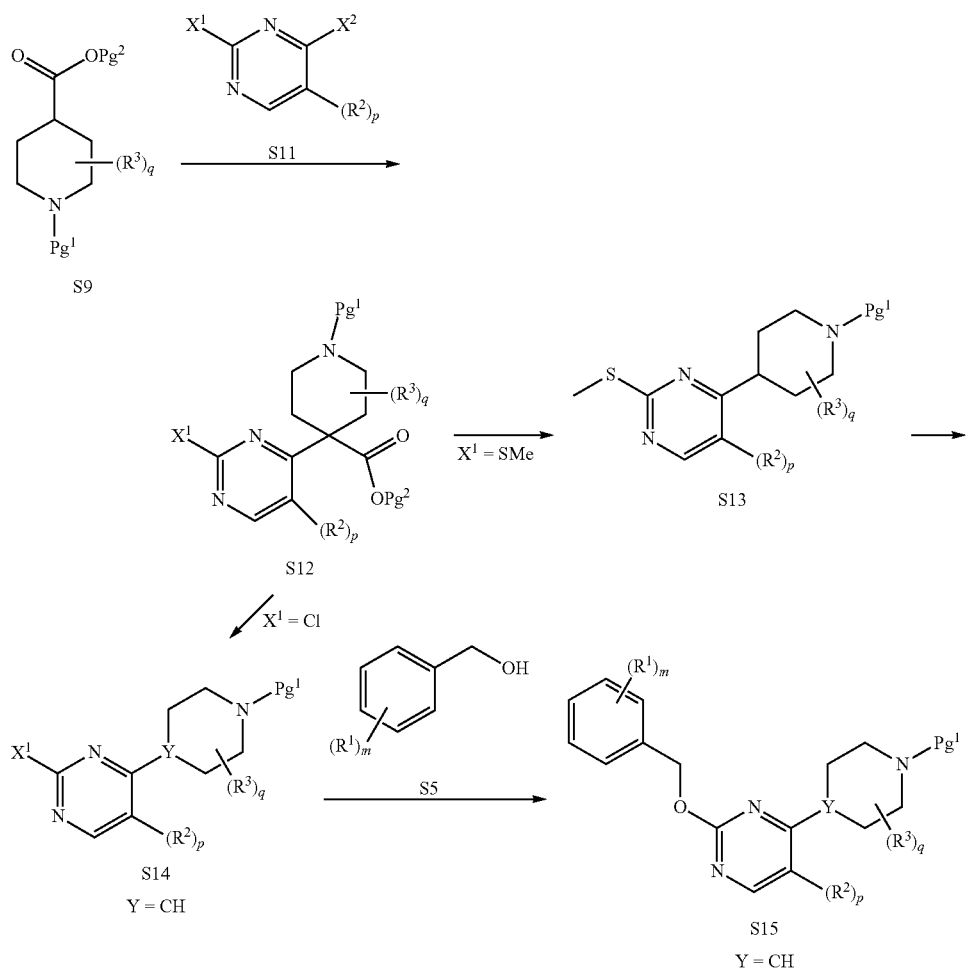

Compounds of general structure S14 where Y=N may also be prepared as discussed in Scheme 4. Substituted pyrimidine S11 may react with piperidines of general structure S8 in the presence of a weak base, such as triethylamine or diisopropylethyl amine, in a solvent, such as methanol, ethanol, water, DMF, or THF, at a temperature around 30° C. to provide compounds of general structure S14. Cl is a preferred $X^2$ substituent. Compounds S14 may then be used to prepare S15 where Y=N as described in Scheme 1. for the preparation of S6 from S4, where preferred $X^1$ substituents include Cl, Br or I.

Scheme 4

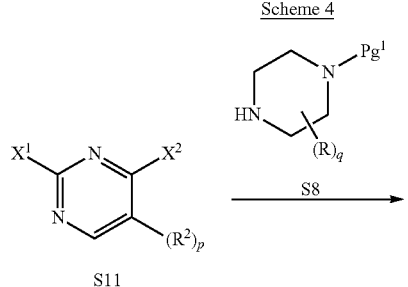

-continued

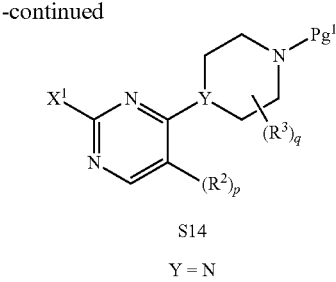

As provided in Scheme 5, reaction of S17 with an appropriately substituted benzyl alcohol S5 in an aprotic solvent such as DMF or THF in the presence of a strong base such as NaH, KOtBu or LiHMDS can deliver compounds of the general structure S18. When electron withdrawing $R^2$ substituents are present bases such as $K_2CO_3$ may be used. Preferred $X^1$ substituents for this reaction include F, Cl, and Br, while $X^2$ substituents may include Cl, Br or I. Alternatively, Buchwald-Hartwig C—O coupling conditions similar to the preparation of S6 may be used to prepare S18 with preferred $X^1$ substituents Cl, Br or I as described in Scheme 1.

Scheme 5

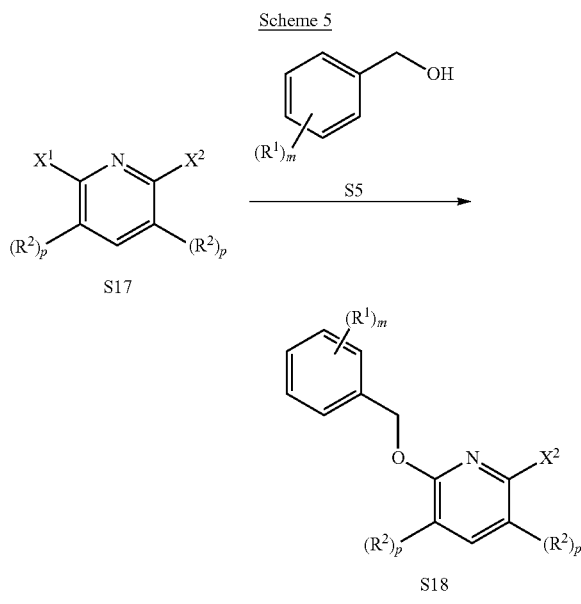

As provided in Scheme 6, reaction of pyrimidine S19 with an appropriately substituted benzyl alcohol S5 in an aprotic solvent such as DMF or THF in the presence of a strong base such as NaH, KOtBu or LiHMDS can deliver compounds of the general structure S20. A preferred $X^2$ substituent for this reaction is Cl.

Scheme 6

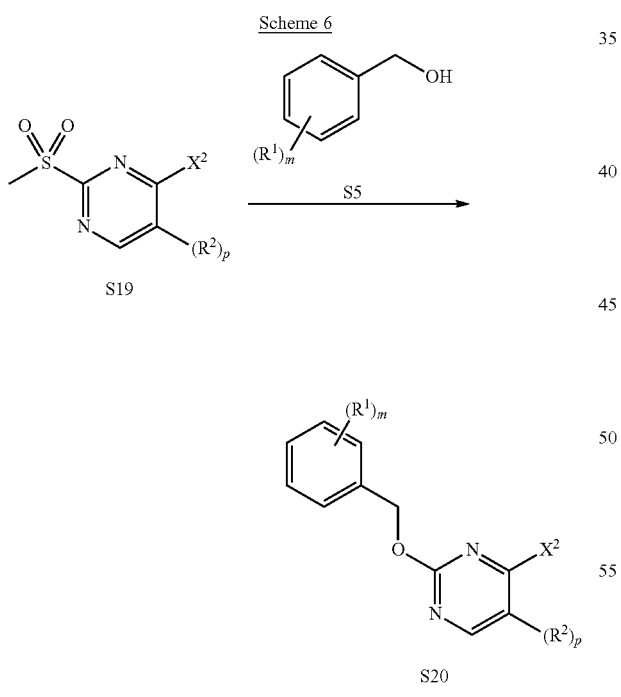

As provided in Scheme 7, reaction of pyrimidine S21 with an appropriately substituted benzyl alcohol S5 in an aprotic solvent such as DMF or THF in the presence of a strong base such as NaH, KOtBu or LiHMDS can deliver compounds of the general structure S22. Preferred $X^1$ and $X^2$ substituent for this reaction are Cl.

Scheme 7

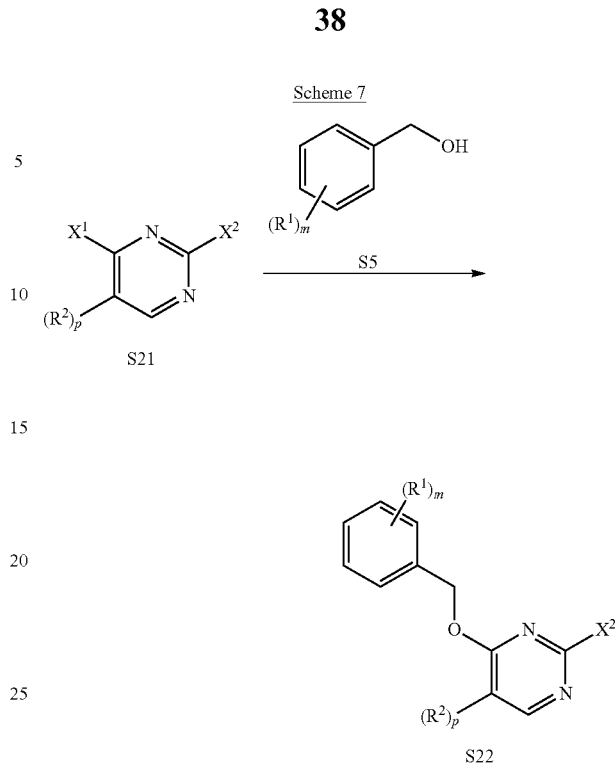

The substituted piperidine of general structure S25 where Y=CH may be prepared as described in Scheme 8. Compounds of general structure S18, S20 and S22, collectively referred to as S23, may be reacted with a substituted boronic acid or boronate ester (S2) as described for S1 in Scheme 1. In the Suzuki reaction, the $X^2$ halogen is preferably Cl, Br or I. Reduction of the olefin as described in Scheme 1 may then provide compounds of general structure S25 where Y=CH.

Scheme 8

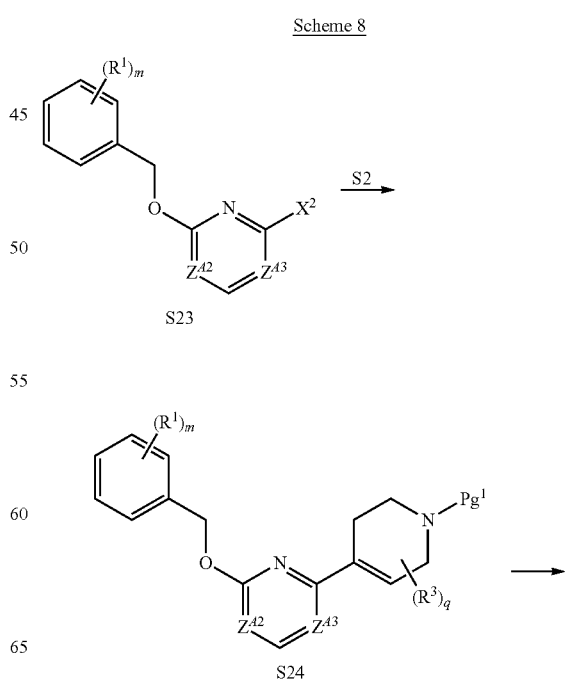

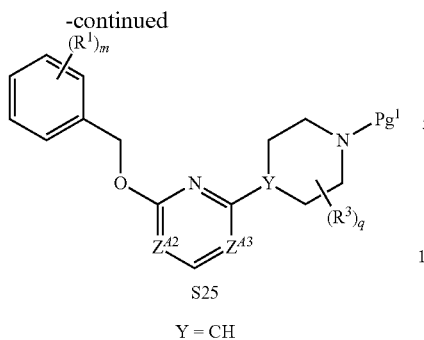

S25

Y = CH

As provided in Scheme 9, conversion of S23 to compounds of general structure S25 where Y=N can be accomplished by such manner as a Buchwald-Hartwig C—N coupling between compounds of the general structure S23 and an appropriately substituted and protected piperazine in the presence of a palladium or copper catalyst and ligand complex as described in Scheme 2 for the conversion of S7 to S6. When $X^2$ is Cl and $Z^{A3}$ is N, S23 and S8 may react to produce S25 in the presence of a weak base, such as triethylamine or diisopropylethyl amine, in a solvent, such as methanol, ethanol, water, DMF, or THF, at a temperature around 30° C.

Scheme 9

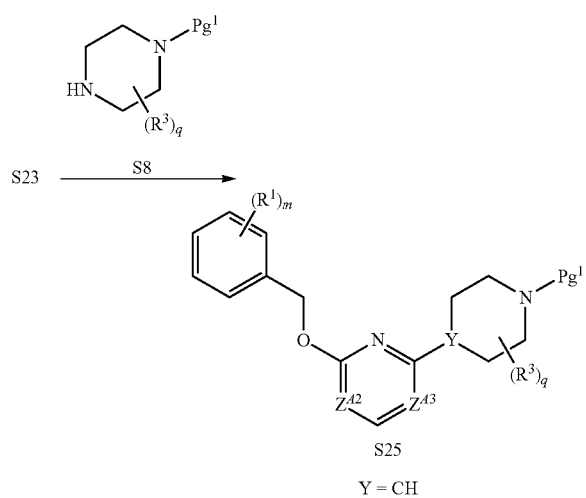

S25

Y = CH

Carboxylic acids of general structure S29 where X=N and L=$CH_2$ may be prepared as discussed in Scheme 10. Compounds of general structures S6, S15 and S25, prepared via methods described in Schemes 1-3, 8 and 9, and collectively referred to as S26, could be deprotected with many methods described in literature to provide amines of general structure S27. Amine compounds S27 can be alkylated with a protected 2-bromoacetate in the presence of a suitable base such as $K_2CO_3$, $Et_3N$, NaH or LiHMDS in a polar aprotic solvent such as but not limited to DMF, DMAc, DMSO or NMP to deliver compounds of the general structure S28 where X=N and L=$CH_2$. If $Pg^2$ is t-butyl, standard acidic deprotection methods such as TFA/DCM, HCl/1,4-dioxane, HCl/EtOAc or other suitable conditions may be used to deliver acids S29. If $Pg^2$ is methyl or ethyl, standard basic deprotection methods such as aqueous NaOH in methanol or ethanol, or other suitable conditions may be used to deliver acids S29.

Scheme 10

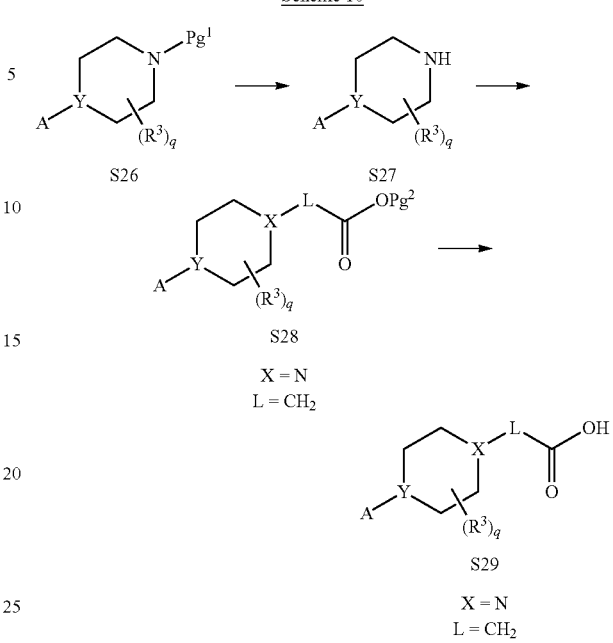

Compounds of general structure S29 where Y=N and X-L=cyclopropyl may be prepared as discussed in Scheme 11. Protected piperidinone S30 may be homologated to unsaturated ester S31 using methods well known to those skilled in the art. For example, Horner-Wadsworth-Emmons olefination of S30 with a phosphonate, such as ethyl (diethoxyphosphoryl)acetate, that has been deprotonated with a strong base such as sodium hydride or potassium tert-butoxide, may provide S31. The reaction is typically conducted in an aprotic solvent like THF or DME, at a temperature around 0 to –50° C. Conversion of S31 to the cyclopropane derivative S32 may be accomplished by treatment with sulfoxonium ylide derived from trimethylsulfoxonium iodide and a base, such as potassium tert-butoxide or sodium hydride. Removal of $Pg^1$ from S32 would then provide amines of general structure S33 where X-L is cyclopropyl. Aryl halides S7, S18, S20, and S22 are collectively represented by general structure S34. Coupling of S33 with compounds of general structure S34 in a manner similar to that described in Scheme 2 for the preparation of S6 from S7 and S8 provides S35 where Y=N and X-L is cyclopropyl. Removal of $Pg^2$ may then provide compounds of general structure S29 where Y=N and X-L=cyclopropyl.

Scheme 11

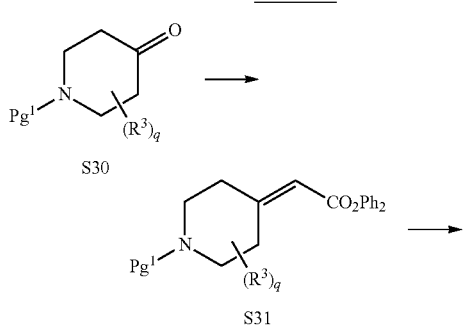

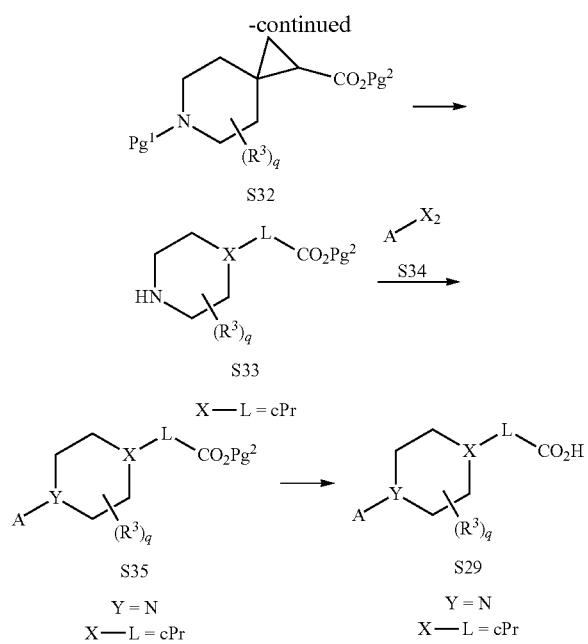

Alternatively, protected carboxylic acids of general structure S33 where X=N and L=CH$_2$ may be prepared as discussed in Scheme 12. Appropriately protected piperazines S8 can be alkylated with a protected 2-bromoacetate as described for the preparation of S28 in Scheme 10 to deliver compounds of the general structure S36. Removal of Pg$^1$ may then provide compounds of general structure S33 that may then be used to prepare S29 where X=N and L=CH$_2$ as described in Scheme 11.

Scheme 12

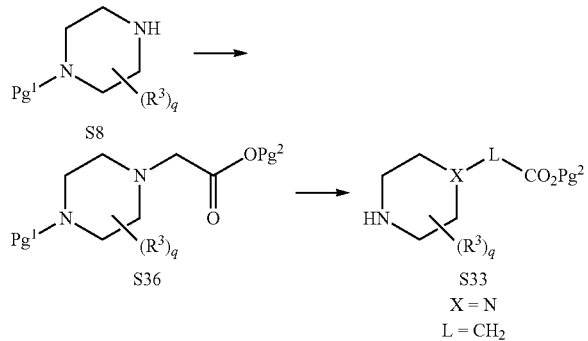

Compounds of general structure S29 where Y=N, A=A2, Z$^{A2}$=N and Z$^{A3}$=CH or CR$^2$ may also be prepared as discussed in Scheme 13. Substituted pyrimidine S16 may react with amines of general structure S33 in the presence of a weak base, such as triethylamine or diisopropylethyl amine, in a solvent, such as methanol, ethanol, water, DMF, or THF, at a temperature around 30° C. to provide compounds of general structure S37. Reaction of S37 with an appropriately substituted benzyl alcohol in an aprotic solvent such as DMF or THF in the presence of a strong base such as NaH, KOtBu or LiHMDS may deliver compounds of the general structure S38. Preferred X$^1$ and X$^2$ substituents for these reactions include Cl. Alternatively, Buchwald-Hartwig C—O coupling conditions similar to the preparation of S6 may be used to prepare S38 with preferred X$^1$ substituent Cl. Removal of Pg$^2$ may then give compounds of general structure S29 where Y=N, A=A2, Z$^{A2}$=N and Z$^{A3}$=CH or CR$^2$.

Scheme 13

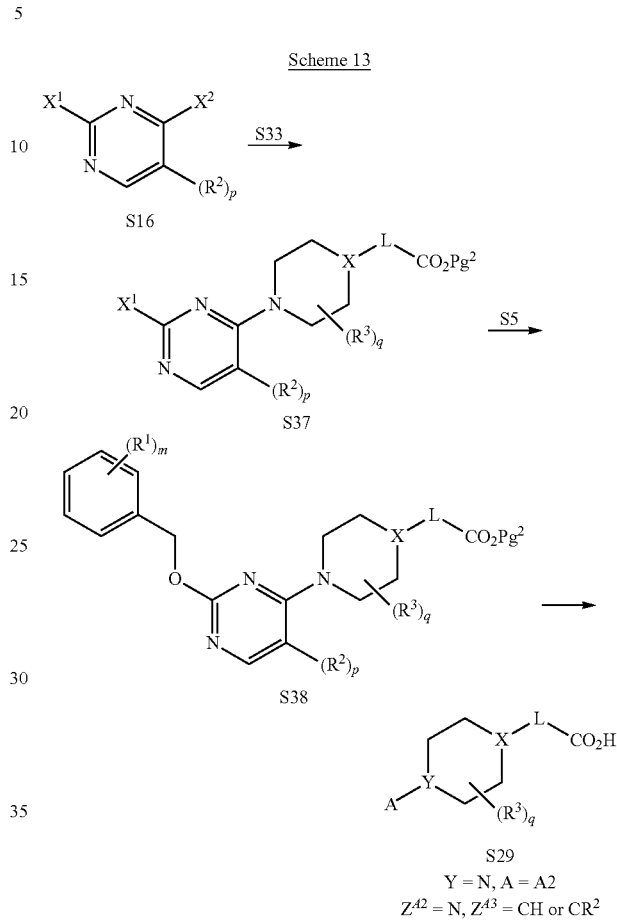

As shown in scheme 14, compounds of general structure S39 can react with amines R$^4$NH$_2$ in the presence of bases such as sodium-, potassium-, or cesium carbonate, -bicarbonate, hydroxide, acetate, or an organic amine base such as Et$_3$N, DIPEA, DBU, and the like in a polar aprotic solvent such as but not limited to THF, DMF, DMAc, DMSO or NMP or a protic solvent such as water, MeOH, EtOH or iPrOH or a mixture thereof to deliver compounds of the general structure S40. One will note that if an example provides an R$^4$ with a resolved enantiomeric center, the other enantiomer or a racemix mixture thereof could be obtained by selection of the appropriate starting material. Preferred X$^3$ substituents include F, Cl, and Br, preferred X$^4$ groups include Cl, Br, —CO$_2$-Pg$^2$. Reduction of the nitro group can be affected by hydrogenation at 1-6 atm H$_2$ with a metal catalyst such as palladium on carbon or Raney nickel in a protic solvent such as MeOH or EtOH or aprotic solvent such as DMF, THF or EtOAc. Alternatively, the nitro group may be reduced with iron, zinc, SnCl$_2$ or other suitable metal in an acidic media such as 1N HCl, AcOH or aqueous NH$_4$Cl in THF to provide compounds of general structure S41 (Scheme 8a). Compounds such as S42 may be acylated by acyl halides by standard fashion or by carboxylates via standard amide coupling protocols to provide compounds S43. Reduction to compounds S44 may be performed under standard conditions with reducing agents such as LAH or BH$_3$-THF or BH$_3$-DMS (Scheme 14b).

Scheme 14

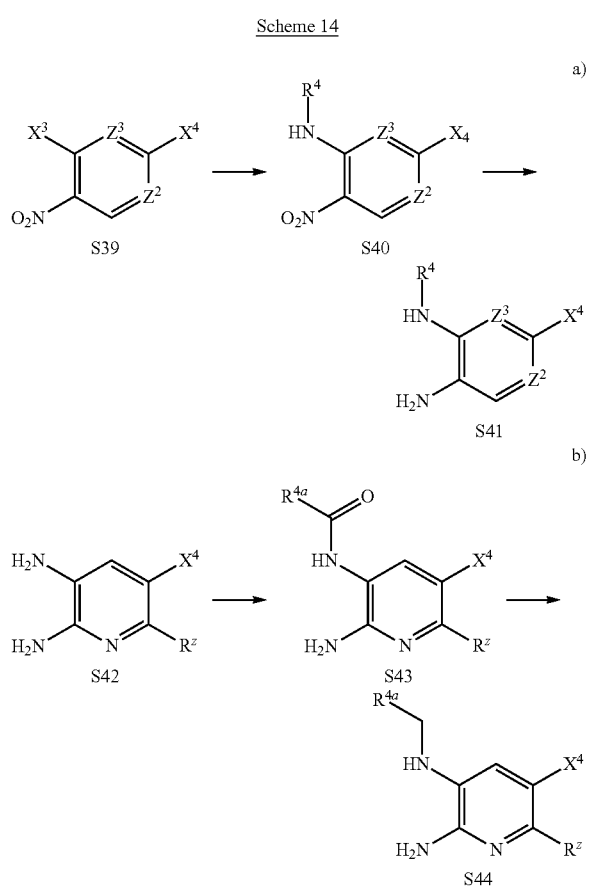

Diamine compounds S41 and S44 prepared via methods described in Schemes 14a and 14b, collectively designated as diamine S45 (Scheme 15), may be acylated with acids of general structure S29 under standard amide coupling protocols to deliver amines S46 which will exist as a mixture from 100% S46a to 100% S46b. This mixture of amines S46 may be cyclized to deliver compounds of general structure S47 by a variety of methods. Amines S46 may be heated with a dehydrating agent such as $T_3P$® or an alkyl alcohol such as n-butanol under microwave conditions (10-60 min at 120-180° C.) to deliver compounds S47. Alternatively, the mixture of compounds S46 may be heated under acidic conditions such as AcOH from 60-100° C. or under basic conditions such as aqueous NaOH or KOH in 1,4-dioxane from 60-100° C. to provide S47. Compounds of general structure S47 ($X^4$=Cl, Br or I) can be converted to esters of structure S48 by palladium-catalyzed carbonylation under a 15-100 psi carbon monoxide atmosphere at a temperature from 20-100 at a temperature from 20-100° C. with an appropriate alcohol such as MeOH or EtOH or other alkyl alcohol. Hydrolysis of ester S48 can be performed as described in Scheme 10 to provide acids S49. For compounds S46 where $X^4$=$CO_2$-$Pg^2$ conversion to ester S48 proceeds under similar conditions as described previously except for use of the basic cyclization method where compound S49 may be isolated directly from the reaction mixture. For compounds S48 where $X^4$ is $CO_2tBu$, deprotection to acid 49 can be performed under acidic conditions described in Scheme 10. Alternatively, for compounds S48 where $Pg^2$ is a $C_1$-$C_8$ alkyl, such as methyl, ethyl, hexyl or octyl, the ester deprotection may be performed with a variety of enzymes including esterases, proteases, peptidases, lipases, and glycosidases which are well known to those skilled in the art. The hydrolysis may also be performed by treating the ester with an aqueous solution of 1,5,7-triazabicyclo[4.4.0]dec-5-ene at RT.

Scheme 15

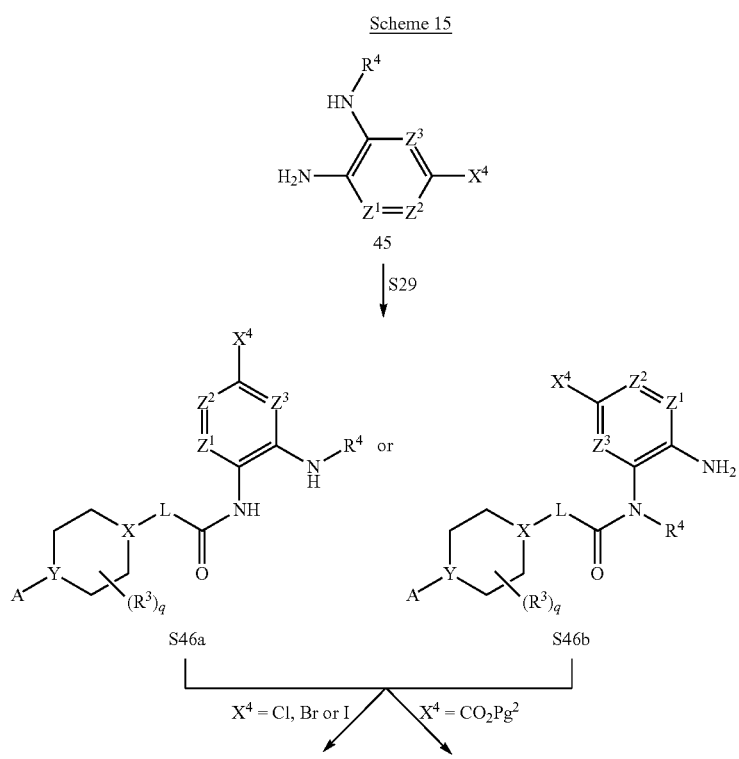

-continued

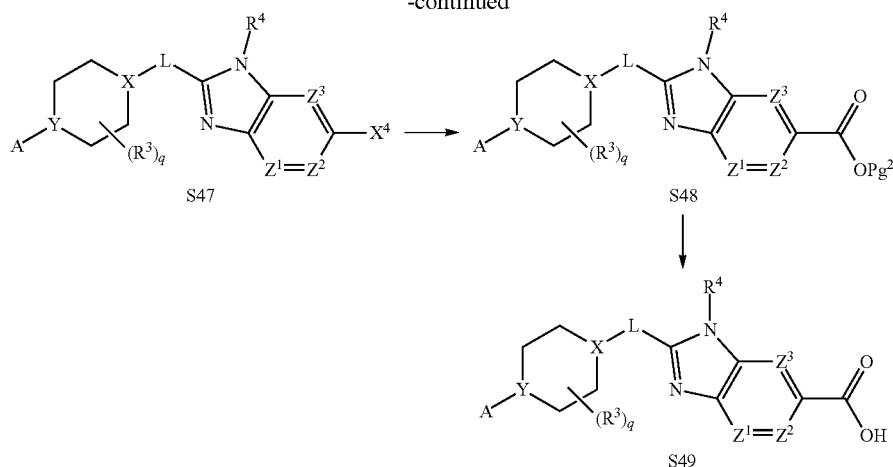

Additionally, diamine S45 may be converted to the 2-chloromethyl benzimidazole S50 (Scheme 16) by several methods. Treatment with 2-chloroacetyl chloride in an aprotic solvent such as 1,4-dioxane followed by heating at 40-100° C. for 2-18 h can deliver the desired benzimidazole S50 where $Z^1$, $Z^2$ and $Z^3$ are CH. In the cases where $Z^1$, $Z^2$ and $Z^3$ are not all $CR^z$, after treatment with 2-chloroacetyl chloride in an aprotic solvent such as 1,4-dioxane for 30 min to 4 h, the solvent is exchanged for an acidic media such as AcOH or TFA followed by heating at 40-100° C. for 2-18 h to provide the desired compound S50. Diamine S45 can also be treated with chloroacetic anhydride at a temperature between 0 and 80° C. in an aprotic solvent such as, but not limited to 1,4-dioxane, THF or MeCN, followed by heating for 2 to 18 h at 60-100° C. to deliver the desired compound S50. In addition, diamine S45 can be treated with 2-chloro-1,1,1-trimethoxyethane in an aprotic solvent such as, but not limited to 1,4-dioxane, THF or MeCN, or a protic solvent, e.g., MeOH or EtOH, in the presence of an acid catalyst, e.g., pTSA, at 20-100° C. Alternatively, diamines S45 may be heated 100-180° C. with 2-hydroxyacetic acid in an aprotic solvent, such as but not limited to mesitylene, to provide a hydroxymethyl intermediate. Conversion of the hydroxymethyl group to the chloromethyl compound S50 may be accomplished by standard methods, including treatment with $SOCl_2$ in an aprotic solvent. Compounds of general structure S50 can be reacted with compounds S27 in the presence of bases such as sodium-, potassium-, or cesium carbonate, -bicarbonate, NaH or an organic amine base such as $Et_3N$, DIPEA, DBU, and the like in a polar aprotic solvent, such as but not limited to THF, MeCN, DMF, DMAc, DMSO or NMP, to deliver compounds S47 ($X^4$=Cl, Br, I) or compounds S48 ($X^4$=$CO_2$-$Pg^2$) that are then used to obtain compounds S49 via methods described in Scheme 15.

Scheme 16

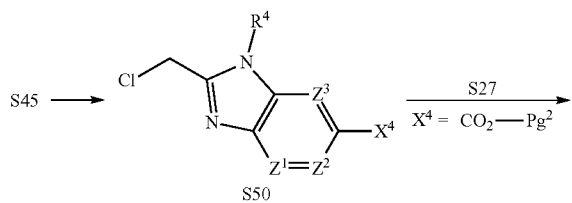

-continued

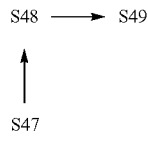

Alternatively, compounds of general structure S50 could be reacted with appropriately substituted and protected piperazines S8 to provide compounds S51 (Scheme 17). Removal of $Pg^1$ could be effected with many methods described in literature to provide amines S52. Conversion to compounds of general structure S47 ($X^4$=Cl, Br or I) or S48 ($X^4$=$CO_2$-$Pg^2$) may be accomplished by such manner as a Buchwald-Hartwig C—N coupling between compounds of the general structures S7 and as described previously in Scheme 2. Compounds of general structure S47 or S48 may then be used to obtain compounds of structure S49 via methods described in Scheme 15.

Scheme 17

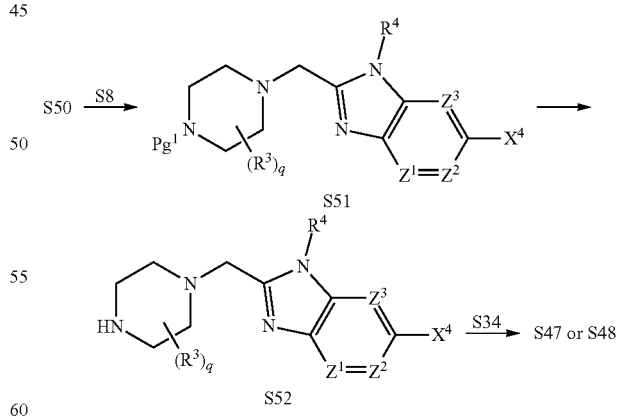

In a manner similar to that described in Scheme 1 for the preparation of S4, compounds of the general structure S29 in which X=Y=CH, L=$CH_2$, A=A2, $Z^{42}$=CH or $CR^2$ and $Z^{43}$=CH or $CR^2$ may also be prepared as described in Scheme 18a. Compounds of general structure S17 may be reacted with boronate esters S53 in the presence of a palladium catalyst and ligand complex in a manner similar to that described for the preparation of S3 from S1 and S2, to provide intermediate olefin S54. In this reaction, preferred X² substituents include Cl and Br. Reduction of the olefin will provide cyclohexyl derivatives S55, with the stereoselectivity of the reduction providing either the cis or the trans isomer, or a mixture thereof, depending on the conditions and the specific nature of the substituents. Reaction of S55 with alcohols S5 as described above will provide compounds of general structure S56. Removal of Pg² will provide compounds S29 (X=Y=CH, L=CH₂, A=A2, Z^{A2}=CH or CR² and Z^{A3}=CH or CR²). Alternatively, compounds of the general structure S29 in which X=Y=CH, L=CH₂ may be prepared from substituted hetaryl halides of general structure S34 by reaction with S53 in the presence of a palladium catalyst and ligand complex (Scheme 18b). Reduction of the resulting olefin (S57) to give S58 followed by removal of Pg² will provide compounds S29 (X=Y=CH, L=CH₂). Compounds S29 prepared in this manner may be converted into compounds of general structure S49 via the methods described above in Scheme 15.

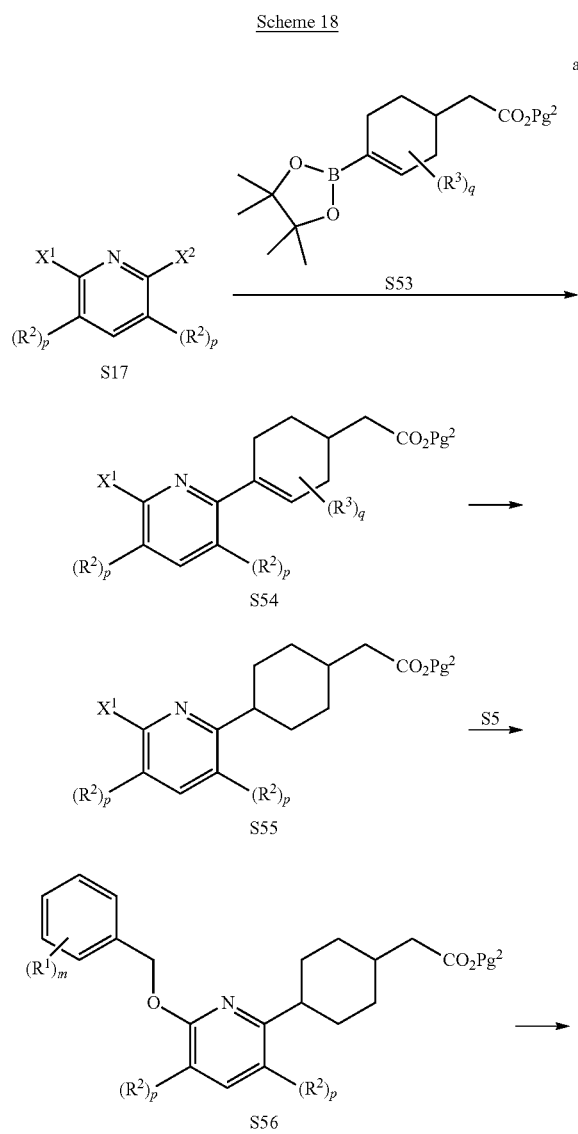

Scheme 18

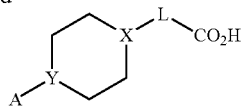

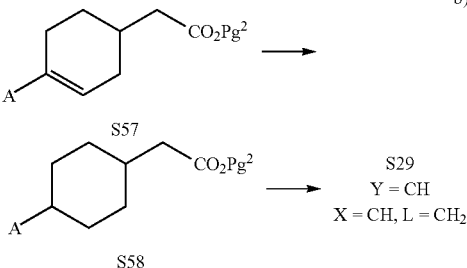

EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide, and THF; b) <180 ppm for methanol, ethanol, 1,4-dioxane, and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. The symbol ♦ denotes that the chlorine isotope pattern was observed in the mass spectrum.

Chiral separations were used to separate enantiomers of some intermediates during the preparation of the compounds of the invention. When such separation was done, the separated enantiomers were designated as ENT-1 or ENT-2, according to their order of elution. For compounds with two chiral centers, the stereoisomers at each stereocenter were separated at different times. The designation of ENT-1 or ENT-2 of an intermediate or an example refers to the chiral center for the separation done at that step. It is recognized that when stereoisomers at a chiral center are separated in a compound with two or more centers, the separated enantiomers are diastereomers of each other. The ENT-1 or ENT-2 designation is used herein for consistency and refers to the separated chiral center. By way of example, but not limitation, Examples 35 and 36 have two chiral centers. The chiral center of the cyclopropyl moiety was separated when intermediate C77 was separated into ENT-1, giving intermediate C78, and ENT-2, giving intermediate C79. C78 was then used to prepare Example 35 that is identified by name as ammonium 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, from C78. In these preparations, after a mixture is subjected to separation procedures, the chiral center is identified with "abs" near that center, with the understanding that the separated enantiomers may not be enantiomerically pure. Typically, the enriched enantiomer at each chiral center is >90% of the isolated material. Preferably, the enriched enantiomer at each center is >98% of the mixture.

In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

Preparation P1

(4-{2-[(4-Chloro-2-fluorobenzyl)oxy]pyridin-3-yl}piperidin-1-yl)acetic Acid (P1)

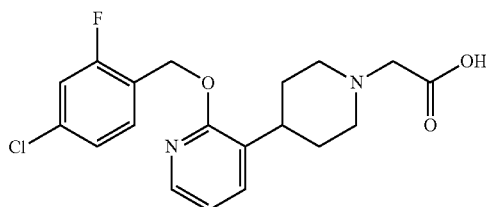

P1

Step 1. Synthesis of tert-butyl 2-fluoro-3',6'-dihydro-3,4'-bipyridine-1'(2'H)-carboxylate (C1)

A mixture of 3-bromo-2-fluoropyridine (14.5 g, 82.4 mmol), tert-butyl 4-(4,4,5,5-tetramethyl-1,3,2-dioxaborolan-2-yl)-3,6-dihydropyridine-1(2H)-carboxylate (28.0 g, 90.6 mmol), [1,1'-bis(diphenylphosphino)ferrocene]dichloropalladium(II) (3.80 g, 5.19 mmol), and potassium carbonate (25.0 g, 181 mmol) in 1,4-dioxane (200 mL) and water (50 mL) was stirred at 100° C. for 16 hours. The reaction mixture was then partitioned between saturated aqueous sodium chloride solution (200 mL) and EtOAc (300 mL); the organic layer was dried over sodium sulfate, filtered, and concentrated in vacuo. Silica gel chromatography (Gradient: 0% to 9% EtOAc in petroleum ether) afforded C1 as a yellow oil. Yield: 20.0 g, 71.9 mmol, 87%.

Step 2. Synthesis of tert-butyl 4-(2-fluoropyridin-3-yl)piperidine-1-carboxylate (C2)

A mixture of C1 (20.0 g, 71.9 mmol) and platinum(IV) oxide (1.97 g) in MeOH (500 mL) was hydrogenated at 15° C. for 16 hours, whereupon the reaction mixture was filtered. The filtrate was concentrated in vacuo, and the residue was subjected to silica gel chromatography (Gradient: 9% to 17% EtOAc in petroleum ether), affording C2 as a pale yellow oil. Yield: 20.0 g, 71.3 mmol, 99%.

Step 3. Synthesis of tert-butyl 4-{2-[(4-chloro-2-fluorobenzyl)oxy]pyridin-3-yl}piperidine-1-carboxylate (C3)

Sodium hydride (60% dispersion in mineral oil; 9.0 g, 220 mmol) was added portion-wise to a 0° C. mixture of C2 (20.0 g, 71.3 mmol) and (4-chloro-2-fluorophenyl)methanol (12.0 g, 74.7 mmol) in N,N-dimethylformamide (150 mL). The reaction mixture was then allowed to warm to 15° C. and stirred at 15° C. for 1 hour, whereupon it was cooled to 0° C. and slowly treated with saturated aqueous ammonium chloride solution (100 mL). The resulting mixture was extracted with EtOAc (300 mL), and the organic layer was washed with saturated aqueous sodium chloride solution (200 mL), dried over sodium sulfate, filtered, and concentrated in vacuo. Silica gel chromatography (Eluent: 20:1 petroleum ether/EtOAc) provided C3 as a white solid. Yield: 21.0 g, 49.9 mmol, 70%.

Step 4. Synthesis of 2-[(4-chloro-2-fluorobenzyl)oxy]-3-(piperidin-4-yl)pyridine (C4)

To a solution of C3 (14.0 g, 33.3 mmol) in dichloromethane (25 mL) was added trifluoroacetic acid (25 mL). After the reaction mixture had been stirred at 20° C. for 1.5 hours, it was concentrated in vacuo, affording C4 as a yellow oil. This material was taken directly into the following step.

Step 5. Synthesis of ethyl (4-{2-[(4-chloro-2-fluorobenzyl)oxy]pyridin-3-yl}piperidin-1-yl)acetate (C5)

Potassium carbonate (30.0 g, 217 mmol) was added to a solution of C4 (from the previous step; ≤33.3 mmol) and ethyl bromoacetate (6.00 g, 35.9 mmol) in N,N-dimethylformamide (150 mL). The reaction mixture was stirred at 50° C. for 2 hours, whereupon it was filtered. The filtrate was diluted with EtOAc (250 mL), washed sequentially with water (250 mL) and with saturated aqueous sodium chloride solution (250 mL), dried over sodium sulfate, filtered, and concentrated in vacuo. Silica gel chromatography (Gradient: 9% to 25% EtOAc in petroleum ether) provided C5 as a yellow oil. Yield: 9.80 g, 24.1 mmol, 72% over 2 steps.

Step 6. Synthesis of (4-{2-[(4-chloro-2-fluorobenzyl)oxy]pyridin-3-yl}piperidin-1-yl)acetic Acid (P1)

To a solution of C5 (8.80 g, 21.6 mmol) in THF (45 mL) and MeOH (45 mL) was added aqueous sodium hydroxide solution (3 M; 90 mL, 270 mmol). After the reaction mixture had been stirred at 20° C. for 2 hours, its pH was adjusted to 4 by addition of 1 M hydrochloric acid. The resulting mixture was filtered, and the collected solid was washed three times with water, whereupon it was taken up in MeOH (20 mL) and water (60 mL). This mixture was concentrated in vacuo to remove organic solvents, and then lyophilized, affording P1 as a white solid. Yield: 5.90 g, 15.6 mmol, 72%. LCMS m/z 378.9♦ [M+H]+. $^1$H NMR (400 MHz, DMSO-$d_6$) δ 8.03 (br d, 1H), 7.60 (br d, 1H), 7.55 (dd, 1H), 7.49 (br d, 1H), 7.32 (dd, 1H), 7.01 (dd, 1H), 5.41 (s, 2H), 3.26-3.17 (m, 4H), 2.90-2.79 (m, 1H), 2.66-2.55 (m, 2H), 1.85-1.73 (m, 4H).

Preparation P2

Ammonium (4-{3-[(4-chloro-2-fluorobenzyl)oxy]pyrazin-2-yl}piperidin-1-yl)acetate (P2)

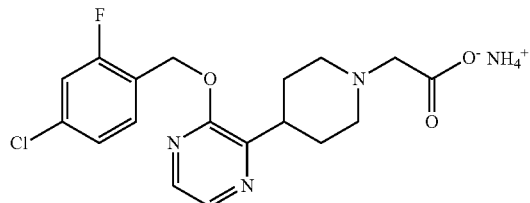

P2

Step 1. Synthesis of tert-butyl 4-(3-chloropyrazin-2-yl)-3,6-dihydropyridine-1(2H)-carboxylate (C6)

A mixture of tert-butyl 4-(4,4,5,5-tetramethyl-1,3,2-dioxaborolan-2-yl)-3,6-dihydropyridine-1(2H)-carboxylate (20.0 g, 64.7 mmol), 2,3-dichloropyrazine (14.5 g, 97.3 mmol), [1,1'-bis(diphenylphosphino)ferrocene]dichloropalladium(II) (2.60 g, 3.55 mmol), and sodium carbonate (15.1 g, 142 mmol) in 1,4-dioxane (120 mL) and water (50 mL) was stirred at 95° C. for 4 hours. The reaction mixture was then diluted with EtOAc (500 mL) and washed sequentially with water (100 mL) and with saturated aqueous sodium chloride solution (300 mL). The organic layer was dried over sodium sulfate, filtered, concentrated in vacuo, and subjected to silica gel chromatography (Gradient: 5% to 17% EtOAc in petroleum ether), affording C6 as a pale yellow oil. Yield: 15.7 g, 53.1 mmol, 82%.

Step 2. Synthesis of tert-butyl 4-(3-chloropyrazin-2-yl)piperidine-1-carboxylate (C7)

To a solution of C6 (12.6 g, 42.6 mmol) in MeOH (400 mL) was added tris(triphenylphosphine)rhodium(I) chloride (2.50 g, 2.70 mmol) and the reaction mixture was stirred for 2 hours at 30° C. under a balloon of hydrogen. After filtration, the filtrate was concentrated in vacuo, and the residue was combined with the product of a similar hydrogenation carried out using C6 (1.08 g, 3.65 mmol); silica gel chromatography (Gradient: 9% to 17% EtOAc in petroleum ether) provided C7 as a pale yellow solid. Combined yield: 12.3 g, 41.3 mmol, 89%.

Step 3. Synthesis of tert-butyl 4-{3-[(4-chloro-2-fluorobenzyl)oxy]pyrazin-2-yl}piperidine-1-carboxylate (C8)

Palladium(II) acetate (271 mg, 1.21 mmol), 1,1'-binaphthalene-2,2'-diylbis(diphenylphosphane) (BINAP; 1.51 g, 2.42 mmol), and cesium carbonate (13.1 mg, 40.3 mmol) were added to a solution of C7 (6.00 g, 20.1 mmol) and (4-chloro-2-fluorophenyl)methanol (3.56 g, 22.2 mmol) in 1,4-dioxane (60 mL). Nitrogen was bubbled through the suspension, after which the reaction mixture was stirred at 90° C. for 18 hours and filtered. The filtrate was concentrated in vacuo and purified using chromatography on silica gel (Gradient: 3% to 20% EtOAc in petroleum ether) to afford C8 as a yellow gum. Yield: 7.96 g, 18.9 mmol, 94%.

Step 4. Synthesis of 2-[(4-chloro-2-fluorobenzyl)oxy]-3-(piperidin-4-yl)pyrazine (C9)

To a solution of C8 (7.00 g, 16.6 mmol) in dichloromethane (80 mL) was added trifluoroacetic acid (20 mL). The reaction mixture was stirred at 15° C. for 1 hour, whereupon it was concentrated, and the residue was carefully treated with saturated aqueous sodium bicarbonate solution (100 mL). The resulting mixture was extracted with EtOAc (3×100 mL), and the combined organic layers were washed with saturated aqueous sodium chloride solution (300 mL), dried over sodium sulfate, filtered, and concentrated in vacuo. Silica gel chromatography (Gradient: 10% to 25% MeOH in dichloromethane) provided C9 as a yellow solid. Yield: 5.2 g, 16 mmol, 96%.

Step 5. Synthesis of ethyl (4-{3-[(4-chloro-2-fluorobenzyl)oxy]pyrazin-2-yl}piperidin-1-yl)acetate (C10)

Ethyl bromoacetate (2.55 g, 15.3 mmol) and potassium carbonate (6.03 g, 43.6 mmol) were added to a solution of C9 (4.68 mg, 14.5 mmol) in N,N-dimethylformamide (50 mL). After the reaction mixture had been stirred at 15° C. for 18 hours, it was diluted with water (100 mL) and extracted with EtOAc (3×100 mL). The combined organic layers were washed sequentially with water (200 mL) and with saturated aqueous sodium chloride solution (200 mL), dried over sodium sulfate, filtered, and concentrated in vacuo to provide C10 as a yellow gum. Yield: 4.75 g, 11.6 mmol, 80%.

Step 6. Synthesis of Ammonium (4-{3-[(4-chloro-2-fluorobenzyl)oxy]pyrazin-2-yl}piperidin-1-yl)acetate (P2)

To a solution of C10 (4.70 g, 11.5 mmol) in MeOH (40 mL) was added aqueous sodium hydroxide solution (3 M; 20 mL, 60 mmol). The reaction mixture was stirred at 15° C. for 2 hours, whereupon it was diluted with water (80 mL) and washed with EtOAc (3×80 mL). The aqueous layer was then adjusted to pH 6 via addition of 1 M hydrochloric acid, and concentrated in vacuo. The residue was treated with a mixture of dichloromethane and MeOH (10:1, 50 mL), stirred at 15° C. for 30 minutes, and filtered through diatomaceous earth. The filtrate was concentrated under reduced pressure and purified via reversed-phase HPLC (Column: Phenomenex Gemini C18, 10 μm; Mobile phase A: 10 mM ammonium bicarbonate in water; Mobile phase B: acetonitrile; Gradient: 10% to 33% B) to afford P2 as a white solid. Yield: 2.30 g, 5.80 mmol, 50%. LCMS m/z 380.1♦ [M+H]+. $^1$H NMR (400 MHz, Methanol-$d_4$) δ 8.13 (d, 1H), 8.06 (d, 1H), 7.55 (dd, 1H), 7.31-7.21 (m, 2H), 5.49 (s, 2H), 3.69 (br d, 2H), 3.61 (s, 2H), 3.43-3.33 (m, 1H), 3.25-3.11 (m, 2H), 2.25-2.06 (m, 4H).

Preparation P3

(4-{2-[(4-Chloro-2-fluorobenzyl)oxy]pyridin-3-yl}piperazin-1-yl)acetic Acid (P3)

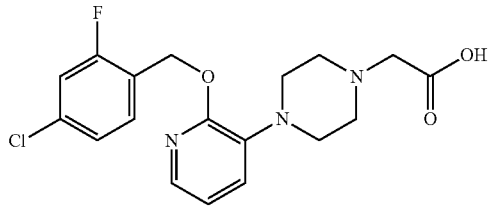

P3

Step 1. Synthesis of 3-bromo-2-[(4-chloro-2-fluorobenzyl)oxy]pyridine (C11)

(4-Chloro-2-fluorophenyl)methanol (2.21 g, 13.8 mmol) was added drop-wise via syringe to a 0° C. suspension of sodium hydride (60% dispersion in mineral oil; 0.80 g, 20.0 mmol) in THF (50 mL). The ice bath was then removed, and the reaction mixture was stirred at room temperature (14° C.) for 40 minutes, whereupon 3-bromo-2-fluoropyridine (2.00 g, 11.4 mmol) was added drop-wise via syringe. Stirring was continued at room temperature (14° C.) for 1 hour, whereupon the reaction mixture was poured into saturated aqueous ammonium chloride solution (20 mL) and extracted with EtOAc (3×20 mL). The combined organic layers were washed with saturated aqueous sodium chloride solution (50 mL), dried over magnesium sulfate, filtered, and concentrated in vacuo. Silica gel chromatography (Gradient: 0% to 5% dichloromethane in petroleum ether) afforded C11 as a white solid. Yield: 1.77 g, 49%.

Step 2. Synthesis of tert-butyl 4-{2-[(4-chloro-2-fluorobenzyl)oxy]pyridin-3-yl}piperazine-1-carboxylate (C12)

A suspension of C11 (1.00 g, 3.16 mmol), tert-butyl piperazine-1-carboxylate (650 mg, 3.49 mmol), 1,1'-binaphthalene-2,2'-diylbis(diphenylphosphane) (236 mg, 0.379 mmol), tris(dibenzylideneacetone)dipalladium(0) (202 mg, 0.221 mmol), and cesium carbonate (2.06 g, 6.32 mmol) in 1,4-dioxane (10 mL) was degassed with nitrogen for 1 minute and then stirred at 85° C. for 16 hours. The reaction mixture was filtered, and the filtrate was concentrated in vacuo; purification of the residue using silica gel chromatography (Eluent: 20:1 petroleum ether/EtOAc) provided C12 as a pale yellow solid. Yield: 920 mg, 69%. LCMS m/z 422.1♦ [M+H]$^+$. $^1$H NMR (400 MHz, Chloroform-d) δ 7.81 (dd, 1H), 7.46 (dd, 1H), 7.18-7.07 (m, 3H), 6.88 (dd, 1H), 5.47 (s, 2H), 3.61-3.52 (m, 4H), 3.07-2.97 (m, 4H), 1.48 (s, 9H).

Step 3. Synthesis of 1-{2-[(4-chloro-2-fluorobenzyl)oxy]pyridin-3-yl}piperazine (C13)

Trifluoroacetic acid (1 mL) was added to a solution of C12 (160 mg, 0.379 mmol) in dichloromethane (2 mL). The reaction mixture was stirred at 20° C. for 30 minutes, whereupon it was concentrated in vacuo to afford C13 as a yellow oil, which was taken directly to the following step.

Step 4. Synthesis of ethyl (4-{2-[(4-chloro-2-fluorobenzyl)oxy]pyridin-3-yl}piperazin-1-yl)acetate (C14)

To a suspension of C13 (from the previous step; 50.379 mmol) and potassium carbonate (262 mg, 1.90 mmol) in N,N-dimethylformamide (1 mL) was added ethyl bromoacetate (82.3 mg, 0.493 mmol). After the reaction mixture had been stirred at 15° C. for 1.5 hours, it was diluted with EtOAc (50 mL) and washed with water (50 mL). The organic layer was then washed with saturated aqueous sodium chloride solution (50 mL), dried over magnesium sulfate, filtered, concentrated in vacuo, and purified via silica gel chromatography (Gradient: 17% to 50% EtOAc in petroleum ether), providing C14 as a yellow oil. Yield: 102 mg, 66% over 2 steps. LCMS m/z 408.0♦ [M+H]$^+$.

Step 5. Synthesis of (4-{2-[(4-chloro-2-fluorobenzyl)oxy]pyridin-3-yl}piperazin-1-yl)acetic Acid (P3)

A solution of C14 (102 mg, 0.250 mmol) and aqueous sodium hydroxide solution (3 M; 0.3 mL, 0.9 mmol) in a mixture of MeOH (1 mL) and THF (1 mL) was stirred at 20° C. for 16 hours. The reaction mixture was then adjusted to pH 7 by addition of 1 M hydrochloric acid, and extracted with a mixture of dichloromethane and MeOH (10:1, 3×30 mL). The combined organic layers were dried over magnesium sulfate, filtered, and concentrated in vacuo to afford P3 as a yellow oil. Yield: 95.0 mg, 100%.

Preparation P4

2-Chloro-3-[(4-chloro-2-fluorobenzyl)oxy]pyrazine (P4)

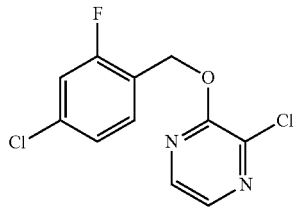

P4

To a 19° C. solution of (4-chloro-2-fluorophenyl)methanol (7.17 g, 44.65 mmol) and 2,3-dichloropyrazine (7.09 g, 47.59 mmol) in 1,4-dioxane (50 mL) was added sodium tert-butoxide (5.42 g, 56.40 mmol). The reaction mixture was stirred at 19° C. for 4 hours, whereupon it was poured into petroleum ether (150 mL) and then filtered through a pad of diatomaceous earth. Concentration of the filtrate in vacuo provided a residue, which was purified using silica gel chromatography (Gradient: 0% to 17% dichloromethane in petroleum ether); P4 was isolated as a white solid. Yield: 8.93 g, 73%. LCMS m/z 272.7 (dichloro isotope pattern observed) [M+H]$^+$. $^1$H NMR (400 MHz, Chloroform-d) δ 8.03 (d, 1H), 7.98 (d, 1H), 7.48 (dd, 1H), 7.21-7.11 (m, 2H), 5.49 (s, 2H).

Preparation P5

Methyl 6-azaspiro[2.5]octane-1-carboxylate (P5)

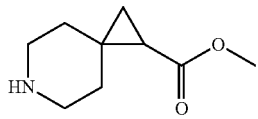

P5

Step 1. Synthesis of tert-butyl 4-(2-ethoxy-2-oxo-ethylidene)piperidine-1-carboxylate (C15)

A solution of potassium tert-butoxide (65.9 g, 587 mmol) in THF (500 mL) was added to a 0° C. solution of ethyl (diethoxyphosphoryl)acetate (132 g, 589 mmol) in THF (500 mL), and the resulting suspension was stirred at 0° C. for 1 hour, whereupon it was cooled to −50° C. A solution of tert-butyl 4-oxopiperidine-1-carboxylate (90.0 g, 452 mmol) in THF (1.5 L) was added drop-wise at −50° C., and the reaction mixture was subsequently allowed to slowly warm to 20° C., and then to stir for 16 hours at 20° C. After addition of water (1 L), the mixture was concentrated in vacuo to remove THF. The aqueous residue was extracted with EtOAc (2×800 mL), and the combined organic layers were washed with saturated aqueous sodium chloride solution (500 mL), dried over sodium sulfate, filtered, and concentrated under reduced pressure. The resulting material was washed several times with petroleum ether (200 mL) to provide C15 as a white solid. Yield: 95.0 g, 353 mmol, 78%. $^1$H NMR (400 MHz, Chloroform-d) δ 5.71 (s, 1H), 4.16 (q, 2H), 3.55-3.43 (m, 4H), 2.94 (br t, 2H), 2.28 (br t, 2H), 1.47 (s, 9H), 1.28 (t, 3H).

Step 2. Synthesis of 6-tert-butyl 1-ethyl 6-azaspiro[2.5]octane-1,6-dicarboxylate (C16)

To a solution of trimethylsulfoxonium iodide (140 g, 636 mmol) in dimethyl sulfoxide (800 mL) was added potassium tert-butoxide (71.2 g, 634 mmol) in one portion at 20° C. After the reaction mixture had been stirred at 20° C. for 1.5 hours, a solution of C15 (95.0 g, 353 mmol) in dimethyl sulfoxide (800 mL) was added drop-wise, and stirring was continued at 20° C. for 16 hours. Saturated aqueous sodium chloride solution (2.0 L) was then added; the resulting mixture was neutralized by addition of ammonium chloride, and extracted with EtOAc (3.0 L). The combined organic layers were washed sequentially with water (2×1.0 L) and with saturated aqueous sodium chloride solution (2.0 L), dried over sodium sulfate, filtered, and concentrated in vacuo. Purification via silica gel chromatography (Eluent: 10:1 petroleum ether/EtOAc) afforded C16 as a yellow oil. $^1$H NMR analysis indicated that extraneous aliphatic material was present. Yield: 80 g, 280 mmol, 79%. $^1$H NMR (400 MHz, Chloroform-d): δ 4.19-4.09 (m, 2H), 3.55-3.39 (m, 3H), 3.27 (ddd, 1H), 1.76-1.64 (m, 2H), 1.56 (dd, 1H, assumed; partially obscured by water peak), 1.47 (s, 9H), 1.47-1.37 (m, 2H), 1.27 (t, 3H), 1.17 (dd, 1H), 0.93 (dd, 1H).

Step 3. Synthesis of 6-(tert-butoxycarbonyl)-6-azaspiro[2.5]octane-1-carboxylic Acid (C17)

To a mixture of C16 (80 g, 280 mmol) in THF (500 mL) and water (500 mL) was added lithium hydroxide monohydrate (37.4 g, 891 mmol) in one portion. The reaction mixture was stirred at 25° C. for 16 hours, whereupon it was diluted with water (600 mL) and washed with EtOAc (3×300 mL). The organic layers were discarded, and the aqueous layer was acidified to pH 3 to 4 by addition of 6 M hydrochloric acid. The resulting mixture was extracted with EtOAc (3×600 mL), and the combined organic layers were dried over sodium sulfate, filtered, and concentrated in vacuo. Trituration of the residue with petroleum ether (300 mL) provided C17 as a white solid. Yield: 42.0 g, 164 mmol, 59%. LCMS m/z 278.2 [M+Na$^+$]. $^1$H NMR (400 MHz, DMSO-d$_6$) δ 12.15-12.03 (br s, 1H), 3.43-3.25 (m, 3H, assumed; partially obscured by water peak), 3.23-3.12 (m, 1H), 1.64-1.50 (m, 2H), 1.52 (dd, 1H), 1.39 (s, 9H), 1.39-1.28 (m, 2H), 0.96-0.88 (m, 2H).

Step 4. Synthesis of methyl 6-azaspiro[2.5]octane-1-carboxylate (P5)

Thionyl chloride (5 mL) was added to a 15° C. solution of C17 (5.00 g, 19.6 mmol) in MeOH (50 mL), and the reaction mixture was stirred at 15° C. for 16 hours. It was then concentrated in vacuo, and the residue was poured into water (20 mL). The resulting mixture was adjusted to pH 9 by addition of aqueous sodium bicarbonate solution, whereupon it was extracted first with EtOAc (3×100 mL), and then with a mixture of dichloromethane and MeOH (10:1 ratio; 5×100 mL). The combined organic layers were dried over sodium sulfate, filtered, and concentrated under reduced pressure to afford P5 as a pale brown solid. Yield: 3.0 g, 18 mmol, 92%. $^1$H NMR (400 MHz, Chloroform-d) δ 3.68 (s, 3H), 2.92-2.88 (m, 2H), 2.88-2.82 (m, 1H), 2.74 (ddd, 1H), 1.76-1.62 (m, 2H), 1.51 (dd, 1H), 1.49-1.36 (m, 2H), 1.13 (dd, 1H), 0.90 (dd, 1H).

Preparation P6

6-{6-[(4-Cyano-2-fluorobenzyl)oxy]pyridin-2-yl}-6-azaspiro[2.5]octane-1-carboxylic Acid (P6)

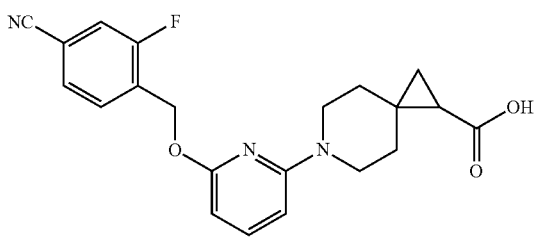

P6

Step 1. Synthesis of 4-{[(6-chloropyridin-2-yl)oxy]methyl}-3-fluorobenzonitrile (C18)

This reaction was carried out in two parallel batches. To a stirred suspension of potassium tert-butoxide (313 g, 2.79 mol) in THF (4.0 L) at 10° C. to 15° C. was added 3-fluoro-4-(hydroxymethyl)benzonitrile (281 g, 1.86 mol) in a portion-wise manner. The reaction mixture was stirred at 15° C. for 45 minutes, whereupon 2,6-dichloropyridine (230 g, 1.55 mol) was added in several portions, while maintaining the reaction temperature at 15° C. After a further 18 hours at 15° C., the reaction mixture was poured into saturated aqueous ammonium chloride solution (10 L). EtOAc (10 L) was added and the mixture was stirred for 15 minutes, then filtered through a pad of diatomaceous earth. The aqueous layer of the filtrate was extracted with EtOAc (2×6 L), and the combined organic layers were washed with saturated aqueous sodium chloride solution (5 L), dried over sodium sulfate, filtered, and concentrated in vacuo. Silica gel chromatography (Gradient: 10% to 15% EtOAc in petroleum ether) afforded C18 as a light yellow solid. Combined yield: 550 g, 2.09 mmol, 67%. $^1$H NMR (400 MHz, CDCl$_3$) δ 7.67 (dd, 1H), 7.58 (dd, 1H), 7.48 (dd, 1H), 7.40 (dd, 1H), 6.97 (d, 1H), 6.75 (d, 1H), 5.49 (s, 2H).

Step 2. Synthesis of methyl 6-{6-[(4-cyano-2-fluorobenzyl)oxy]pyridin-2-yl}-6-azaspiro[2.5]octane-1-carboxylate (C19)

To a solution of C18 (3.00 g, 11.4 mmol) in toluene (80 mL) were added P5 (1.93 g, 11.4 mmol), tris(dibenzylideneacetone)dipalladium(0) (523 mg, 0.571 mmol), 1,1'-binaphthalene-2,2'-diylbis(diphenylphosphane) (711 mg, 1.14 mmol), and cesium carbonate (11.2 g, 34.3 mmol). The reaction mixture was stirred at 100° C. for 16 hours, whereupon it was filtered through diatomaceous earth. The filtrate was concentrated in vacuo and purified using silica gel chromatography (Gradient: 0% to 15% EtOAc in petroleum ether) to provide C19 as a pale yellow oil. Yield: 2.30 g, 5.82 mmol, 51%. LCMS m/z 395.9 [M+H]$^+$. $^1$H NMR (400 MHz, CDCl$_3$) δ 7.61 (dd, 1H), 7.44 (dd, 1H), 7.42 (dd, 1H), 7.36 (dd, 1H), 6.21 (d, 1H), 6.13 (d, 1H), 5.45 (s, 2H), 3.69 (s, 3H), 3.63-3.49 (m, 3H), 3.38 (ddd, 1H), 1.83-1.70 (m, 2H), 1.60 (dd, 1H), 1.51-1.45 (m, 2H), 1.21 (dd, 1H), 0.99 (dd, 1H).

Step 3. Synthesis of 6-{6-[(4-cyano-2-fluorobenzyl)oxy]pyridin-2-yl}-6-azaspiro[2.5]octane-1-carboxylic Acid (P6)

To a solution of C19 (770 mg, 1.95 mmol) in a mixture of THF (8.0 mL) and MeOH (8.0 mL) was added aqueous lithium hydroxide solution (2 M; 5.8 mL, 12 mmol), and the reaction mixture was stirred at 15° C. for 60 hours. It was then concentrated to remove organic solvents, and the aqueous residue was adjusted to pH 6 by addition of 1 M hydrochloric acid. The resulting mixture was extracted with dichloromethane (3×30 mL), and the combined organic layers were dried over magnesium sulfate, filtered, and concentrated in vacuo. Purification was carried out via chromatography on silica gel (Gradient: 0% to 1% MeOH in dichloromethane) followed by preparative thin-layer chromatography (Eluent: 20:1 dichloromethane/MeOH), affording P6 as a red gum. Yield: 530 mg, 1.39 mmol, 71%. LCMS m/z 382.1 [M+H]$^+$.

Preparation P7

Ammonium 6-{2-[(4-chloro-2-fluorobenzyl)oxy]-5-fluoropyrimidin-4-yl}-6-azaspiro[2.5]octane-1-carboxylate, ENT-2 (P7)

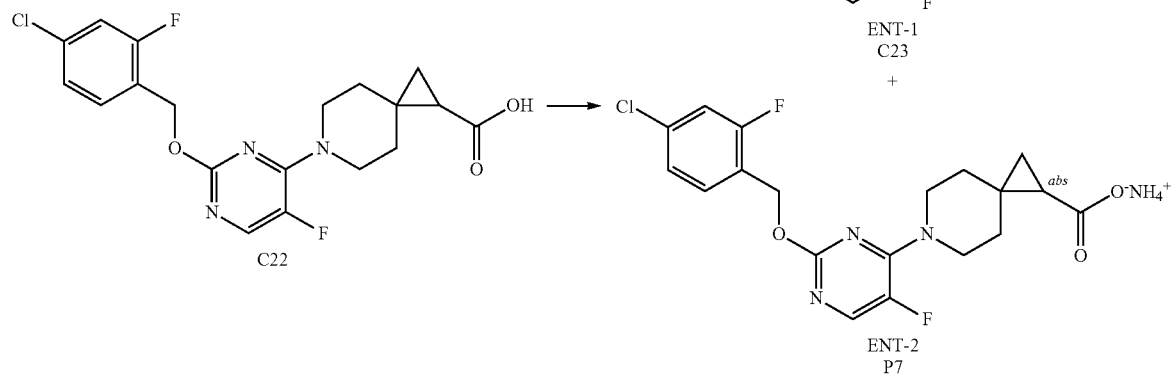

Step 1. Synthesis of methyl 6-azaspiro[2.5]octane-1-carboxylate, Hydrochloride Salt (P5, HCl Salt)

Thionyl chloride (8 mL) was added to a solution of C17 (12.4 g, 48.6 mmol) in MeOH (200 mL), and the reaction mixture was stirred at 30° C. for 16 hours. Concentration in vacuo afforded P5, HCl salt as a beige solid. Yield: 10.0 g, 48.6 mmol, quantitative. $^1$H NMR (400 MHz, DMSO-d$_6$) δ 9.29 (br s, 2H), 3.61 (s, 3H), 3.09-2.97 (m, 3H), 2.92-2.81 (m, 1H), 1.91-1.76 (m, 2H), 1.74 (dd, 1H), 1.73-1.57 (m, 2H), 1.06 (dd, 1H), 1.02 (dd, 1H).

Step 2. Synthesis of methyl 6-(2-chloro-5-fluoropyrimidin-4-yl)-6-azaspiro[2.5]octane-1-carboxylate (C20)

To a solution of P5, HCl salt (8.0 g, 39 mmol) and 2,4-dichloro-5-fluoropyrimidine (7.80 g, 46.7 mmol) in MeOH (150 mL) was added triethylamine (16.5 mL, 118 mmol). After the reaction mixture had been stirred at room temperature (30° C.) for 16 hours, it was concentrated in vacuo. The resulting gum was partitioned between EtOAc (80 mL) and water (80 mL); the aqueous layer was then further extracted with EtOAc (3×80 mL). The combined organic layers were washed with saturated aqueous sodium chloride solution (2×50 mL), dried over sodium sulfate, filtered, and concentrated under reduced pressure. Silica gel chromatography (Gradient: 0% to 21% EtOAc in petroleum ether) provided C20 as a yellow oil. Yield: 11.5 g, 38.4 mmol, 98%. $^1$H NMR (400 MHz, CDCl$_3$) δ 7.91 (d, 1H), 3.88-3.78 (m, 3H), 3.74-3.65 (m, 1H), 3.70 (s, 3H), 1.92-1.79 (m, 2H), 1.65 (dd, 1H, assumed; partially obscured by water peak), 1.59-1.54 (m, 2H), 1.25 (dd, 1H), 1.02 (dd, 1H).

Step 3. Synthesis of methyl 6-{2-[(4-chloro-2-fluorobenzyl)oxy]-5-fluoropyrimidin-4-yl}-6-azaspiro[2.5]octane-1-carboxylate (C21)

Palladium(II) acetate (888 mg, 3.96 mmol), di-tert-butyl [2',4',6'-tri(propan-2-yl)biphenyl-2-yl]phosphane (t-Bu XPhos; 3.27 g, 7.70 mmol), and cesium carbonate (31.6 g, 96.9 mmol) were added to a solution of C20 (11.5 g, 38.4 mmol) and (4-chloro-2-fluorophenyl)methanol (7.47 g, 46.5 mmol) in toluene (200 mL), whereupon the reaction vessel was evacuated and charged with nitrogen. This evacuation cycle was repeated twice, and the reaction mixture was then stirred at 110° C. for 16 hours. After filtration, the filtrate was concentrated in vacuo and purified via silica gel chromatography (Gradient: 0% to 22% EtOAc in petroleum ether) to afford C21 as a pale yellow oil. Yield: 13.4 g, 31.6 mmol, 82%. LCMS m/z 424.0♦ [M+H]$^+$. $^1$H NMR (400 MHz, CDCl$_3$) δ 7.87 (d, 1H), 7.45 (dd, 1H), 7.15-7.07 (m, 2H), 5.33 (s, 2H), 3.84-3.73 (m, 3H), 3.70 (s, 3H), 3.70-3.63 (m, 1H), 1.88-1.75 (m, 2H), 1.63 (dd, 1H), 1.56-1.50 (m, 2H), 1.23 (dd, 1H), 1.00 (dd, 1H).

Step 4. Synthesis of 6-{2-[(4-chloro-2-fluorobenzyl)oxy]-5-fluoropyrimidin-4-yl}-6-azaspiro[2.5]octane-1-carboxylic Acid (C22)

To a solution of C21 (21 g, 50 mmol) in a mixture of MeOH (80 mL) and THF (80 mL) was added aqueous sodium hydroxide solution (5 M; 30 mL, 150 mmol). The reaction mixture was stirred at 30° C. for 15 hours, whereupon it was concentrated in vacuo, adjusted to a pH of 6 to 7 by addition of 1 M hydrochloric acid, and extracted with a mixture of dichloromethane and MeOH (10:1, 4×100 mL). The combined organic layers were dried over sodium sulfate, filtered, concentrated under reduced pressure, and combined with the product of a similar reaction carried out using C21 (13.4 g, 31.6 mmol). Silica gel chromatography (Gradient: 0% to 10% MeOH in dichloromethane) provided C22 as a yellow gum. Combined yield: 27.0 g, 65.9 mmol, 81%. LCMS m/z 410.1♦ [M+H]$^+$.

Step 5. Isolation of ammonium 6-{2-[(4-chloro-2-fluorobenzyl)oxy]-5-fluoropyrimidin-4-yl}-6-azaspiro[2.5]octane-1-carboxylate, ENT-1 (C23) and ammonium 6-{2-[(4-chloro-2-fluorobenzyl)oxy]-5-fluoropyrimidin-4-yl}-6-azaspiro[2.5]octane-1-carboxylate, ENT-2 (P7)

Separation of C22 (27.0 g, 65.9 mmol) into its component enantiomers was carried out via supercritical fluid chromatography [Column: Chiral Technologies Chiralpak AD, 10 μm; Mobile phase: 7:3 carbon dioxide/(MeOH containing 0.1% ammonium hydroxide)]. The first-eluting enantiomer, isolated as a white solid, was designated as ENT-1 (C23). Yield: 10.27 g, 25.06 mmol, 38%. LCMS m/z 410.0♦ [M+H]$^+$. $^1$H NMR (400 MHz, CDCl$_3$) δ 7.88 (d, 1H), 7.44 (dd, 1H), 7.12 (dd, 1H), 7.09 (dd, 1H), 5.33 (s, 2H), 3.89-3.69 (m, 4H), 1.86 (t, 2H), 1.63 (dd, 1H), 1.60-1.48 (m, 2H), 1.25 (dd, 1H), 1.05 (dd, 1H).

The second-eluting enantiomer, designated as ENT-2 (P7), was further purified using reversed-phase HPLC (Column: Phenomenex Gemini C18, 10 μm; Mobile phase A: 0.05% ammonium hydroxide in water; Mobile phase B: acetonitrile; Gradient: 15% to 38% B); this material was also obtained as a white solid. Yield: 9.86 g, 24.1 mmol, 37%. LCMS m/z 410.0♦ [M+H]$^+$. $^1$H NMR (400 MHz, CDCl$_3$) δ 7.88 (d, 1H), 7.45 (dd, 1H), 7.12 (dd, 1H), 7.09 (dd, 1H), 5.33 (s, 2H), 3.88-3.69 (m, 4H), 1.86 (t, 2H), 1.64 (dd, 1H), 1.61-1.49 (m, 2H), 1.26 (dd, 1H), 1.07 (dd, 1H).

Preparation P8

4-Chloro-2-[(4-chloro-2-fluorobenzyl)oxy]pyrimidine (P8)

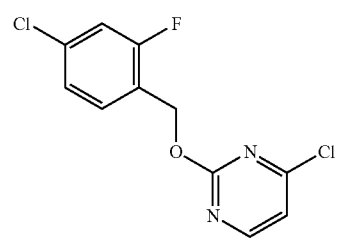

This reaction was carried out in two identical batches. A solution of (4-chloro-2-fluorophenyl)methanol (5.42 g, 33.8 mmol) in THF (60 mL) was added drop-wise, over a period of 25 minutes, to a −25° C. suspension of 4-chloro-2-(methylsulfonyl)pyrimidine (13.0 g, 67.5 mmol) and sodium hydride (60% dispersion in mineral oil; 2.43 g, 60.8 mmol) in THF (180 mL). The reaction mixture was allowed to stir at room temperature (25° C.) for 18 hours, whereupon the two batches were combined and concentrated in vacuo. The residue was diluted with saturated aqueous ammonium chloride solution (120 mL) and extracted with EtOAc (3×100 mL); the combined organic layers were dried over sodium sulfate, filtered, concentrated under reduced pressure, and purified via silica gel chromatography (Gradient: 0% to 6% EtOAc in petroleum ether), affording P8 as a white solid. Combined yield: 9.93 g, 36.4 mmol, 54%. LCMS m/z 272.7 (dichloro isotope pattern observed) [M+H]$^+$. $^1$H NMR (400 MHz, Chloroform-d) δ 8.41 (d, 1H), 7.48 (dd, 1H), 7.17-7.10 (m, 2H), 7.02 (d, 1H), 5.46 (s, 2H).

Preparation P9

6-{4-[(4-Chloro-2-fluorobenzyl)oxy]-5-fluoropyrimidin-2-yl}-6-azaspiro[2.5]octane-1-carboxylic Acid (P9)

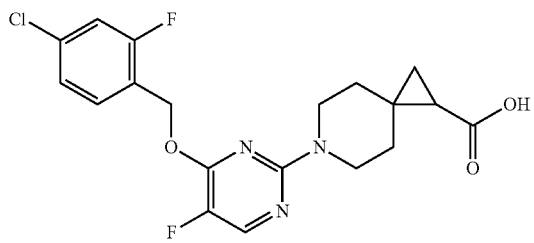

Step 1. Synthesis of 2-chloro-4-[(4-chloro-2-fluorobenzyl)oxy]-5-fluoropyrimidine (C24)

Sodium hydride (60% dispersion in mineral oil; 264 mg, 6.59 mmol) was added in portions to a 0° C. solution of (4-chloro-2-fluorophenyl)methanol (1.06 g, 6.59 mmol) in THF (15 mL), and the resultant mixture was stirred at 10° C. for 30 minutes. A solution of 2,4-dichloro-5-fluoropyrimidine (1.00 mg, 5.99 mmol) in THF (5 mL) was then added portion-wise, and the reaction mixture was stirred at 10° C. for 3 hours, whereupon it was poured into aqueous ammonium chloride solution (100 mL) and extracted with EtOAc (2×50 mL). The combined organic layers were dried over sodium sulfate, filtered, and concentrated under reduced pressure. Silica gel chromatography (Gradient: 0% to 5% EtOAc in petroleum ether) provided C24 as a white solid. Yield: 1.21 g, 69%.

Step 2. Synthesis of methyl 6-{4-[(4-chloro-2-fluorobenzyl)oxy]-5-fluoropyrimidin-2-yl}-6-azaspiro[2.5]octane-1-carboxylate (C25)

A solution of C24 (1.10 g, 3.78 mmol), P5, HCl salt (855 mg, 4.16 mmol), and triethylamine (1.15 g, 11.3 mmol) in N,N-dimethylformamide (20 mL) was stirred at 100° C. for 6 hours, whereupon it was combined with a similar reaction carried out using C24 (100 mg, 0.344 mmol), poured into water (300 mL), and extracted with EtOAc (2×60 mL). The combined organic layers were dried over sodium sulfate, filtered, and concentrated in vacuo; purification via silica gel chromatography (Gradient: 0% to 10% EtOAc in petroleum ether) afforded C25 as an orange oil. Combined yield: 813 mg, 1.92 mmol, 47%.

Step 3. Synthesis of 6-{4-[(4-chloro-2-fluorobenzyl)oxy]-5-fluoropyrimidin-2-yl}-6-azaspiro[2.5]octane-1-carboxylic Acid (P9)

To a solution of C25 (1.79 g, 4.22 mmol) in MeOH (50 mL) was added aqueous sodium hydroxide solution (2 M; 21.1 mL, 42.2 mmol). The reaction mixture was stirred at 20° C. for 3 hours, then at 40° C. for 4 hours, whereupon it was acidified to pH 5 by addition of 12 M hydrochloric acid, diluted with water (300 mL), and extracted with dichloromethane (2×200 mL). The combined organic layers were dried over sodium sulfate, filtered, and concentrated in vacuo. Purification was carried out using silica gel chromatography (Gradient: 0% to 5% MeOH in dichloromethane) followed by reversed-phase HPLC (Column: Phenomenex Synergi C18, 30×150 mm, 4 μm; Mobile phase A: 0.225% formic acid in water; Mobile phase B: acetonitrile; Gradient: 50% to 80% B). The fractions from the HPLC separation were concentrated under reduced pressure to half of the original volume, and then extracted with dichloromethane (2×100 mL); the combined organic layers were dried over sodium sulfate, filtered, and concentrated in vacuo, providing P9 as a white foamy solid. Yield: 1.04 g, 60%. LCMS m/z 409.8♦ [M+H]⁺. ¹H NMR (400 MHz, Chloroform-d) δ 7.97 (d, 1H), 7.42 (dd, 1H), 7.15 (br dd, 1H), 7.12 (dd, 1H), 5.43 (s, 2H), 3.86-3.74 (m, 3H), 3.73-3.64 (m, 1H), 1.79 (t, 2H), 1.63 (dd, 1H), 1.49 (t, 2H), 1.26 (dd, 1H), 1.07 (dd, 1H).

Preparation P10

6-{6-[(4-Cyano-2-fluorobenzyl)oxy]-5-fluoropyridin-2-yl}-6-azaspiro[2.5]octane-1-carboxylic Acid (P10)

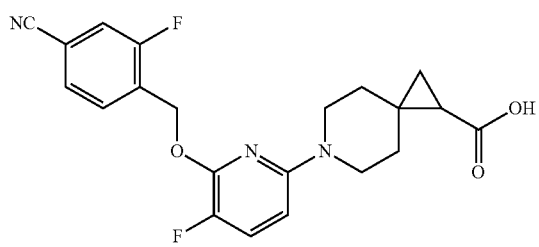

Step 1. Synthesis of 4-{[(3,6-difluoropyridin-2-yl)oxy]methyl}-3-fluorobenzonitrile (C26)

To a solution of 2,3,6-trifluoropyridine (4.40 g, 33.1 mmol) and 3-fluoro-4-(hydroxymethyl)benzonitrile (5.00 g, 33.1 mmol) in 1-methylpyrrolidin-2-one (60 mL) was added potassium carbonate (13.7 g, 99.2 mmol). The reaction mixture was stirred at 100° C. for 16 hours, whereupon it was poured into water (100 mL) and extracted with EtOAc (3×300 mL). After the combined organic layers had been washed with saturated aqueous sodium chloride solution (4×200 mL), they were dried over sodium sulfate, filtered, concentrated in vacuo, and combined with the product of a similar reaction carried out using 2,3,6-trifluoropyridine (200 mg, 1.50 mmol). Silica gel chromatography (Gradient: 0% to 5% EtOAc in petroleum ether) provided C26 as a white solid. Combined yield: 6.93 g, 26.2 mmol, 76%. MS (ESI) m/z 265.1 [M+H]⁺. ¹H NMR (400 MHz, CDCl₃) δ 7.69 (dd, 1H), 7.53-7.45 (m, 2H), 7.41 (dd, 1H), 6.50 (ddd, 1H), 5.52 (s, 2H).

Step 2. Synthesis of methyl 6-{6-[(4-cyano-2-fluorobenzyl)oxy]-5-fluoropyridin-2-yl}-6-azaspiro[2.5]octane-1-carboxylate (C27)

This reaction was carried out in two identical batches. Triethylamine (766 mg, 7.57 mmol) was added to a solution of C26 (1.00 g, 3.78 mmol) and P5 (640 mg, 3.78 mmol) in dimethyl sulfoxide (9 mL), and the reaction mixture was stirred at 140° C. for 14 hours in a microwave reactor. The two reaction mixtures were then combined, poured into water (50 mL), and extracted with dichloromethane (3×50 mL). The combined organic layers were dried over sodium sulfate, filtered, concentrated in vacuo, and subjected to silica gel chromatography (Eluent: 20% EtOAc in petroleum ether) to afford C27 as a yellow oil. Combined yield: 696 mg, 1.68 mmol, 22%. LCMS m/z 413.9 [M+H]$^+$. $^1$H NMR (400 MHz, CDCl$_3$): δ 7.65 (dd, 1H), 7.46 (dd, 1H), 7.37 (dd, 1H), 7.24 (dd, 1H), 6.12 (dd, 1H), 5.52 (s, 2H), 3.70 (s, 3H), 3.56-3.42 (m, 3H), 3.30 (ddd, 1H), 1.85-1.72 (m, 2H), 1.60 (dd, 1H), 1.53-1.46 (m, 2H), 1.21 (dd, 1H), 0.99 (dd, 1H).

Step 3. Synthesis of 6-{6-[(4-cyano-2-fluorobenzyl)oxy]-5-fluoropyridin-2-yl}-6-azaspiro[2.5]octane-1-carboxylic Acid (P10)

To a solution of C27 (646 mg, 1.56 mmol) in a mixture of THF (10 mL) and MeOH (1 mL) was added aqueous lithium hydroxide solution (2 M; 4.7 mL, 9.4 mmol). After the reaction mixture had been stirred at 25° C. for 16 hours, it was combined with a similar reaction carried out using C27 (50 mg, 0.12 mmol) and concentrated to dryness in vacuo. The residue was dissolved in water (5 mL) and adjusted to pH 6 via addition of 1 M hydrochloric acid; the precipitate was collected via filtration and washed with water (5 mL) to afford P10 as a yellow solid. Combined yield: 645 mg, 1.61 mmol, 96%. LCMS m/z 400.1 [M+H]$^+$.

Preparation P11

6-(6-Bromo-3-fluoropyridin-2-yl)-6-azaspiro[2.5]octane-1-carboxylic Acid (P11)

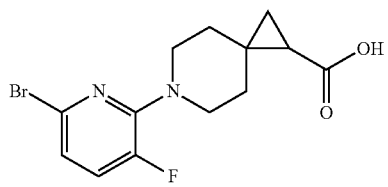

P11

Step 1. Synthesis of methyl 6-(6-bromo-3-fluoropyridin-2-yl)-6-azaspiro[2.5]octane-1-carboxylate (C28)

Potassium carbonate (2.44 g, 17.7 mmol) was added to a solution of 2,6-dibromo-3-fluoropyridine (1.50 g, 5.88 mmol) and P5 (1.10 g, 6.50 mmol) in N,N-dimethylformamide (25 mL), and the resulting suspension was stirred at 100° C. for 16 hours. The reaction mixture was then combined with two similar reactions carried out using 2,6-dibromo-3-fluoropyridine (1.50 g, 5.88 mmol and 1.0 g, 3.9 mmol), and poured into water (300 mL). After extraction with tert-butyl methyl ether (2×200 mL), the combined organic layers were washed with saturated aqueous sodium chloride solution (200 mL), dried over sodium sulfate, filtered, and concentrated in vacuo. Silica gel chromatography (Gradient: 0% to 10% EtOAc in petroleum ether), followed by reversed-phase HPLC (Column: Phenomenex Gemini C18, 10 μm; Mobile phase A: 0.05% ammonium hydroxide in water; Mobile phase B: acetonitrile; Gradient: 60% to 88% B), afforded C28 as a white solid. Combined yield: 2.25 g, 6.56 mmol, 42%. LCMS m/z 344.7 (bromine isotope pattern observed) [M+H]$^+$. $^1$H NMR (400 MHz, CDCl$_3$) δ 7.06 (dd, 1H), 6.80 (dd, 1H), 3.69 (s, 3H), 3.63-3.50 (m, 3H), 3.40 (ddd, 1H), 1.91-1.78 (m, 2H), 1.64-1.50 (m, 3H, assumed; partially obscured by water peak), 1.22 (dd, 1H), 0.99 (dd, 1H).

Step 2. Synthesis of 6-(6-bromo-3-fluoropyridin-2-yl)-6-azaspiro[2.5]octane-1-carboxylic Acid (P11)

Aqueous sodium hydroxide solution (2 M; 6.56 mL, 13.1 mmol) was added to a solution of C28 (2.25 g, 6.56 mmol) in THF (35 mL) and MeOH (25 mL), and the reaction mixture was stirred at room temperature for 73 hours, whereupon it was concentrated under reduced pressure to two-thirds of the original volume, and acidified to pH 6 to 7 by careful addition of concentrated hydrochloric acid. The resulting mixture was diluted with saturated aqueous sodium chloride solution (100 mL) and extracted with dichloromethane (2×80 mL); the combined organic layers were dried over sodium sulfate, filtered, and concentrated in vacuo to provide P11 as an off-white solid. Yield: 2.15 g, 6.53 mmol, quantitative. LCMS m/z 330.7 (bromine isotope pattern observed) [M+H]$^+$. $^1$H NMR (400 MHz, CDCl$_3$) δ 7.06 (dd, 1H), 6.80 (dd, 1H), 3.62-3.44 (m, 4H), 1.90 (dd, 2H), 1.65-1.56 (m, 3H), 1.26 (dd, 1H), 1.07 (dd, 1H).

Preparation P12

6-{6-[(4-Cyano-2-fluorobenzyl)oxy]-3,5-difluoropyridin-2-yl}-6-azaspiro[2.5]octane-1-carboxylic Acid (P12)

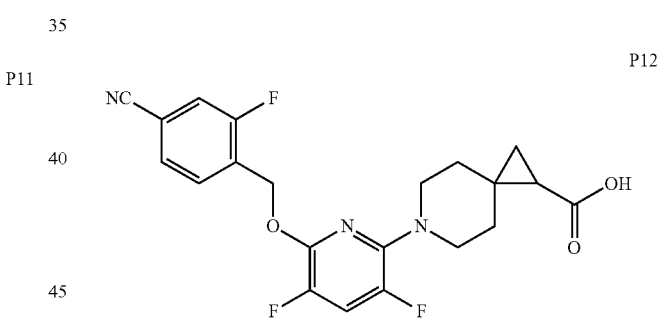

P12

Step 1. Synthesis of 3-fluoro-4-{[(3,5,6-trifluoropyridin-2-yl)oxy]methyl}benzonitrile (C29)

Reaction of 3-fluoro-4-(hydroxymethyl)benzonitrile with 2,3,5,6-tetrafluoropyridine was carried out using the method described for synthesis of C26 in Preparation P10. Compound C29 was obtained as a white solid. Yield: 1.15 g, 40%. $^1$H NMR (400 MHz, Chloroform-d) δ 7.66 (dd, 1H), 7.49 (dd, 1H), 7.46-7.38 (m, 2H), 5.49 (s, 2H).

Step 2. Synthesis of methyl 6-{6-[(4-cyano-2-fluorobenzyl)oxy]-3,5-difluoropyridin-2-yl}-6-azaspiro[2.5]octane-1-carboxylate (C30)

To a solution of C29 (522 mg, 1.85 mmol) in N,N-dimethylformamide (10 mL) were added P5 (348 mg, 2.06 mmol) and potassium carbonate (281 mg, 2.04 mmol). The reaction mixture was stirred at 110° C. for 10 hours, whereupon it was diluted with water (30 mL) and extracted with EtOAc (3×25 mL). The combined organic layers were washed with saturated aqueous sodium chloride solution (2×20 mL), dried over sodium sulfate, filtered, and concentrated in vacuo. Silica gel chromatography (Gradient: 0% to 4% EtOAc in petroleum ether) afforded C30 as a light yellow gum. Yield: 400 mg, 50%. LCMS m/z 431.9 [M+H]$^+$.

Step 3. Synthesis of 6-{6-[(4-cyano-2-fluorobenzyl)oxy]-3,5-difluoropyridin-2-yl}-6-azaspiro[2.5]octane-1-carboxylic Acid (P12)

To a solution of C30 (540 mg, 1.25 mmol) in THF (16 mL) were added aqueous lithium hydroxide solution (2 M; 1.9 mL, 3.8 mmol) and MeOH (1.8 mL). After the reaction mixture had been stirred at 25° C. for 16 hours, aqueous lithium hydroxide solution (2 M; 1.9 mL, 3.8 mmol) was again added, and stirring was continued at 25° C. for 20 hours, whereupon the pH was adjusted to 5 to 6 by addition of 1 M hydrochloric acid, and the mixture was extracted with dichloromethane (2×25 mL). The combined organic layers were dried over sodium sulfate, filtered, and concentrated in vacuo to provide P12 (540 mg, assumed quantitative) as a white solid. This material was used in further chemistry without additional purification. LCMS m/z 417.9 [M+H]$^+$.

Preparation P13

2-[(4-Chloro-2-fluorobenzyl)oxy]-4-(piperidin-4-yl)pyrimidine, bis(p-toluenesulfonic Acid) Salt (P13)

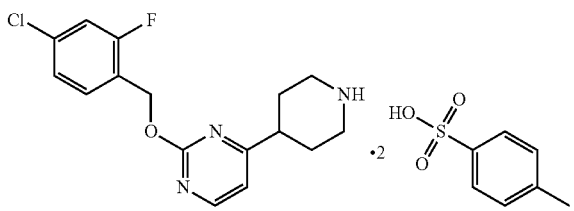

P13

Step 1. Synthesis of 1-tert-butyl 4-ethyl 4-[2-(methylthio)pyrimidin-4-yl]piperidine-1,4-dicarboxylate (C31)

A solution of lithium bis(trimethylsilyl)amide in THF (1 M; 2.3 L, 2.3 mol) was added to a −60° C. solution of 1-tert-butyl 4-ethyl piperidine-1,4-dicarboxylate (500 g, 1.93 mol) in THF (5 L). After the reaction mixture had stirred at −60° C. for 30 minutes, a solution of 4-chloro-2-(methylthio)pyrimidine (300 g, 1.87 mol) in THF (1.5 L) was added in a drop-wise manner. The reaction mixture was allowed to warm to room temperature over 1.5 hours and was then stirred at room temperature for 1 hour, before being cooled to 0° C. A solution of citric acid (386 g, 2.01 mol) in water (5 L) was then added, followed by saturated aqueous sodium chloride solution (5 L), and the resulting mixture was extracted with EtOAc (2×10 L). The combined organic layers were dried over sodium sulfate, filtered, concentrated in vacuo, and purified via silica gel chromatography (Gradient: 75% to 100% EtOAc in petroleum ether), affording C31 as a yellow oil. Yield: 690 g, 1.81 mol, 97%. LCMS m/z 382.2 [M+H]$^+$. $^1$H NMR (400 MHz, DMSO-d$_6$) δ 8.61 (d, 1H), 7.25 (d, 1H), 4.13 (q, 2H), 3.69 (ddd, 2H), 3.16-2.96 (m, 2H), 2.48 (s, 3H), 2.27-2.18 (m, 2H), 1.96 (ddd, 2H), 1.39 (s, 9H), 1.13 (t, 3H).

Step 2. Synthesis of tert-butyl 4-[2-(methylthio)pyrimidin-4-yl]piperidine-1-carboxylate (C32)

A solution of C31 (690 g, 1.81 mol) in MeOH (4.6 L) and THF (2.3 L) was heated to 40° C., whereupon aqueous sodium hydroxide solution (2.0 M, 2 equivalents) was added. After the reaction mixture had been stirred at 40° C. for 8 hours, it was allowed to cool to room temperature and then adjusted to pH 4 by addition of 1 M aqueous citric acid solution. The resulting mixture was diluted with saturated aqueous sodium chloride solution (5 L) and extracted with EtOAc (3×5 L); the combined organic layers were dried over sodium sulfate, filtered, and concentrated in vacuo to provide C32, which was advanced directly into the following step. Yield: 550 g, 1.78 mol, 98%. LCMS m/z 310.2 [M+H]$^+$. $^1$H NMR (400 MHz, DMSO-d$_6$) δ 8.52 (d, 1H), 7.12 (d, 1H), 4.10-3.98 (m, 2H), 2.90-2.74 (m, 2H), 2.80 (tt, 1H), 2.49 (s, 3H), 1.82 (br d, 2H), 1.60-1.47 (m, 2H), 1.41 (s, 9H).

Step 3. Synthesis of tert-butyl 4-[2-(methylsulfonyl)pyrimidin-4-yl]piperidine-1-carboxylate (C33)

3-Chloroperoxybenzoic acid (80%; 765 g, 3.55 mol) was added to a 0° C. solution of C32 (550 g, 1.78 mol) in dichloromethane (14 L). The reaction mixture was allowed to warm to room temperature over 1.5 hours and was then stirred for an additional 15 hours before being filtered through a pad of diatomaceous earth. The filter pad was rinsed with dichloromethane (3×5 L), and the combined filtrates were washed sequentially with saturated aqueous sodium bicarbonate solution (2×1.1 L) and with saturated aqueous sodium chloride solution (1.5 L), dried over magnesium sulfate, filtered, and concentrated in vacuo. Silica gel chromatography (Eluent: 50:1 dichloromethane/MeOH) afforded C33 as a yellow solid. Yield: 420 g, 1.23 mol, 69%. LCMS m/z 364.2 [M+Na]$^+$. $^1$H NMR (400 MHz, CDCl$_3$) δ 8.83 (d, 1H), 7.40 (d, 1H), 4.28 (br d, 2H), 3.37 (s, 3H), 2.99 (tt, 1H), 2.85 (ddd, 2H), 1.98 (br d, 2H), 1.81-1.67 (m, 2H), 1.48 (s, 9H).

Step 4. Synthesis of tert-butyl 4-{2-[(4-chloro-2-fluorobenzyl)oxy]pyrimidin-4-yl}piperidine-1-carboxylate (C34)

To a solution of (4-chloro-2-fluorophenyl)methanol (201 g, 1.25 mol) in THF (12 L) was added a solution of sodium bis(trimethylsilyl)amide in THF (2 M; 1.2 equivalents). After the reaction mixture had been stirred for 15 minutes, a solution of C33 (410 g, 1.20 mol) in THF (1 L) was added, and stirring was continued at room temperature for 1 hour. Water (5 L) was then added, and the mixture was extracted with EtOAc (2×5 L); the combined organic layers were washed with saturated aqueous sodium chloride solution (5 L), dried over magnesium sulfate, filtered, and concentrated in vacuo. Purification via silica gel chromatography (Eluent: 5:1 petroleum ether/EtOAc) provided C34. Yield: 252 g, 597 mmol, 50%. LCMS m/z 422.1♦ [M+H]$^+$. $^1$H NMR (400 MHz, CDCl$_3$) δ 8.43 (d, 1H), 7.48 (dd, 1H), 7.15-7.08 (m, 2H), 6.82 (d, 1H), 5.44 (s, 2H), 4.32-4.15 (m, 2H), 2.88-2.74 (m, 2H), 2.75 (tt, 1H), 1.88 (br d, 2H), 1.77-1.63 (m, 2H), 1.47 (s, 9H).

Step 5. Synthesis of 2-[(4-chloro-2-fluorobenzyl)oxy]-4-(piperidin-4-yl)pyrimidine, bis(p-toluenesulfonic Acid) Salt (P13)

p-Toluenesulfonic acid monohydrate (17.1 g, 89.9 mmol) was added in one portion to a solution of C34 (16.2 g, 38.4 mmol) in EtOAc (220 mL). The reaction mixture was heated to an internal temperature of 60° C. for 35 minutes, whereupon it was allowed to cool to room temperature overnight while stirring in the oil bath. LCMS analysis at this point indicated conversion to P13: LCMS m/z 322.2♦ [M+H]+. The solid was collected via filtration and washed with EtOAc (100 mL), affording P13 as a pink-white solid. Yield: 23.7 g, 35.6 mmol, 93%. $^1$H NMR (400 MHz, DMSO-$d_6$) δ 8.64-8.53 (br m, 1H), 8.56 (d, 1H), 8.37-8.23 (br m, 1H), 7.60 (dd, 1H), 7.53-7.48 (m, 1H), 7.49 (d, 4H), 7.34 (br d, 1H), 7.12 (d, 4H), 7.09 (d, 1H), 5.41 (s, 2H), 3.37 (br d, 2H), 3.08-2.93 (m, 3H), 2.29 (s, 6H), 2.01 (br d, 2H), 1.92-1.77 (m, 2H).

Preparation P14 tert-Butyl (2S)-4-{2-[(4-chloro-2-fluorobenzyl)oxy]-5-fluoropyrimidin-4-yl}-2-methylpiperazine-1-carboxylate (P14)

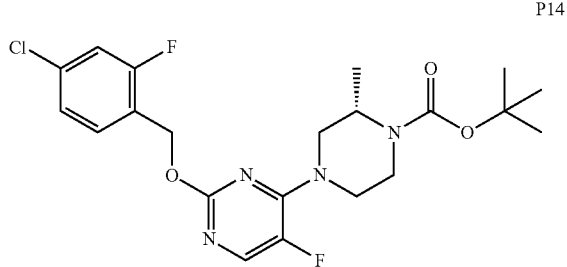 [SMILES: C[C@H]1CN(c2nc(OCc3ccc(Cl)cc3F)ncc2F)CCN1C(=O)OC(C)(C)C]

P14

Step 1. Synthesis of tert-butyl (2S)-4-(2-chloro-5-fluoropyrimidin-4-yl)-2-methylpiperazine-1-carboxylate (C35)

To a 0° C. solution of 2,4-dichloro-5-fluoropyrimidine (12.0 g, 71.9 mmol) in dichloromethane (130 mL) was added triethylamine (20 mL, 140 mmol), followed by a solution of tert-butyl (2S)-2-methylpiperazine-1-carboxylate (15.0 g, 74.9 mmol) in dichloromethane (70 mL). The reaction mixture was stirred at 30° C. for 15 hours, whereupon it was washed sequentially with water (150 mL) and with saturated aqueous sodium chloride solution (100 mL), dried over magnesium sulfate, filtered, and concentrated in vacuo. Purification via chromatography on silica gel (Gradient: 20% to 50% EtOAc in petroleum ether) afforded C35 as a white solid. Yield: 21.4 g, 64.7 mmol, 90%. LCMS m/z 330.9♦ [M+H]+. $^1$H NMR (400 MHz, CDCl$_3$) δ 7.94 (d, 1H), 4.54-4.45 (m, 1H), 4.39-4.29 (m, 1H), 4.28 (br d, 1H), 3.94 (br d, 1H), 3.35 (dd, 1H), 3.25-3.06 (m, 2H), 1.48 (s, 9H), 1.17 (d, 3H).

Step 2. Synthesis of tert-butyl (2S)-4-{2-[(4-chloro-2-fluorobenzyl)oxy]-5-fluoropyrimidin-4-yl}-2-methylpiperazine-1-carboxylate (P14)

Conversion of C35 to P14 was carried out via the method described for synthesis of C21 from C20 in Preparation P7. In this case, the crude product was purified using silica gel chromatography (Gradient: 0% to 20% EtOAc in petroleum ether) to afford P14 as a pale yellow oil. Yield: 10.7 g, 23.5 mmol, 98%. $^1$H NMR (400 MHz, Chloroform-d) δ 7.88 (d, 1H), 7.44 (dd, 1H), 7.15-7.06 (m, 2H), 5.33 (s, 2H), 4.50-4.42 (m, 1H), 4.35-4.20 (m, 2H), 3.90 (br d, 1H), 3.28 (dd, 1H), 3.16 (ddd, 1H), 3.05 (ddd, 1H), 1.47 (s, 9H), 1.14 (d, 3H).

Preparation P15

2-[(4-Chloro-2-fluorobenzyl)oxy]-4-[(3S)-3-methylpiperazin-1-yl]pyrimidine, bis(p-toluenesulfonate) Salt (P15)

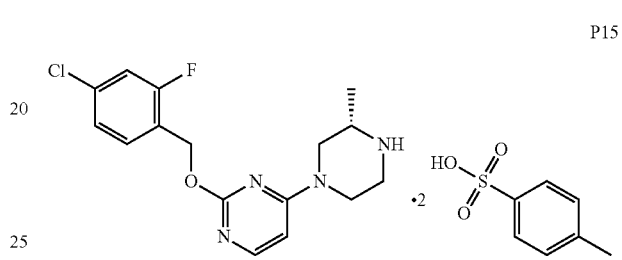

P15

Step 1. Synthesis of tert-butyl (2S)-4-(2-chloropyrimidin-4-yl)-2-methylpiperazine-1-carboxylate (C36)

A solution of tert-butyl (2S)-2-methylpiperazine-1-carboxylate (22.2 g, 111 mmol), 2,4-dichloropyrimidine (15.0 g, 101 mmol), and triethylamine (30 mL) in dichloromethane (200 mL) was stirred at 30° C. for 15 hours, whereupon it was washed sequentially with water (150 mL) and with saturated aqueous sodium chloride solution (100 mL), dried over magnesium sulfate, filtered, and concentrated in vacuo. Chromatography on silica gel (Gradient: 20% to 50% EtOAc in petroleum ether) afforded C36 as a white solid. Yield: 25.0 g, 79.9 mmol, 79%.

Step 2. Synthesis of tert-butyl (2S)-4-{2-[(4-chloro-2-fluorobenzyl)oxy]pyrimidin-4-yl}-2-methylpiperazine-1-carboxylate (C37)

A solution of sodium bis(trimethylsilyl)amide in THF (1.0 M; 90.0 mL, 90.0 mmol) was added in a drop-wise manner to a solution of (4-chloro-2-fluorophenyl)methanol (13.3 g, 82.8 mmol) in THF (50 mL), and the resulting mixture was stirred at 60° C. for 15 minutes, whereupon it was added to a solution of C36 (20.0 g, 63.9 mmol) in THF (120 mL). Stirring was continued at 60° C. for 1 hour, and then the reaction mixture was partitioned between EtOAc and water, and combined with material from a similar reaction carried out using C36 (5.00 g, 16.0 mmol). The aqueous layer was extracted with EtOAc (2×120 mL), and the combined organic layers were dried over sodium sulfate, filtered, and concentrated in vacuo. Silica gel chromatography (Gradient: 0% to 30% EtOAc in petroleum ether) provided C37 as a yellow gum. Combined yield: 33.6 g, 76.9 mmol, 96%.

Step 3. Synthesis of 2-[(4-chloro-2-fluorobenzyl)oxy]-4-[(3S)-3-methylpiperazin-1-yl]pyrimidine, bis(p-toluenesulfonate) Salt (P15)

p-Toluenesulfonic acid monohydrate (17.8 g, 93.6 mmol) was added in one portion to a mixture of C37 (15.7 g, 35.9 mmol) and EtOAc (220 mL). The reaction mixture was heated to an internal temperature of 60° C. for 35 minutes, whereupon it was allowed to cool to room temperature in the oil bath while stirring overnight. The resulting solid was collected via filtration and washed with EtOAc (100 mL) to afford P15 as an off-white solid. Yield: 24.5 g, quantitative. LCMS m/z 337.2♦ [M+H]$^+$. $^1$H NMR (400 MHz, DMSO-d$_6$), characteristic peaks: δ 9.21-9.06 (m, 1H), 8.89-8.73 (m, 1H), 8.22 (d, 1H), 7.62 (dd, 1H), 7.55 (dd, 1H), 7.48 (d, 4H), 7.37 (dd, 1H), 7.11 (d, 4H), 6.87 (d, 1H), 5.53 (s, 2H), 3.22 (dd, 1H), 3.18-3.05 (m, 1H), 2.29 (s, 6H), 1.27 (d, 3H).

Preparation P16

Methyl 4-amino-3-{[(2S)-oxetan-2-ylmethyl]amino}benzoate (P16)

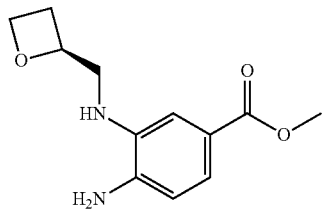

P16

This entire sequence was carried out on large scale. In general, before reactions, as well as after addition of reagents, reactors were evacuated to −0.08 to −0.05 MPa and then filled with nitrogen to normal pressure. This process was generally repeated 3 times, and then oxygen content was assessed to ensure that it was ≤1.0%. For the processes of extraction and washing of organic layers, mixtures were generally stirred for 15 to 60 minutes and then allowed to settle for 15 to 60 minutes before separation of layers.

Step 1. Synthesis of (2S)-2-[(benzyloxy)methyl]oxetane (C38)

This reaction was carried out in three batches of approximately the same scale. A 2000 L glass-lined reactor was charged with 2-methylpropan-2-ol (774.7 kg). Potassium tert-butoxide (157.3 kg, 1402 mol) was added via a solid addition funnel, and the mixture was stirred for 30 minutes. Trimethylsulfoxonium iodide (308.2 kg, 1400 mol) was then added in the same manner, and the reaction mixture was heated at 55° C. to 65° C. for 2 to 3 hours, whereupon (2S)-2-[(benzyloxy)methyl]oxirane (92.1 kg, 561 mol) was added at a rate of 5 to 20 kg/hour. After the reaction mixture had been maintained at 55° C. to 65° C. for 25 hours, it was cooled to 25° C. to 35° C., and filtered through diatomaceous earth (18.4 kg). The filter cake was rinsed with tert-butyl methyl ether (3×340 kg), and the combined filtrates were transferred to a 5000 L reactor, treated with purified water (921 kg), and stirred for 15 to 30 minutes at 15° C. to 30° C. The organic layer was then washed twice using a solution of sodium chloride (230.4 kg) in purified water (920.5 kg), and concentrated under reduced pressure (≤−0.08 MPa) at ≤45° C. n-Heptane (187 kg) was added, and the resulting mixture was concentrated under reduced pressure (≤−0.08 MPa) at ≤45° C.; the organic phase was purified using silica gel chromatography (280 kg), with sodium chloride (18.5 kg) on top of the column. The crude material was loaded onto the column using n-heptane (513 kg), and then eluted with a mixture of n-heptane (688.7 kg) and EtOAc (64.4 kg). The three batches were combined, providing C38 as an 85% pure light yellow oil (189.7 kg, 906 mmol, 54%). $^1$H NMR (400 MHz, Chloroform-d), C38 peaks only: δ 7.40-7.32 (m, 4H), 7.32-7.27 (m, 1H), 4.98 (dddd, 1H), 4.72-4.55 (m, 4H), 3.67 (dd, 1H), 3.62 (dd, 1H), 2.72-2.53 (m, 2H).

Step 2. Synthesis of (2S)-oxetan-2-ylmethanol (C39)

10% Palladium on carbon (30.7 kg) was added through an addition funnel to a 10° C. to 30° C. solution of 85% pure C38 (from previous step; 185.3 kg, 884.8 mol) in THF (1270 kg) in a 3000 L stainless steel autoclave reactor. The addition funnel was rinsed with purified water and THF (143 kg), and the rinses were added to the reaction mixture. After the reactor contents had been purged with nitrogen, they were similarly purged with hydrogen, increasing the pressure to 0.3 to 0.5 MPa and then venting to 0.05 MPa. This hydrogen purge was repeated 5 times, whereupon the hydrogen pressure was increased to 0.3 to 0.4 MPa. The reaction mixture was then heated to 35° C. to 45° C. After 13 hours, during which the hydrogen pressure was maintained at 0.3 to 0.5 MPa, the mixture was vented to 0.05 MPa, and purged five times with nitrogen, via increasing the pressure to 0.15 to 0.2 MPa and then venting to 0.05 MPa. After the mixture had been cooled to 10° C. to 25° C., it was filtered, and the reactor was rinsed with THF (2×321 kg). The filter cake was soaked twice with this rinsing liquor and then filtered; concentration at reduced pressure (≤−0.06 MPa) was carried out at ≤40° C., affording C39 (62.2 kg, 706 mol, 80%) in THF (251 kg)

Step 3. Synthesis of (2S)-oxetan-2-ylmethyl 4-methylbenzenesulfonate (C40)

4-(Dimethylamino)pyridine (17.5 kg, 143 mol) was added to a 10° C. to 25° C. solution of C39 (from the previous step; 62.2 kg, 706 mol) in THF (251 kg) and triethylamine (92.7 kg, 916 mol) in dichloromethane (1240 kg). After 30 minutes, p-toluenesulfonyl chloride (174.8 kg, 916.9 mol) was added in portions at intervals of 20 to 40 minutes, and the reaction mixture was stirred at 15° C. to 25° C. for 16 hours and 20 minutes. Purified water (190 kg) was added; after stirring, the organic layer was washed with aqueous sodium bicarbonate solution (prepared using 53.8 kg of sodium bicarbonate and 622 kg of purified water), and then washed with aqueous ammonium chloride solution (prepared using 230 kg of ammonium chloride and 624 kg of purified water). After a final wash with purified water (311 kg), the organic layer was filtered through a stainless steel Nutsche filter that had been preloaded with silica gel (60.2 kg). The filter cake was soaked with dichloromethane (311 kg) for 20 minutes, and then filtered; the combined filtrates were concentrated at reduced pressure (≤−0.05 MPa) and ≤40° C. until 330 to 400 L remained. THF (311 kg) was then added, at 15° C. to 30° C., and the mixture was concentrated in the same manner, to a final volume of 330 to 400 L. The THF addition and concentration was repeated, again to a volume of 330 to 400 L, affording a light yellow solution of C40 (167.6 kg, 692 mmol, 98%) in THF (251.8 kg) $^1$H NMR (400 MHz, Chloroform-d), C40 peaks only: δ 7.81 (d, 2H), 7.34 (d, 2H), 4.91 (ddt, 1H), 4.62-4.55 (m, 1H), 4.53-4.45 (m, 1H), 4.14 (d, 2H), 2.75-2.63 (m, 1H), 2.60-2.49 (m, 1H), 2.44 (s, 3H).

Step 4. Synthesis of (2S)-2-(azidomethyl)oxetane (C41)

N,N-Dimethylformamide (473 kg), sodium azide (34.7 kg, 534 mol), and potassium iodide (5.2 kg, 31 mol) were combined in a 3000 L glass-lined reactor at 10° C. to 25° C. After addition of C40 (83.5 kg, 344.6 mol) in THF (125.4 kg), the reaction mixture was heated to 55° C. to 65° C. for 17 hours and 40 minutes, whereupon it was cooled to 25° C. to 35° C., and nitrogen was bubbled from the bottom valve for 15 minutes. tert-Butyl methyl ether (623 kg) and purified water (840 kg) were then added, and the resulting aqueous layer was extracted twice with tert-butyl methyl ether (312 kg and 294 kg). The combined organic layers were washed with purified water (2×419 kg) while maintaining the temperature at 10° C. to 25° C., affording C41 (31.2 kg, 276 mol, 80%) in a solution of the above organic layer (1236.8 kg).

Step 5. Synthesis of 1-[(2S)-oxetan-2-yl]methanamine (C42)

10% Palladium on carbon (3.7 kg) was added through an addition funnel to a 10° C. to 30° C. solution of C41 (from the previous step; 1264 kg, 31.1 kg, 275 mol) in THF (328 kg) in a 3000 L stainless steel autoclave reactor. The addition funnel was rinsed with THF (32 kg), and the rinse was added to the reaction mixture. After the reactor contents had been purged with nitrogen, they were similarly purged with hydrogen, increasing the pressure to 0.05 to 0.15 MPa and then venting to 0.03 to 0.04 MPa. This hydrogen purge was repeated 5 times, whereupon the hydrogen pressure was increased to 0.05 to 0.07 MPa. The reaction temperature was increased to 25° C. to 33° C., and the hydrogen pressure was maintained at 0.05 to 0.15 MPa for 22 hours, while exchanging the hydrogen every 3 to 5 hours. The mixture was then purged five times with nitrogen, via increasing the pressure to 0.15 to 0.2 MPa and then venting to 0.05 MPa. After filtration, THF (92 kg and 93 kg) was used to wash the reactor and then soak the filter cake. The combined filtrates were concentrated at reduced pressure (≤−0.07 MPa) and ≤45° C., affording C42 (18.0 kg, 207 mol, 75%) in THF (57.8 kg) $^1$H NMR (400 MHz, DMSO-$d_6$), C42 peaks only: δ 4.62 (ddt, 1H), 4.49 (ddd, 1H), 4.37 (dt, 1H), 2.69 (d, 2H), 2.55-2.49 (m, 1H), 2.39 (m, 1H).

Step 6. Synthesis of methyl 4-nitro-3-{[(2S)-oxetan-2-ylmethyl]amino}benzoate (C43)

Potassium carbonate (58.1 kg, 420 mol) was added to a solution of methyl 3-fluoro-4-nitrobenzoate (54.8 kg, 275 mol) in THF (148 kg) in a 100 L glass-lined reactor, and the mixture was stirred for 10 minutes. A solution of C42 (29.3 kg, 336 mol) in THF (212.9 kg) was added, and the reaction mixture was stirred at 20° C. to 30° C. for 12 hours, whereupon EtOAc (151 kg) was added, and the mixture was filtered through silica gel (29 kg). The filter cake was rinsed with EtOAc (150 kg and 151 kg), and the combined filtrates were concentrated at reduced pressure (≤−0.08 MPa) and ≤45° C. to a volume of 222 to 281 L. After the mixture had been cooled to 10° C. to 30° C., n-heptane (189 kg) was added, stirring was carried out for 20 minutes, and the mixture was concentrated at reduced pressure (≤−0.08 MPa) and ≤45° C. to a volume of 222 L. n-Heptane (181 kg) was again added into the mixture at a reference rate of 100 to 300 kg/hour, and stirring was continued for 20 minutes. The mixture was sampled until residual THF was ≤5% and residual EtOAc was 10% to 13%. The mixture was heated to 40° C. to 45° C. and stirred for 1 hour, whereupon it was cooled to 15° C. to 25° C. at a rate of 5° C. to 10° C. per hour, and then stirred at 15° C. to 25° C. for 1 hour. Filtration using a stainless steel centrifuge provided a filter cake, which was rinsed with a mixture of EtOAc (5.0 kg) and n-heptane (34 kg), and then stirred with THF (724 kg) at 10° C. to 30° C. for 15 minutes; filtration provided a yellow solid of C43 (57.3 kg, 210 mol, 76%). $^1$H NMR (400 MHz, DMSO-$d_6$) δ 8.34 (t, 1H), 8.14 (d, 1H), 7.63 (d, 1H), 7.13 (dd, 1H), 4.99 (dddd, 1H), 4.55 (ddd, 1H), 4.43 (dt, 1H), 3.87 (s, 3H), 3.67-3.61 (m, 2H), 2.67 (dddd, 1H), 2.57-2.47 (m, 1H).

Step 7. Synthesis of methyl 4-amino-3-{[(2S)-oxetan-2-ylmethyl]amino}benzoate (P16)

To a solution of C43 (5.00 g, 18.8 mmol) in MeOH (150 mL) was added wet palladium on carbon (500 mg), and the mixture was stirred at 15° C. for 3 hours under a balloon of hydrogen. The reaction mixture was filtered; concentration of the filtrate in vacuo afforded P16 as a colorless oil. Yield: 4.40 g, 18.6 mmol, 99%. $^1$H NMR (400 MHz, DMSO-$d_6$) δ 7.16 (dd, 1H), 7.02 (d, 1H), 6.55 (d, 1H), 5.48 (s, 2H), 4.92-4.87 (m, 1H), 4.70 (t, 1H), 4.54 (ddd, 1H), 4.47 (ddd, 1H), 3.72 (s, 3H), 3.39-3.23 (m, 2H, assumed; partially obscured by water peak), 2.72-2.61 (m, 1H), 2.5-2.40 (m, 1H, assumed; partially obscured by solvent peak).

Preparation P17

Methyl 2-(chloromethyl)-1-[(2S)-oxetan-2-ylmethyl]-1H-benzimidazole-6-carboxylate (P17)

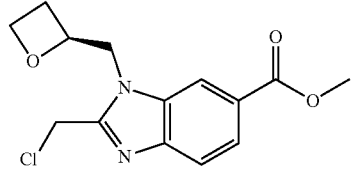

P17

A solution of C43 (from step 6 of Preparation P16; 51.8 kg, 190 mol) in THF (678 kg), in a 3000 L autoclave reactor, was treated with 10% palladium on carbon (5.2 kg) at 10° C. to 30° C. The addition pipe was rinsed with THF (46 kg) and the rinse was added to the reaction mixture. After the reactor contents had been purged with nitrogen, they were similarly purged with hydrogen, increasing the pressure to 0.1 to 0.2 MPa and then venting to 0.02 to 0.05 MPa. This hydrogen purge was repeated 5 times, whereupon the hydrogen pressure was increased to 0.1 to 0.25 MPa. The reaction mixture was stirred at 20° C. to 30° C., and every 2 to 3 hours, the mixture was purged with nitrogen three times, and then purged with hydrogen five times; after each final hydrogen exchange, the hydrogen pressure was increased to 0.1 to 0.25 MPa. After 11.25 hours total reaction time, the reaction mixture was vented to normal pressure, and purged five times with nitrogen, via increasing the pressure to 0.15 to 0.2 MPa and then venting to 0.05 MPa. It was then filtered, and the filter cake was rinsed twice with THF (64 kg and 63 kg); the combined rinse and filtrate were concentrated under reduced pressure (≤−0.08 MPa) and ≤40° C. to a volume of 128 to 160 L. THF (169 kg) was added, and the mixture was again concentrated to a volume of 128 to 160 L; this process was repeated a total of 4 times, affording a solution of the intermediate P16.

THF (150 kg) was added to this solution, followed by 2-chloro-1,1,1-trimethoxyethane (35.1 kg, 227 mol) and p-toluenesulfonic acid monohydrate (1.8 kg, 9.5 mol). After the reaction mixture had been stirred for 25 minutes, it was heated at 40° C. to 45° C. for 5 hours, whereupon it was concentrated under reduced pressure to a volume of 135 to 181 L. 2-Propanol (142 kg) was added, and the mixture was again concentrated to a volume of 135 to 181 L, whereupon 2-propanol (36.5 kg) and purified water (90 kg) were added, and stirring was continued until a solution was obtained. This was filtered with an in-line liquid filter, and then treated with purified water (447 kg) at a reference rate of 150 to 400 kg/hour at 20° C. to 40° C. After the mixture had been cooled to 20° C. to 30° C., it was stirred for 2 hours, and the solid was collected via filtration with a centrifuge. The filter cake was rinsed with a solution of 2-propanol (20.5 kg) and purified water (154 kg); after drying, P17 was obtained as a white solid (32.1 kg, 109 mol, 57%). $^1$H NMR (400 MHz, Chloroform-d) δ 8.14-8.11 (m, 1H), 8.01 (dd, 1H), 7.79 (br d, 1H), 5.26-5.18 (m, 1H), 5.04 (s, 2H), 4.66-4.58 (m, 2H), 4.53 (dd, 1H), 4.34 (dt, 1H), 3.96 (s, 3H), 2.82-2.71 (m, 1H), 2.48-2.37 (m, 1H).

Preparation P18

Methyl 3-methyl-2-{[(2S)-2-methylpiperazin-1-yl]methyl}-3H-imidazo[4,5-b]pyridine-5-carboxylate (P18)

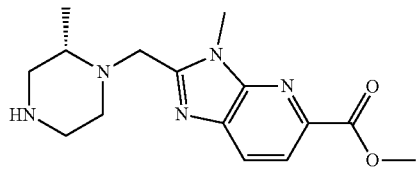

P18

Step 1. Synthesis of tert-butyl (3S)-4-(2-ethoxy-2-oxoethyl)-3-methylpiperazine-1-carboxylate (C44)

To a solution of tert-butyl (3S)-3-methylpiperazine-1-carboxylate (1.20 g, 5.99 mmol) in N,N-dimethylformamide (15 mL) were added ethyl bromoacetate (1.20 g, 7.19 mmol) and potassium carbonate (2.48 g, 18.0 mmol). After the reaction mixture had been stirred at 50° C. for 2 hours, it was cooled to room temperature, diluted with EtOAc (25 mL), and washed with water (25 mL). The aqueous layer was extracted with EtOAc (2×30 mL), and the combined organic layers were washed with saturated aqueous sodium chloride solution (3×20 mL), dried over sodium sulfate, filtered, and concentrated in vacuo. Purification via silica gel chromatography (Gradient: 0% to 10% MeOH in dichloromethane) afforded C44 as a yellow oil. Yield: 1.6 g, 5.6 mmol, 93%.

Step 2. Synthesis of [(2S)-4-(tert-butoxycarbonyl)-2-methylpiperazin-1-yl]acetic Acid (C45)

Aqueous sodium hydroxide solution (2 M; 5.34 mL, 10.7 mmol) and water (1 mL) were added to a solution of C44 (612 mg, 2.14 mmol) in MeOH (5 mL) and the reaction mixture was stirred at room temperature (10° C.) for 2 hours. After removal of organic solvent in vacuo, the residue was acidified to pH 7 by addition of 1 M hydrochloric acid, and the resulting mixture was concentrated under reduced pressure. The solid residue was then stirred with a mixture of dichloromethane and MeOH (10:1, 45 mL) at room temperature (10° C.) for 20 hours, whereupon it was filtered; the filtrate was concentrated in vacuo to provide C45 as a light yellow gum. Yield: 300 mg, 1.16 mmol, 54%.

Step 3. Synthesis of tert-butyl (3S)-4-(2-{[6-chloro-2-(methylamino)pyridin-3-yl]amino}-2-oxoethyl)-3-methylpiperazine-1-carboxylate (C46)

To a solution of C45 (270 mg, 1.04 mmol) and 2,4,6-tripropyl-1,3,5,2,4,6-trioxatriphosphinane 2,4,6-trioxide (50% solution in EtOAc; 1.27 g, 2.00 mmol) in N,N-dimethylformamide (3 mL) were added 6-chloro-N$^2$-methylpyridine-2,3-diamine (182 mg, 1.15 mmol) and N,N-diisopropylethylamine (465 mg, 3.60 mmol). The reaction mixture was stirred at 25° C. for 16 hours, whereupon it was combined with a similar reaction carried out using C45 (25.5 mg, 98.8 μmol), diluted with water (20 mL), and extracted with EtOAc (3×20 mL). The combined organic layers were washed with saturated aqueous sodium chloride solution (2×20 mL), dried over sodium sulfate, filtered, concentrated in vacuo, and purified via silica gel chromatography (Gradient: 0% to 44% EtOAc in petroleum ether) to afford C46 as a black gum. Combined yield: 320 mg, 0.804 mmol, 70%.

Step 4. Synthesis of tert-butyl (3S)-4-[(5-chloro-3-methyl-3H-imidazo[4,5-b]pyridin-2-yl)methyl]-3-methylpiperazine-1-carboxylate (C47)

A mixture of C46 (320 mg, 0.804 mmol) in acetic acid (4 mL) was stirred at 100° C. for 16 hours, and then concentrated in vacuo. After the residue had been mixed with dichloromethane (10 mL), di-tert-butyl dicarbonate (287 mg, 1.32 mmol) and triethylamine (200 mg, 1.97 mmol) were added, and the reaction mixture was stirred at room temperature (15° C.) for 2 hours, whereupon it was washed with water (20 mL) and extracted with dichloromethane (3×20 mL). The combined organic layers were dried over sodium sulfate, filtered, concentrated in vacuo, and subjected to chromatography on silica gel (Gradient: 0% to 45% EtOAc in petroleum ether), providing C47 as a yellow gum. Yield: 180 mg, 0.474 mmol, 59%.

Step 5. Synthesis of methyl 2-{[(2S)-4-(tert-butoxycarbonyl)-2-methylpiperazin-1-yl]methyl}-3-methyl-3H-imidazo[4,5-b]pyridine-5-carboxylate (C48)

1,3-Bis(diphenylphosphino)propane (43.0 mg, 0.104 mmol), palladium(II) acetate (12.7 mg, 56.6 μmol), and triethylamine (528 mg, 5.22 mmol) were added to a solution of C47 (180 mg, 0.474 mmol) in a mixture of MeOH (7 mL) and N,N-dimethylformamide, and the reaction mixture was stirred at 80° C., under carbon monoxide (50 psi), for 20 hours. It was then concentrated in vacuo and purified by chromatography on silica gel (Gradient: 0% to 78% EtOAc in petroleum ether), affording C48 as a yellow gum. Yield: 150 mg, 0.372 mmol, 78%.

Step 6. Synthesis of methyl 3-methyl-2-{[(2S)-2-methylpiperazin-1-yl]methyl}-3H-imidazo[4,5-b]pyridine-5-carboxylate (P18)

To a solution of C48 (100 mg, 0.248 mmol) in dichloromethane (4 mL) was added trifluoroacetic acid (1 mL), and the reaction mixture was stirred at room temperature (15° C.) for 2 hours. It was then concentrated in vacuo and subjected to strong cation exchange via solid-phase extraction (Agela Cleanert SCX column), affording P18 as a brown gum. Yield: 70 mg, 0.23 mmol, 93%. LCMS m/z 304.1 [M+H]⁺. ¹H NMR (400 MHz, Chloroform-d) δ 8.08 (AB quartet, 2H), 4.34 (d, 1H), 4.06 (s, 3H), 4.03 (s, 3H), 3.59 (d, 1H), 2.99-2.91 (m, 1H), 2.89-2.82 (m, 1H), 2.80-2.71 (m, 1H), 2.65-2.55 (m, 2H), 2.53-2.43 (m, 1H), 2.32-2.22 (m, 1H), 1.19 (d, 3H).

Preparation P19

Methyl 2-(6-azaspiro[2.5]oct-1-yl)-1-(2-methoxyethyl)-1H-benzimidazole-6-carboxylate (P19)

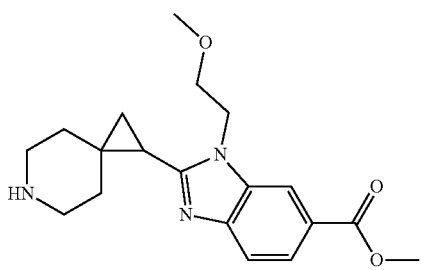

Step 1. Synthesis of methyl 3-[(2-methoxyethyl)amino]-4-nitrobenzoate (C49)

To a colorless solution of methyl 3-fluoro-4-nitrobenzoate (50 g, 250 mmol) in THF (400 mL) was added triethylamine (40.7 g, 402 mmol, 55.8 mL) followed by addition of 2-methoxyethanamine (30.2 g, 402 mmol) in THF (100 mL), drop-wise, at room temperature. The resultant yellow solution was stirred at 55° C. for 18 hours. The solution was cooled to room temperature and concentrated under reduced pressure to remove THF. The resultant yellow solid was dissolved in EtOAc (800 mL) and washed with saturated aqueous ammonium chloride solution (250 mL). The aqueous phase was separated and extracted with EtOAc (200 mL). The combined organic layers were washed with saturated aqueous sodium chloride solution (3×250 mL), dried over sodium sulfate, filtered, and concentrated under reduced pressure to yield C49 (60.2 g, 94%) as a yellow solid. ¹H NMR (CDCl₃) δ 8.23 (d, 1H), 8.17 (br s, 1H), 7.58 (d, 1H), 7.25 (dd, 1H), 3.95 (s, 3H), 3.69-3.73 (m, 2H), 3.56 (m, 2H), 3.45 (s, 3H); LCMS m/z 255.4 [M+H]⁺.

Step 2. Synthesis of methyl 4-amino-3-[(2-methoxyethyl)amino]benzoate (C50)

To solution of C49 (30 g, 118 mmol) in MeOH (500 mL) was added palladium on carbon (10 g, 94 mmol). This reaction was stirred at room temperature under 15 psi hydrogen for 18 hours. The black suspension was filtered through diatomaceous earth and the filter cake was washed with MeOH (500 mL). The combined filtrates were concentrated in vacuo to give C50 (26.5 g, quantitative) as a brown oil, which solidified on standing. ¹H NMR (400 MHz, CDCl₃) δ 7.48 (dd, 1H), 7.36 (d, 1H), 6.69 (d, 1H), 3.87 (s, 3H), 3.77 (br s, 2H), 3.68 (t, 2H), 3.41 (s, 3H), 3.32 (t, 2H); LCMS m/z 224.7 [M+H]⁺.

Step 3. Synthesis of tert-butyl 1-({4-(methoxycarbonyl)-2-[(2-methoxyethyl)amino]phenyl}carbamoyl)-6-azaspiro[2.5]octane-6-carboxylate (C51)

To a room temperature (15° C.) solution of C17 (1.50 g, 5.88 mmol) and C50 (1.49 g, 6.64 mmol) in N,N-dimethylformamide (30 mL) was added O-(7-azabenzotriazol-1-yl)-N,N,N',N'-tetramethyluronium hexafluorophosphate (HATU; 3.35 g, 8.81 mmol). The reaction mixture was stirred at 15° C. for 20 minutes, whereupon triethylamine (1.19 g, 11.8 mmol) was added, and the reaction mixture was stirred at 50° C. for 4 hours. It was then poured into water (160 mL) and extracted with EtOAc (3×100 mL); the combined organic layers were washed with saturated aqueous sodium chloride solution (3×100 mL), dried over sodium sulfate, filtered, and concentrated in vacuo. Purification using silica gel chromatography (Gradient: 0% to 5% MeOH in dichloromethane) afforded C51 as a yellow oil. Yield: 2.70 g, 5.85 mmol, 99%.

Step 4. Synthesis of methyl 2-[6-(tert-butoxycarbonyl)-6-azaspiro[2.5]oct-1-yl]-1-(2-methoxyethyl)-1H-benzimidazole-6-carboxylate (C52)

A solution of C51 (2.70 g, 5.85 mmol) in acetic acid (25 mL) was stirred at 50° C. for 16 hours, whereupon it was carefully basified by addition of saturated aqueous potassium carbonate solution. The resulting mixture was extracted with EtOAc (2×100 mL), and the combined organic layers were dried over magnesium sulfate, filtered, and concentrated in vacuo. Chromatography on silica gel (Gradient: 50% to 100% EtOAc in petroleum ether) provided C52 as a yellow solid. Yield: 1.45 g, 3.27 mmol, 56%.

Step 5. Synthesis of methyl 2-(6-azaspiro[2.5]oct-1-yl)-1-(2-methoxyethyl)-1H-benzimidazole-6-carboxylate (P19)

To a solution of C52 (550 mg, 1.24 mmol) in dichloromethane (10 mL) was added a solution of hydrogen chloride in EtOAc (4 M; 10 mL). The reaction mixture was stirred at 20° C. for 2 hours, whereupon it was concentrated under reduced pressure. The residue was treated with saturated aqueous potassium carbonate solution (10 mL) and extracted with dichloromethane (3×40 mL); the combined organic layers were dried over magnesium sulfate, filtered, and concentrated in vacuo to provide P19 as a yellow solid. Yield: 400 mg, 1.16 mmol, 94%. ¹H NMR (400 MHz, Chloroform-d) δ 8.06-8.02 (m, 1H), 7.93 (dd, 1H), 7.66 (d, 1H), 4.51 (ddd, component of ABXY pattern; 1H), 4.38 (ddd, component of ABXY pattern; 1H), 3.93 (s, 3H), 3.81-3.69 (m, 2H), 3.30 (s, 3H), 3.08-3.00 (m, 1H), 2.93 (ddd, 1H), 2.80-2.66 (m, 2H), 2.09 (dd, 1H), 1.88-1.77 (m, 1H), 1.67 (dd, 1H), 1.51-1.41 (m, 2H), 1.40-1.30 (m, 1H), 1.12 (dd, 1H).

Preparation P20

Methyl 2-(chloromethyl)-1-(2-methoxyethyl)-1H-benzimidazole-6-carboxylate (P20)

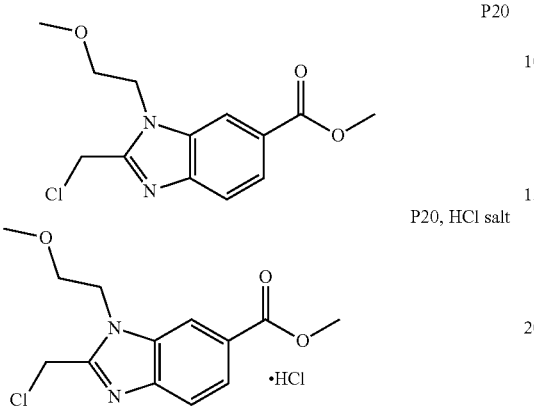

P20

P20, HCl salt

Step 1. Synthesis of methyl 2-(chloromethyl)-1-(2-methoxyethyl)-1H-benzimidazole-6-carboxylate (P20)

To a solution of C50 (5.00 g, 22.3 mmol) in THF (100 mL) was added 2-chloro-1,1,1-trimethoxyethane (3.31 mL, 24.6 mmol), followed by p-toluenesulfonic acid monohydrate (84.8 mg, 0.446 mmol). The reaction mixture was heated at 45° C. for 5 hours, whereupon it was concentrated in vacuo; the residual oil was dissolved in EtOAc (10 mL) and heated until a solution formed. This was slowly stirred while cooling to room temperature overnight. The precipitate was collected via filtration and washed with heptane to afford P20 as a gray solid. Yield: 5.73 g, 20.3 mmol, 91%. $^1$H NMR (600 MHz, Chloroform-d) δ 8.12 (br s, 1H), 8.01 (br d, 1H), 7.79 (d, 1H), 4.96 (s, 2H), 4.52 (t, 2H), 3.96 (s, 3H), 3.74 (t, 2H), 3.28 (s, 3H).

Step 2. Synthesis of methyl 2-(chloromethyl)-1-(2-methoxyethyl)-1H-benzimidazole-6-carboxylate, Hydrochloride Salt (P20, HCl Salt)

A solution of C50 (5.0 g, 24 mmol) in 1,4-dioxane (100 mL) was heated to 100° C., a solution of chloroacetic anhydride (4.1 g, 24.5 mmol) in 1,4-dioxane (60 mL) was added via addition funnel over a period of 10 hours, and the reaction mixture was stirred for another 12 hours at 100° C. The following day, the reaction was cooled to room temperature and the 1,4-dioxane was removed under reduced pressure. The crude reaction mixture was dissolved in EtOAc and washed with saturated aqueous sodium bicarbonate solution. The EtOAc layer was separated, dried over sodium sulfate, and filtered. A solution of 4 M hydrogen chloride in 1,4-dioxane (1.1 equiv.) was added to the EtOAc solution of the product with constant stirring. The HCl salt of the desired product precipitated out as a pale yellow solid. The suspension was stirred for 1 hour and the product was then collected by filtration to obtain P20, HCl salt as a yellow solid (6.1 g, 86%). $^1$H NMR (600 MHz, CD$_3$OD) δ 8.64 (s, 1H), 8.30 (d, 1H), 7.92 (d, 1H), 5.32 (s, 2H), 4.84 (m, 2H), 3.99 (s, 3H), 3.83 (t, 2H), 3.31 (s, 3H). LCMS m/z 283.2 [M+H]$^+$.

Preparation P21

Methyl 1-(2-methoxyethyl)-2-(piperazin-1-ylmethyl)-1H-benzimidazole-6-carboxylate (P21)

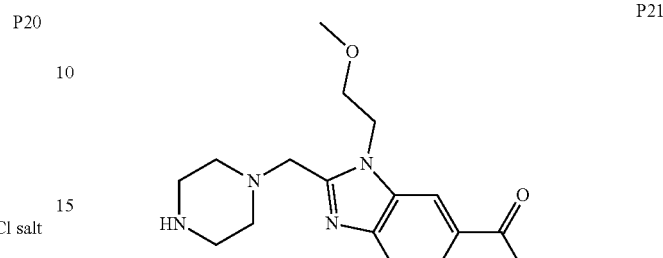

P21

Step 1. Synthesis of methyl 2-{[4-(tert-butoxycarbonyl)piperazin-1-yl]methyl}-1-(2-methoxyethyl)-1H-benzimidazole-6-carboxylate (C53)

Compound P20 (1.59 g, 5.62 mmol) was added to a 15° C. mixture of tert-butyl piperazine-1-carboxylate (1.00 g, 5.37 mmol) and potassium carbonate (2.97 g, 21.5 mmol) in acetonitrile (15 mL), and the reaction mixture was stirred at 55° C. for 12 hours. It was then combined with a similar reaction carried out using P20 and tert-butyl piperazine-1-carboxylate (200 mg, 1.07 mmol), and the mixture was filtered. After the filtrate had been concentrated in vacuo, the residue was purified via chromatography on silica gel (Gradient: 0% to 60% EtOAc in petroleum ether) to provide C53 as a pale yellow solid. Combined yield: 2.30 g, 5.32 mmol, 83%. LCMS m/z 433.0 [M+H]$^+$. $^1$H NMR (400 MHz, Chloroform-d) δ 8.12 (d, 1H), 7.96 (dd, 1H), 7.73 (d, 1H), 4.58 (t, 2H), 3.95 (s, 3H), 3.89 (s, 2H), 3.73 (t, 2H), 3.46-3.37 (br m, 4H), 3.28 (s, 3H), 2.54-2.44 (br m, 4H), 1.45 (s, 9H).

Step 2. Synthesis of methyl 1-(2-methoxyethyl)-2-(piperazin-1-ylmethyl)-1H-benzimidazole-6-carboxylate (P21)

To a solution of C53 (2.30 g, 5.32 mmol) in dichloromethane (80 mL) was added a solution of hydrogen chloride in EtOAc (20 mL). The reaction mixture was stirred at 20° C. for 2 hours, whereupon it was concentrated in vacuo. The residue was diluted with water (20 mL), adjusted to a pH of 9 to 10 by addition of saturated aqueous sodium bicarbonate solution, and extracted with a mixture of EtOAc and MeOH (10:1, 15×50 mL). The combined organic layers were dried over sodium sulfate, filtered, and concentrated in vacuo to afford P21 as a pale yellow solid. Yield: 1.68 g, 5.05 mmol, 95%. LCMS m/z 332.8 [M+H]$^+$. $^1$H NMR (400 MHz, Chloroform-d) δ 8.13 (br s, 1H), 7.96 (br d, 1H), 7.72 (d, 1H), 4.59 (t, 2H), 3.95 (s, 3H), 3.86 (s, 2H), 3.75 (t, 2H), 3.29 (s, 3H), 2.87 (t, 4H), 2.50 (br m, 4H).

Preparation P22

Methyl 2-(chloromethyl)-1-methyl-1H-benzimidazole-6-carboxylate (P22)

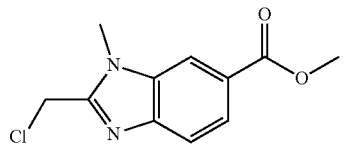

Methyl 4-amino-3-(methylamino)benzoate (206 mg, 1.14 mmol) was dissolved in 1,4-dioxane (11.5 mL) and treated with chloroacetyl chloride (109 µL, 1.37 mmol). The mixture was stirred at 100° C. for 3 hours and cooled to room temperature. Triethylamine (0.8 mL, 7 mmol) and heptane (10 mL) were added and filtered. The filtrate was concentrated under reduced pressure and the crude product was purified by chromatography on silica gel (Eluent: 40% EtOAc in heptane) to afford 120 mg of P22 (44%). $^1$H NMR (400 MHz, Chloroform-d) δ 8.14 (s, 1H), 8.01 (d, 1H), 7.78 (d, 1H), 4.87 (s, 2H), 3.97 (s, 3H), 3.94 (s, 3H); LCMS m/z 239.1 [M+H]$^+$.

Preparation P23

Methyl 4-amino-3-{[(1-ethyl-1H-imidazol-5-yl)methyl]amino}benzoate (P23)

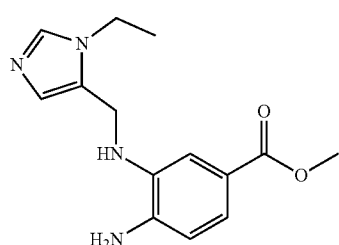

Step 1. Synthesis of methyl 3-{[(1-ethyl-1H-imidazol-5-yl)methyl]amino}-4-nitrobenzoate (C54)

Triethylamine (3.65 mL, 26.2 mmol) was added to a solution of methyl 3-fluoro-4-nitrobenzoate (1.00 g, 5.02 mmol) and 1-(1-ethyl-1H-imidazol-5-yl)methanamine, dihydrochloride salt (1.00 g, 5.05 mmol) in a mixture of THF (12 mL) and MeOH (8 mL). The reaction mixture was stirred at 60° C. for 40 hours, whereupon it was concentrated in vacuo and purified using silica gel chromatography (Gradient: 0% to 2% MeOH in dichloromethane). Compound C54 was obtained as an orange solid. Yield: 1.27 g, 4.17 mmol, 83%. $^1$H NMR (400 MHz, Chloroform-d) δ 8.24 (d, 1H), 7.98-7.91 (m, 1H), 7.68 (d, 1H), 7.57 (br s, 1H), 7.33 (dd, 1H), 7.11 (br s, 1H), 4.53 (d, 2H), 3.99 (q, 2H), 3.95 (s, 3H), 1.47 (t, 3H).

Step 2. Synthesis of methyl 4-amino-3-{[(1-ethyl-1H-imidazol-5-yl)methyl]amino}benzoate (P23)

A mixture of wet palladium on carbon (144 mg) and C54 (412 mg, 1.35 mmol) in MeOH (13 mL) was stirred under a balloon of hydrogen for 16 hours at 25° C. The reaction mixture was then filtered through a pad of diatomaceous earth and the filtrate was concentrated in vacuo to afford P23 as a gray solid. Yield: 340 mg, 1.24 mmol, 92%. $^1$H NMR (400 MHz, Methanol-d$_4$) δ 7.66 (br s, 1H), 7.38-7.29 (m, 2H), 6.97 (br s, 1H), 6.67 (d, 1H), 4.35 (s, 2H), 4.11 (q, 2H), 3.81 (s, 3H), 1.44 (t, 3H).

Preparation P24

Methyl 2-(chloromethyl)-1-[(1-methyl-1H-imidazol-5-yl)methyl]-1H-benzimidazole-6-carboxylate, Hydrochloride Salt (P24)

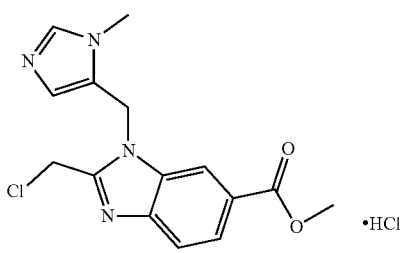

Step 1. Synthesis of methyl 3-{[(1-methyl-1H-imidazol-5-yl)methyl]amino}-4-nitrobenzoate (C55)

To a colorless solution of methyl 3-fluoro-4-nitrobenzoate (1.0 g, 5.0 mmol) in N,N-dimethylformamide (10 mL) was added 1-(1-methyl-1H-imidazol-5-yl)methanamine (670 mg, 6.0 mmol) and triethylamine (762 mg, 7.53 mmol), slowly. The solution was stirred at 60° C. for 16 hours. The reaction mixture was poured into water (30 mL) and extracted with dichloromethane (3×30 mL). The combined organic extracts were dried over sodium sulfate, filtered, and concentrated under reduced pressure. The crude product was purified by flash chromatography (20% MeOH/dichloromethane). The obtained yellow solid was triturated with 30:1 petroleum ether/EtOAc to deliver C55 (1.2 g, 82%) as a yellow solid. $^1$H NMR (CDCl$_3$) δ 8.26 (d, 1H), 7.96 (br s, 1H), 7.71 (d, 1H), 7.50 (s, 1H), 7.35 (dd, 1H), 7.13 (s, 1H), 4.55 (d, 2H), 3.97 (s, 3H), 3.68 (s, 3H).

Step 2. Synthesis of methyl 4-amino-3-{[(1-methyl-1H-imidazol-5-yl)methyl]amino}benzoate (C56)

To a yellow suspension of C55 (5.46 g, 18.8 mmol) in MeOH (160 mL) was added wet 10% palladium on carbon (1 g). The mixture was stirred under 1 atmosphere of hydrogen for 36 hours at 20° C. The reaction mixture was filtered and the filter cake was rinsed with MeOH (200 mL). The filtrate was concentrated under reduced pressure to deliver C56 (4.8 g, 98%) as a brown solid. $^1$H NMR (DMSO-d$_6$) δ 7.56 (s, 1H), 7.18 (d, 1H), 7.13 (s, 1H), 6.87 (s, 1H), 6.55 (d, 1H), 5.50 (s, 2H), 4.84 (t, 1H), 4.23 (d, 2H), 3.73 (s, 3H), 3.63 (s, 3H).

Step 3. Synthesis of methyl 2-(hydroxymethyl)-1-[(1-methyl-1H-imidazol-5-yl)methyl]-1H-benzimidazole-6-carboxylate (C57)

A red mixture of C56 (780 mg, 3.00 mmol) and hydroxyacetic acid (342 mg, 4.49 mmol) in 1,3,5-trimethylbenzene (8 mL) was stirred at 140° C. under N₂ for 14 hours and at 25° C. for 48 hours. The clear yellow solution was decanted off to give a brown residue that was dissolved in MeOH (50 mL) and concentrated under reduced pressure. The crude product was purified by flash chromatography (20% MeOH/dichloromethane) to give C57 (318 mg, 35%) as a yellow foam. ¹H NMR (DMSO-d₆) δ 8.13 (d, 1H), 7.83 (dd, 1H), 7.71 (d, 1H), 7.60 (s, 1H), 6.59 (s, 1H), 5.69 (s, 2H), 4.76 (s, 2H), 3.91 (s, 1H), 3.84 (s, 3H), 3.53 (s, 3H).

Step 4. Synthesis of methyl 2-(chloromethyl)-1-[(1-methyl-1H-imidazol-5-yl)methyl]-1H-benzimidazole-6-carboxylate, Hydrochloride Salt (P24)

To a yellow suspension of C57 (500 mg, 1.66 mmol) in dichloromethane (10 mL) and N,N-dimethylformamide (3 mL) was added SOCl₂ (990 mg, 0.60 mL, 8.32 mmol), drop-wise, at room temperature. The reaction mixture was stirred at room temperature for 1 hour, concentrated under reduced pressure, and the resultant brown residue was triturated with dichloromethane (10 mL). The solids were collected by filtration, rinsed with dichloromethane (5 mL), and dried under vacuum to give P24 (431 mg, 73%) as an off-white solid. ¹H NMR (400 MHz, DMSO-d₆) δ 9.17 (s, 1H), 8.31 (s, 1H), 7.91-7.99 (m, 1H), 7.77-7.87 (m, 1H), 7.11 (s, 1H), 5.92 (s, 2H), 5.13 (s, 2H), 3.87 (s, 3H), 3.86 (s, 3H); MS (ES+): 319.0 (M+H).

Preparation P25 tert-Butyl 4-nitro-3-[(1,3-oxazol-2-ylmethyl)amino]benzoate (P25)

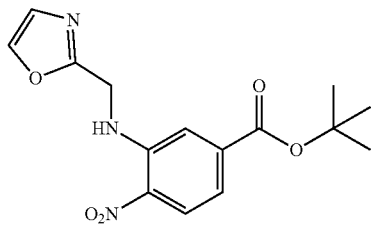

P25

To a suspension of 1-(1,3-oxazol-2-yl)methanamine, hydrochloride salt (491 mg, 3.65 mmol) and tert-butyl 3-fluoro-4-nitrobenzoate (800 mg, 3.32 mmol) in N,N-dimethylformamide (5 mL) was added potassium carbonate (1.04 g, 6.63 mmol). The reaction was stirred at 60° C. for 2 hours. Additional 1-(1,3-oxazol-2-yl)methanamine, hydrochloride salt (100 mg, 1.0 mmol) was added and the reaction was stirred for an additional 30 minutes at 60° C. The reaction was cooled to room temperature then diluted with water (30 mL) and extracted with EtOAc (60 mL). The organic layer was washed with water, then saturated aqueous sodium chloride solution, dried over sodium sulfate, filtered and concentrated under reduced pressure. The orange residue was purified by flash chromatography (12 g silica gel, 0-50% EtOAc/heptane gradient) to deliver P25 (764 mg, 75%) as an orange solid. ¹H NMR (CDCl₃) δ 8.48 (br s, 1H), 8.23 (d, 1H), 7.68 (d, 1H), 7.61 (d, 1H), 7.28 (dd, 1H), 7.15 (s, 1H), 4.72 (d, 2H), 1.60 (s, 9H).

Preparation P26

Methyl 5-amino-6-{[(2S)-oxetan-2-ylmethyl]amino}pyridine-2-carboxylate (P26)

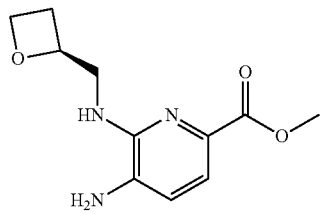

P26

Step 1. Synthesis of methyl 5-nitro-6-{[(2S)-oxetan-2-ylmethyl]amino}pyridine-2-carboxylate (C58)

Methyl 6-chloro-5-nitropyridine-2-carboxylate (270 g, 1.25 mol) and triethylamine (500 g, 5.1 mol) were added to a solution of C42 (152 g, 1.7 mol) in N,N-dimethylformamide (3 L) and THF (3 L) at 25° C. The mixture was stirred at 25° C. for 16 hours. The mixture was concentrated under reduced pressure to remove the THF, and water (5 L) was added. The mixture was extracted with EtOAc (2×5 L) and the combined organic solutions were washed with saturated aqueous sodium chloride solution (2×), dried and concentrated under reduced pressure. The crude material was combined with a second batch of crude product from a similar experiment (70 g) and the solids were triturated with petroleum ether:EtOAc (4:1, 500 mL) for 2 hours. The solids were collected by filtration and dried to provide C58 (304 g, 52%) as a yellow solid. ¹H NMR (400 MHz, CDCl₃) δ 8.58 (br s, 1H), 8.56 (d, 1H), 7.39 (d, 1H), 5.08-5.18 (m, 1H), 4.73 (ddd, 1H), 4.61 (td, 1H), 4.06-4.16 (m, 1H), 3.98 (s, 3H), 3.88-3.97 (m, 1H), 2.68-2.80 (m, 1H), 2.55 (tdd, 1H).

Step 2. Synthesis of methyl 5-amino-6-{[(2S)-oxetan-2-ylmethyl]amino}pyridine-2-carboxylate (P26)

Compound C58 (10 g, 37 mmol) was suspended in MeOH (150 mL) and treated with 10% palladium on carbon (1.0 g) and the mixture was stirred at room temperature under 50 psi H₂ for 4 hours. The mixture was filtered through Celite® and the filtrate was concentrated under reduced pressure to yield P26 (8.4 g, 95%) as a yellow oil that solidified on standing. ¹H NMR (600 MHz, CDCl₃) δ 7.49 (d, 1H), 6.86 (d, 1H), 5.06-5.15 (m, 1H), 4.68-4.77 (m, 1H), 4.53-4.63 (m, 2H), 3.91 (s, 3H), 3.80-3.86 (m, 2H), 3.72 (br s, 2H), 2.68-2.78 (m, 1H), 2.52-2.61 (m, 1H).

Preparation P27

Methyl 2-(chloromethyl)-3-[(2S)-oxetan-2-ylmethyl]-3H-imidazo[4,5-b]pyridine-5-carboxylate (P27)

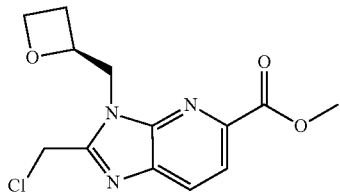

In a 2 L, 3-neck flask equipped with a mechanical overhead stirrer P26 (43.0 g, 181 mmol) was taken up in THF (780 mL). The resultant pale pink suspension was treated with a solution of chloroacetic anhydride (33.5 g, 190 mmol in 100 mL THF) via addition funnel over 30 minutes. The resultant light amber solution was stirred at room temperature for 2 hours and then heated at 60° C. for 7 hours. The reaction mixture was cooled to room temperature. Approximately 400 mL of solvent from the reaction was removed under reduced pressure on a rotary evaporator. The resulting solution was diluted with EtOAc (500 mL) and treated with saturated aqueous sodium bicarbonate solution (200 mL). The biphasic mixture was stirred at room temperature for 30 minutes. The organic layer was separated and the aqueous layer was extracted with EtOAc (500 mL). The combined organic layers were washed with saturated aqueous sodium chloride solution (500 mL), dried over sodium sulfate, filtered and concentrated under reduced pressure to yield P27 (52.5 g, 98%) as a yellowish brown solid. $^1$H NMR (600 MHz, CDCl$_3$) δ 8.14 (d, 2H), 5.19-5.28 (m, 1H), 4.99-5.16 (m, 2H), 4.70-4.88 (m, 2H), 4.55-4.67 (m, 1H), 4.24-4.44 (m, 1H), 4.01 (s, 3H), 2.70-2.88 (m, 1H), 2.37-2.53 (m, 1H); LC-MS (ES+): 296.4 (M+H).

Preparation P28

5-Chloro-2-(chloromethyl)-3-methyl-3H-imidazo[4,5-b]pyridine (P28)

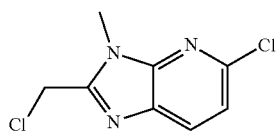

Step 1. Synthesis of 6-chloro-N-methyl-3-nitropyridin-2-amine (C59)

To a suspension of 2,6-dichloro-3-nitropyridine (200 g, 1.04 mol) and sodium carbonate (132 g, 1.24 mol) in ethanol (1 L) was added 2.0 M methylamine in THF (622 mL, 1.24 mol), drop-wise, at 0° C. via syringe. After the addition, the reaction mixture was stirred at 18° C. for 6 hours. The yellow mixture was filtered and the filtrate was concentrated under reduced pressure to give a yellow solid. The crude product was purified by flash chromatography (petroleum ether/EtOAc 0-5%) to afford C59 (158 g, 81% yield) as a yellow solid. $^1$H NMR (DMSO-d$_6$) δ 8.72 (br s, 1H), 8.41 (d, 1H), 6.76 (d, 1H), 3.00 (d, 3H).

Step 2. Synthesis of 6-chloro-N$^2$-methylpyridine-2,3-diamine (C60)

To a mixture of C59 (15.8 g, 84.2 mmol) in acetic acid (100 mL) was added iron powder (15.4 g, 276 mmol). The yellow mixture was stirred at 80° C. for 3 hours. The reaction was cooled to room temperature and filtered. The filter cake was washed with EtOAc (2×100). The combined organic layers were concentrated under reduced pressure and the crude product was purified by flash chromatography (120 g silica gel, 50% EtOAc/petroleum ether) to afford C60 (8.40 g, 63% yield) as a brown solid. $^1$H NMR (CDCl$_3$) δ 6.80 (d, 1H), 6.50 (d, 1H), 3.39 (br s, 2H), 3.01 (s, 3H).

Step 3. Synthesis of 5-chloro-2-(chloromethyl)-3-methyl-3H-imidazo[4,5-b]pyridine (P28)

To a solution of C60 (50.0 g, 317 mmol) in 1,4-dioxane (1.2 L) was added chloroacetyl chloride (55.5 mL, 698 mmol) and the mixture was stirred at 15° C. for 50 minutes. The brown mixture was concentrated under reduced pressure to give a brown solid which was taken up in trifluoroacetic acid (1.2 L) and stirred at 80° C. for 60 hours. The mixture was concentrated under reduced pressure to give a brown oil. The oil was diluted with EtOAc (1 L) and neutralized with saturated aqueous sodium bicarbonate solution. When CO$_2$ evolution subsided, the layers were separated and the aqueous layer was extracted with EtOAc (200 mL). The organic extracts were combined, dried over sodium sulfate, filtered and concentrated under reduced pressure. The crude product was purified by flash chromatography (10-25% EtOAc/petroleum ether gradient) to afford P28 (61.0 g, 79%) as a yellow solid. $^1$H NMR (400 MHz, DMSO-d$_6$) δ 8.13 (d, 1H), 7.37 (d, 1H), 5.11 (s, 2H), 3.84 (s, 3H).

Preparation P29

5-Bromo-N$^3$,6-dimethylpyridine-2,3-diamine (P29)

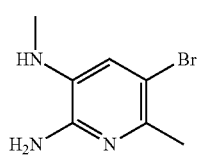

Compound P29 was synthesized according to the literature procedure (Choi, J. Y. et al., *J. Med. Chem.* 2012, 55, 852-870).

Preparation P30

Methyl 2-(6-azaspiro[2.5]oct-1-yl)-1-(2-methoxy-ethyl)-1H-imidazo[4,5-b]pyridine-6-carboxylate, Hydrochloride Salt (P30)

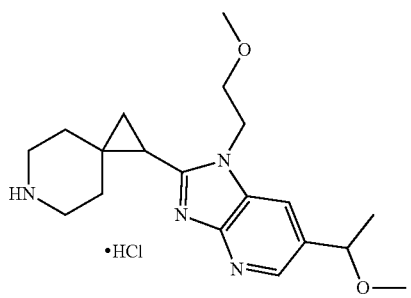

Step 1. Synthesis of tert-butyl 1-(6-bromo-1H-imidazo[4,5-b]pyridin-2-yl)-6-azaspiro[2.5]octane-6-carboxylate (C61)

A mixture of C17 (1.00 g, 3.92 mmol), O-(7-azabenzotriazol-1-yl)-N,N,N',N'-tetramethyluronium hexafluorophosphate (2.98 g, 7.83 mmol), 5-bromopyridine-2,3-diamine (1.10 g, 5.85 mmol), and triethylamine (1.64 mL, 11.8 mmol) was dissolved in N,N-dimethylformamide, and the reaction mixture was stirred at room temperature overnight, whereupon it was diluted with water and extracted with EtOAc. The organic layer was concentrated in vacuo, and purified using silica gel chromatography. The resulting amide was dissolved in 1,4-dioxane (8 mL), treated with aqueous potassium hydroxide solution (4 M; 2 mL, 8 mmol), and stirred for 15 hours at 100° C. After a standard work-up, chromatography on silica gel (Gradient: EtOAc in hydrocarbon solvent), both C61 (255 mg) and uncyclized amide (255 mg) were obtained. The amide was resubjected to the potassium hydroxide reaction conditions, affording additional C61 (250 mg) as a solid. Combined yield: 505 mg, 1.24 mmol, 32%.

Step 2. Synthesis of tert-butyl 1-[6-bromo-1-(2-methoxyethyl)-1H-imidazo[4,5-b]pyridin-2-yl]-6-azaspiro[2.5]octane-6-carboxylate (C62)

A solution of C61 (225 mg, 0.552 mmol) and potassium tert-butoxide (136 mg, 1.21 mmol) in THF was stirred at room temperature for 20 minutes, whereupon 2-bromoethyl methyl ether (0.125 mL, 1.33 mmol) was added, and the reaction mixture was heated at 60° C. for 15 hours. LCMS analysis indicated formation of two isomers of the product. Silica gel chromatography provided purified C62 (120 mg) as a gum, and C63 (69 mg). The indicated regiochemistries for C62 and C63 were determined using nuclear Overhauser effect experiments. Yield of C62: 120 mg, 0.258 mmol, 47%. LCMS m/z 465.3 (bromine isotope pattern observed) [M+H]$^+$. $^1$H NMR (400 MHz, Chloroform-d), characteristic peaks: δ 8.40 (s, 1H), 7.70 (s, 1H), 4.40-4.20 (m, 2H), 3.75-3.58 (m, 3H), 3.36-3.25 (m, 2H), 3.21 (s, 3H), 3.14-3.08 (m, 1H), 1.98 (dd, 1H), 1.74 (dd, 1H), 1.70-1.63 (m, 1H), 1.48-1.42 (m, 2H), 1.36 (s, 9H), 1.11 (dd, 1H).

Step 3. Synthesis of methyl 2-(6-azaspiro[2.5]oct-1-yl)-1-(2-methoxyethyl)-1H-imidazo[4,5-b]pyridine-6-carboxylate, Hydrochloride Salt (P30)

A mixture of C62 (120 mg, 0.258 mmol), 1,3-bis(diphenylphosphino)propane (31.9 mg, 77.4 μmol), and palladium (II) acetate (11.6 mg, 51.7 μmol) in N,N-dimethylformamide (0.5 mL) was treated with MeOH (4 mL) and triethylamine (0.36 mL, 2.6 mmol), and then heated at 80° C. under carbon monoxide (50 psi) for 20 hours. After a standard work-up, purification via silica gel chromatography (Eluent: 10:1 dichloromethane/MeOH) provided material that was then deprotected using a solution of hydrogen chloride in 1,4-dioxane to provide P30 as a solid. Yield: 40 mg, 0.105 mmol, 41%. LCMS m/z 345.3 [M+H]$^+$.

Preparation P31

5-Bromo-N$^3$-(2-methoxyethyl)pyridine-2,3-diamine (P31)

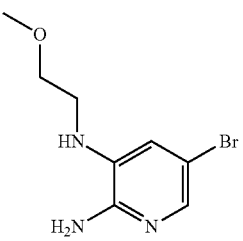

Step 1. Synthesis of N-(2-amino-5-bromopyridin-3-yl)-2-methoxyacetamide (C64)

To a flask containing a solution of methoxyacetic acid (1.00 g, 11.1 mmol) in N,N-dimethylformamide (30 mL) was added O-(7-azabenzotriazol-1-yl)-N,N,N',N'-tetramethyluronium hexafluorophosphate (6.33 g, 16.7 mmol) and triethylamine (3.37 g, 33.3 mmol). After stirring for 20 minutes, 5-bromopyridine-2,3-diamine (2.3 g, 12 mmol) was added portion-wise, and the resulting reaction mixture was stirred overnight. After 15 hours, water was added, and the solution was extracted with EtOAc. The combined organic layers were dried, and the solvent was removed under reduced pressure. The crude compound was purified by flash chromatography (Gradient: 0% to 80% EtOAc in heptane) to yield C64 (2.3 g, 80%). $^1$H NMR (400 MHz, CDCl$_3$) δ 8.09 (s, 1H), 8.06 (d, 1H), 8.03 (s, 1H), 7.83 (d, 1H), 4.08 (s, 2H), 3.53 (s, 3H); LC-MS (ES+): 260.2 (M+H).

Step 2. Synthesis of 5-bromo-N$^3$-(2-methoxyethyl)pyridine-2,3-diamine (P31)

To a solution of C64 (3.3 g, 13 mmol) in THF was added a solution of BH$_3$ in THF (1 M; 14 mL, 14 mmol) over the period of 10 minutes, and stirred at room temperature overnight, Water was added to the reaction slowly to quench the excess borane, and the mixture was then extracted with EtOAc. The EtOAc layer was dried and concentrated under reduced pressure. The crude product was dissolved in MeOH and HCl in 1,4-dioxane (1.0 equiv) was added and stirred for 2 hours. Excess MeOH was removed under reduced pressure to obtain the crude product. The compound was purified by flash chromatography with a gradient ranging from 0% to 70% EtOAc in heptane to obtain P31 as a brown oil (1.1 g, 35%). $^1$H NMR (600 MHz, CDCl$_3$) δ 7.83 (d, 1H), 6.95 (d, 1H), 5.56 (s, 2H), 3.77 (t, 1H), 3.66 (t, 2H), 3.42 (s, 3H), 3.22 (q, 2H); LC-MS (ES+): 246.1.

Preparation P32

6-Bromo-2-(chloromethyl)-1-(2-methoxyethyl)-1H-imidazo[4,5-b]pyridine (P32)

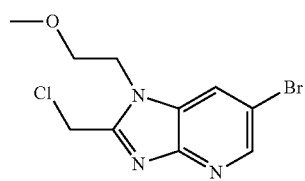

Compound P31 (400 mg, 1.63 mmol) was taken up in 1,4-dioxane (8 mL) and treated with chloroacetyl chloride (0.284 mL, 3.58 mmol). The mixture was stirred at room temperature. The solvent was removed under reduced pressure and the resultant residue was taken up in trifluoroacetic acid (8 mL) and stirred at 80° C. for 18 hours. The reaction was cooled to room temperature and concentrated under reduced pressure. The resultant brown oil was taken up in EtOAc (50 mL) and neutralized with saturated aqueous sodium bicarbonate solution. After the carbon dioxide evolution had subsided, the layers were separated and the aqueous layer was extracted with additional EtOAc (20 mL). The organic extracts were combined, dried over sodium sulfate, filtered and concentrated under reduced pressure. The resultant crude product was purified by flash chromatography (Gradient: 0% to 80% EtOAc in heptane) to yield P32 (176 mg, 36%) as a tan solid. $^1$H NMR (600 MHz, CDCl$_3$) δ 8.59 (s, 1H), 7.90 (s, 1H), 4.93 (s, 2H), 4.45 (m, 2H), 3.72 (m, 2H), 3.29 (s, 3H); LC-MS (ES+): 306.1 (M+H).

Preparation P33

6-Bromo-N$^4$-(2-methoxyethyl)pyridine-3,4-diamine (P33)

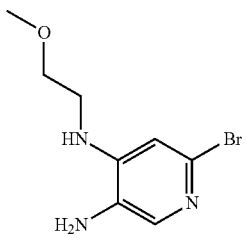

Step 1. Synthesis of 2-bromo-N-(2-methoxyethyl)-5-nitropyridin-4-amine (C65)

A solution of 2,4-dibromo-5-nitropyridine (8.65 g, 30.7 mmol) in THF (100 mL) was treated with triethylamine (5.11 mL, 36.8 mmol) and 2-methoxyethanamine (2.77 g, 36.8 mmol), and the reaction mixture was stirred at 20° C. for 1 hour. It was then poured into water (200 mL) and extracted with EtOAc (2×200 mL); the combined organic layers were dried over sodium sulfate, filtered, concentrated in vacuo, and combined with a similar reaction carried out using 2,4-dibromo-5-nitropyridine (600 mg, 2.13 mmol). Purification using silica gel chromatography (Gradient: 0% to 35% EtOAc in petroleum ether) afforded C65 as a yellow solid. Combined yield: 9.02 g, 32.7 mmol, 99%.

Step 2. Synthesis of 6-bromo-N$^4$-(2-methoxyethyl)pyridine-3,4-diamine (P33)

Reduced iron powder (607 mg, 10.9 mmol) and ammonium chloride (3.49 g, 65.2 mmol) were added to a solution of C65 (1.00 g, 3.62 mmol) in a mixture of MeOH (10 mL) and water (4 mL). The reaction mixture was stirred at 80° C. for 4 hours, whereupon it was poured into water (30 mL) and extracted with EtOAc (4×50 mL). The combined organic layers were washed with saturated aqueous sodium chloride solution (50 mL), dried over sodium sulfate, filtered, and concentrated in vacuo to provide P33 as a pale brown solid. Yield: 900 mg, assumed quantitative. $^1$H NMR (400 MHz, Chloroform-d) δ 7.63 (s, 1H), 6.59 (s, 1H), 4.58 (br s, 1H), 3.63 (t, 2H), 3.40 (s, 3H), 3.34-3.26 (m, 2H).

Preparation P34

(4-{6-[(4-chloro-2-fluorobenzyl)oxy]pyridin-2-yl}cyclohexyl)acetic Acid (P34)

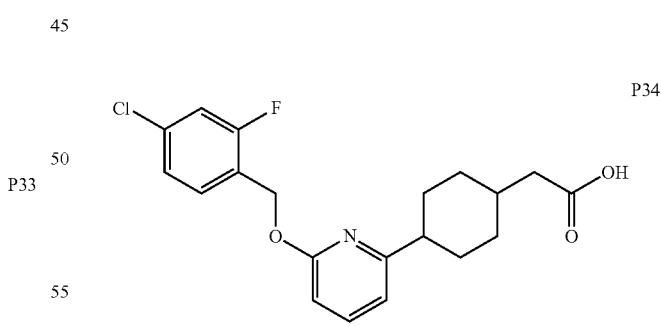

Compound P34 was prepared as a mixture of cis and trans isomers by a route analogous to that employed in the preparation of P2 beginning from 2,6-dichloropyridine and methyl [4-(4,4,5,5-tetramethyl-1,3,2-dioxaborolan-2-yl)cyclohex-3-en-1-yl]acetate, via Suzuki coupling, chemoselective reduction, palladium-catalyzed etherification and ester hydrolysis. LCMS m/z 378.1 [M+H]$^+$.

Example 1

Ammonium 2-[(4-{2-[(4-chloro-2-fluorobenzyl)oxy]pyridin-3-yl}piperidin-1-yl)methyl]-1-[(2S)-oxetan-2-ylmethyl]-1H-benzimidazole-6-carboxylate (1)

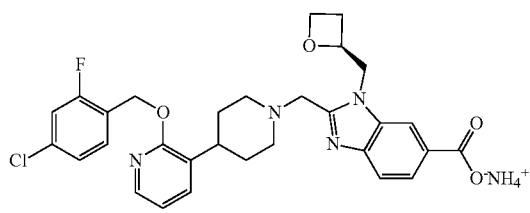

Step 1. Synthesis of methyl 4-{[(4-{2-[(4-chloro-2-fluorobenzyl)oxy]pyridin-3-yl}piperidin-1-yl)acetyl]amino}-3-{[(2S)-oxetan-2-ylmethyl]amino}benzoate (C66)

To a solution of P1 (100 mg, 0.264 mmol) in N,N-dimethylformamide (5 mL) was added O-(7-azabenzotriazol-1-yl)-N,N,N',N'-tetramethyluronium hexafluorophosphate (151 mg, 0.396 mmol). After this mixture had been stirred at room temperature (10° C.) for 10 minutes, P16 (62.4 mg, 0.264 mmol) and N,N-diisopropylethylamine (102 mg, 0.792 mmol) were added, and the reaction mixture was stirred at room temperature (10° C.) for 16 hours. It was then treated with saturated aqueous ammonium chloride solution (10 mL) and extracted with a mixture of dichloromethane and MeOH (10:1, 3×30 mL). The combined organic layers were washed with saturated aqueous sodium chloride solution, dried over sodium sulfate, filtered, and concentrated in vacuo; purification via preparative thin-layer chromatography (Eluent: 20:1 dichloromethane/MeOH) afforded C66 as a colorless oil. Yield: 90 mg, 0.15 mmol, 57%.

Step 2. Synthesis of methyl 2-[(4-{2-[(4-chloro-2-fluorobenzyl)oxy]pyridin-3-yl}piperidin-1-yl)methyl]-1-[(2S)-oxetan-2-ylmethyl]-1H-benzimidazole-6-carboxylate (C67)

A solution of C66 (90 mg, 0.15 mmol) in acetic acid (5 mL) was stirred at 50° C. for 16 hours. After the reaction mixture had been concentrated in vacuo, the residue was dissolved in a mixture of dichloromethane and MeOH (10:1, 30 mL) and washed with saturated aqueous sodium carbonate solution (20 mL). The aqueous layer was extracted with a mixture of dichloromethane and MeOH (10:1, 3×30 mL), and the combined organic layers were washed with saturated aqueous sodium chloride solution, dried over sodium sulfate, filtered, and concentrated in vacuo to provide C67 (90 mg) as a colorless oil, a portion of which was used directly in the following step.

Step 3. Synthesis of Ammonium 2-[(4-{2-[(4-chloro-2-fluorobenzyl)oxy]pyridin-3-yl}piperidin-1-yl)methyl]-1-[(2S)-oxetan-2-ylmethyl]-1H-benzimidazole-6-carboxylate (1)

To a solution of C67 (from the previous step; 80 mg, ≤0.13 mmol) in MeOH (2 mL) was added lithium hydroxide (4.96 mg, 0.209 mmol) and water (0.5 mL), and the reaction mixture was stirred at 50° C. for 16 hours. It was then concentrated in vacuo and purified via reversed-phase HPLC (Column: Agela Durashell C18, 5 μm; Mobile phase A: 0.05% ammonium hydroxide in water; Mobile phase B: acetonitrile; Gradient: 13% to 33% B) to provide 1 as a white solid. Yield: 28 mg, 48 μmol, 37% over 2 steps. LCMS m/z 565.1♦ [M+H]⁺. ¹H NMR (400 MHz, Methanol-d₄) δ 8.30 (d, 1H), 8.00-7.94 (m, 2H), 7.65 (d, 1H), 7.58 (dd, 1H), 7.51 (dd, 1H), 7.29-7.21 (m, 2H), 6.94 (dd, 1H), 5.42 (s, 2H), 5.29-5.21 (m, 1H), 4.9-4.83 (m, 1H, assumed; partially obscured by water peak), 4.71 (dd, 1H), 4.67-4.60 (m, 1H), 4.45 (dt, 1H), 3.99 (AB quartet, 2H), 3.11-3.04 (m, 1H), 3.02-2.94 (m, 1H), 2.92-2.74 (m, 2H), 2.57-2.47 (m, 1H), 2.40-2.25 (m, 2H), 1.90-1.69 (m, 4H).

The compounds listed in Table 1 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 1

| Ex. No. | Structure | IUPAC Name |
|---|---|---|
| 2 | 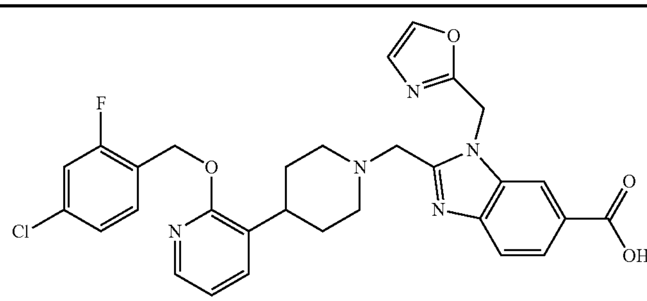 | 2-[(4-{2-[(4-chloro-2-fluorobenzyl)oxy]pyridin-3-yl}piperidin-1-yl)methyl]-1-(1,3-oxazol-2-ylmethyl)-1H-benzimidazole-6-carboxylic acid, trifluoroacetate salt |

Structure and IUPAC name for Examples 2 to 18

TABLE 1-continued

Structure and IUPAC name for Examples 2 to 18

| Ex. No. | Structure | IUPAC Name |
|---|---|---|
| 3 | 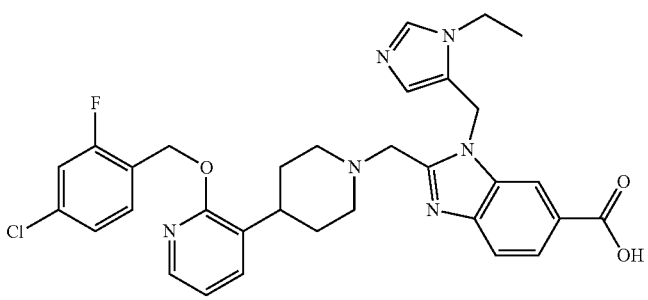 •CF₃COOH | 2-[(4-{2-[(4-chloro-2-fluorobenzyl)oxy]pyridin-3-yl}piperidin-1-yl)methyl]-1-[(1-ethyl-1H-imidazol-5-yl)methyl]-1H-benzimidazole-6-carboxylic acid, trifluoroacetate salt |
| 4 | 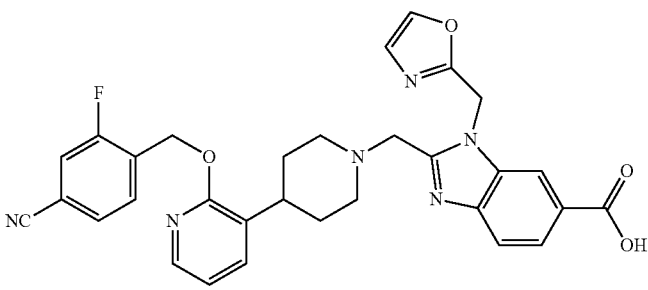 •CF₃COOH | 2-[(4-{2-[(4-cyano-2-fluorobenzyl)oxy]pyridin-3-yl}piperidin-1-yl)methyl]-1-(1,3-oxazol-2-ylmethyl)-1H-benzimidazole-6-carboxylic acid, trifluoroacetate salt |
| 5 | 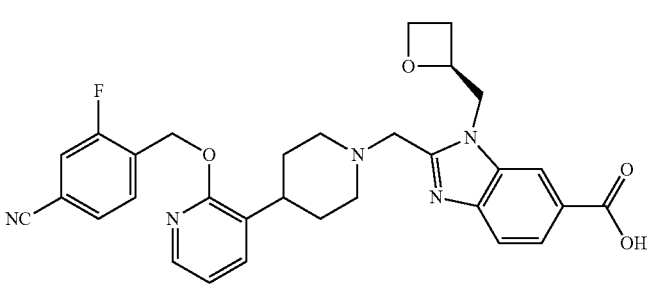 [SMILES: N#Cc1ccc(COc2ncccc2C2CCN(Cc3nc4ccc(C(=O)O)cc4n3C[C@@H]3CCO3)CC2)c(F)c1] | 2-[(4-{2-[(4-cyano-2-fluorobenzyl)oxy]pyridin-3-yl}piperidin-1-yl)methyl]-1-[(2S)-oxetan-2-ylmethyl]-1H-benzimidazole-6-carboxylic acid |
| 6 | 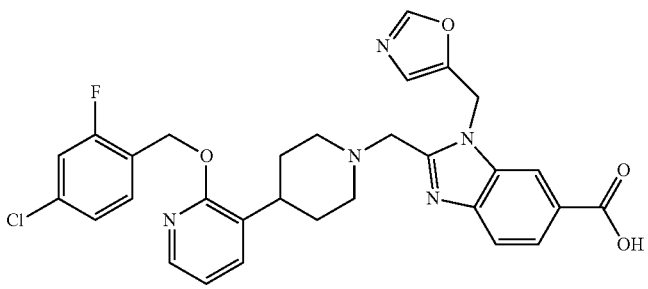 •CF₃COOH | 2-[(4-{2-[(4-chloro-2-fluorobenzyl)oxy]pyridin-3-yl}piperidin-1-yl)methyl]-1-(1,3-oxazol-5-ylmethyl)-1H-benzimidazole-6-carboxylic acid, trifluoroacetate salt |

TABLE 1-continued

Structure and IUPAC name for Examples 2 to 18

| Ex. No. | Structure | IUPAC Name |
|---|---|---|
| 7 | 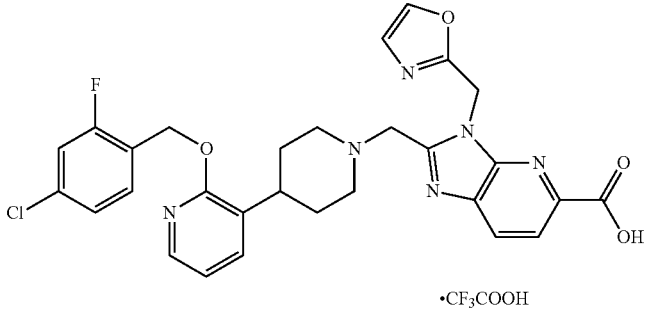 [SMILES: O=C(O)c1ccc2nc(CN3CCC(c4cccnc4OCc4ccc(Cl)cc4F)CC3)n(Cc3ncco3)c2n1 ; "·CF3COOH"] | 2-[(4-{2-[(4-chloro-2-fluorobenzyl)oxy]pyridin-3-yl}piperidin-1-yl)methyl]-3-(1,3-oxazol-2-ylmethyl)-3H-imidazo[4,5-b]pyridine-5-carboxylic acid, trifluoroacetate salt |
| 8 | 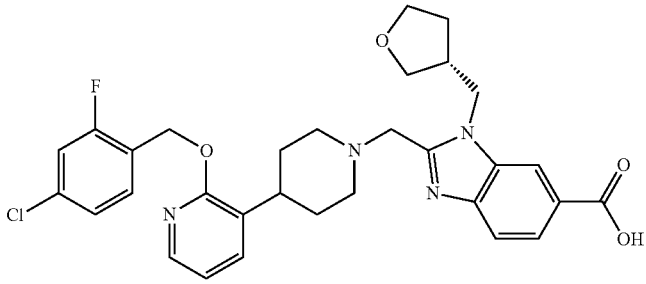 | 2-[(4-{2-[(4-chloro-2-fluorobenzyl)oxy]pyridin-3-yl}piperidin-1-yl)methyl]-1-[(3R)-tetrahydrofuran-3-ylmethyl]-1H-benzimidazole-6-carboxylic acid, trifluoroacetate salt |
| 9 | 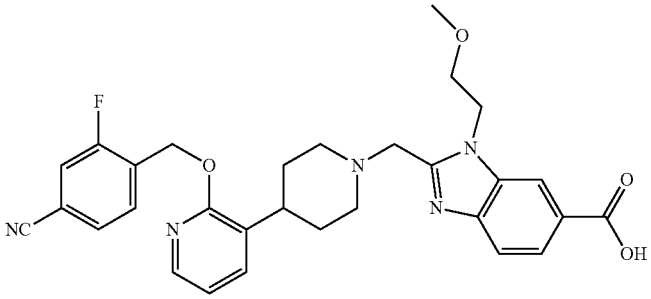 | 2-[(4-{2-[(4-cyano-2-fluorobenzyl)oxy]pyridin-3-yl}piperidin-1-yl)methyl]-1-(2-methoxyethyl)-1H-benzimidazole-6-carboxylic acid, trifluoroacetate salt |
| 10 | 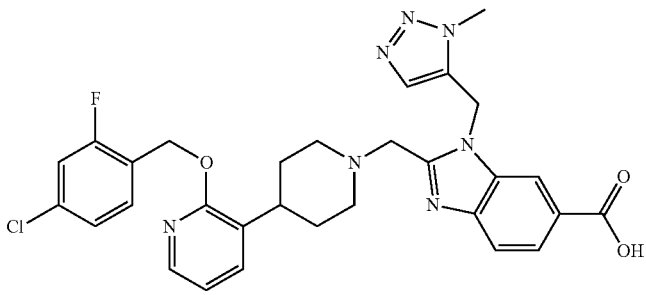 | 2-[(4-{2-[(4-chloro-2-fluorobenzyl)oxy]pyridin-3-yl}piperidin-1-yl)methyl]-1-[(1-methyl-1H-1,2,3-triazol-5-yl)methyl]-1H-benzimidazole-6-carboxylic acid, trifluoroacetate salt |

TABLE 1-continued

Structure and IUPAC name for Examples 2 to 18

| Ex. No. | Structure | IUPAC Name |
|---|---|---|
| 11 | 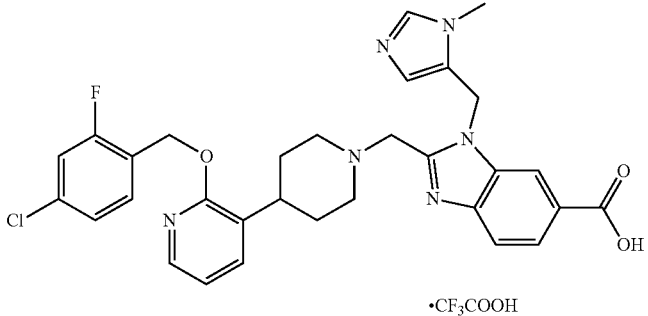 •CF₃COOH | 2-[(4-{2-[(4-chloro-2-fluorobenzyl)oxy]pyridin-3-yl}piperidin-1-yl)methyl]-1-[(1-methyl-1H-imidazol-5-yl)methyl]-1H-benzimidazole-6-carboxylic acid, trifluoroacetate salt |
| 12 | 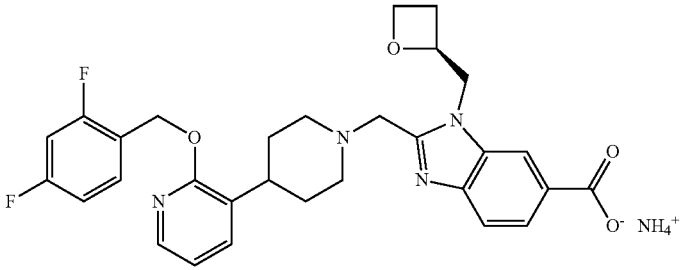 [SMILES: O=C([O-])c1ccc2nc(CN3CCC(c4cccnc4OCc4ccc(F)cc4F)CC3)n(C[C@@H]3CCO3)c2c1 ; [NH4+]] | ammonium 2-[(4-{2-[(2,4-difluorobenzyl)oxy]pyridin-3-yl}piperidin-1-yl)methyl]-1-[(2S)-oxetan-2-ylmethyl]-1H-benzimidazole-6-carboxylate |
| 13 | 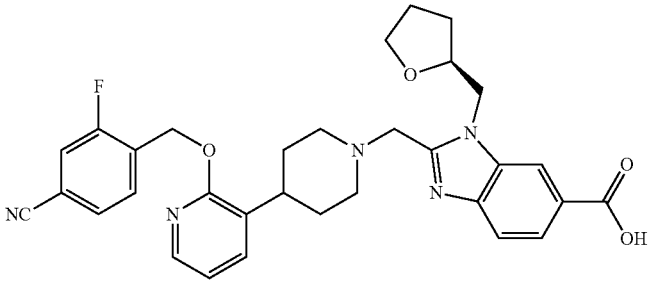 •CF₃COOH | 2-[(4-{2-[(4-cyano-2-fluorobenzyl)oxy]pyridin-3-yl}piperidin-1-yl)methyl]-1-[(2S)-tetrahydrofuran-2-ylmethyl]-1H-benzimidazole-6-carboxylic acid, trifluoroacetate salt |
| 14 | 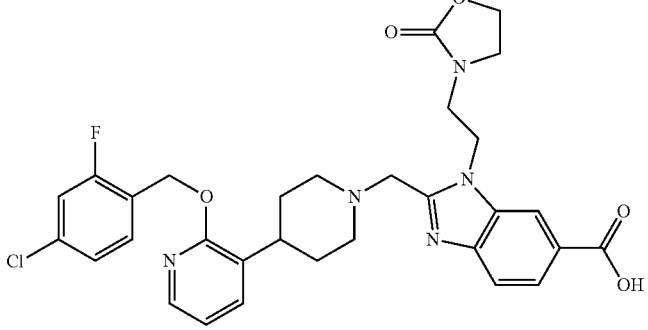 •CF₃COOH | 2-[(4-{2-[(4-chloro-2-fluorobenzyl)oxy]pyridin-3-yl}piperidin-1-yl)methyl]-1-[2-(2-oxo-1,3-oxazolidin-3-yl)ethyl]-1H-benzimidazole-6-carboxylic acid, trifluoroacetate salt |

TABLE 1-continued

Structure and IUPAC name for Examples 2 to 18

| Ex. No. | Structure | IUPAC Name |
|---|---|---|
| 15 | 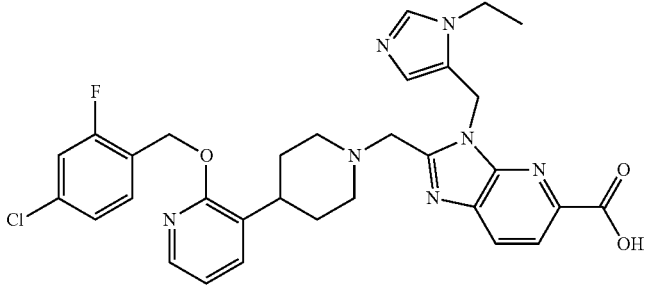 •CF₃COOH | 2-[(4-{2-[(4-chloro-2-fluorobenzyl)oxy]pyridin-3-yl}piperidin-1-yl)methyl]-3-[(1-ethyl-1H-imidazol-5-yl)methyl]-3H-imidazo[4,5-b]pyridine-5-carboxylic acid, trifluoroacetate salt |
| 16 | 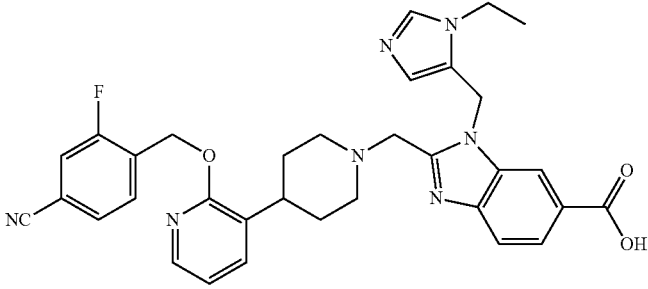 •CF₃COOH | 2-[(4-{2-[(4-cyano-2-fluorobenzyl)oxy]pyridin-3-yl}piperidin-1-yl)methyl]-1-[(1-ethyl-1H-imidazol-5-yl)methyl]-1H-benzimidazole-6-carboxylic acid, trifluoroacetate salt |
| 17 | 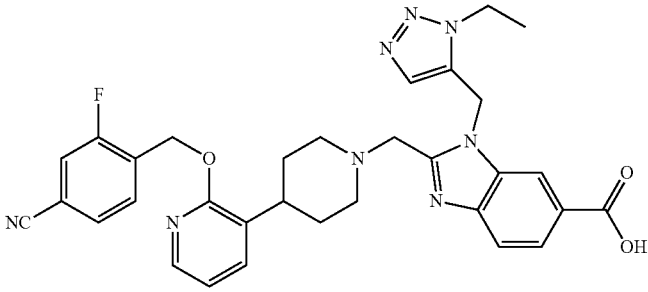 •CF₃COOH | 2-[(4-{2-[(4-cyano-2-fluorobenzyl)oxy]pyridin-3-yl}piperidin-1-yl)methyl]-1-[(1-ethyl-1H-1,2,3-triazol-5-yl)methyl]-1H-benzimidazole-6-carboxylic acid, trifluoroacetate salt |
| 18[1] | 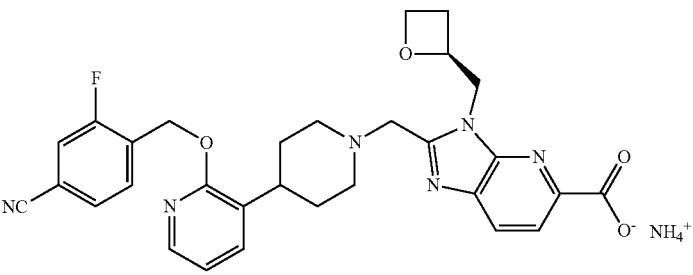 [SMILES: N#Cc1ccc(COc2ncccc2C2CCN(Cc3nc4ccc(C(=O)[O-])nc4n3C[C@@H]3CCO3)CC2)c(F)c1 ; [NH4+]] | ammonium 2-[(4-{2-[(4-cyano-2-fluorobenzyl)oxy]pyridin-3-yl}piperidin-1-yl)methyl]-3-[(2S)-oxetan-2-ylmethyl]-3H-imidazo[4,5-b]pyridine-5-carboxylate |

TABLE 1A

Physicochemical data for Examples 2 to 18

| Ex. No. | Mass spectrum, observed ion m/z [M + H]⁺; HPLC retention time or ¹H NMR |
|---|---|
| 2 | 576.0♦; ¹H NMR (400 MHz, Methanol-d₄): δ 8.36 (d, 1H), 8.09 (dd, 1H), 8.06 (dd, 1H), 7.98 (d, 1H), 7.82 (d, 1H), 7.66 (dd, 1H), 7.56 (t, 1H), 7.31-7.22 (m, 2H), 7.19 (d, 1H), 7.03 (dd, 1H), 5.86 (s, 2H), 5.48 (s, 2H), 4.89 (s, 2H), 3.96 (d, 2H), 3.41 (t, 2H), 3.29-3.18 (m, 1H), 2.28-2.04 (m, 4H) |
| 3 | 603.1♦; 2.43 minutes (Column: Waters XBridge C18, 2.1 × 50 mm, 5 μm; Mobile phase A: water containing 0.1% formic acid; Mobile phase B: acetonitrile; Gradient: 1.0% to 5% B over 0.6 minutes, then 5% to 100% B over 3.4 minutes; Flow rate: 0.8 mL/minute) |
| 4 | 567.0; ¹H NMR (400 MHz, Methanol-d₄): δ 8.36 (dd, 1H), 8.09-8.04 (m, 2H), 7.98 (d, 1H), 7.82 (d, 1H), 7.73 (t, 1H), 7.67 (dd, 1H), 7.63 (dd, 1H), 7.59 (dd, 1H), 7.20 (d, 1H), 7.04 (dd, 1H), 5.86 (s, 2H), 5.60 (s, 2H), 4.88 (s, 2H, assumed; partially obscured by water), 3.94 (d, 2H), 3.45-3.33 (m, 2H), 3.32-3.22 (m, 1H), 2.26-2.06 (m, 4H) |
| 5 | 556.5; ¹H NMR (600 MHz, DMSO-d₆): δ 12.76 (br s, 1H), 8.27 (s, 1H), 8.00 (d, 1H), 7.92 (d, 1H), 7.80 (d, 1H), 7.77-7.72 (m, 1H), 7.71-7.58 (m, 3H), 7.05-6.97 (m, 1H), 5.51 (s, 2H), 5.09 (d, 1H), 4.87-4.75 (m, 1H), 4.72-4.60 (m, 1H), 4.49 (d, 1H), 4.43-4.32 (m, 1H), 3.95 (d, 1H), 3.80 (d, 1H), 3.01 (d, 1H), 2.88 (d, 1H), 2.81 (t, 1H), 2.75-2.64 (m, 1H), 2.43 (d, 1H), 2.29-2.12 (m, 2H), 1.86-1.73 (m, 2H), 1.72-1.54 (m, 2H) |
| 6 | 576.1♦; 2.63 minutes (Analytical conditions identical to those used for Ex. 3) |
| 7 | 577.0♦; 2.63 minutes (Column: Waters XBridge C18, 2.0 × 50 mm, 5 μm; Mobile phase A: water containing 0.1% formic acid; Mobile phase B: acetonitrile containing 0.1% formic acid; Gradient: 1.0% to 5% B over 0.6 minutes, then 5% to 100% B over 3.4 minutes; Flow rate: 0.8 mL/minute) |
| 8 | 579.1♦; 1.85 minutes (Column: Chiral Technologies Chiralpak AD-3, 4.6 × 50 mm, 3 μm; Mobile phase A: carbon dioxide; Mobile phase B: 0.05% diethylamine in 2-propanol; Gradient: 5% B for 0.2 minutes, then 5% to 40% B over 1.4 minutes, then 40% B for 1.05 minutes; Flow rate: 4 mL/minute; Column temperature: 40° C.) |
| 9 | 544.1; 2.52 minutes (Analytical conditions identical to those used for Ex. 3) |
| 10 | 590.1♦; 2.70 minutes (Analytical conditions identical to those used for Ex. 3) |
| 11 | 589.0♦; 2.47 minutes (Analytical conditions identical to those used for Ex. 3) |
| 12 | 549.1; 1.45 minutes (Column: Chiral Technologies Chiralpak AD-3, 4.6 × 50 mm, 3 μm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.) |
| 13 | 570.1; 1.81 minutes (Analytical conditions identical to those used for Ex. 8) |
| 14 | 608.0♦; 2.57 minutes (Analytical conditions identical to those used for Ex. 7) |
| 15 | 604.0♦; 2.29 minutes (Analytical conditions identical to those used for Ex. 7) |
| 16 | 594.1; 2.27 minutes (Analytical conditions identical to those used for Ex. 3) |
| 17 | 595.0; 2.58 minutes (Column: Waters XBridge C18, 2.0 × 50 mm, 5 μm; Mobile phase A: water containing 10 mM ammonium carbonate; Mobile phase B: acetonitrile; Gradient: 1% to 5% B over 0.6 minutes, then 5% to 100% B over 3.4 minutes; Flow rate: 0.8 mL/minute) |
| 18[1] | 557.0; 4.34 minutes (Column: Chiral Technologies Chiralpak AD-3, 4.6 × 100 mm, 3 μm; Mobile phase A: carbon dioxide; Mobile phase B: 0.05% diethylamine in ethanol; Gradient: 5% to 40% B over 4.5 minutes, then 40% B for 2.5 minutes; Flow rate: 2.8 mL/minute; Column temperature: 40° C.) |

Table 1/1A: [1]Treatment of methyl 5-{[(4-{2-[(4-cyano-2-fluorobenzyl)oxy]pyridin-3-yl}piperidin-1-yl)acetyl]amino}-6-{[(2S)-oxetan-2-ylmethyl]amino}pyridine-2-carboxylate with aqueous sodium hydroxide solution in 1,4-dioxane at elevated temperature served to effect both ring closure and ester hydrolysis, delivering Example 18 after purification.

Example 19

Ammonium 2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylate (19)

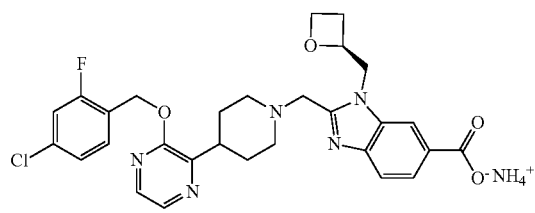

19

Step 1. Synthesis of methyl 4-{[(4-{3-[(4-chloro-2-fluorobenzyl)oxy]pyrazin-2-yl}piperidin-1-yl)acetyl]amino}-3-{[(2S)-oxetan-2-ylmethyl]amino}benzoate (C68)

To a solution of P2 (800 mg, 2.02 mmol) and P16 (476 mg, 2.02 mmol) in N,N-dimethylformamide (12 mL) were added O-(7-azabenzotriazol-1-yl)-N,N,N',N'-tetramethyluronium hexafluorophosphate (1.15 g, 3.02 mmol) and triethylamine (408 mg, 4.03 mmol). The reaction mixture was stirred at 30° C. for 18 hours, whereupon it was diluted with saturated aqueous ammonium chloride solution (20 mL) and extracted with EtOAc (3×20 mL). The combined organic layers were washed with saturated aqueous sodium chloride solution (40 mL), dried over sodium sulfate, filtered, and concentrated in vacuo to afford C68 as a yellow gum. Yield: 1.07 g, 1.79 mmol, 89%.

Step 2. Synthesis of methyl 2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylate (C69)

A solution of C68 (1.08 g, 1.81 mmol) in acetic acid (8 mL) was stirred at 50° C. for 18 hours, whereupon it was concentrated in vacuo, carefully poured into saturated aqueous sodium bicarbonate solution (20 mL), and extracted with EtOAc (3×20 mL). The combined organic layers were washed with saturated aqueous sodium chloride solution (50 mL), dried over sodium sulfate, filtered, and concentrated in vacuo. Silica gel chromatography (Eluent: EtOAc) provided C69 as a yellow gum. Yield: 550 mg, 0.948 mmol, 52%.

Step 3. Synthesis of Ammonium 2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylate (19)

To a suspension of C69 (550 mg, 0.948 mmol) in a mixture of MeOH (5 mL) and THF (5 mL) was added aqueous sodium hydroxide solution (3 M; 6.32 mL, 19.0 mmol), and the reaction mixture was stirred at 15° C. for 3 hours. It was then concentrated in vacuo, diluted with water (8 mL), and washed with EtOAc (8 mL). The aqueous layer was adjusted to pH 6 to 7 by addition of 1 M hydrochloric acid, and extracted with EtOAc (3×10 mL). The combined organic extracts were washed with saturated aqueous sodium chloride solution (30 mL), dried over sodium sulfate, filtered, and concentrated under reduced pressure. Purification via reversed-phase HPLC (Column: Agela Durashell C18, 5 μm; Mobile phase A: 0.05% ammonium hydroxide in water; Mobile phase B: acetonitrile; Gradient: 26% to 56% B) afforded 19 as a white solid. Yield: 294 mg, 0.504 mmol, 53%. LCMS m/z 566.1◆ [M+H]$^+$. $^1$H NMR (400 MHz, Methanol-d$_4$) δ 8.25 (br s, 1H), 8.06 (d, 1H), 7.99 (d, 1H), 7.95 (dd, 1H), 7.61 (d, 1H), 7.52 (dd, 1H), 7.28-7.21 (m, 2H), 5.46 (s, 2H), 5.30-5.22 (m, 1H), 4.93-4.83 (m, 1H, assumed; largely obscured by water peak), 4.70 (dd, 1H), 4.67-4.59 (m, 1H), 4.47 (dt, 1H), 3.96 (AB quartet, 2H), 3.13-3.02 (m, 2H), 2.95 (br d, 1H), 2.85-2.75 (m, 1H), 2.57-2.47 (m, 1H), 2.38-2.23 (m, 2H), 2.00-1.78 (m, 4H).

The compounds listed in Table 2 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 2

Structure and IUPAC name for Examples 20 to 28

| Ex. No. | Structure | IUPAC Name |
|---|---|---|
| 20 | 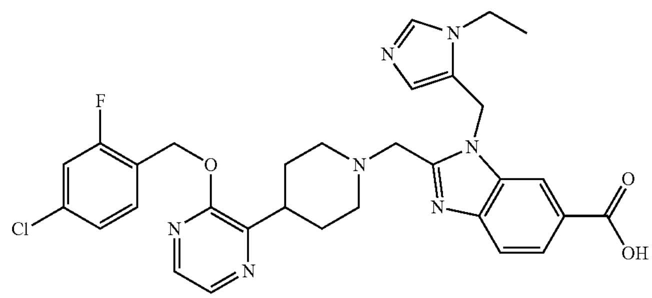 | 2-[(4-{3-[(4-chloro-2-fluorobenzyl)oxy]pyrazin-2-yl}piperidin-1-yl)methyl]-1-[(1-ethyl-1H-imidazol-5-yl)methyl]-1H-benzimidazole-6-carboxylic acid, trifluoroacetate salt |
| 21 | 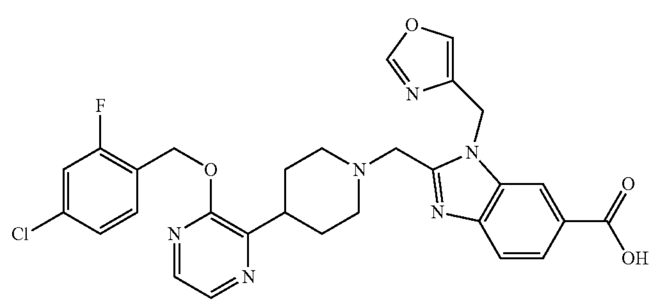 | 2-[(4-{3-[(4-chloro-2-fluorobenzyl)oxy]pyrazin-2-yl}piperidin-1-yl)methyl]-1-(1,3-oxazol-4-ylmethyl)-1H-benzimidazole-6-carboxylic acid, trifluoroacetate salt |

TABLE 2-continued

Structure and IUPAC name for Examples 20 to 28

| Ex. No. | Structure | IUPAC Name |
|---|---|---|
| 22 | 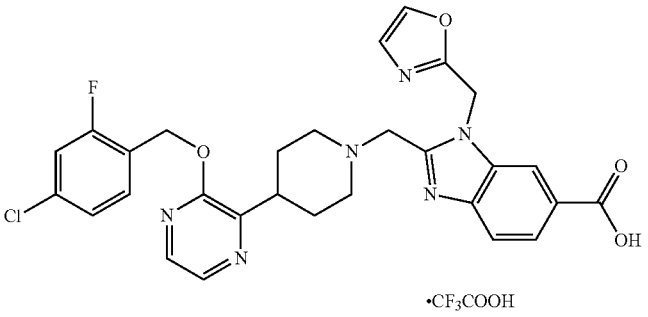 [SMILES: O=C(O)c1ccc2nc(CN3CCC(c4nccnc4OCc4ccc(Cl)cc4F)CC3)n(Cc3ncco3)c2c1 ; "·CF3COOH"] •CF₃COOH | 2-[(4-{3-[(4-chloro-2-fluorobenzyl)oxy]pyrazin-2-yl}piperidin-1-yl)methyl]-1-(1,3-oxazol-2-ylmethyl)-1H-benzimidazole-6-carboxylic acid, trifluoroacetate salt |
| 23 | 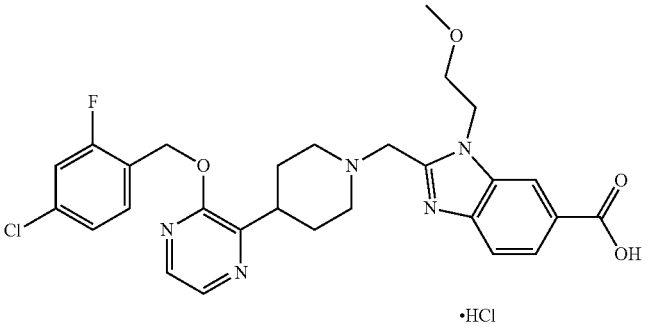 [SMILES: COCCn1c(CN2CCC(c3nccnc3OCc3ccc(Cl)cc3F)CC2)nc2ccc(C(=O)O)cc21 ; Cl] •HCl | 2-[(4-{3-[(4-chloro-2-fluorobenzyl)oxy]pyrazin-2-yl}piperidin-1-yl)methyl]-1-(2-methoxyethyl)-1H-benzimidazole-6-carboxylic acid, hydrochloride salt |
| 24 | 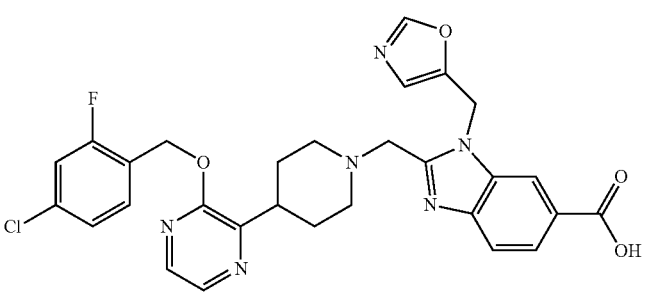 •CF₃COOH | 2-[(4-{3-[(4-chloro-2-fluorobenzyl)oxy]pyrazin-2-yl}piperidin-1-yl)methyl]-1-(1,3-oxazol-5-ylmethyl)-1H-benzimidazole-6-carboxylic acid, trifluoroacetate salt |
| 25 | 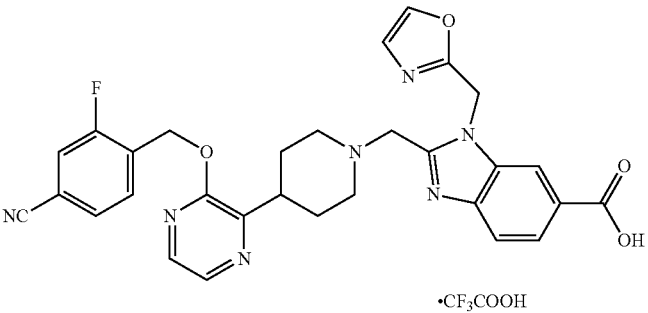 [SMILES: N#Cc1ccc(COc2nccnc2C2CCN(Cc3nc4ccc(C(=O)O)cc4n3Cc3ncco3)CC2)c(F)c1 ; "·CF3COOH"] •CF₃COOH | 2-[(4-{3-[(4-cyano-2-fluorobenzyl)oxy]pyrazin-2-yl}piperidin-1-yl)methyl]-1-(1,3-oxazol-2-ylmethyl)-1H-benzimidazole-6-carboxylic acid, trifluoroacetate salt |

TABLE 2-continued

Structure and IUPAC name for Examples 20 to 28

| Ex. No. | Structure | IUPAC Name |
|---|---|---|
| 26 | 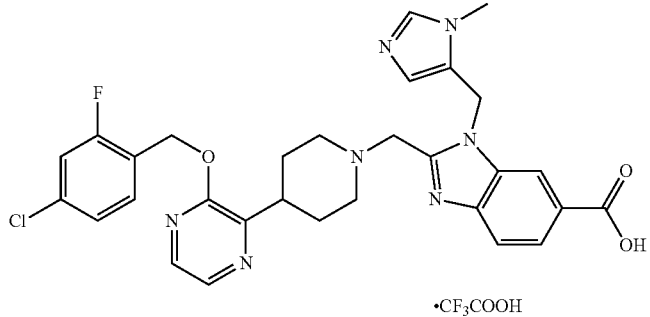 [SMILES: Cn1cncc1Cn1c(CN2CCC(c3nccnc3OCc3ccc(Cl)cc3F)CC2)nc2ccc(C(=O)O)cc21 ; "·CF3COOH"] ·CF₃COOH | 2-[(4-{3-[(4-chloro-2-fluorobenzyl)oxy]pyrazin-2-yl}piperidin-1-yl)methyl]-1-[(1-methyl-1H-imidazol-5-yl)methyl]-1H-benzimidazole-6-carboxylic acid, trifluoroacetate salt |
| 27 | 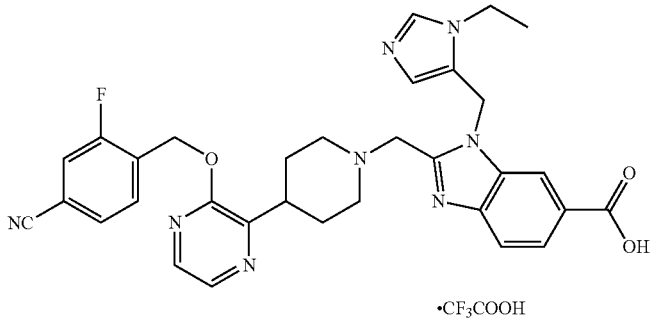 [SMILES: CCn1cncc1Cn1c(CN2CCC(c3nccnc3OCc3ccc(C#N)cc3F)CC2)nc2ccc(C(=O)O)cc21 ; "·CF3COOH"] ·CF₃COOH | 2-[(4-{3-[(4-cyano-2-fluorobenzyl)oxy]pyrazin-2-yl}piperidin-1-yl)methyl]-1-[(1-ethyl-1H-imidazol-5-yl)methyl]-1H-benzimidazole-6-carboxylic acid, trifluoroacetate salt |
| 28 | 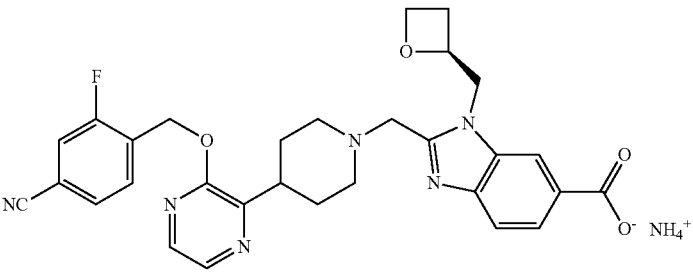 [SMILES: N#Cc1ccc(COc2nccnc2C2CCN(Cc3nc4ccc(C(=O)[O-])cc4n3C[C@@H]3CCO3)CC2)c(F)c1 ; [NH4+]] | ammonium 2-[(4-{3-[(4-cyano-2-fluorobenzyl)oxy]pyrazin-2-yl}piperidin-1-yl)methyl]-1-[(2S)-oxetan-2-ylmethyl]-1H-benzimidazole-6-carboxylate |

TABLE 2A

Physicochemical data for Examples 20 to 28

Ex. No. Mass spectrum, observed ion m/z [M + H]⁺; HPLC retention time or ¹H NMR 20  604.1♦; 2.38 minutes (Column: Waters XBridge C18, 2.1 × 50 mm, 5 µm; Mobile phase A: water containing 0.1% formic acid; Mobile phase B: acetonitrile; Gradient: 1.0% to 5% B over 0.6 minutes, then 5% to 100% B over 3.4 minutes; Flow rate: 0.8 mL/minute)
21  577.0♦; 2.64 minutes (Analytical conditions identical to those used for Ex. 20)
22  577.0♦; 2.66 minutes (Analytical conditions identical to those used for Ex. 20)
23  554.2♦; ¹H NMR (600 MHz, DMSO-d₆), characteristic peaks: δ 8.31 (s, 1H), 8.22 (s, 1H), 8.14 (s, 1H), 7.89 (d, 1H), 7.78 (d, 1H), 7.61 (dd, 1H), 7.52 (d, 1H), 7.34 (d, 1H), 5.45 (s, 2H), 4.86-4.68 (br m, 2H), 4.67-4.58 (m, 2H), 3.87-3.71 (br m, 2H), 3.69-3.61 (m, 2H), 3.5-3.2 (m, 2H, assumed; partially obscured by water peak), 3.20 (s, 3H), 2.17-1.99 (br m, 4H)
24  577.0♦; 2.60 minutes (Analytical conditions identical to those used for Ex. 20)
25  568.1; 2.45 minutes (Analytical conditions identical to those used for Ex. 20)
26  590.0♦; 2.31 minutes (Analytical conditions identical to those used for Ex. 20)
27  595.1; 2.16 minutes (Analytical conditions identical to those used for Ex. 20)
28  557.1; 1.52 minutes (Column: Chiral Technologies Chiralpak AD-3, 4.6 × 50 mm, 3 µm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.)

Example 29

2-[(4-{3-[(4-Chloro-2-fluorobenzyl)oxy]pyrazin-2-yl}piperidin-1-yl)methyl]-1-methyl-1H-imidazo[4,5-c]pyridine-6-carboxylic Acid, Trifluoroacetate Salt (29)

Step 1. Synthesis of N-[6-bromo-4-(methylamino)pyridin-3-yl]-2-(4-{3-[(4-chloro-2-fluorobenzyl)oxy]pyrazin-2-yl}piperidin-1-yl)acetamide (C70)

To a solution of P2, HCl salt (180 mg, 0.47 mmol) in N,N-dimethylformamide (5 mL) were added 6-bromo-N$^4$-methylpyridine-3,4-diamine (96 mg, 0.47 mmol), O-(7-azabenzotriazol-1-yl)-N,N,N',N'-tetramethyluronium hexafluorophosphate (270 mg, 0.71 mmol), and N,N-diisopropylethylamine (0.25 mL, 1.4 mmol). The reaction mixture was stirred at 25° C. for 16 hours, whereupon it was diluted with water (60 mL) and extracted with EtOAc (3×50 mL). The combined organic layers were dried over sodium sulfate, filtered, and concentrated in vacuo. The residue was purified by preparative thin-layer chromatography (EtOAc) to afford C70 as a red gum. Yield: 200 mg, 0.36 mmol, 75%.

Step 2. Synthesis of 6-bromo-2-[(4-{3-[(4-chloro-2-fluorobenzyl)oxy]pyrazin-2-yl}piperidin-1-yl)methyl]-1-methyl-1H-imidazo[4,5-c]pyridine (C71)

To a solution of C70 (200 mg, 0.36 mmol) in 1,4-dioxane (9 mL) was added aqueous sodium hydroxide solution (2 M; 1.8 mL, 4 mmol). The solution was stirred at 100° C. for 2 hours. The mixture was then diluted with water (30 mL) and extracted with EtOAc (3×40 mL). The combined organic layers were dried over sodium sulfate, filtered, and concentrated in vacuo. The material was combined with further crude material and purified by preparative thin-layer chromatography (EtOAc) to afford C71 as a yellow solid (140 mg, 0.26 mmol, 48% based on combined starting materials).

Step 3. Synthesis of methyl 2-[(4-{3-[(4-chloro-2-fluorobenzyl)oxy]pyrazin-2-yl}piperidin-1-yl)methyl]-1-methyl-1H-imidazo[4,5-c]pyridine-6-carboxylate (C72)

1,3-Bis(diphenylphosphino)propane (25 mg, 62 µmol), palladium(II) acetate (26 mg, 0.12 mmol), and triethylamine (0.35 mL, 2.5 mmol) were added to a solution of C71 (140 mg, 0.26 mmol) in a mixture of MeOH (3 mL) and N,N-dimethylformamide (2 mL), and the reaction mixture was stirred at 80° C., under carbon monoxide (50 psi), for 16 hours. It was then concentrated in vacuo and purified by preparative thin-layer chromatography (EtOAc) to afford C72 as a yellow solid (110 mg, 0.21 mmol, 82%).

Step 4. Synthesis of 2-[(4-{3-[(4-chloro-2-fluorobenzyl)oxy]pyrazin-2-yl}piperidin-1-yl)methyl]-1-methyl-1H-imidazo[4,5-c]pyridine-6-carboxylic Acid, Trifluoroacetate Salt (29)

Aqueous lithium hydroxide solution (2 M; 0.4 mL, 0.8 mmol) was added to a solution of C72 (80 mg, 0.15 mmol) in a mixture of THF (2 mL) and MeOH (2 mL), and the reaction mixture was stirred at 30° C. for 2 hours. After concentration in vacuo, the residue was adjusted to pH 4 with trifluoroacetic acid, and then purified using reversed-phase HPLC (Column: Waters XBridge C18 OBD, 5 µm; Mobile phase A: water containing 0.1% trifluoroacetic acid; Mobile phase B: acetonitrile; Gradient: 5% to 95% B); 29 was isolated as a white solid. Yield: 52.4 mg, 83.8 µmol, 56%. LCMS m/z 511.2♦ [M+H]$^+$. $^1$H NMR (400 MHz, Methanol-d$_4$) δ 9.11 (s, 1H), 8.60 (s, 1H), 8.16 (d, 1H), 8.09 (d, 1H), 7.56 (dd, 1H), 7.30-7.22 (m, 2H), 5.50 (s, 2H), 4.91 (s, 2H), 4.02-3.93 (m, 2H), 4.01 (s, 3H), 3.54-3.41 (m, 3H), 2.38-2.18 (m, 4H).

The compounds listed in Table 3 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 3

Structure and IUPAC name for Examples 30 to 32

| Ex. No. | Structure | IUPAC Name |
|---|---|---|
| 30 | 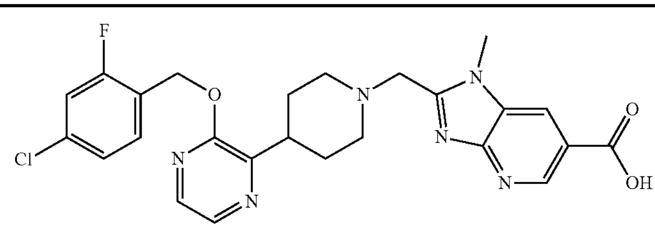 | 2-[(4-{3-[(4-chloro-2-fluorobenzyl)oxy]pyrazin-2-yl}piperidin-1-yl)methyl]-1-methyl-1H-imidazo[4,5-b]pyridine-6-carboxylic acid, hydrochloride salt |

TABLE 3-continued

Structure and IUPAC name for Examples 30 to 32

| Ex. No. | Structure | IUPAC Name |
|---|---|---|
| 31 | 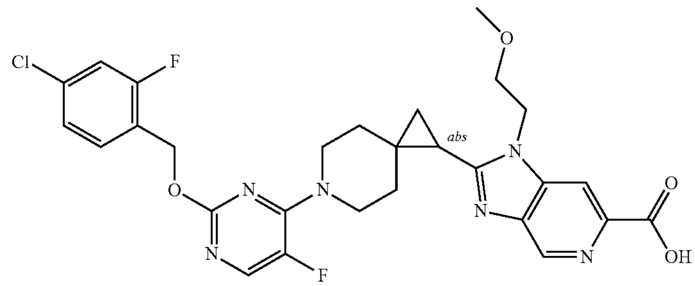 | 2-(6-{2-[(4-chloro-2-fluorobenzyl)oxy]-5-fluoropyrimidin-4-yl}-6-azaspiro[2.5]oct-1-yl)-1-(2-methoxyethyl)-1H-imidazo[4,5-c]pyridine-6-carboxylic acid, trifluoroacetate salt, single enantiomer; from P7 |
| 32 | 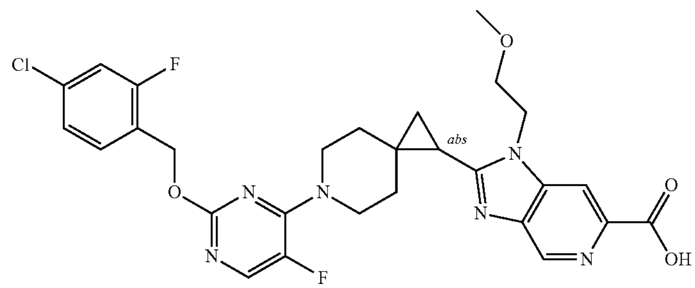 | 2-(6-{2-[(4-chloro-2-fluorobenzyl)oxy]-5-fluoropyrimidin-4-yl}-6-azaspiro[2.5]oct-1-yl)-1-(2-methoxyethyl)-1H-imidazo[4,5-c]pyridine-6-carboxylic acid, trifluoroacetate salt, single enantiomer; from C23 |

TABLE 3A

Physicochemical data for Examples 30 to 32

| Ex. No. | Mass spectrum, observed ion m/z [M + H]⁺; HPLC retention time or ¹H NMR |
|---|---|
| 30 | 511.3; $^1$H NMR (600 MHz, DMSO-$d_6$), characteristic peaks: δ 9.02 (s, 1H), 8.65 (s, 1H), 8.22 (s, 1H), 8.13 (s, 1H), 7.61 (dd, 8.0, 1H), 7.52 (d, 1H), 7.34 (d, 1H), 5.46 (s, 2H), 4.95-4.71 (br m, 2H), 3.96 (s, 3H), 3.90-3.69 (br m, 2H), 3.5-3.2 (m, 2H, assumed; partially obscured by water peak), 2.22-1.92 (br m, 4H) |
| 31 | 585.1◆; 9.26 minutes (Column: Chiral Technologies Chiralcel AS-RH, 4.6 × 150 mm, 5 μm: Mobile phase A: 0.069% trifluoroacetic acid in water; Mobile phase B: acetonitrile; Eluent: 20% B; Flow rate: 0.8 mL/minute) |
| 32 | 585.1◆; 9.79 minutes (Column: Chiral Technologies Chiralcel OJ-RH, 4.6 × 150 mm, 5 μm: Mobile phase A: 0.069% trifluoroacetic acid in water; Mobile phase B: acetonitrile; Gradient: 10% to 80% B over 25 minutes; Flow rate: 0.8 mL/minute) |

Example 33

Ammonium 2-[(4-{2-[(4-chloro-2-fluorobenzyl)oxy]pyridin-3-yl}piperazin-1-yl)methyl]-1-[(2S)-oxetan-2-ylmethyl]-1H-benzimidazole-6-carboxylate (33)

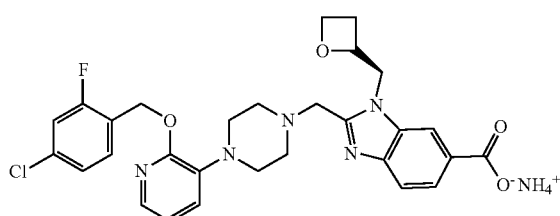

Step 1. Synthesis of methyl 4-{[(4-{2-[(4-chloro-2-fluorobenzyl)oxy]pyridin-3-yl}piperazin-1-yl)acetyl]amino}-3-{[(2S)-oxetan-2-ylmethyl]amino}benzoate (C73)

A solution of P3 (95.0 mg, 0.250 mmol), P16 (70.5 mg, 0.298 mmol) and O-(7-azabenzotriazol-1-yl)-N,N,N',N'-tetramethyluronium hexafluorophosphate (143 mg, 0.376 mmol) in N,N-dimethylformamide (1 mL) was stirred at 20° C. for 30 minutes, whereupon triethylamine (50.6 mg, 0.500 mmol) was added. After the reaction mixture had been stirred at 15° C. for 2 hours, it was diluted with EtOAc (50 mL) and washed with water (50 mL). The organic layer was washed with saturated aqueous sodium chloride solution (50 mL), dried over magnesium sulfate, filtered, and concentrated in vacuo; preparative thin-layer chromatography (Eluent: EtOAc) provided C73 as a yellow oil (150 mg), which was advanced directly to the following step.

Step 2. Synthesis of methyl 2-[(4-{2-[(4-chloro-2-fluorobenzyl)oxy]pyridin-3-yl}piperazin-1-yl)methyl]-1-[(2S)-oxetan-2-ylmethyl]-1H-benzimidazole-6-carboxylate (C74)

A solution of C73 (from the previous step; 150 mg, 50.250 mmol) in acetic acid (2 mL) was stirred at 50° C. for 16 hours, whereupon it was concentrated in vacuo to dryness, mixed with EtOAc (60 mL), and washed with saturated aqueous sodium carbonate solution (50 mL). The organic layer was dried over magnesium sulfate, filtered, concentrated under reduced pressure, and purified using preparative thin-layer chromatography (Eluent: EtOAc) to afford C74 as a yellow oil. Yield: 80.5 mg, 0.139 mmol, 56% over 2 steps.

Step 3. Synthesis of Ammonium 2-[(4-{2-[(4-chloro-2-fluorobenzyl)oxy]pyridin-3-yl}piperazin-1-yl)methyl]-1-[(2S)-oxetan-2-ylmethyl]-1H-benzimidazole-6-carboxylate (33)

A solution of C74 (80.0 mg, 0.138 mmol) and aqueous sodium hydroxide solution (3 M; 0.3 mL, 0.9 mmol) in MeOH (1 mL) and THF (1 mL) was stirred at 50° C. for 1 hour. The reaction mixture was then adjusted to pH 7 by addition of 1 M hydrochloric acid, and extracted with a mixture of dichloromethane and MeOH (10:1, 3×30 mL). The combined organic layers were dried over magnesium sulfate, filtered, and concentrated in vacuo; purification using reversed-phase HPLC (Column: Agela Durashell C18, 5 μm; Mobile phase A: 0.05% ammonium hydroxide in water; Mobile phase B: acetonitrile; Gradient: 20% to 50% B) provided 33 as a white solid. Yield: 39.7 mg, 68.0 μmol, 49%. LCMS m/z 566.0♦ [M+H]$^+$. $^1$H NMR (400 MHz, Methanol-d$_4$) δ 8.32 (d, 1H), 7.97 (dd, 1H), 7.75 (dd, 1H), 7.67 (d, 1H), 7.55 (dd, 1H), 7.28-7.20 (m, 3H), 6.92 (dd, 1H), 5.42 (s, 2H), 5.29-5.21 (m, 1H), 4.9-4.81 (m, 1H, assumed; partially obscured by water peak), 4.70 (dd, 1H), 4.66-4.59 (m, 1H), 4.46 (dt, 1H), 3.98 (AB quartet, 2H), 3.16-3.04 (br m, 4H), 2.84-2.74 (m, 1H), 2.74-2.61 (m, 4H), 2.56-2.45 (m, 1H).

Example 34

2-{[(2S)-4-{3-[(4-Chloro-2-fluorobenzyl)oxy]pyrazin-2-yl}-2-methylpiperazin-1-yl]methyl}-3-methyl-3H-imidazo[4,5-b]pyridine-5-carboxylic Acid, Trifluoroacetate Salt (34)

Step 1. Synthesis of methyl 2-{[(2S)-4-{3-[(4-chloro-2-fluorobenzyl)oxy]pyrazin-2-yl}-2-methylpiperazin-1-yl]methyl}-3-methyl-3H-imidazo[4,5-b]pyridine-5-carboxylate (C75)

To a suspension of P18 (60.0 mg, 0.198 mmol), P4 (64.8 mg, 0.237 mmol), 1,1'-binaphthalene-2,2'-diylbis(diphenylphosphane) (24.6 mg, 39.6 μmol), and tris(dibenzylideneacetone)dipalladium(0) (18.1 mg, 19.8 μmol) in toluene (2 mL) was added cesium carbonate (129 mg, 0.396 mmol). The reaction mixture was purged with nitrogen for 30 seconds and stirred at 100° C. for 16 hours, whereupon it was diluted with water (10 mL) and extracted with dichloromethane (3×10 mL). The combined organic layers were dried over sodium sulfate, filtered, and concentrated in vacuo. Preparative thin-layer chromatography (Eluent: 20:1 dichloromethane/MeOH) afforded C75 as a yellow solid. Yield: 60 mg, 0.11 μmol, 56%.

Step 2. Synthesis of 2-{[(2S)-4-{3-[(4-chloro-2-fluorobenzyl)oxy]pyrazin-2-yl}-2-methylpiperazin-1-yl]methyl}-3-methyl-3H-imidazo[4,5-b]pyridine-5-carboxylic Acid, Trifluoroacetate Salt (34)

To a solution of C75 (60 mg, 0.11 mmol) in MeOH (5 mL) was added THF (1 mL) and a solution of sodium hydroxide (22.2 mg, 0.556 mmol) in water (1 mL). After the reaction mixture had been stirred at 40° C. for 2 hours, it was concentrated in vacuo and acidified to pH 7 by addition of 1 M hydrochloric acid. The resulting mixture was extracted with dichloromethane (3×20 mL), and the combined organic layers were dried over sodium sulfate, filtered, and concentrated under reduced pressure. Purification via reversed-phase HPLC (Column: Waters XBridge C18 OBD, 5 μm; Mobile phase A: water containing 0.1% trifluoroacetic acid; Mobile phase B: acetonitrile; Gradient: 5% to 95% B) afforded 34 as a solid. Yield: 43.4 mg, 67.8 μmol, 62%. LCMS m/z 526.0♦ [M+H]$^+$. $^1$H NMR (400 MHz, Methanol-d$_4$) δ 8.20 (AB quartet, 2H), 7.80 (d, 1H), 7.70 (d, 1H), 7.54 (dd, 1H), 7.27 (dd, 1H), 7.24 (br dd, 1H), 5.49 (AB quartet, 2H), 5.01 (d, 1H), 4.68 (d, 1H), 4.14-4.01 (m, 2H), 3.99 (s, 3H), 3.87-3.69 (m, 2H), 3.67-3.40 (m, 3H), 1.49 (d, 3H).

Examples 35 and 36

Ammonium 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, from C78 (35) and Ammonium 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, from C79 (36)

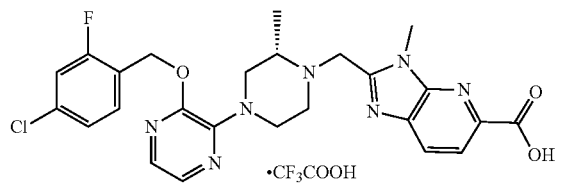

34

·CF₃COOH

C77

C78 (ENT-1)        C79 (ENT-2)

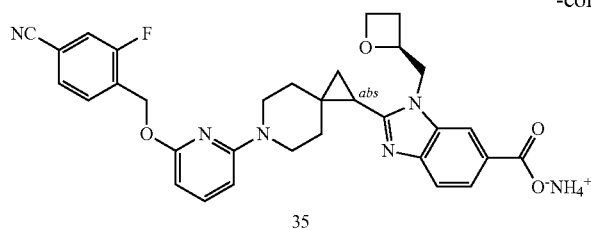

35

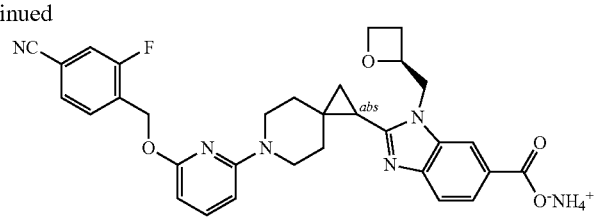

36

Step 1. Synthesis of methyl 4-{[(6-{6-[(4-cyano-2-fluorobenzyl)oxy]pyridin-2-yl}-6-azaspiro[2.5]oct-1-yl)carbonyl]amino}-3-{[(2S)-oxetan-2-ylmethyl]amino}benzoate (C76)

To a solution of P6 (530 mg, 1.39 mmol), O-(7-azabenzotriazol-1-yl)-N,N,N',N'-tetramethyluronium hexafluorophosphate (794 mg, 2.09 mmol), and N,N-diisopropylethylamine (0.70 mL, 4.1 mmol) in N,N-dimethylformamide (4.0 mL) was added a solution of P16 (324 mg, 1.37 mmol) in N,N-dimethylformamide (4.0 mL). After the reaction mixture had been stirred at 25° C. for 15 hours, it was concentrated in vacuo to remove N,N-dimethylformamide. The resulting gum was washed with saturated aqueous sodium chloride solution (20 mL), and extracted with EtOAc (3×20 mL). The combined organic layers were dried over magnesium sulfate, filtered, concentrated under reduced pressure, and purified via silica gel chromatography (Gradient: 0% to 1.3% MeOH in dichloromethane) followed by preparative thin-layer chromatography (Eluent: 4:1 EtOAc/petroleum ether). Compound C76 was isolated as a red gum. Yield: 530 mg, 0.884 mmol, 64%.

Step 2. Synthesis of methyl 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate (C77)

A solution of C76 (530 mg, 0.884 mmol) in acetic acid (5.0 mL) was stirred at 60° C. for 16 hours, whereupon it was concentrated in vacuo, washed with saturated aqueous sodium bicarbonate solution (10 mL), and extracted with EtOAc (3×20 mL). The combined organic layers were dried over sodium sulfate, filtered, and concentrated under reduced pressure. Purification was carried out twice using preparative thin-layer chromatography (Eluent for #1: 1:1 petroleum ether/EtOAc; Eluent for #2: 10:1 dichloromethane/MeOH), and then via reversed-phase HPLC (Column: Phenomenex Gemini C18, 10 μm; Mobile phase A: 0.05% ammonium hydroxide in water; Mobile phase B: acetonitrile; Gradient: 60% to 90% B), affording C77 as a solid that consisted of a mixture of two stereoisomers at the cyclopropane. Yield: 140 mg, 0.241 mmol, 27%.

Step 3. Isolation of methyl 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, ENT-1 (C78) and methyl 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, ENT-2 (C79)

Separation of C77 (185 mg, 0.318 mmol) into the component stereoisomers at the cyclopropane was carried out using supercritical fluid chromatography [Column: Chiral Technologies Chiralcel OJ-H, 5 μm; Mobile phase: 3:2 carbon dioxide/(MeOH containing 0.1% ammonium hydroxide)]. The first-eluting stereoisomer, obtained as a yellow gum, was designated as ENT-1 (C78). Yield: 80 mg, 0.14 mmol, 44%. The second-eluting stereoisomer, isolated as a green gum, was designated as ENT-2 (C79). Yield: 100 mg, 0.17 mmol, assumed 50%.

Step 4. Synthesis of Ammonium 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, from C78 (35)

A solution of C78 (75 mg, 0.13 mmol) in a mixture of THF (5.0 mL) and MeOH (2.0 mL) was treated with aqueous lithium hydroxide solution (2 M; 0.32 mL, 0.64 mmol), and the reaction mixture was stirred at 30° C. for 60 hours. It was then adjusted to pH 6 to 7 by addition of 1 M hydrochloric acid, and extracted with dichloromethane (4×15 mL); the combined organic layers were dried over magnesium sulfate, filtered, and concentrated in vacuo. Purification using reversed-phase HPLC (Column: Agela Durashell C18, 5 μm; Mobile phase A: 0.05% ammonium hydroxide in water; Mobile phase B: acetonitrile; Gradient: 20% to 40% B) afforded 35 as a white solid. Yield: 11.3 mg, 18.8 μmol, 14%. LCMS m/z 568.1 [M+H]$^+$. $^1$H NMR (400 MHz, Methanol-$d_4$) δ 8.22 (d, 1H), 7.94 (dd, 1H), 7.64-7.57 (m, 2H), 7.53-7.47 (m, 2H), 7.41 (dd, 1H), 6.27 (d, 1H), 6.09 (d, 1H), 5.40 (AB quartet, 2H), 5.23-5.15 (m, 1H), 4.69 (dd, 1H), 4.63-4.53 (m, 2H), 4.41 (dt, 1H), 3.98-3.90 (m, 1H), 3.61-3.52 (m, 1H), 3.42 (ddd, 1H), 3.23 (ddd, 1H), 2.84-2.73 (m, 1H), 2.58-2.48 (m, 1H), 2.38 (dd, 1H), 1.86 (ddd, 1H), 1.65 (dd, 1H), 1.54-1.44 (m, 2H), 1.36-1.27 (m, 1H), 1.24 (dd, 1H).

Step 5. Synthesis of Ammonium 2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylate, from C79 (36)

A solution of C79 (95 mg, 0.16 mmol) in a mixture of THF (5.0 mL) and MeOH (2.0 mL) was treated with aqueous lithium hydroxide solution (2 M; 0.40 mL, 0.80 mmol), and the reaction mixture was stirred at 30° C. for 50 hours. It was then adjusted to pH 5 to 6 by addition of 1 M hydrochloric acid, and extracted with dichloromethane (4×20 mL); the combined organic layers were dried over magnesium sulfate, filtered, and concentrated in vacuo. Purification using reversed-phase HPLC (Column: Agela Durashell C18, 5 μm; Mobile phase A: 0.05% ammonium hydroxide in water; Mobile phase B: acetonitrile; Gradient: 21% to 41% B) afforded 36 as a white solid. Yield: 21.9 mg, 38.5 μmol, 24%. LCMS m/z 568.1 [M+H]$^+$. $^1$H NMR (400 MHz, Methanol-$d_4$) δ 8.21 (d, 1H), 7.95 (dd, 1H), 7.62 (d, 1H), 7.60 (dd, 1H), 7.53-7.47 (m, 2H), 7.40 (dd, 1H), 6.25 (d, 1H), 6.08 (d, 1H), 5.40 (AB quartet, 2H), 5.28-5.20 (m, 1H), 4.69 (dd, 1H), 4.58-4.48 (m, 2H), 4.31 (dt, 1H), 3.95-3.86 (m, 1H), 3.59-3.50 (m, 1H), 3.41 (ddd, 1H), 3.22 (ddd, 1H), 2.81-2.71 (m, 1H), 2.52-2.41 (m, 2H), 1.86-1.77 (m, 1H), 1.66 (dd, 1H), 1.56-1.42 (m, 2H), 1.36-1.27 (m, 1H), 1.23 (dd, 1H).

Example 37, in Table 4 below, was synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. Example 37 was purified using methods well-known to those skilled in the art and may include silica gel chromatography, HPLC, or precipitation from the reaction mixture.

TABLE 4

Structure and IUPAC name for Example 37

| Ex. No. | Structure | IUPAC Name |
|---|---|---|
| 37 | 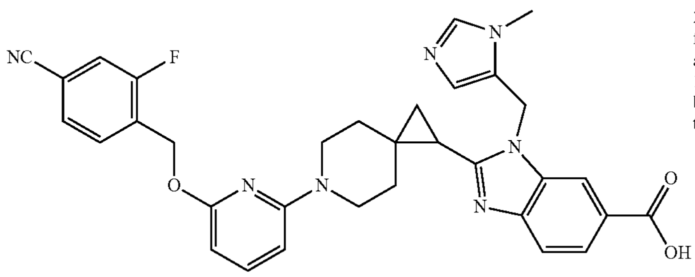 | 2-(6-{6-[(4-cyano-2-fluorobenzyl)oxy]pyridin-2-yl}-6-azaspiro[2.5]oct-1-yl)-1-[(1-methyl-1H-imidazol-5-yl)methyl]-1H-benzimidazole-6-carboxylic acid, trifluoroacetate salt |

TABLE 4A

Physicochemical data for Example 37

| Ex No. | Mass spectrum, observed ion m/z [M + H]⁺; HPLC retention time or ¹H NMR |
|---|---|
| 37 | 592.2; 2.68 minutes (Column: Waters XBridge C18, 2.1 × 50 mm, 5 μm; Mobile phase A: water containing 0.1% formic acid; Mobile phase B: acetonitrile; Gradient: 1.0% to 5% B over 0.6 minutes, then 5% to 100% B over 3.4 minutes; Flow rate: 0.8 mL/minute) |

Example 38

Ammonium 2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylate, from P7 (38)

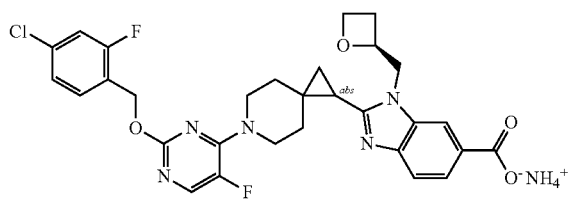

Step 1. Synthesis of methyl 4-{[(6-{2-[(4-chloro-2-fluorobenzyl)oxy]-5-fluoropyrimidin-4-yl}-6-azaspiro[2.5]oct-1-yl)carbonyl]amino}-3-{[(2S)-oxetan-2-ylmethyl]amino}benzoate, from P7 (C80)

To a solution of P16 (540 mg, 2.29 mmol) and P7 (1.03 g, 2.51 mmol) in pyridine (10 mL) was added 1-[3-(dimethylamino)propyl]-3-ethylcarbodiimide hydrochloride (1.31 g, 6.86 mmol). The reaction mixture was stirred at 30° C. for 16 hours, whereupon it was poured into water (20 mL) and extracted with EtOAc (3×20 mL). The combined organic layers were dried over sodium sulfate, filtered, and concentrated in vacuo; silica gel chromatography (Eluent: 85% EtOAc in petroleum ether) afforded C80 as a white foam. Yield: 1.4 g, 2.23 mmol, 97%.

Step 2. Synthesis of methyl 2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylate, from P7 (C81)

A solution of C80 (1.4 g, 2.2 mmol) in acetic acid (20 mL) was stirred at 60° C. for 21 hours, whereupon the reaction mixture was concentrated to dryness in vacuo and neutralized by addition of aqueous sodium bicarbonate solution (20 mL). The resulting mixture was extracted with EtOAc (3×20 mL), and the combined organic layers were dried over sodium sulfate, filtered, and concentrated in vacuo. Silica gel chromatography (Eluent: EtOAc) provided C81 as a foamy white solid. Yield: 1.1 g, 1.8 mmol, 82%.

Step 3. Synthesis of Ammonium 2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylate, from P7 (38)

Aqueous sodium hydroxide solution (2 M; 4.5 mL, 9.0 mmol) was added to a solution of C81 (1.1 g, 1.8 mmol) in a mixture of THF (11 mL) and MeOH (4.5 mL), and the reaction mixture was stirred at 25° C. for 16 hours. It was then combined with a similar reaction carried out using C81 (366 mg, 0.600 mmol), concentrated to dryness in vacuo, taken up in water (10 mL), and adjusted to pH 5 by addition of 1 M hydrochloric acid. The resulting mixture was extracted with dichloromethane (4×50 mL); the combined organic layers were dried over sodium sulfate, filtered, and concentrated under reduced pressure. Silica gel chromatography (Eluent: 20% MeOH in dichloromethane) provided a white solid, which was dissolved in acetonitrile (5 mL), and then treated with water (20 mL) and concentrated ammonium hydroxide (1 mL). This mixture was lyophilized to afford 38 as a white solid. Yield: 1.09 g, 1.78 mmol, 74%. LCMS m/z 596.0♦ [M+H]⁺. ¹H NMR (400 MHz, Methanol-d₄) δ 8.20 (d, 1H), 7.95 (dd, 1H), 7.86 (d, 1H), 7.62 (d, 1H), 7.44 (dd, 1H), 7.18-7.11 (m, 2H), 5.30 (s, 2H), 5.28-5.20 (m, 1H), 4.73 (dd, 1H), 4.59-4.49 (m, 2H), 4.34 (dt, 1H), 4.28-4.20 (m, 1H), 3.99-3.90 (m, 1H), 3.70-3.60 (m, 1H), 3.53-3.44 (m, 1H), 2.84-2.73 (m, 1H), 2.56-2.44 (m, 2H), 2.00-1.89 (m, 1H), 1.69 (dd, 1H), 1.65-1.50 (m, 2H), 1.43-1.34 (m, 1H), 1.28 (dd, 1H).

The compounds listed in Table 5 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 5

Structure and IUPAC name for Examples 39 to 45

| Ex. No. | Structure | IUPAC Name |
|---|---|---|
| 39 | 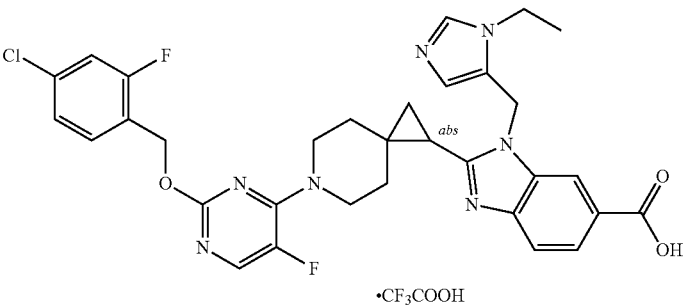 [SMILES: CCn1cncc1Cn1c(C2CC23CCN(c2nc(OCc4ccc(Cl)cc4F)ncc2F)CC3)nc2ccc(C(=O)O)cc21 ; "·CF3COOH"] | 2-(6-{2-[(4-chloro-2-fluorobenzyl)oxy]-5-fluoropyrimidin-4-yl}-6-azaspiro[2.5]oct-1-yl)-1-[(1-ethyl-1H-imidazol-5-yl)methyl]-1H-benzimidazole-6-carboxylic acid, trifluoroacetate salt, from P7 |
| 40[1] | 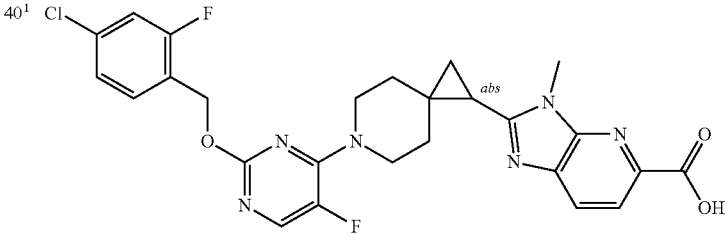 | 2-(6-{2-[(4-chloro-2-fluorobenzyl)oxy]-5-fluoropyrimidin-4-yl}-6-azaspiro[2.5]oct-1-yl)-3-methyl-3H-imidazo[4,5-b]pyridine-5-carboxylic acid, trifluoroacetate salt, from P7 |
| 41[2] | 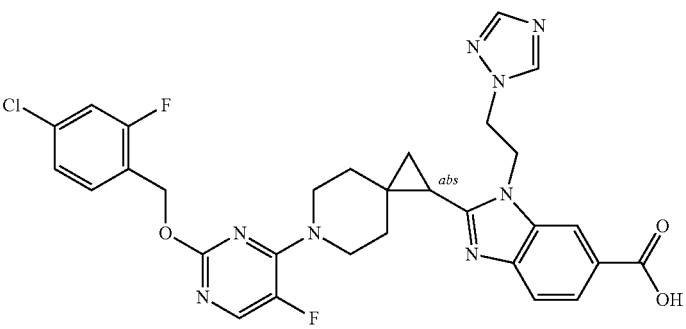 | 2-(6-{2-[(4-chloro-2-fluorobenzyl)oxy]-5-fluoropyrimidin-4-yl}-6-azaspiro[2.5]oct-1-yl)-1-[2-(1H-1,2,4-triazol-1-yl)ethyl]-1H-benzimidazole-6-carboxylic acid, trifluoroacetate salt, from P7 |

TABLE 5-continued

Structure and IUPAC name for Examples 39 to 45

| Ex. No. | Structure | IUPAC Name |
|---|---|---|
| 42[3] | 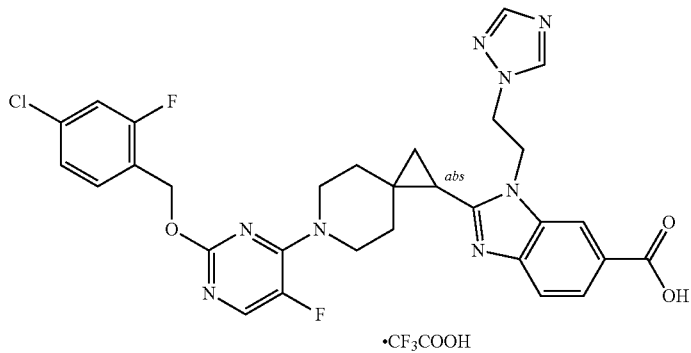 [SMILES: O=C(O)c1ccc2nc(C3CC34CCN(c3nc(OCc5ccc(Cl)cc5F)ncc3F)CC4)n(CCn3cncn3)c2c1 ; "·CF3COOH"] | 2-(6-{2-[(4-chloro-2-fluorobenzyl)oxy]-5-fluoropyrimidin-4-yl}-6-azaspiro[2.5]oct-1-yl)-1-[2-(1H-1,2,4-triazol-1-yl)ethyl]-1H-benzimidazole-6-carboxylic acid, trifluoroacetate salt, from C23 |
| 43 | 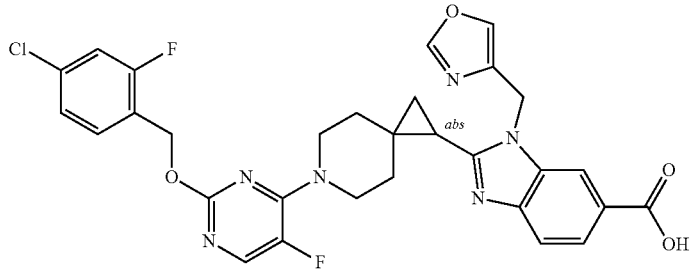 | 2-(6-{2-[(4-chloro-2-fluorobenzyl)oxy]-5-fluoropyrimidin-4-yl}-6-azaspiro[2.5]oct-1-yl)-1-(1,3-oxazol-4-ylmethyl)-1H-benzimidazole-6-carboxylic acid, trifluoroacetate salt, from P7 |
| 44 | 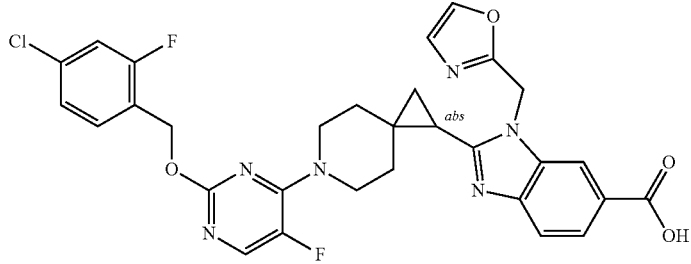 | 2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid, trifluoroacetate salt, from P7 |
| 45 | 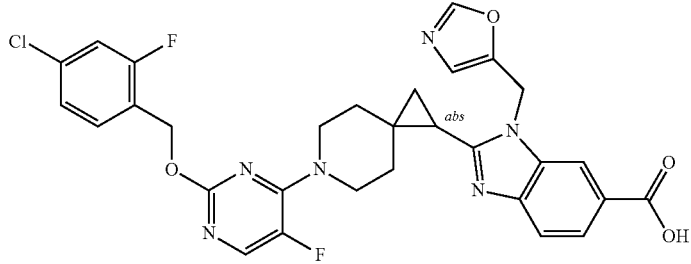 | 2-(6-{2-[(4-chloro-2-fluorobenzyl)oxy]-5-fluoropyrimidin-4-yl}-6-azaspiro[2.5]oct-1-yl)-1-(1,3-oxazol-5-ylmethyl)-1H-benzimidazole-6-carboxylic acid, trifluoroacetate salt, from P7 |

TABLE 5A

Physicochemical data for Examples 39 to 45

| Ex. No. | Mass spectrum, observed ion m/z [M + H]$^+$; HPLC retention time or $^1$H NMR |
|---|---|
| 39 | 634.1♦; 2.02 minutes (Column: Chiral Technologies Chiralpak AD-3, 4.6 × 50 mm, 3 μm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.) |
| 40[1] | 541.1♦; 3.54 minutes (Column: Chiral Technologies Chiralpak AS-3, 4.6 × 100 mm, 3 μm; Mobile phase A: carbon dioxide; Mobile phase B: 0.05% diethylamine in ethanol; Gradient: 5% to 40% B for 4.5 minutes, then 40% B over 2.5 minutes; Flow rate: 2.8 mL/minute; Column temperature: 40° C.) |
| 41[2] | 621.3♦; 5.81 minutes (Column: Chiral Technologies Chiralpak AD-3, 4.6 × 100 mm, 3 μm; Mobile phase A: carbon dioxide; Mobile phase B: 0.05% diethylamine in ethanol; Gradient: 5% to 40% B over 4.5 minutes, then 40% B over 2.5 minutes; Flow rate: 2.8 mL/minute; Column temperature: 40° C.) |
| 42[3] | 621.3♦; 4.96 minutes (Analytical conditions identical to those used for Example 41) |
| 43 | 607.1♦; 3.51 minutes (Column: Chiral Technologies Chiralcel OJ-3, 4.6 × 100 mm, 3 μm; Mobile phase A: carbon dioxide; Mobile phase B: 0.05% diethylamine in MeOH; Gradient: 5% to 40% B over 4.5 minutes, then 40% B for 2.5 minutes; Flow rate: 2.8 mL/minute; Column temperature: 40° C.) |
| 44 | 607.1♦; 1.49 minutes (Column: Chiral Technologies Chiralcel OJ-3, 4.6 × 50 mm, 3 μm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.) |
| 45 | 607.1♦; 3.84 minutes (Analytical conditions identical to those used for Example 43) |

Table 5/5A:[1]The amide product from coupling of P7 with C60 was cyclized by heating in trimethylsilyl polyphosphate at 120° C. for 30 minutes, affording a single enantiomer of 5-chloro-2-(6-{2-[(4-chloro-2-fluorobenzyl)oxy]-5-fluoropyrimidin-4-yl}-6-azaspiro[2.5]oct-1-yl)-3-methyl-3H-imidazo[4,5-b]pyridine.
[2]The amide product from coupling of P7 with methyl 4-amino-3-{[2-(1H-1,2,4-triazol-1-yl)ethyl]amino}benzoate was cyclized by heating at elevated temperature with aqueous sodium hydroxide solution in 1,4-dioxane; ester hydrolysis was also effected, providing Example 41 after purification.
[3]The amide product from coupling of C23 with methyl 4-amino-3-{[2-(1H-1,2,4-triazol-1-yl)ethyl]amino}benzoate was cyclized by heating to elevated temperature with aqueous sodium hydroxide solution in 1,4-dioxane; ester hydrolysis was also effected, providing Example 42 after purification.

Examples 46 and 47

Ammonium 2-(6-{2-[(4-chloro-2-fluorobenzyl)oxy]pyrimidin-4-yl}-6-azaspiro[2.5]oct-1-yl)-1-(2-methoxyethyl)-1H-benzimidazole-6-carboxylate, ENT-1 (46) and Ammonium 2-(6-{2-[(4-chloro-2-fluorobenzyl)oxy]pyrimidin-4-yl}-6-azaspiro[2.5]oct-1-yl)-1-(2-methoxyethyl)-1H-benzimidazole-6-carboxylate, ENT-2 (47)

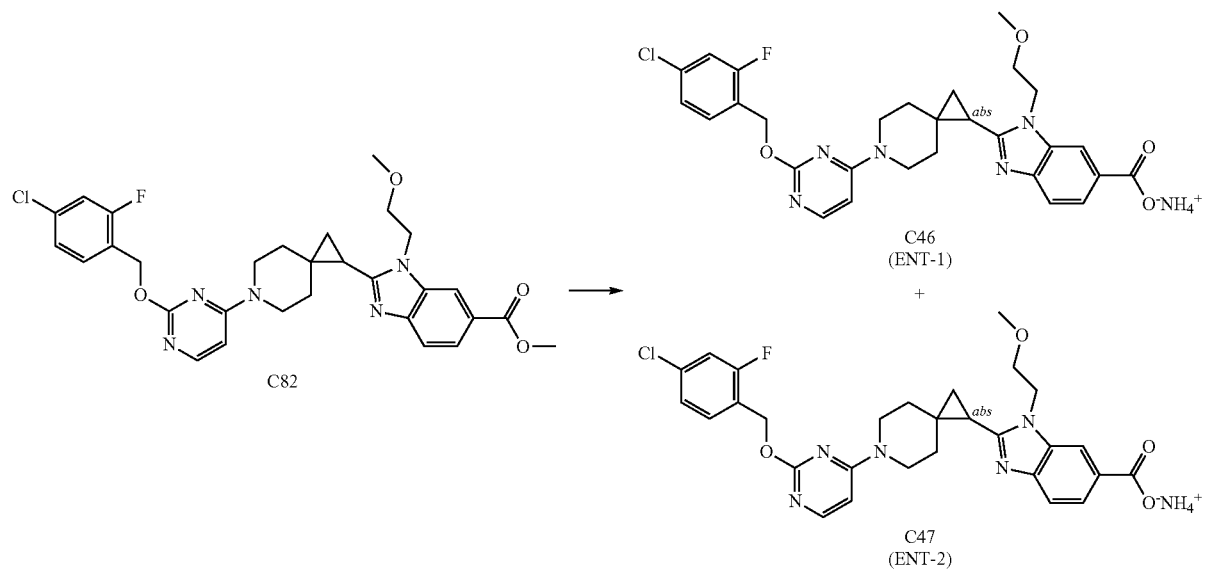

Step 1. Synthesis of methyl 2-(6-{2-[(4-chloro-2-fluorobenzyl)oxy]pyrimidin-4-yl}-6-azaspiro[2.5]oct-1-yl)-1-(2-methoxyethyl)-1H-benzimidazole-6-carboxylate (C82)

A vial containing a mixture of P8 (61 mg, 0.22 mmol), P19 (55 mg, 0.16 mmol), tris(dibenzylideneacetone)dipalladium(0) (14.7 mg, 16.0 μmol), 1,1'-binaphthalene-2,2'-diylbis(diphenylphosphane) (20 mg, 32 μmol), and cesium carbonate (104 mg, 0.319 mmol) was evacuated and then purged with nitrogen for 10 minutes. After addition of 1,4-dioxane (0.8 mL), the reaction mixture was heated to 100° C. for 23 hours, whereupon it was diluted with dichloromethane (0.5 mL) and directly purified via silica gel chromatography (Gradient: 15% to 100% EtOAc in heptane). Compound C82 was isolated as a yellow solid (37.5 mg), which was taken directly into the following reaction.

Step 2. Synthesis of Ammonium 2-(6-{2-[(4-chloro-2-fluorobenzyl)oxy]pyrimidin-4-yl}-6-azaspiro[2.5]oct-1-yl)-1-(2-methoxyethyl)-1H-benzimidazole-6-carboxylate, ENT-1 (46) and Ammonium 2-(6-{2-[(4-chloro-2-fluorobenzyl)oxy]pyrimidin-4-yl}-6-azaspiro[2.5]oct-1-yl)-1-(2-methoxyethyl)-1H-benzimidazole-6-carboxylate, ENT-2 (47)

Aqueous sodium hydroxide solution (2 M; 150 μL, 0.3 mmol) was added to a mixture of C82 (from the previous step; 37.5 mg, 564.6 μmol) in MeOH (0.4 mL) and THF (0.4 mL). The reaction mixture stirred at 35° C. for 2.25 hours, whereupon hydrochloric acid (1 M; 0.35 mL, 0.35 mmol) was added, and the reaction mixture was allowed to cool to room temperature. After removal of solvents in vacuo, the residue was separated into its component enantiomers using supercritical fluid chromatography [Column: Chiral Technologies Chiralpak AD-H, 5 μm; Mobile phase: 65:35 carbon dioxide/(MeOH containing 0.2% ammonium hydroxide)]. The first-eluting enantiomer was designated as ENT-1 (46). Yield: 4.3 mg, 7.3 μmol, 5% over 2 steps. LCMS m/z 566.4◆ [M+H]⁺. Retention time: 2.12 minutes [Analytical conditions, Column: Chiral Technologies Chiralpak AD-H, 4.6×100 mm, 5 μm; Mobile phase: 1:1 carbon dioxide/(MeOH containing 0.2% ammonium hydroxide); Flow rate: 1.5 mL/minute; Back pressure: 120 bar].

The second-eluting enantiomer was designated as ENT-2 (47). Yield: 4.1 mg, 7.0 μmol, 4% over 2 steps. LCMS m/z 566.4◆ [M+H]⁺. Retention time: 2.74 minutes (Analytical conditions identical to those used for 46).

The compounds listed in Table 6 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 6

Structure and IUPAC name for Examples 48 and 49

| Ex. No. | Structure | IUPAC Name |
|---|---|---|
| 48[1] | 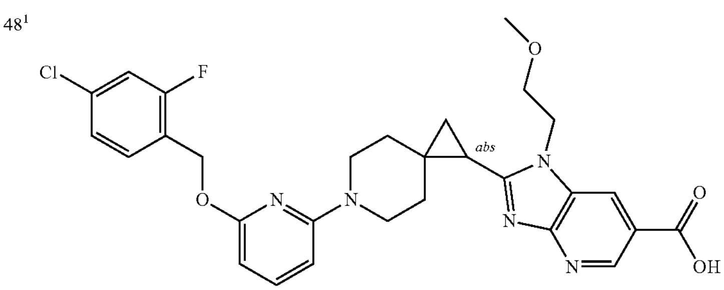 | 2-(6-{6-[(4-chloro-2-fluorobenzyl)oxy]pyridin-2-yl}-6-azaspiro[2.5]oct-1-yl)-1-(2-methoxyethyl)-1H-imidazo[4,5-b]pyridine-6-carboxylic acid, ENT-1[1,2] |
| 49[1] | 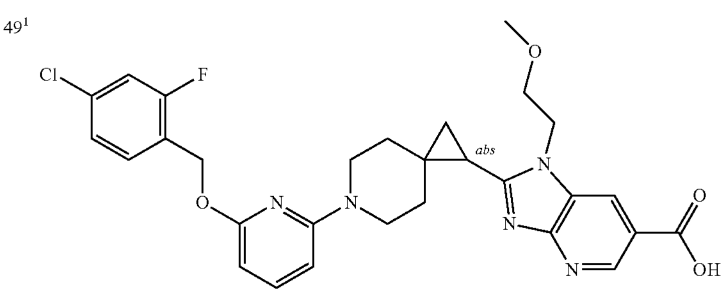 | 2-(6-{6-[(4-chloro-2-fluorobenzyl)oxy]pyridin-2-yl}-6-azaspiro[2.5]oct-1-yl)-1-(2-methoxyethyl)-1H-imidazo[4,5-b]pyridine-6-carboxylic acid, ENT-2[1,2] |

[1]In this case, the coupling between P30 and 2-chloro-6-[(4-chloro-2-fluorobenzyl)oxy]pryidine was catalyzed by chloro(2-dicyclohexylphosphino-2',6'-diisopropoxy-1,1'-biphenyl)[2-(2'-amino-1,1'-biphenyl)]palladium(II) (RuPhos Pd G2) and 2-dicyclohexylphosphino-2',6'-diisopropxybiphenyl.

[2]A racemic mixture of Examples 48 and 49 was separated into its component enantiomers using supercritical fluid chromatography [Column: Phenomenex Lux Cellulose-2, 5 μm; Mobile phase: 7:3 carbon dioxide/(MeOH containing 0.2% ammonium hydroxide and 5% water)]. The first-eluting enantiomer was designated as ENT-1 (48), and the second-eluting enantiomer was designated as ENT-2 (49).

TABLE 6A

Physicochemical data for Examples 48 and 49

| Ex. No. | Mass spectrum, observed ion m/z [M + H]⁺; HPLC retention time or ¹H NMR |
|---|---|
| 48 | 566.3; 8.04 minutes [Column: Phenomenex Lux Cellulose-2, 4.6 × 100 mm, 5 µm; Mobile phase: 3:2 carbon dioxide/(MeOH containing 0.2% ammonium hydroxide and 5% water); Flow rate: 1.5 mL/minute; Column temperature: 40° C.; Back pressure: 200 bar] |
| 49 | 566.3; 11.33 minutes (Analytical conditions identical to those used for Ex. 48) |

Example 50 and 51

Ammonium 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate, from C85 (50) and Ammonium 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate, from C86 (51)

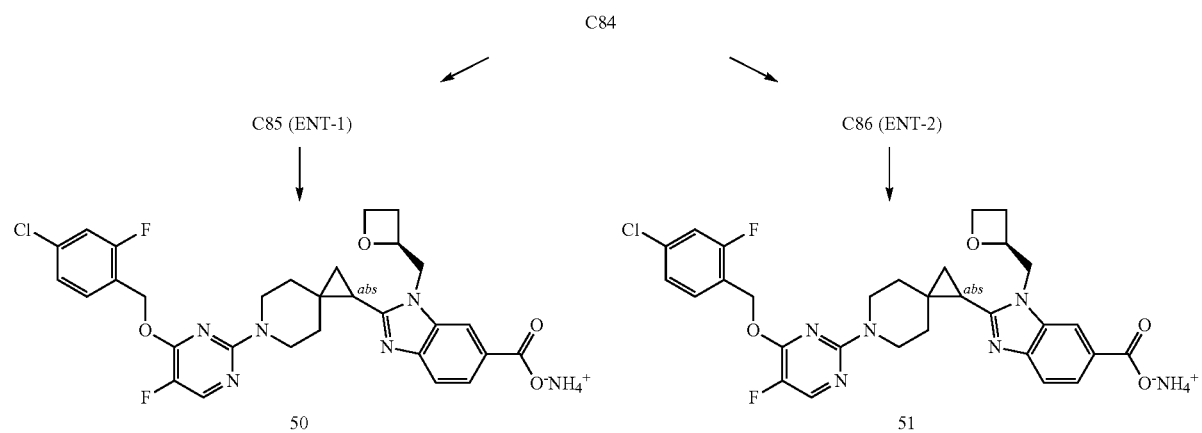

Step 1. Synthesis of methyl 4-{[(6-{4-[(4-chloro-2-fluorobenzyl)oxy]-5-fluoropyrimidin-2-yl}-6-azaspiro[2.5]oct-1-yl)carbonyl]amino}-3-{[(2S)-oxetan-2-ylmethyl]amino}benzoate (C83)

Reaction of P16 with P9 was carried out using the method described for synthesis of C80 from P16 and P7 in Example 38. In this case, purification was carried out using silica gel chromatography (Gradient: 0% to 2.1% MeOH in dichloromethane), affording C83, a mixture of stereoisomers at the cyclopropane, as a yellow foamy solid. Yield: 504 mg, 0.802 mmol, 94%.

Step 2. Synthesis of methyl 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate (C84)

A solution of C83 (270 mg, 0.430 mmol) in acetic acid (4.5 mL) was stirred at 60° C. for 7 hours, whereupon it was poured into water, basified to pH 8 by addition of sodium carbonate, and extracted with EtOAc (3×30 mL). The combined organic layers were dried over sodium sulfate, filtered, concentrated in vacuo, and purified via silica gel chromatography (Gradient: 0% to 80% EtOAc in petroleum ether) to provide C84, a mixture of stereoisomers at the cyclopropane, as a yellow oil. Yield: 250 mg, 0.410 mmol, 95%.

Step 3. Isolation of methyl 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate, ENT-1 (C85) and methyl 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate, ENT-2 (C86)

Separation of C84 (250 mg, 0.410 mmol) into its component stereoisiomers at the cyclopropane center was carried out via supercritical fluid chromatography [Column: Chiral Technologies Chiralcel OJ-H, 5 µm; Mobile phase: 3:2 carbon dioxide/(ethanol containing 0.1% ammonium hydroxide)]. This first-eluting stereoisomer, a colorless oil, was designated as ENT-1 (C85). Yield: 104 mg, 0.170 mmol, 41%.

The second-eluting stereoisomer, a white solid, was designated as ENT-2 (C86). Yield: 109 mg, 0.179 mmol, 44%.

Step 4. Synthesis of Ammonium 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate, from C85 (50)

Aqueous sodium hydroxide solution (0.767 mL, 2 M, 1.53 mmol) was added to a solution of C85 (104 mg, 0.170 mmol) in MeOH (3 mL). After the reaction mixture had stirred at 30° C. for 6 hours, it was acidified by careful

Examples 52 and 53

Ammonium 2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylate, ENT-1 (52) and Ammonium 2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylate, ENT-2 (53)

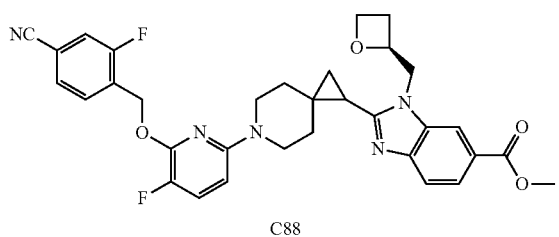

C88

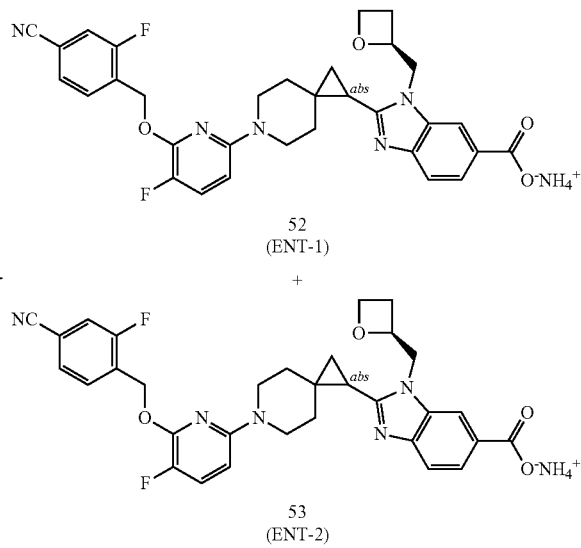

52
(ENT-1)

+

53
(ENT-2)

addition of 12 M hydrochloric acid, diluted with water (30 mL), and extracted with dichloromethane (3×30 mL). The combined organic layers were dried over sodium sulfate, filtered, concentrated in vacuo, and purified via reversed-phase HPLC (Column: Phenomenex Gemini C18, 10 μm; Mobile phase A: 0.05% ammonium hydroxide in water; Mobile phase B: acetonitrile; Gradient: 25% to 55% B) to afford 50 as a white solid. Yield: 47.1 mg, 76.8 μmol, 45%. LCMS m/z 596.0♦ [M+H]$^+$. $^1$H NMR (400 MHz, Methanol-d$_4$) δ 8.20 (d, 1H), 7.97-7.92 (m, 2H), 7.61 (d, 1H), 7.45 (dd, 1H), 7.20-7.13 (m, 2H), 5.42 (s, 2H), 5.28-5.20 (m, 1H), 4.70 (dd, 1H), 4.58-4.49 (m, 2H), 4.33 (dt, 1H), 4.24-4.16 (m, 1H), 3.92-3.83 (m, 1H), 3.56 (ddd, 1H), 3.39 (ddd, 1H), 2.82-2.71 (m, 1H), 2.54-2.42 (m, 2H), 1.90-1.80 (m, 1H), 1.68 (dd, 1H), 1.54-1.43 (m, 2H), 1.35-1.28 (m, 1H), 1.25 (dd, 1H).

Step 5. Synthesis of Ammonium 2-(6-{4-[(4-chloro-2-fluorobenzyl)oxy]-5-fluoropyrimidin-2-yl}-6-azaspiro[2.5]oct-1-yl)-1-[(2S)-oxetan-2-ylmethyl]-1H-benzimidazole-6-carboxylate, from C86 (51)

Conversion of C86 to 51 was carried out using the method described for synthesis of 50 from C85 in step 4 above. Compound 51 was isolated as a white solid. Yield: 46.0 mg, 75.0 μmol, 42%. LCMS m/z 596.0♦ [M+H]$^+$. $^1$H NMR (400 MHz, Methanol-d$_4$) δ 8.23 (d, 1H), 7.97 (d, 1H), 7.95 (dd, 1H), 7.62 (d, 1H), 7.45 (dd, 1H), 7.20-7.13 (m, 2H), 5.43 (s, 2H), 5.23-5.15 (m, 1H), 4.70 (dd, 1H), 4.63-4.54 (m, 2H), 4.40 (dt, 1H), 4.29-4.21 (m, 1H), 3.96-3.87 (m, 1H), 3.57 (ddd, 1H), 3.41 (ddd, 1H), 2.85-2.74 (m, 1H), 2.59-2.48 (m, 1H), 2.42 (dd, 1H), 1.95-1.86 (m, 1H), 1.67 (dd, 1H), 1.54-1.42 (m, 2H), 1.36-1.24 (m, 2H).

Step 1. Synthesis of methyl 4-{[(6-{6-[(4-cyano-2-fluorobenzyl)oxy]-5-fluoropyridin-2-yl}-6-azaspiro[2.5]oct-1-yl)carbonyl]amino}-3-{[(2S)-oxetan-2-ylmethyl]amino}benzoate (C87)

To a solution of P10 (695 mg, 1.74 mmol), P16 (411 mg, 1.74 mmol), and O-(7-azabenzotriazol-1-yl)-N,N,N',N'-tetramethyluronium hexafluorophosphate (860 mg, 2.26 mmol) in N,N-dimethylformamide (7 mL) was added triethylamine (880 mg, 8.70 mmol). The reaction mixture was stirred at 35° C. for 16 hours, whereupon it was combined with a similar reaction carried out using P10 (50 mg, 0.12 mmol), poured into water (20 mL), and extracted with EtOAc (3×20 mL). The combined organic layers were washed with aqueous ammonium chloride solution (2×30 mL), dried over sodium sulfate, filtered, and concentrated in vacuo. Purification was carried out via silica gel chromatography (Eluent: 80% EtOAc in petroleum ether) followed by preparative thin-layer chromatography (Eluent: EtOAc) to provide C87, a mixture of stereoisomers at the cyclopropane, as a yellow foam. Combined yield: 525 mg, 0.850 mmol, 46%.

Step 2. Synthesis of methyl 2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylate (C88)

A solution of C87 (351 mg, 0.568 mmol) in acetic acid (4 mL) was stirred at 60° C. for 16 hours, whereupon it was combined with a similar reaction carried out using C87 (174 mg, 0.282 mmol) and concentrated to dryness in vacuo. The residue was neutralized with aqueous sodium bicarbonate solution and extracted with dichloromethane (3×10 mL); the combined organic layers were dried over sodium sulfate, filtered, and concentrated under reduced pressure to afford C88, a mixture of stereoisomers at the cyclopropane, as a yellow, foamy solid. Combined yield: 510 mg, 0.850 mmol, quantitative.

Step 3. Synthesis of Ammonium 2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylate, ENT-1 (52) and Ammonium 2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylate, ENT-2 (53)

To a solution of C88 (490 mg, 0.817 mmol) in a mixture of THF (8 mL) and MeOH (1 mL) was added aqueous lithium hydroxide solution (2 M; 1.63 mL, 3.26 mmol), and the reaction mixture was stirred at 25° C. for 16 hours. It was then combined with a similar reaction carried out using C88 (20 mg, 33 μmol), concentrated in vacuo, and diluted with water (5 mL). The resulting mixture was adjusted to pH 6 by addition of 1 M hydrochloric acid and extracted with a mixture of dichloromethane and MeOH (9:1, 3×10 mL). After the combined organic layers had been dried over sodium sulfate, they were filtered, concentrated in vacuo, and purified using reversed-phase HPLC (Column: Agela Durashell C18, 5 μm; Mobile phase A: 0.05% ammonium hydroxide in water; Mobile phase B: acetonitrile; Gradient: 17% to 47% B) to provide a mixture of stereoisomers at the cyclopropane center 52 and 53 (161 mg, 0.275 mmol, 32%) as a white solid.

The stereoisomers at the cyclopropane center were separated using supercritical fluid chromatography [Column: Chiral Technologies Chiralcel OJ-H, 5 μm; Mobile phase: 3:2 carbon dioxide/(ethanol containing 0.1% ammonium hydroxide)]. The first-eluting stereoisomer, obtained as a white solid, was designated as ENT-1 (52). Yield: 49.2 mg, 81.6 μmol, 30% for the separation. LCMS m/z 586.1 [M+H]⁺. ¹H NMR (400 MHz, Methanol-d₄) δ 8.23 (s, 1H), 7.94 (d, 1H), 7.67-7.59 (m, 2H), 7.55-7.49 (m, 2H), 7.28 (dd, 1H), 6.22 (dd, 1H), 5.48 (AB quartet, 2H), 5.23-5.14 (m, 1H), 4.70 (dd, 1H), 4.63-4.54 (m, 2H), 4.41 (dt, 1H), 3.90-3.82 (m, 1H), 3.54-3.45 (m, 1H), 3.38 (ddd, 1H), 3.19 (ddd, 1H), 2.84-2.73 (m, 1H), 2.59-2.48 (m, 1H), 2.39 (dd, 1H), 1.88 (ddd, 1H), 1.69-1.62 (m, 1H), 1.56-1.46 (m, 2H), 1.38-1.30 (m, 1H), 1.24 (dd, 1H).

The second-eluting stereoisomer, which was also isolated as a white solid, was designated as ENT-2 (53). Yield: 37.9 mg, 62.9 μmol, 23% for the separation. LCMS m/z 586.1 [M+H]⁺. ¹H NMR (400 MHz, Methanol-d₄) δ 8.21 (d, 1H), 7.94 (dd, 1H), 7.66-7.59 (m, 2H), 7.55-7.50 (m, 2H), 7.26 (dd, 1H), 6.20 (dd, 1H), 5.47 (AB quartet, 2H), 5.29-5.20 (m, 1H), 4.70 (dd, 1H), 4.58-4.48 (m, 2H), 4.32 (dt, 1H), 3.87-3.78 (m, 1H), 3.51-3.43 (m, 1H), 3.37 (ddd, 1H), 3.17 (ddd, 1H), 2.82-2.71 (m, 1H), 2.53-2.41 (m, 2H), 1.84 (ddd, 1H), 1.65 (dd, 1H), 1.59-1.44 (m, 2H), 1.38-1.27 (m, 1H), 1.23 (dd, 1H).

Examples 54 and 55

Ammonium 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate, from C92 (54) and Ammonium 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate, from C93 (55)

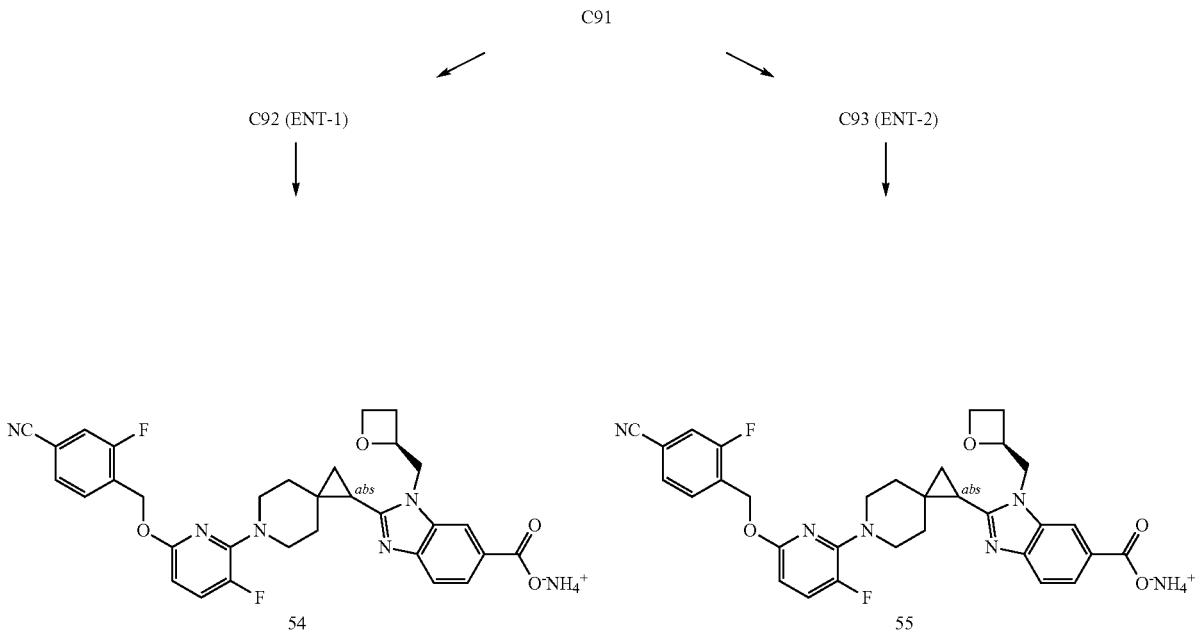

Step 1. Synthesis of methyl 4-({[6-(6-bromo-3-fluoropyridin-2-yl)-6-azaspiro[2.5]oct-1-yl]carbonyl}amino)-3-{[(2S)-oxetan-2-ylmethyl]amino}benzoate (C89)

Using the method described for synthesis of C73 in Example 33, P11 was reacted with P16. Chromatography on silica gel afforded C89, a mixture of stereoisomers at the cyclopropane, as an off-white solid. Yield: 1.31 g, 2.39 mmol, 79%.

Step 2. Synthesis of methyl 2-[6-(6-bromo-3-fluoropyridin-2-yl)-6-azaspiro[2.5]oct-1-yl]-1-[(2S)-oxetan-2-ylmethyl]-1H-benzimidazole-6-carboxylate (C90)

A solution of C89 (900 mg, 1.64 mmol) in acetic acid (18 mL) was stirred at 60° C. for 16 hours, whereupon it was diluted with water (200 mL), carefully neutralized by addition of sodium carbonate, and extracted with EtOAc (3×100 mL). The combined organic layers were dried over sodium sulfate, filtered, and concentrated under reduced pressure; the residue was combined with the product of a similar reaction carried out using C89 (400 mg, 0.731 mmol) and purified using chromatography on silica gel (Gradient: 0% to 60% EtOAc in petroleum ether) to afford C90, a mixture of stereoisomers at the cyclopropane, as a white solid. Combined yield: 823 mg, 1.55 mmol, 65%.

Step 3. Synthesis of methyl 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate (C91)

A mixture of C90 (400 mg, 0.756 mmol), 3-fluoro-4-(hydroxymethyl)benzonitrile (228 mg, 1.51 mmol), 4,5-bis(diphenylphosphino)-9,9-dimethylxanthene (Xantphos; 43.7 mg, 75.6 µmol), palladium(II) acetate (8.48 mg, 37.8 µmol), and cesium carbonate (739 mg, 2.27 mmol) in toluene (8 mL) was stirred at 100° C. for 2 hours. The reaction mixture was combined with a similar reaction carried out using C90 (100 mg, 0.189 mmol), diluted with dichloromethane (50 mL), and filtered. The filtrate was then concentrated in vacuo and purified using silica gel chromatography (Gradient: 0% to 45% EtOAc in petroleum ether) to afford C91, a mixture of stereoisomers at the cyclopropane, as a light yellow foamy solid. Combined yield: 385 mg, 0.642 mmol, 68%.

Step 4. Isolation of methyl 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate, ENT-1 (C92) and methyl 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate, ENT-2 (C93)

The stereoisomers at the cyclopropane comprising C91 (385 mg, 0.642 mmol) were separated using supercritical fluid chromatography [Column: Chiral Technologies Chiralpak AD, 5 µm; Mobile phase: 3:2 carbon dioxide/(ethanol containing 0.1% ammonium hydroxide)]. The first-eluting stereoisomer, isolated as a white foam, was designated as ENT-1 (C92). Yield: 192 mg, 0.320 mmol, 50%.

The second-eluting stereoisomer, also isolated as a white foam, was designated as ENT-2 (C93). Yield: 193 mg, 0.322 mmol, 50%.

Step 5. Synthesis of Ammonium 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate, from C92. (54)

To a solution of C92 (100 mg, 0.167 mmol) in a mixture of THF (1 mL) and MeOH (1 mL) was added aqueous lithium hydroxide solution (2 M; 0.834 mL, 1.67 mmol). After the reaction mixture had been stirred at 30° C. for 3 hours, it was carefully neutralized by addition of 12 M hydrochloric acid, diluted with water (30 mL), and extracted with dichloromethane (3×50 mL). The combined organic layers were dried over sodium sulfate, filtered, and concentrated in vacuo; the residue was combined with the product of a similar reaction carried out using C92 (90 mg, 0.15 mmol) and purified via reversed-phase HPLC (Column: Agela Durashell C18, 5 µm; Mobile phase A: 0.05% ammonium hydroxide in water; Mobile phase B: acetonitrile; Gradient: 27% to 47% B) to provide 54 as a white solid. Combined yield: 39 mg, 65 µmol, 20%. LCMS m/z 586.1 [M+H]$^+$. $^1$H NMR (400 MHz, Methanol-d$_4$) δ 8.24 (d, 1H), 7.95 (dd, 1H), 7.62 (d, 1H), 7.60 (dd, 1H), 7.51 (dd, 1H), 7.47 (dd, 1H), 7.28 (dd, 1H), 6.22 (dd, 1H), 5.39 (s, 2H), 5.26-5.17 (m, 1H), 4.72 (dd, component of ABX pattern, 1H), 4.66-4.55 (m, 2H), 4.43 (dt, 1H), 3.84-3.74 (m, 1H), 3.50-3.34 (m, 2H), 3.19 (ddd, 1H), 2.87-2.75 (m, 1H), 2.61-2.49 (m, 1H), 2.39 (dd, 1H), 1.95 (ddd, 1H), 1.65 (dd, 1H), 1.61-1.49 (m, 2H), 1.42-1.32 (m, 1H), 1.23 (dd, 1H).

Step 6. Synthesis of Ammonium 2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylate, from C93. (55)

Conversion of C93 to 55 was carried out using the method described for synthesis of 54 from C92 in step 5 above. Compound 55 was obtained as a white solid. Yield: 59.4 mg, 98.5 µmol, 31%. LCMS m/z 586.1 [M+H]$^+$. $^1$H NMR (400 MHz, Methanol-d$_4$) δ 8.23 (d, 1H), 7.95 (dd, 1H), 7.62 (d, 1H), 7.59 (dd, 1H), 7.51 (dd, 1H), 7.46 (dd, 1H), 7.26 (dd, 1H), 6.20 (dd, 1H), 5.38 (s, 2H), 5.30-5.22 (m, 1H), 4.71 (dd, 1H), 4.61-4.50 (m, 2H), 4.35 (dt, 1H), 3.80-3.72 (m, 1H), 3.47-3.33 (m, 2H), 3.17 (ddd, 1H), 2.83-2.72 (m, 1H), 2.54-2.46 (m, 1H), 2.44 (dd, 1H), 1.95-1.84 (m, 1H), 1.65 (dd, 1H), 1.62-1.47 (m, 2H), 1.39-1.31 (m, 1H), 1.22 (dd, 1H).

Examples 56, 57, and 58

Ammonium 2-(6-{6-[(4-cyano-2-fluorobenzyl)oxy]-3,5-difluoropyridin-2-yl}-6-azaspiro[2.5]oct-1-yl)-1-[(2S)-oxetan-2-ylmethyl]-1H-benzimidazole-6-carboxylate (56), Ammonium 2-(6-{6-[(4-cyano-2-fluorobenzyl)oxy]-3,5-difluoropyridin-2-yl}-6-azaspiro[2.5]oct-1-yl)-1-[(2S)-oxetan-2-ylmethyl]-1H-benzimidazole-6-carboxylate, ENT-1 (57), and Ammonium 2-(6-{6-[(4-cyano-2-fluorobenzyl)oxy]-3,5-difluoropyridin-2-yl}-6-azaspiro[2.5]oct-1-yl)-1-[(2S)-oxetan-2-ylmethyl]-1H-benzimidazole-6-carboxylate, ENT-2 (58)

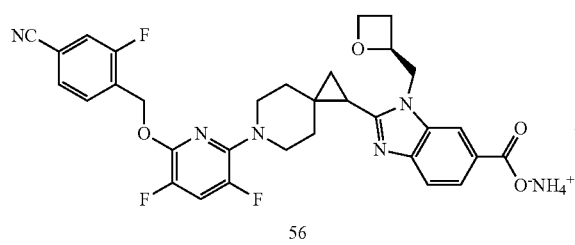

56

→

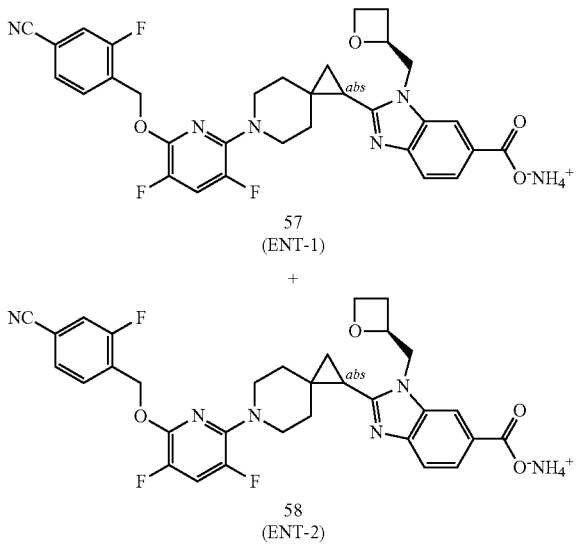

57
(ENT-1)

+

58
(ENT-2)

Step 1. Synthesis of methyl 2-(6-{6-[(4-cyano-2-fluorobenzyl)oxy]-3,5-difluoropyridin-2-yl}-6-azaspiro[2.5]oct-1-yl)-1-[(2S)-oxetan-2-ylmethyl]-1H-benzimidazole-6-carboxylate (C94)

To a solution of P12 (488 mg, 1.17 mmol) and O-(7-azabenzotriazol-1-yl)-N,N,N',N'-tetramethyluronium hexafluorophosphate (522 mg, 1.37 mmol) in N,N-dimethylformamide (8 mL) were added P16 (276 mg, 1.17 mmol) and N,N-diisopropylethylamine (515 mg, 3.99 mmol). The reaction mixture was stirred at 25° C. for 16 hours, whereupon it was diluted with water (35 mL) and extracted with EtOAc (3×30 mL). The combined organic layers were washed with saturated aqueous sodium chloride solution (2×25 mL), dried over sodium sulfate, filtered, and concentrated in vacuo; silica gel chromatography (Gradient: 0% to 60% EtOAc in petroleum ether) provided the intermediate amide (500 mg, 0.787 mmol, 67%) as a colorless gum. This material was dissolved in acetic acid and heated at 60° C. for 16 hours, whereupon it was combined with a similar reaction mixture (derived from P12, 52.2 mg, 0.125 mmol) and concentrated in vacuo. The residue was dissolved in dichloromethane (25 mL) and washed with saturated aqueous sodium bicarbonate solution (30 mL). The aqueous layer was extracted with dichloromethane (2×20 mL), and the combined organic layers were dried over sodium sulfate, filtered, and concentrated in vacuo. Preparative thin-layer chromatography (Eluent: 1:1 EtOAc/petroleum ether) afforded C94, a mixture of stereoisomers at the cyclopropane, as a yellow gum. Combined yield: 280 mg, 0.453 mmol, 35%.

Step 2. Synthesis of Ammonium 2-(6-{6-[(4-cyano-2-fluorobenzyl)oxy]-3,5-difluoropyridin-2-yl}-6-azaspiro[2.5]oct-1-yl)-1-[(2S)-oxetan-2-ylmethyl]-1H-benzimidazole-6-carboxylate (56)

Hydrolysis of C94 was carried out using the method described for synthesis of P12 from C30 in Preparation P12 providing 56, a mixture of stereoisomers at the cyclopropane, as a solid. The crude product was purified via reversed-phase HPLC (Column: Agela Durashell C18, 5 μm; Mobile phase A: 0.05% ammonium hydroxide in water; Mobile phase B: acetonitrile; Gradient: 23% to 53% B). The first-eluting stereoisomer, isolated as a white solid, was designated as ENT-1 (57). Yield: 11.0 mg, 17.7 μmol, 21%. LCMS m/z 604.1 [M+H]$^+$. $^1$H NMR (400 MHz, Methanol-d$_4$) δ 8.22 (br s, 1H), 7.95 (dd, 1H), 7.66-7.60 (m, 2H), 7.54 (dd, 1H), 7.49 (dd, 1H), 7.38 (dd, 1H), 5.48 (s, 2H), 5.31-5.22 (m, 1H), 4.72 (dd, 1H), 4.62-4.52 (m, 2H), 4.36 (dt, 1H), 3.69-3.60 (m, 1H), 3.36-3.25 (m, 2H, assumed; largely obscured by solvent peak), 3.16-3.07 (m, 1H), 2.84-2.73 (m, 1H), 2.55-2.47 (m, 1H), 2.45 (dd, 1H), 1.99-1.86 (m, 1H), 1.65 (dd, 1H), 1.62-1.49 (m, 2H), 1.42-1.33 (m, 1H), 1.22 (dd, 1H).

The second-eluting stereoisomer, also isolated as a white solid, was designated as ENT-2 (58). Yield: 23.5 mg, 39.0 μmol, 32%. LCMS m/z 604.1 [M+H]$^+$. $^1$H NMR (400 MHz, Methanol-d₄) δ 8.25 (br s, 1H), 7.95 (dd, 1H), 7.67-7.60 (m, 2H), 7.54 (br d, 1H), 7.49 (br d, 1H), 7.40 (dd, 1H), 5.49 (s, 2H), 5.26-5.18 (m, 1H), 4.74 (dd, component of ABX system; 1H), 4.66-4.57 (m, 2H), 4.44 (dt, 1H), 3.71-3.63 (m, 1H), 3.37-3.26 (m, 2H, assumed; largely obscured by solvent peak), 3.17-3.08 (m, 1H), 2.88-2.76 (m, 1H), 2.61-2.50 (m, 1H), 2.40 (dd, 1H), 2.03-1.93 (m, 1H), 1.65 (dd, 1H), 1.63-1.52 (m, 2H), 1.43-1.34 (m, 1H), 1.24 (dd, 1H).

The compounds listed in Table 7 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 7

Structure and IUPAC name for Examples 59 to 61

| Ex No. | Structure | IUPAC Name |
|---|---|---|
| 59 | 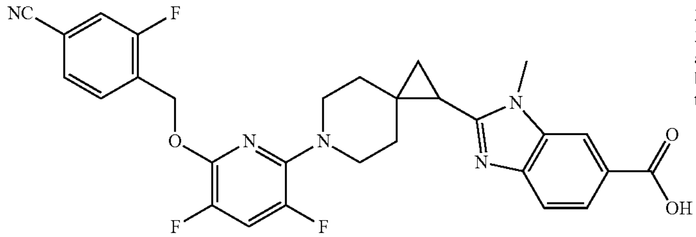 | 2-(6-{6-[(4-cyano-2-fluorobenzyl)oxy]-3,5-difluoropyridin-2-yl}-6-azaspiro[2.5]oct-1-yl)-1-methyl-1H-benzimidazole-6-carboxylic acid, trifluoroacetate salt |
| 60 | 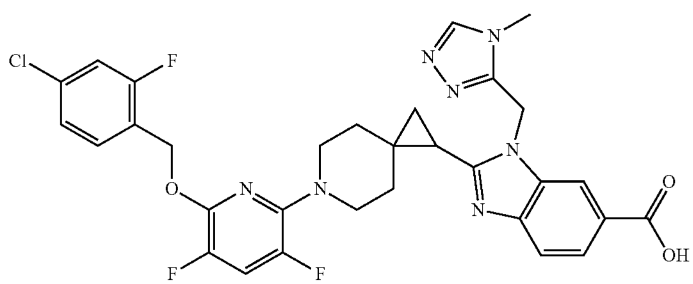 | 2-(6-{6-[(4-chloro-2-fluorobenzyl)oxy]-3,5-difluoropyridin-2-yl}-6-azaspiro[2.5]oct-1-yl)-1-[(4-methyl-4H-1,2,4-triazol-3-yl)methyl]-1H-benzimidazole-6-carboxylic acid, trifluoroacetate salt |
| 61 | 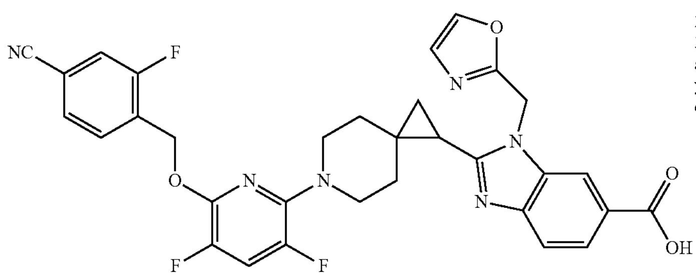 | 2-(6-{6-[(4-cyano-2-fluorobenzyl)oxy]-3,5-difluoropyridin-2-yl}-6-azaspiro[2.5]oct-1-yl)-1-(1,3-oxazol-2-ylmethyl)-1H-benzimidazole-6-carboxylic acid, trifluoroacetate salt |

TABLE 7A

Physicochemical data for Examples 59 to 61

| Ex. No. | Mass spectrum, observed ion m/z [M + H]⁺; HPLC retention time or ¹H NMR |
|---|---|
| 59 | 548.1; 2.91 minutes (Column: Waters XBridge C18, 2.1 × 50 mm, 5 µm; Mobile phase A: water containing 0.1% formic acid; Mobile phase B: acetonitrile; Gradient: 1.0% to 5% B over 0.6 minutes, then 5% to 100% B over 3.4 minutes; Flow rate: 0.8 mL/minute) |
| 60 | 638.3♦; 3.17 minutes (Analytical conditions identical to those used for Ex. 59) |
| 61 | 615.1; 3.19 minutes (Analytical conditions identical to those used for Ex. 59) |

Example 62

2-[(4-{2-[(4-Chloro-2-fluorobenzyl)oxy]pyrimidin-4-yl}piperidin-1-yl)methyl]-1-[(2S)-oxetan-2-ylmethyl]-1H-benzimidazole-6-carboxylic Acid (62)

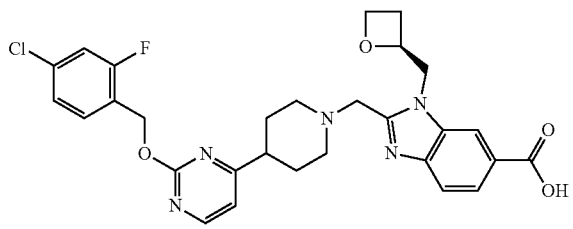

Step 1. Synthesis of methyl 2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylate (C95)

A mixture of P13 (14.34 g, 21.5 mmol), P17 (6.34 g, 21.5 mmol), and potassium carbonate (19.3 g, 140 mmol) in 1,4-dioxane (144 mL) was stirred at 58° C. After 1.5 hours, additional potassium carbonate (5.0 g, 36 mmol) was introduced; 30 minutes later, acetonitrile (50 mL) was added, and after another 50 minutes, more acetonitrile (25 mL) was added. The reaction temperature was then increased to 63° C. overnight, whereupon it was removed from the heat and slowly diluted with water (300 mL). The resulting mixture was extracted with EtOAc (3×200 mL), and the combined organic layers were dried over sodium sulfate, filtered, and concentrated in vacuo. Silica gel chromatography (Gradient: 0% to 10% MeOH in dichloromethane) provided C95 as an off-white solid. Yield: 10.7 g, 18.4 mmol, 86%.

Step 2. Synthesis of 2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylic Acid (62)

A mixture of C95 (9.33 g, 16.1 mmol), MeOH (100 mL), and aqueous sodium hydroxide solution (1.0 M; 40.2 mL, 40.2 mmol) was treated with sufficient THF (12 mL) to form a solution; the reaction mixture was then stirred at room temperature overnight. LCMS analysis at this point indicated conversion to the product: LCMS m/z 566.3 [M+H]$^+$. The reaction mixture was concentrated in vacuo to a final volume of approximately 50 mL, and then treated with 10% aqueous citric acid solution to a pH of 6. After extraction with a mixture of 2-propanol and dichloromethane (1:4; 3×75 mL), the combined organic layers were dried over sodium sulfate, filtered, and concentrated under reduced pressure. The resulting white solid was diluted with cyclohexane and dichloromethane and then concentrated in vacuo to remove residual 2-propanol, affording 62. Yield: 9.25 g, 16 mmol, quantitative. $^1$H NMR (400 MHz, DMSO-d$_6$) δ 8.50 (d, 1H), 8.26 (br s, 1H), 7.80 (dd, 1H), 7.63 (d, 1H), 7.57 (dd, 1H), 7.48 (dd, 1H), 7.32 (dd, 1H), 7.09 (d, 1H), 5.39 (s, 2H), 5.13-5.04 (m, 1H), 4.80 (dd, 1H), 4.66 (dd, 1H), 4.52-4.44 (m, 1H), 4.37 (dt, 1H), 3.87 (AB quartet, 2H), 2.99 (br d, 1H), 2.86 (br d, 1H), 2.76-2.58 (m, 2H), 2.47-2.37 (m, 1H), 2.29-2.12 (m, 2H), 1.88-1.77 (m, 2H), 1.77-1.59 (m, 2H).

The compounds listed in Table 8 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 8

Structure and IUPAC name for Examples 63 to 68

| Ex. No. | Structure | IUPAC Name |
|---|---|---|
| 63 | 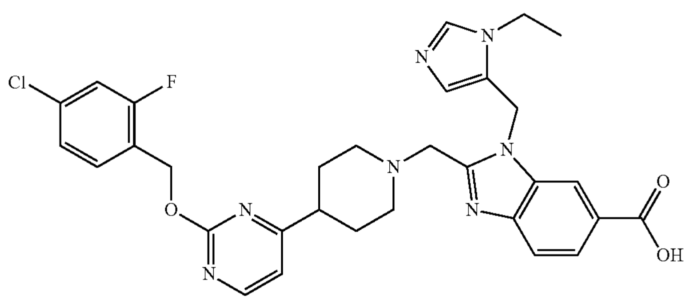 [SMILES: CCn1cncc1Cn1c(CN2CCC(c3ccnc(OCc4ccc(Cl)cc4F)n3)CC2)nc2ccc(C(=O)O)cc21] | 2-[(4-{2-[(4-chloro-2-fluorobenzyl)oxy]pyrimidin-4-yl}piperidin-1-yl)methyl]-1-[(1-ethyl-1H-imidazol-5-yl)methyl]-1H-benzimidazole-6-carboxylic acid |

TABLE 8-continued

Structure and IUPAC name for Examples 63 to 68

| Ex. No. | Structure | IUPAC Name |
|---|---|---|
| 64 | 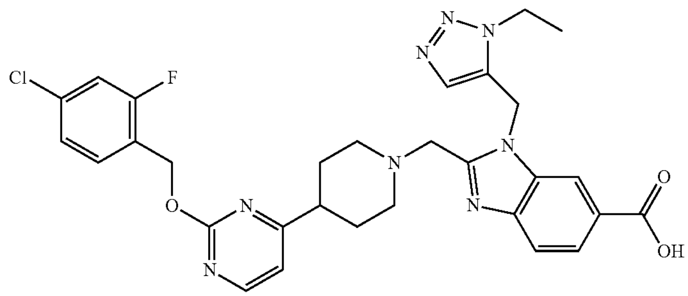 [SMILES: CCn1nncc1Cn1c(CN2CCC(c3ccnc(OCc4ccc(Cl)cc4F)n3)CC2)nc2ccc(C(=O)O)cc21] | 2-[(4-{2-[(4-chloro-2-fluorobenzyl)oxy]pyrimidin-4-yl}piperidin-1-yl)methyl]-1-[(1-ethyl-1H-1,2,3-triazol-5-yl)methyl]-1H-benzimidazole-6-carboxylic acid |
| 65 | 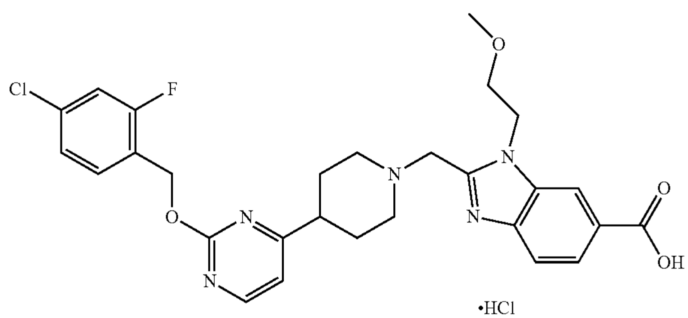 [SMILES: COCCn1c(CN2CCC(c3ccnc(OCc4ccc(Cl)cc4F)n3)CC2)nc2ccc(C(=O)O)cc21 ; Cl] | 2-[(4-{2-[(4-chloro-2-fluorobenzyl)oxy]pyrimidin-4-yl}piperidin-1-yl)methyl]-1-(2-methoxyethyl)-1H-benzimidazole-6-carboxylic acid, hydrochloride salt |
| 66 | 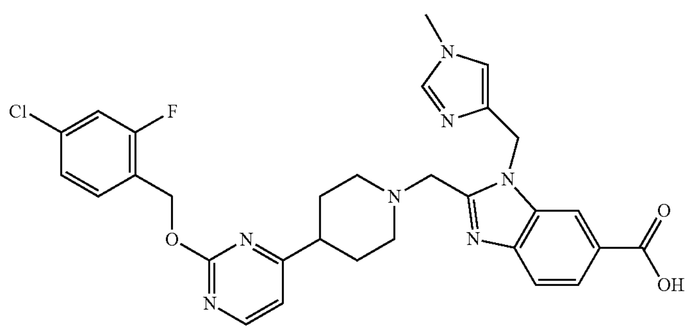 [SMILES: Cn1cnc(Cn2c(CN3CCC(c4ccnc(OCc5ccc(Cl)cc5F)n4)CC3)nc3ccc(C(=O)O)cc32)c1] | 2-[(4-{2-[(4-chloro-2-fluorobenzyl)oxy]pyrimidin-4-yl}piperidin-1-yl)methyl]-1-[(1-methyl-1H-imidazol-4-yl)methyl]-1H-benzimidazole-6-carboxylic acid |
| 67[1] | 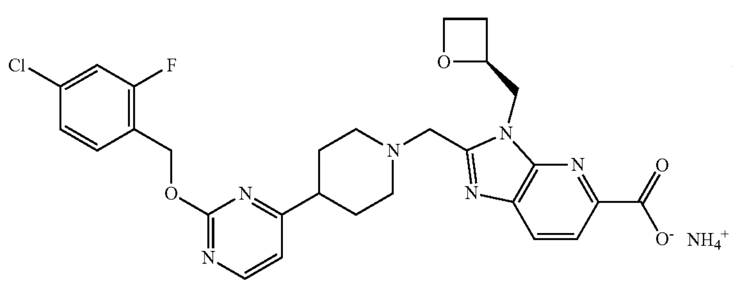 [SMILES: O=C([O-])c1ccc2nc(CN3CCC(c4ccnc(OCc5ccc(Cl)cc5F)n4)CC3)n(C[C@@H]3CCO3)c2n1 ; [NH4+]] | ammonium 2-[(4-{2-[(4-chloro-2-fluorobenzyl)oxy]pyrimidin-4-yl}piperidin-1-yl)methyl]-3-[(2S)-oxetan-2-ylmethyl]-3H-imidazo[4,5-b]pyridine-5-carboxylate |
| 68 | 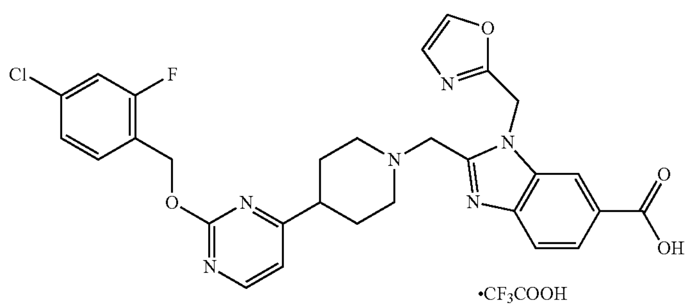 [SMILES: O=C(O)c1ccc2nc(CN3CCC(c4ccnc(OCc5ccc(Cl)cc5F)n4)CC3)n(Cc3ncco3)c2c1 ; "·CF3COOH"] | 2-[(4-{2-[(4-chloro-2-fluorobenzyl)oxy]pyrimidin-4-yl}piperidin-1-yl)methyl]-1-(1,3-oxazol-2-ylmethyl)-1H-benzimidazole-6-carboxylic acid, trifluoroacetate salt |

TABLE 8A

Physicochemical data for Examples 63 to 68

Ex. No. Mass spectrum, observed ion m/z [M + H]+; HPLC retention time or 1H NMR 63   604; 2.64 minutes (Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute)

64   605; 2.22 minutes (Column: Waters XBridge C18, 2.1 × 50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute 65   554.2♦; 1H NMR (600 MHz, DMSO-d6), characteristic peaks: δ 8.58 (s, 1H), 8.31 (s, 1H), 7.89 (d, 1H), 7.78 (d, 1H), 7.65-7.57 (m, 1H), 7.50 (d, 1H), 7.34 (d, 1H), 7.15 (s, 1H), 5.42 (s, 2H), 4.89-4.72 (br m, 2H), 4.70-4.59 (m, 2H), 3.88-3.71 (br m, 2H), 3.70-3.57 (b m, 3H), 3.21 (s, 3H), 3.07-2.93 (br m, 2H), 2.24-2.01 (br m, 4H)

66   590; 2.80 minutes (Analytical conditions identical to those used for Ex. 63

67[1]   566.9♦; 1.81 minutes (Column: Chiral Technologies Chiralpak AD-3, 4.6 × 50 mm, 3 μm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.)

68   577.0♦; 2.55 minutes (Column: Waters XBridge C18, 2.1 × 50 mm, 5 μm; Mobile phase A: water containing 0.1% formic acid; Mobile phase B: acetonitrile; Gradient: 1.0% to 5% B over 0.6 minutes, then 5% to 100% B over 3.4 minutes; Flow rate: 0.8 mL/minute)

Table 8/8A: [1]Treatment of methyl 5-{[(4-{2-[(4-chloro-2-fluorobenzyl)oxy]pyrimidin-4-yl}piperidin-1-yl)acetyl]amino}-6-{[(2S)-oxetan-2-ylmethyl]amino}pyridine-2-carboxylate with aqueous sodium hydroxide solution in 1,4-dioxane at elevated temperature served to effect both ring closure and ester hydrolysis, delivering Example 67 after purification.

Example 69

Ammonium 2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylate (69)

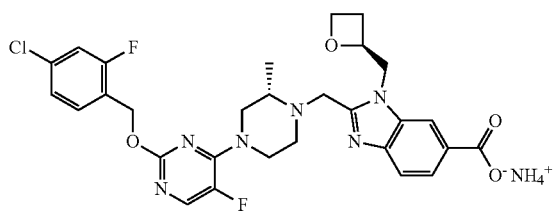

69

Step 1. Synthesis of 2-[(4-chloro-2-fluorobenzyl)oxy]-5-fluoro-4-[(3S)-3-methylpiperazin-1-yl]pyrimidine, Trifluoroacetate Salt (C96)

Trifluoroacetic acid (36 mL) was added to a solution of P14 (7.62 g, 16.8 mmol) in dichloromethane (75 mL) and the reaction mixture was stirred at 18° C. for 1 hour, whereupon it was combined with a similar reaction carried out using P14 (3.09 g, 6.79 mmol). Concentration in vacuo afforded C96 as a brown oil. Combined yield: 11.0 g, 23.5 mmol, quantitative.

Step 2. Synthesis of methyl 2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylate (C97)

A suspension of C96 (11.0 g, 23.5 mmol), P17 (6.94 g, 23.5 mmol), and potassium carbonate (16.3 g, 118 mmol) in acetonitrile (150 mL) was stirred at 50° C. for 19 hours, whereupon it was partitioned between water (300 mL) and EtOAc (300 mL). After extraction of the aqueous layer with EtOAc (2×200 mL), the combined organic layers were concentrated in vacuo and purified via silica gel chromatography (Gradient: 35% to 60% EtOAc in petroleum ether) to provide C97 as a white gum. Yield: 11.1 g, 18.1 mmol, 77%.

Step 3. Synthesis of Ammonium 2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylate (69)

Aqueous sodium hydroxide solution (2 M; 22 mL, 44 mmol) was added to a solution of C97 (5.00 g, 8.16 mmol) in a mixture of MeOH (73 mL) and THF (73 mL). After the reaction mixture had been stirred at 18° C. for 16 hours, it was heated to 45° C. for 3 hours, whereupon it was neutralized to pH 7 by addition of 1 M hydrochloric acid and concentrated in vacuo. The residue was diluted with water (100 mL) and extracted with a mixture of dichloromethane and MeOH (10:1, 4×100 mL); the combined organic layers were concentrated under reduced pressure and then purified using reversed-phase HPLC (Column: Phenomenex Gemini C18, 10 μm; Mobile phase A: 0.05% ammonium hydroxide in water; Mobile phase B: acetonitrile; Gradient: 20% to 40% B) to afford 69 as a white solid. Yield: 2.75 g, 4.59 mmol, 56%. LCMS m/z 598.9♦ [M+H]+. 1H NMR (400 MHz, Methanol-d4) δ 8.23 (dd, 1H), 7.96 (dd, 1H), 7.89 (d, 1H), 7.62 (dd, 1H), 7.46 (dd, 1H), 7.24-7.17 (m, 2H), 5.33 (s, 2H), 5.33-5.26 (m, 1H), 4.9-4.84 (m, 1H, assumed; partially obscured by water peak), 4.75 (dd, 1H), 4.60 (ddd, 1H), 4.49 (d, 1H), 4.33 (dt, 1H), 4.14-4.07 (m, 1H), 4.02 (br d, 1H), 3.70 (d, 1H), 3.52 (ddd, 1H), 3.36-3.29 (m, 1H, assumed; partially obscured by solvent peak), 2.81-2.70 (m, 2H), 2.72-2.63 (m, 1H), 2.54-2.44 (m, 1H), 2.39 (ddd, 1H), 1.18 (d, 3H).

The compounds listed in Table 9 below below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 9

Structure and IUPAC name for Examples 70 to 72

| Ex. No. | Structure | IUPAC Name |
|---|---|---|
| 70 | 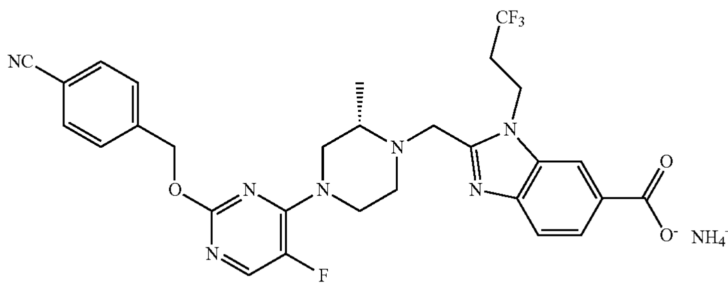 [SMILES: C[C@H]1CN(c2nc(OCc3ccc(C#N)cc3)ncc2F)CCN1Cc1nc2ccc(C(=O)[O-])cc2n1CCC(F)(F)F ; [NH4+]] | ammonium 2-{[(2S)-4-{2-[(4-cyanobenzyl)oxy]-5-fluoropyrimidin-4-yl}-2-methylpiperazin-1-yl]methyl}-1-(3,3,3-trifluoropropyl)-1H-benzimidazole-6-carboxylate |
| 71 | 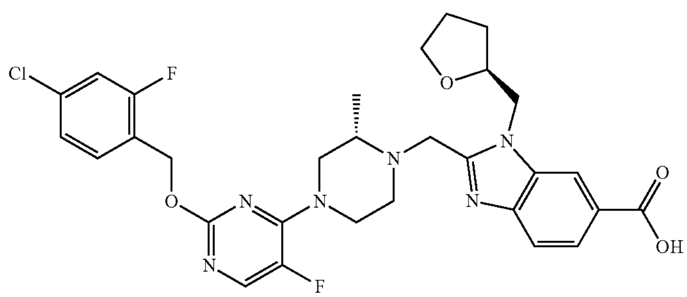 [SMILES: C[C@H]1CN(c2nc(OCc3ccc(Cl)cc3F)ncc2F)CCN1Cc1nc2ccc(C(=O)O)cc2n1C[C@@H]1CCCO1] | 2-{[(2S)-4-{2-[(4-chloro-2-fluorobenzyl)oxy]-5-fluoropyrimidin-4-yl}-2-methylpiperazin-1-yl]methyl}-1-[(2S)-tetrahydrofuran-2-ylmethyl]-1H-benzimidazole-6-carboxylic acid |
| 72 | 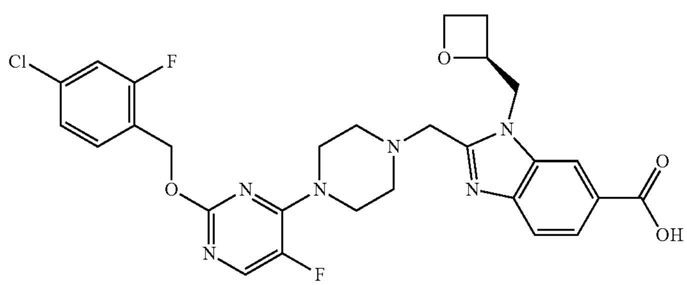 [SMILES: O=C(O)c1ccc2nc(CN3CCN(c4nc(OCc5ccc(Cl)cc5F)ncc4F)CC3)n(C[C@@H]3CCO3)c2c1] | 2-[(4-{2-[(4-chloro-2-fluorobenzyl)oxy]-5-fluoropyrimidin-4-yl}piperazin-1-yl)methyl]-1-[(2S)-oxetan-2-ylmethyl]-1H-benzimidazole-6-carboxylic acid |

TABLE 9A

Physicochemical data for Examples 70 to 72

| Ex. No. | Mass spectrum, observed ion m/z [M + H]$^+$; HPLC retention time or $^1$H NMR |
|---|---|
| 70 | 598.3; 2.41 minutes (Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute) |
| 71 | 613; 2.36 minutes (Column: Waters XBridge C18, 2.1 × 50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute) |
| 72 | 585.2♦; 1.87 minutes (Column: Chiral Technologies Chiralpak AD-3, 4.6 × 50 mm, 3 μm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.) |

Example 73

2-{[(2S)-4-{2-[(4-Chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic Acid (73)

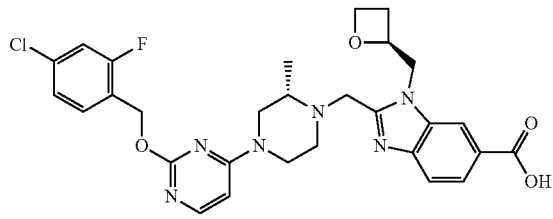

Step 1. Synthesis of methyl 2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylate (C98)

This reaction was carried out in two identical batches. A mixture of P15 (26.3 g 38.6 mmol) and potassium carbonate (31.0 g, 225 mmol) in acetone (190 mL) was stirred at room temperature for 5 minutes, placed in a 70° C. oil bath for 5 minutes, removed from the heat, and stirred for another 5 minutes. To this mixture was added P17 (11.0 g, 37.3 mmol) and the reaction mixture was heated at reflux for 24 hours. After cooling to room temperature, the reaction mixture was diluted with water (350 mL), stirred at room temperature for 1 hour, and extracted with EtOAc (2×250 mL). The EtOAc extracts from both reactions were combined, dried over sodium sulfate, filtered, and concentrated in vacuo; repeated chromatography on silica gel (Gradient: 0% to 10% MeOH in dichloromethane) provided C98 as a white solid. Combined yield: 29.2 g, 49.1 mmol, 66%.

Step 2. Synthesis of 2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic Acid (73)

Aqueous sodium hydroxide solution (1 M; 110 mL, 110 mmol) was added to a 0° C. solution of C98 (18.8 g, 31.6 mmol) in MeOH (220 mL); THF (40 mL) was then added until the mixture became clear. After the reaction mixture had been stirred at room temperature overnight, LCMS analysis indicated conversion to the product: LCMS m/z 581.2♦ [M+H]$^+$. The reaction mixture was concentrated in vacuo to a volume of approximately 125 mL, diluted to 150 mL by addition of water, and slowly adjusted to pH 7 with 10% aqueous citric acid solution. The resulting slurry was filtered, and the filter cake was washed with copious water, affording 73 as a white solid. Yield: 18.2 g, 31.3 mmol, 99%. $^1$H NMR (400 MHz, Methanol-d$_4$) δ 8.30 (br s, 1H), 7.98 (dd, 1H), 7.94 (d, 1H), 7.67 (d, 1H), 7.49 (dd, 1H), 7.26-7.18 (m, 2H), 6.40 (d, 1H), 5.38 (s, 2H), 5.34-5.26 (m, 1H), 4.95-4.85 (m, 1H, assumed; partially obscured by water peak), 4.78 (dd, 1H), 4.62 (td, 1H), 4.50 (d, 1H), 4.35 (dt, 1H), 4.10-3.97 (br m, 1H), 3.97-3.83 (br m, 1H), 3.72 (d, 1H), 3.45-3.3 (m, 1H, assumed; partially obscured by solvent peak), 3.23 (dd, 1H), 2.82-2.70 (m, 2H), 2.70-2.59 (m, 1H), 2.53-2.42 (m, 1H), 2.36 (ddd, 1H), 1.19 (d, 3H).

The compounds listed in Table 10 below were synthesized via procedures analogous to those described herein for syntheses of Examples and Preparations by using appropriate starting materials, which are available commercially, prepared using preparations well-known to those skilled in the art, or prepared in a manner analogous to routes described herein for other intermediates. The compounds were purified using methods well-known to those skilled in the art and may include silica gel chromatography, HPLC, or precipitation from the reaction mixture.

TABLE 10

Structure and IUPAC name for Examples 74 to 78

| Ex. No. | Structure | IUPAC Name |
|---|---|---|
| 74[1] | 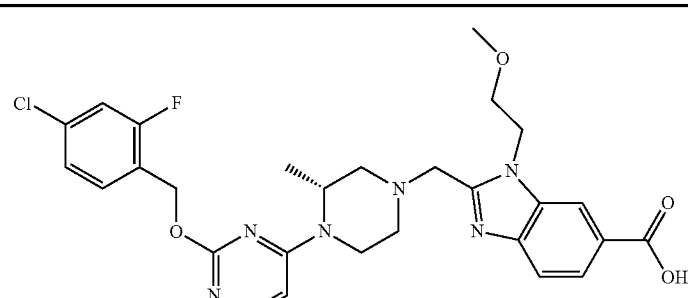 | 2-{[(3R)-4-{2-[(4-chloro-2-fluorobenzyl)oxy]pyrimidin-4-yl}-3-methylpiperazin-1-yl]methyl}-1-(2-methoxyethyl)-1H-benzimidazole-6-carboxylic acid, trifluoroacetate salt |

TABLE 10-continued

Structure and IUPAC name for Examples 74 to 78

| Ex. No. | Structure | IUPAC Name |
|---|---|---|
| 75 | 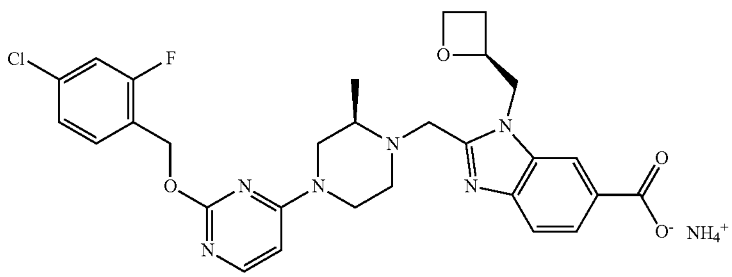 [SMILES: C[C@@H]1CN(c2ccnc(OCc3ccc(Cl)cc3F)n2)CCN1Cc1nc2ccc(C(=O)[O-])cc2n1C[C@@H]1CCO1 ; [NH4+]] | ammonium 2-{[(2R)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylate |
| 76 | 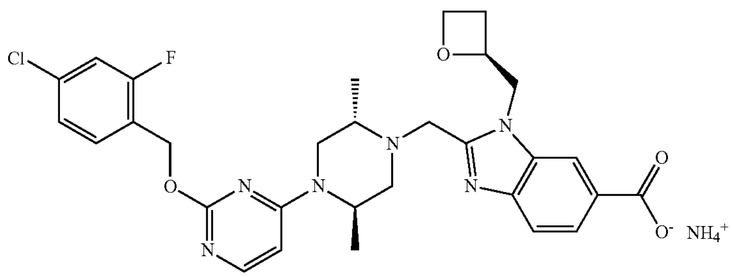 [SMILES: C[C@@H]1CN(Cc2nc3ccc(C(=O)[O-])cc3n2C[C@@H]2CCO2)[C@@H](C)CN1c1ccnc(OCc2ccc(Cl)cc2F)n1 ; [NH4+]] | ammonium 2-{[(2S,5R)-4-{2-[(4-chloro-2-fluorobenzyl)oxy]pyrimidin-4-yl}-2,5-dimethylpiperazin-1-yl]methyl}-1-[(2S)-oxetan-2-ylmethyl]-1H-benzimidazole-6-carboxylate |
| 77 | 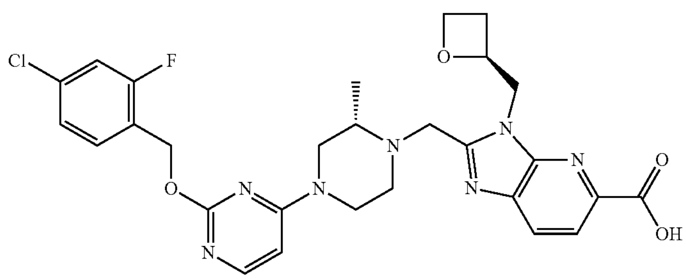 [SMILES: C[C@H]1CN(c2ccnc(OCc3ccc(Cl)cc3F)n2)CCN1Cc1nc2ccc(C(=O)O)nc2n1C[C@@H]1CCO1] | 2-{[(2S)-4-{2-[(4-chloro-2-fluorobenzyl)oxy]pyrimidin-4-yl}-2-methylpiperazin-1-yl]methyl}-3-[(2S)-oxetan-2-ylmethyl]-3H-imidazo[4,5-b]pyridine-5-carboxylic acid |
| 78 | 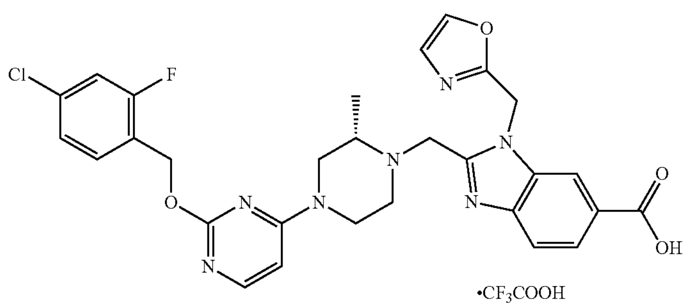 [SMILES: C[C@H]1CN(c2ccnc(OCc3ccc(Cl)cc3F)n2)CCN1Cc1nc2ccc(C(=O)O)cc2n1Cc1ncco1 ; "·CF3COOH"] | 2-{[(2S)-4-{2-[(4-chloro-2-fluorobenzyl)oxy]pyrimidin-4-yl}-2-methylpiperazin-1-yl]methyl}-1-(1,3-oxazol-2-ylmethyl)-1H-benzimidazole-6-carboxylic acid, trifluoroacetate salt |

TABLE 10A

Physicochemical data for Examples 74 to 78

Ex. No. Mass spectrum, observed ion m/z [M + H]$^+$; HPLC retention time or $^1$H NMR 74[1]  569; 2.16 minutes (Column: Waters XBridge C18, 2.1 × 50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute)

75  581.0♦; 2.13 minutes (Column: Chiral Technologies Chiralpak AD-3, 4.6 × 50 mm, 3 μm; Mobile phase A: carbon dioxide; Mobile phase B: 0.05% diethylamine in ethanol; Gradient: 5% B for 0.2 minutes, then 5% to 40% B over 1.4 minutes, then 40% B for 1.05 minutes; Flow rate: 4 mL/minute; Column temperature: 40° C.)

TABLE 10A-continued

Physicochemical data for Examples 74 to 78

| Ex. No. | Mass spectrum, observed ion m/z [M + H]⁺; HPLC retention time or ¹H NMR |
|---|---|
| 76 | 595.0◆; 2.97 minutes (Column: Chiral Technologies Chiralcel OJ-3, 4.6 × 100 mm, 3 µm; Mobile phase A: carbon dioxide; Mobile phase B: 0.05% diethylamine in ethanol; Gradient: 5% to 40% B over 4.5 minutes, then 40% B for 2.5 minutes; Flow rate: 2.8 mL/minute; Column temperature: 40° C.) |
| 77 | 582.1◆; 1.18 minutes (Column: Chiral Technologies Chiralcel OJ-3, 4.6 × 50 mm, 3 µm; Mobile phase A: carbon dioxide; Mobile phase B: 0.05% diethylamine in MeOH; Gradient: 5% B for 0.2 minutes, then 5% to 40% B over 1.4 minutes, then 40% B for 1.05 minutes; Flow rate: 4 mL/minute; Column temperature: 40° C.) |
| 78 | 592.2◆; 1.31 minutes (Analytical conditions identical to those used for Ex. 77) |

Table 10/10A,
[1]Reaction of P8 with tert-butyl (3R)-3-methylpiperazine-1-carboxylate was carried out using cesium fluoride and N,N-diisopropylethylamine in acetonitrile at ≥100° C.

Example 79 and 80

Ammonium 2-[(4-{6-[(4-chloro-2-fluorobenzyl)oxy] pyridin-2-yl}cyclohexyl)methyl]-1-[(2S)-oxetan-2-ylmethyl]-1H-benzimidazole-6-carboxylate, Isomer 1 (79) and Ammonium 2-[(4-{6-[(4-chloro-2-fluorobenzyl)oxy] pyridin-2-yl}cyclohexyl)methyl]-1-[(2S)-oxetan-2-ylmethyl]-1H-benzimidazole-6-carboxylate, Isomer 2 (80)

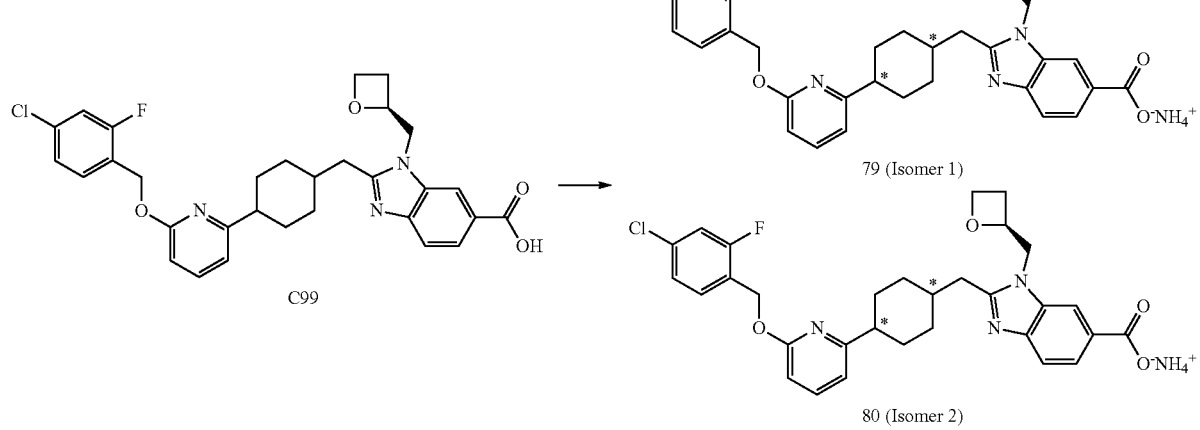

Compound C99, a mixture of cis and trans isomers at the cyclohexyl group, was prepared from P34 and P16 in a manner analogous to the preparation of Example 1 from intermediate P1. The isomeric mixture was subjected to separation by HPLC with the retention times shown below. Column: Chiral Technologies Chiralpak AD-H, 21×250 mm, 5 µm; Mobile phase A: carbon dioxide; Mobile phase B: 0.2% ammonium hydroxide in methanol; Eluent: 30% B; Flow rate: 75 mL/minute; Column temperature: 40° C.).

The first eluting isomer was assigned as isomer 1 (79). Retention time 1.60 min, LCMS m/z 564.5 [M+H]⁺.

The second eluting isomer was assigned as isomer 2 (80). Retention time 1.86 min, LCMS m/z 564.4 [M+H]⁺.

CHO GLP-1R Clone H6—Assay 1

GLP-1R-mediated agonist activity was determined with a cell-based functional assay utilizing an HTRF (Homogeneous Time-Resolved Fluorescence) cAMP detection kit (cAMP HI Range Assay Kit; CisBio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either standard or experimental sample.

The human GLP-1R coding sequence (NCBI Reference Sequence NP_002053.3, including naturally-occurring variant Gly168Ser) was subcloned into pcDNA3 (Invitrogen) and a cell line stably expressing the receptor was isolated (designated Clone H6). Saturation binding analyses (filtration assay procedure) using $^{125}$I-GLP-1$_{7-36}$ (Perkin Elmer) showed that plasma membranes derived from this cell line express a high GLP-1R density ($K_d$: 0.4 nM, $B_{max}$: 1900 fmol/mg protein).

Cells were removed from cryopreservation, re-suspended in 40 mL of Dulbecco's Phosphate Buffered Saline (DPBS—Lonza Cat #17-512Q) and centrifuged at 800×g for 5 min at 22° C. The cell pellet was then re-suspended in 10 mL of growth medium [DMEM/F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081) and 500 µg/mL Geneticin (G418) (Invitrogen #10131035)]. A 1 mL sample of the cell suspension in growth media was counted on a Becton Dickinson ViCell to determine cell viability and cell count per mL. The remaining cell suspension was then adjusted with growth media to deliver 2000 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment in 5% carbon dioxide.

Varying concentrations of each compound to be tested (in DMSO) were diluted in assay buffer (HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E) containing 100 µM 3-isobutyl-1-methylxanthin (IBMX; Sigma cat #15879). The final DMSO concentration is 1%.

After 48 hours, the growth media was removed from the assay plate wells, and the cells were treated with 20 µL of the serially diluted compound in assay buffer for 30 minutes at 37° C. in a humidified environment in 5% carbon dioxide. Following the 30 minute incubation, 10 µL of labeled d2 cAMP and 10 µL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1$_{7-36}$ (1 µM) included on each plate. $EC_{50}$ determinations were made from agonist dose-response curves analyzed with a curve fitting program using a 4-parameter logistic dose response equation.

CHO GLP-1R Clone C6—Assay 2

GLP-1R-mediated agonist activity was determined with a cell-based functional assay utilizing an HTRF (Homogeneous Time-Resolved Fluorescence) cAMP detection kit (cAMP HI Range Assay Kit; Cis Bio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either a standard or an experimental sample.

The human GLP-1R coding sequence (NCBI Reference Sequence NP_002053.3, including naturally-occurring variant Leu260Phe) was subcloned into pcDNA5-FRT-TO and a clonal CHO cell line stably expressing a low receptor density was isolated using the Flp-In™ T-Rex™ System, as described by the manufacturer (ThermoFisher). Saturation binding analyses (filtration assay procedure) using $^{125}$I-GLP-1 (Perkin Elmer) showed that plasma membranes derived from this cell line (designated clone C6) express a low GLP-1R density ($K_d$: 0.3 nM, $B_{max}$: 240 fmol/mg protein), relative to the clone H6 cell line.

Cells were removed from cryopreservation, re-suspended in 40 mL of Dulbecco's Phosphate Buffered Saline (DPBS—Lonza Cat #17-512Q) and centrifuged at 800×g for 5 min at 22° C. The DPBS was aspirated, and the cell pellet was re-suspended in 10 mL of complete growth medium (DMEM:F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081), 700 µg/mL Hygromycin (Invitrogen Cat #10687010) and 15 µg/mL Blasticidin (Gibco Cat #R21001). A 1 mL sample of the cell suspension in growth media was counted on a Becton Dickinson ViCell to determine cell viability and cell count per mL. The remaining cell suspension was then adjusted with growth media to deliver 1600 viable cells per well using a Matrix Combi Multidrop reagent dispenser, and the cells were dispensed into a white 384 well tissue culture treated assay plate (Corning 3570). The assay plate was then incubated for 48 h at 37° C. in a humidified environment (95% $O_2$, 5% $CO_2$)

Varying concentrations of each compound to be tested (in DMSO) were diluted in assay buffer [HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E)] containing 100 µM 3-isobutyl-1-methylxanthin (IBMX; Sigma cat #15879). The final DMSO concentration in the compound/assay buffer mixture is 1%.

After 48 h, the growth media was removed from the assay plate wells, and the cells were treated with 20 µL of the serially diluted compound in assay buffer for 30 min at 37° C. in a humidified environment (95% $O_2$, 5% $CO_2$). Following the 30 min incubation, 10 µL of labeled d2 cAMP and 10 µL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1 (1 µM) included on each plate. $EC_{50}$ determinations were made from agonist dose response curves analyzed with a curve fitting program using a 4-parameter logistic dose response equation.

In Table 11, assay data are presented to two (2) significant figures as the geometric mean ($EC_{50}$s) and arithmetic mean (Emax) based on the number of replicates listed (Number). A blank cell means there was no data for that Example or the Emax was not calculated.

TABLE 11

Biological activity for Examples 1-80.

| Example Number | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| 1 | 1.0 | 84 | 5 | 20 | 95 | 7 |
| 2 | 3.2 | 79 | 8 | 38 | 81 | 3 |
| 3 | 0.58 | 79 | 4 | 9.0 | 88 | 5 |
| 4 | 3.0 | 77 | 6 | 40 | 98 | 3 |
| 5* | 2.2 | 82 | 5 | 42 | 95 | 6 |
| 6 | 4.5 | 68 | 3 | 84 | 83 | 4 |
| 7 | 8.9 | 81 | 3 | 190 | 81 | 3 |
| 8 | 6.0 | 72 | 3 | 230 | 76 | 3 |
| 9 | 28 | 77 | 3 | 700 | 81 | 3 |
| 10 | 9.7 | 76 | 3 | 220 | 100 | 3 |
| 11 | 1.9 | 83 | 4 | 49 | 100 | 3 |
| 12 | 4.7 | 78 | 4 | 110 | 93 | 3 |
| 13 | 6.0 | 80 | 4 | 270 | 91 | 3 |

TABLE 11-continued

Biological activity for Examples 1-80.

| Example Number | Assay 1 EC$_{50}$ (nM) | Assay 1 Emax (%) | Assay 1 Number | Assay 2 EC$_{50}$ (nM) | Assay 2 Emax (%) | Assay 2 Number |
|---|---|---|---|---|---|---|
| 14 | 14 | 77 | 3 | 540 | 120 | 3 |
| 15 | 0.96 | 81 | 4 | 21 | 91 | 3 |
| 16 | 0.99 | 87 | 3 | 18 | 130 | 4 |
| 17 | 6.0 | 86 | 3 | 150 | 91 | 3 |
| 18 | 1.8 | 95 | 3 | 59 | 100 | 3 |
| 19 | 5.3 | 90 | 8 | 42 | 94 | 6 |
| 20 | 0.34 | 80 | 5 | 6.1 | 91 | 4 |
| 21 | 14 | 73 | 3 | 370 | 91 | 3 |
| 22 | 2.8 | 85 | 5 | 23 | 82 | 3 |
| 23 | 41 | 89 | 4 | 450 | 94 | 4 |
| 24 | 2.0 | 76 | 3 | 33 | 89 | 3 |
| 25 | 6.3 | 80 | 4 | 73 | 91 | 3 |
| 26 | 5.1 | 86 | 3 | 38 | 86 | 3 |
| 27 | 0.84 | 86 | 4 | 16 | 85 | 5 |
| 28 | 6.8 | 94 | 3 | 150 | 98 | 3 |
| 29 | 1800 | 65 | 4 | | | |
| 30 | 140 | 79 | 3 | 2800 | 110 | 4 |
| 31 | 300 | 65 | 3 | | | |
| 32 | >20000 | | 1 | | | |
| 33 | 3.1 | 93 | 3 | 84 | 110 | 3 |
| 34 | 1900 | 92 | 3 | | | |
| 35 | 330 | 85 | 3 | 13000 | 100 | 3 |
| 36 | 0.48 | 83 | 3 | 15 | 90 | 5 |
| 37 | 9.3 | 88 | 3 | 190 | 92 | 3 |
| 38 | 1.1 | 75 | 6 | 35 | 91 | 7 |
| 39 | 1.6 | 90 | 3 | 29 | 95 | 3 |
| 40 | 150 | 77 | 3 | 2000 | 100 | 3 |
| 41 | 7.6 | 84 | 4 | 130 | 96 | 3 |
| 42 | 3400 | 89 | 3 | | | |
| 43 | 13 | 75 | 3 | 250 | 70 | 3 |
| 44 | 6.5 | 81 | 3 | 120 | 77 | 3 |
| 45 | 12 | 72 | 3 | 230 | 83 | 3 |
| 46 | >9700 | 100 | 2 | | | |
| 47 | 86 | 92 | 4 | 1700 | 100 | 1 |
| 48 | 2600 | 56 | 3 | | | |
| 49 | 18 | 75 | 3 | 290 | 87 | 3 |
| 50 | 0.71 | 78 | 3 | 19 | 80 | 3 |
| 51 | 470 | 71 | 4 | >20000 | | 1 |
| 52 | 100 | 74 | 3 | 6400 | 100 | 3 |
| 53 | 0.57 | 83 | 3 | 14 | 90 | 3 |
| 54 | 63 | 76 | 3 | 3400 | 93 | 3 |
| 55 | 0.33 | 83 | 3 | 5.8 | 82 | 5 |
| 56 | 0.38 | 80 | 3 | 4.2 | 90 | 3 |
| 57 | 0.30 | 88 | 3 | 4.1 | 98 | 5 |
| 58 | 43 | 74 | 3 | | | |
| 59 | 6.8 | 80 | 3 | 120 | 85 | 3 |
| 60 | 5.0 | 91 | 3 | 110 | 110 | 3 |
| 61 | 1.1 | 68 | 3 | 26 | 74 | 3 |
| 62** | 4.4 | 86 | 8 | 110 | 98 | 12 |
| 63 | 0.98 | 92 | 1 | 10 | 97 | 3 |
| 64 | 24 | 96 | 3 | 100 | 100 | 4 |
| 65 | 88 | 85 | 3 | 1700 | 110 | 3 |
| 66 | 170 | 110 | 4 | | | |
| 67 | 3.3 | 90 | 3 | 52 | 120 | 3 |
| 68 | 8.3 | 77 | 3 | 310 | 92 | 3 |
| 69 | 0.91 | 89 | 3 | 18 | 110 | 5 |
| 70 | 700 | 79 | 3 | | | |
| 71 | 8.9 | 82 | 4 | 160 | 90 | 3 |
| 72* | 6.0 | 96 | 7 | 120 | 130 | 4 |
| 73*** | 2.4 | 84 | 7 | 89 | 100 | 14 |
| 74 | 500 | 86 | 3 | 11000 | 96 | 3 |
| 75 | 21 | 88 | 3 | 370 | 100 | 3 |
| 76 | 12 | 88 | 3 | 180 | 100 | 3 |
| 77* | 4.4 | 100 | 3 | 110 | 110 | 3 |
| 78 | 17 | 79 | 3 | 440 | 81 | 3 |
| 79 | >12000 | | 4 | >20000 | | 2 |
| 80 | 12 | 98 | 4 | 160 | 100 | 3 |

*Tested as ammonium salt and free acid
**Tested as ammonium and tris salts
***Tested as ammonium and tris salts, and free acid All patents, patent applications and references referred to herein are hereby incorporated by reference in their entirety.

It is claimed:

1. A compound of Formula I:

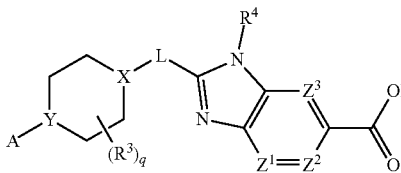

or a pharmaceutically acceptable salt thereof, wherein A is A1 or A2,

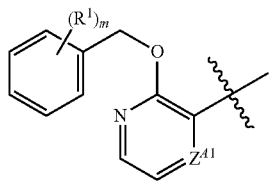

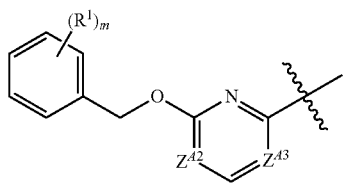

and wherein
each $R^1$ is independently halogen, —CN, —C$_{1-3}$alkyl, or —OC$_{1-3}$alkyl, wherein the alkyl of C$_{1-3}$alkyl and OC$_{1-3}$alkyl is substituted with 0 to 3 F atoms;
m is 0, 1, 2, or 3;
X—L is N—CH$_2$, CHCH$_2$, or cyclopropyl;
Y is CH or N;
$Z^{A1}$ is CH, CR$^2$, or N;
$Z^{A2}$ is CH, CR$^2$, or N;
$Z^{A3}$ is CH, CR$^2$, or N, provided that $Z^{A2}$ and $Z^{A3}$ are not simultaneously N; and further provided that one of $Z^{A2}$ and $Z^{A3}$ is N when X—L is N—CH$_2$;
each $R^2$ is independently F, C, or —CN;
each $R^3$ is independently F, —OH, —CN, —C$_{1-3}$alkyl, —OC$_{1-3}$alkyl, or —C$_{3-4}$cycloalkyl, or 2 R$^3$s may together cyclize to form —C$_{3-4}$spirocycloalkyl, wherein the alkyl of C$_{1-3}$alkyl and OC$_{1-3}$alkyl, cycloalkyl, or spirocycloalkyl may be substituted as valency allows with 0 to 3 F atoms and with 0 to 1 —OH;
q is 0, 1, or 2;
$R^4$ is —C$_{1-3}$alkyl, —C$_{0-3}$alkylene-C$_{3-9}$cycloalkyl, —C$_{0-3}$alkylene-R$^5$, or —C$_{1-3}$alkylene-R$^6$, wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, and —N(R$^N$)$_2$, and
wherein said alkylene of —C$_{0-3}$alkylene-C$_{3-6}$cycloalkyl, —C$_{0-3}$alkylene-R$^5$, or —C$_{1-3}$alkylene-R$^6$ and said cycloalkyl may be independently substituted as valency allows with 0 to 2 substituents independently selected from 0 to 2 F atoms and 0 to 1 substituent selected from C$_{0-1}$alkylene-CN, C$_{0-1}$alkylene-OR$^O$, and —N(R$^N$)$_2$;

R⁵ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
0 to 3 F atoms,
0 to 1 —CN, and
0 to 1 —OR$^O$;
R⁶ is a 5- to 6-membered heteroaryl, wherein said heteroaryl may be substituted with 0 to 2 substituents as valency allows independently selected from:
0 to 2 halogens,
0 to 1 substituent selected from —OR$^O$ and —N(R$^N$)$_2$, and
0 to 2 —C$_{1-3}$alkyl, wherein the alkyl may be substituted with 0 to 3 substituents as valency allows independently selected from:
0 to 3 F atoms, and
0 to 1 —OR$^O$;
each R$^O$ is independently H, or —C$_{1-3}$alkyl, wherein C$_{1-3}$alkyl may be substituted with 0 to 3 F atoms;
each R$^N$ is independently H, or —C$_{1-3}$alkyl;
Z¹, Z², and Z³ are each —CR$^Z$, or
one of Z¹, Z², and Z³ is N and the other two are —CR$^Z$; and
each R$^Z$ is independently H, F, Cl, or —CH$_3$.

2. The compound of claim 1, wherein the compound is a compound of Formula II

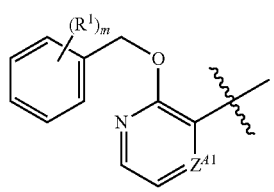

II or a pharmaceutically acceptable salt thereof, wherein A is A1 or A2,

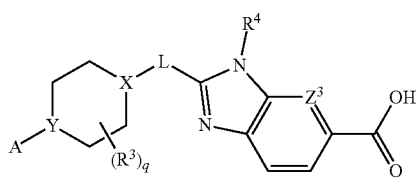

A1

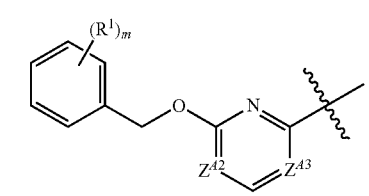

A2 and wherein
each R¹ is independently F, Cl, or —CN; and
m is 0, 1, or 2.

3. The compound of claim 1, wherein the compound is a compound of Formula III

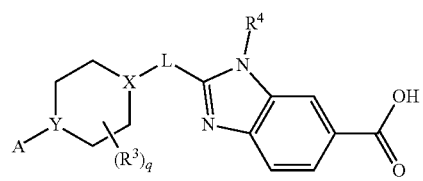

III or a pharmaceutically acceptable salt thereof, wherein A is A1 or A2,

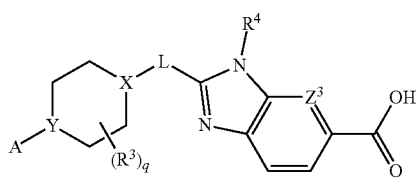

A1

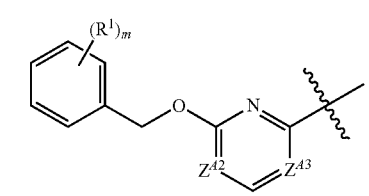

A2 and wherein
each R¹ is independently F, Cl, or —CN; and
m is 0, 1, or 2.

4. The compound of claim 1, wherein A is A1, or a pharmaceutically acceptable salt thereof.

5. The compound of claim 4, wherein the compound is a compound of Formula IV

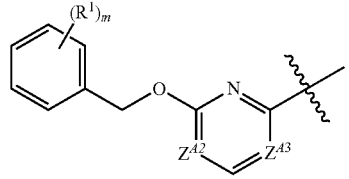

IV or a pharmaceutically acceptable salt thereof, wherein
each R¹ is independently F, Cl, or —CN;
m is 0, or 1;
q is 0 or 1; and
R³ is —CH$_3$.

6. The compound of claim 5, wherein Z$^{A1}$ is CH, or CR²; and R² is F; or a pharmaceutically acceptable salt thereof.

7. The compound of claim 5, wherein Z$^{A1}$ is N, or a pharmaceutically acceptable salt thereof.

8. The compound of claim 1, wherein A is A2;
q is 0 or 1; and
$R^3$ is —$CH_3$;
or a pharmaceutically acceptable salt thereof.

9. The compound of claim 8, wherein $Z^{42}$ is CH, or $CR^2$; and $Z^{43}$ is N; or a pharmaceutically acceptable salt thereof.

10. The compound of claim 8, wherein $Z^{42}$ is N and $Z^{43}$ is CH, or $CR^2$, or a pharmaceutically acceptable salt thereof.

11. The compound of claim 1, wherein the compound is a compound of Formula V

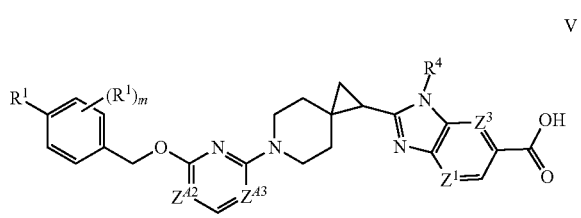

V or a pharmaceutically acceptable salt thereof, wherein
each $R^1$ is independently F, C, or —CN;
m is 0, or 1;
$Z^{42}$ is CH, $CR^2$, or N;
$Z^{43}$ is CH, $CR^2$, or N, provided that $Z^{42}$ and $Z^{43}$ are not simultaneously N; and
each $R^2$ is F.

12. The compound of claim 1, wherein the compound is a compound of Formula VI

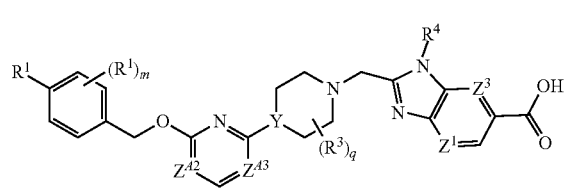

VI or a pharmaceutically acceptable salt thereof, wherein
each $R^1$ is independently F, Cl, or —CN;
m is 0, or 1;
$R^3$ is —$CH_3$;
q is 0, 1, or 2;
$Z^{42}$ is CH, $CR^2$, or N;
$Z^{43}$ is CH, $CR^2$, or N, $Z^{42}$ and $Z^{43}$ are not simultaneously N; and further provided that one of $Z^{42}$ and $Z^{43}$ is N;
$R^2$ is F; and
Y is CH or N.

13. The compound of claim 1, wherein $R^4$ is —$CH_2$—$R^5$, wherein $R^5$ is 4- to 5-membered heterocycloalkyl, wherein said heterocycloalkyl may be substituted with 0 to 2 substituents as valency allows independently selected from:
0 to 2 F atoms, and
0 to 1 substituent selected from oxo (=O), —$OCH_3$ and —$CH_2OCH_3$;
or a pharmaceutically acceptable salt thereof.

14. The compound of claim 1, wherein $R^4$ is —$CH_2$—$R^6$, wherein $R^6$ is 5-membered heteroaryl, wherein said heteroaryl may be substituted with 0 to 2 substitutents as valency allows independently selected from:
0 to 2 halogens, wherein the halogen is independently selected from F and Cl,
0 1 —$OCH_3$, and
0 to 1 —$CH_3$, —$CH_2CH_3$, —$CF_3$, or —$CH_2CH_2OCH_3$;
or a pharmaceutically acceptable salt thereof.

15. The compound of claim 1, wherein $R^4$ is —$C_{1-3}$alkyl, wherein said alkyl may be substituted as valency allows with 0 to 3 substituents independently selected from 0 to 3 F atoms and 0 to 1 substituent that is $C_{0-1}$alkylene-$OR^O$.

16. A compound of claim 1 that is
2-[(4-{2-[(4-chloro-2-fluorobenzyl)oxy]pyridin-3-yl}piperidin-1-yl)methyl]-1-[(2S)-oxetan-2-ylmethyl]-1H-benzimidazole-6-carboxylic acid;
2-[(4-{2-[(4-chloro-2-fluorobenzyl)oxy]pyridin-3-yl}piperidin-1-yl)methyl]-1-(1,3-oxazol-2-ylmethyl)-1H-benzimidazole-6-carboxylic acid;
2-[(4-{2-[(4-cyano-2-fluorobenzyl)oxy]pyridin-3-yl}piperidin-1-yl)methyl]-1-(1,3-oxazol-2-ylmethyl)-1H-benzimidazole-6-carboxylic acid;
2-[(4-{2-[(4-cyano-2-fluorobenzyl)oxy]pyridin-3-yl}piperidin-1-yl)methyl]-1-[(2S)-oxetan-2-ylmethyl]-1H-benzimidazole-6-carboxylic acid; or
2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylic acid;
or a pharmaceutically acceptable salt thereof.

17. A compound of claim 1 that is
2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylic acid;
2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylic acid;
2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid;
2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylic acid; or
2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylic acid;
or a pharmaceutically acceptable salt thereof.

18. A compound of claim 1 that is
2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylic acid;
2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylic acid; or
2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic acid;
or a pharmaceutically acceptable salt thereof.

19. A pharmaceutical composition comprising the compound of claim 1, or a pharmaceutically acceptable salt thereof, and a pharmaceutically acceptable excipient.

20. A method of treating a disease or disorder in a mammal comprising administering to the mammal a therapeutically effective amount of the compound of claim 1, or a pharmaceutically acceptable salt thereof, wherein the disease or disorder is Type 1 diabetes (T1 D), Type 2 diabetes mellitus (T2DM), pre-diabetes, idiopathic T1D, latent autoimmune diabetes in adults, early-onset T2DM, youth-onset atypical diabetes, maturity onset diabetes of the young, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity, eating disorders, weight gain from use of other agents, excessive sugar craving, dyslipidemia, hyperinsulinemia, nonalcoholic fatty liver disease (NAFLD), non-alcoholic steatohepatitis (NASH), fibrosis, cirrhosis, hepatocellular carcinoma, cardiovascular disease, atherosclerosis, coronary artery disease, peripheral vascular disease, hypertension, endothelial dysfunction, impaired vascular compliance, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, Polycystic Ovary Syndrome, and addiction.

* * * * *